United States Patent
Emanuel et al.

(10) Patent No.: US 11,597,746 B2
(45) Date of Patent: Mar. 7, 2023

(54) CYCLIC DINUCLEOTIDES AS STING AGONISTS

(71) Applicant: JANSSEN BIOTECH, INC., Horsham, PA (US)

(72) Inventors: Stuart Emanuel, Spring House, PA (US); Mark Richter, Spring House, PA (US); Peter J. Connolly, Spring House, PA (US); James P. Edwards, Spring House, PA (US); Guangyi Wang, Irvine, CA (US); Santhosh Kumar Thatikonda, San Mateo, CA (US); Leonid Beigelman, San Mateo, CA (US); Gilles Bignan, Spring House, PA (US); Wim Bert Griet Schepens, Beerse (BE); Marcel Viellevoye, Beerse (BE); Johannes Wilhelmus J. F. Thuring, Beerse (BE)

(73) Assignee: Janssen Biotech, Inc., Horsham, PA (US)

( * ) Notice: Subject to any disclaimer, the term of this patent is extended or adjusted under 35 U.S.C. 154(b) by 29 days.

(21) Appl. No.: 17/260,886

(22) PCT Filed: Jul. 16, 2019

(86) PCT No.: PCT/IB2019/056075
§ 371 (c)(1),
(2) Date: Jan. 15, 2021

(87) PCT Pub. No.: WO2020/016782
PCT Pub. Date: Jan. 23, 2020

(65) Prior Publication Data
US 2021/0277046 A1    Sep. 9, 2021

Related U.S. Application Data

(60) Provisional application No. 62/699,001, filed on Jul. 17, 2018.

(51) Int. Cl.
*C07H 19/207*    (2006.01)
*C07H 19/23*    (2006.01)
*A61P 35/00*    (2006.01)

(52) U.S. Cl.
CPC .......... *C07H 19/207* (2013.01); *A61P 35/00* (2018.01); *C07H 19/23* (2013.01)

(58) Field of Classification Search
None
See application file for complete search history.

(56) References Cited

FOREIGN PATENT DOCUMENTS

| WO | 2017/161349 A1 | 9/2017 | |
|----|----------------|--------|---|
| WO | 2018/045204 A1 | 3/2018 | |
| WO | WO-2018045204 A1 * | 3/2018 | ......... A61K 31/7084 |

OTHER PUBLICATIONS

Beckett et al., "A minimal peptide substrate in biotin holoenzyme synthetase-catalyzed biotinylation", Protein Science, 1999, 8, 921-929.
Bhat et al., "Recognition of Cytosolic DNA by cGAS and other STING-dependent sensors". Eur J Immunol. Mar. 2014; 44(3):634-40.
Chen H, et al. "Activation of STAT6 by STING Is Critical for Antiviral Innate Immunity" Cell. 2011, vol. 14: 433-446.
Chou, et al., "Quantitative Analysis of Dose-Effect Relationships: The Combined Effects of Multiple Drugs or Enzyme Inhibitors", 1984, Adv. Enzyme Regul. 22, 27-55.
Corrales, L. et al., "Direct activation of STING in the tumor microenvironment leads to potent and systemic tumor regression and immunity" Cell Reports, 2015, vol. II: 1-13.
Danilchanka, et al., "Cyclic Dinucleotides and the Innate Immune Response" Cell. 2013. vol. 154: 962-970.
Holford, et al., "Understanding the Dose-Effect Relationship: Clinical Applications of Pharmacokinetic-Pharmacodynamic Models" Clin. Pharmacokinet., 1981, 6: 429-453.
Konno, H. et al., "Cyclic dinucleotides trigger ULK1 (ATG1) phosphorylation of STING to prevent sustained innate immune signaling" Cell, 2013, vol. 155: 688-698.
Liu, et al., "Phosphorylation of innate immune adaptor proteins MAVS, STING, and TRIF induces IRF3 activation" Science. 2015:2630-2637.
Liu, et al., "Systematic identification of type I and type II interferon-induced antiviral factors". Proc. Natl. Acad. Sci. 2012: vol. 109: 4239-4244.
Loewe, et al., "Effect of combinations: mathematical basis of problem", Arch. Exp. Pathol Pharmacol., 1926, 114: 313-326.
Sun, L. et al., "Cyclic GMP-AMP Synthase Is a Cytosolic DNA Sensor That Activates the Type I Interferon Pathway" Science, 2013, vol. 339: 786-791.
Yi, et. al., "Single 20 Nucleotide Polymorphisms of Human STING can affect innate immune response to cyclic dinucleotides" PLOS One. 2013, 8(10), e77846.

(Continued)

*Primary Examiner* — Traviss C McIntosh, III
(74) *Attorney, Agent, or Firm* — BakerHostetler

(57) ABSTRACT

Disclosed are compounds, compositions and methods for treating of diseases, syndromes, or disorders that are affected by the modulation of STING. Such compounds are represented by Formula (I), wherein $R_1$, $R_1'$, $X_1$, $B_1$, $R_2$, $R_2'$, $B_2$, $X_2$, $R_3$, Z-M-Y, and $Y_1$-$M_1$-$Z_1$ are as defined herein.

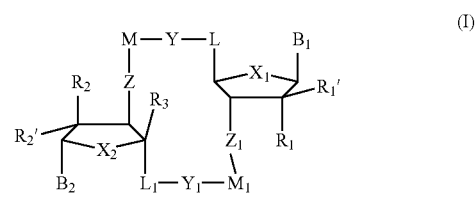

(I)

53 Claims, No Drawings

(56) References Cited

OTHER PUBLICATIONS

Zhang X, et al., "Cyclic GMP-AMP Containing Mixed Phosphodiester Linkages Is An Endogenous High-Affinity Ligand for STING" Molecular Cell, 2013, vol. 51: 226-235.

Zhong B, et al., "The Adaptor Protein MITA Links Virus Sensing Receptors to IRF3 Transcription Factor Activation". Immunity. 2008. vol. 29: 538-550.

* cited by examiner

US 11,597,746 B2

CYCLIC DINUCLEOTIDES AS STING AGONISTS

CROSS-REFERENCE TO RELATED APPLICATIONS

This application is a U.S. National Stage application of International Patent Application No. PCT/IB2019/056075 filed Jul. 16, 2019, which claims the benefit of priority of U.S. Provisional Patent Application No. 62/699,001, filed Jul. 17, 2018, both of which are incorporated by reference herein, in their entirety and for all purposes.

FIELD OF THE INVENTION

The present invention relates to novel compounds which are STING (Stimulator of Interferon Genes) agonists and are useful for the treatment of disorders that are affected by the modulation of the STING protein. The invention also relates to pharmaceutical compositions comprising one or more of such compounds, processes to prepare such compounds and compositions, and use of such compounds or pharmaceutical compositions for the treatment of various diseases, syndromes and disorders. The invention may be involved in the activation of the downstream signaling pathway, further resulting in the activation of second messengers and growth factors, and the production of interferon involved in innate and adaptive immunity. More particularly, the present invention relates to the use of such compounds or pharmaceutical compositions for the treatment of various infections, diseases, syndromes and disorders including, but not limited to, melanoma, colon cancer, breast cancer, prostate cancer, lung cancer, fibrosarcoma, and antiviral therapy.

BACKGROUND OF THE INVENTION

STING (stimulator of interferon genes), also known as TMEM173, MITA, MPYS, and ERIS, is a transmembrane receptor located inside the cell and a key sensor of cytosolic nucleic acids (Zhong B, et al. "The Adaptor Protein MITA Links Virus-Sensing Receptors to IRF3 Transcription Factor Activation". *Immunity.* 2008. vol. 29: 538-550). Recent studies have revealed the biology of STING and its role in mobilizing an innate immune response resulting in robust antitumor activity in mouse models. Activation of the STING pathway results in production of Type I interferons (mainly IFN-α and IFN-β) induced through the IRF3 (interferon regulatory factor 3) pathway. Activation of IRF3 is thought to be mediated by TBK1 that recruits and phosphorylates IRF3 thus forming an IRF3 homodimer capable of entering the nucleus to transcribe type I interferon and other genes (Liu S, et al. "Phosphorylation of innate immune adaptor proteins MAVS, STING, and TRIF induces IRF3 activation" Science. 2015: 2630-2637). TBK1 also activates the nuclear factor kappa-light-chain-enhancer of activated B cells pathway which leads to production of pro-inflammatory cytokines (IL-1α, IL-1β, IL-2, IL-6, TNF-α, etc.), via the oncogenic transcription factor NF-κB. In addition, STING activates STAT6 (signal transducer and activator of transcription 6) to induce (Th2-type), increase (IL-12) or decrease (IL-10) production of various cytokines, including the chemokines CCL2, CCL20, and CCL26 (Chen H, et al. "Activation of STAT6 by STING Is Critical for Antiviral Innate Immunity" *Cell.* 2011, vol. 14: 433-446). Direct phosphorylation of STING on Ser366 upon activation has also been reported to occur through TBK1 (Corrales, L. et al "Direct activation of STING in the tumor microenvironment leads to potent and systemic tumor regression and immunity" *Cell Reports,* 2015, vol. 11: 1-13; Konno, H. et al. "Cyclic dinucleotides trigger ULK1 (ATG1) phosphorylation of STING to prevent sustained innate immune signaling" *Cell,* 2013, vol. 155: 688-698).

The natural ligand that binds to and activates STING (2',3')cyclic guanosine monophosphate-adenosine monophosphate (2',3'-cGAMP) and the enzyme responsible for its synthesis (cGAS, also known as C6orf150 or MB21D1) have been elucidated providing an opportunity to modulate this pathway. cGAMP is a high affinity ligand for STING produced in mammalian cells that serves as an endogenous second messenger to activate the STING pathway. It is a cyclic dinucleotide with a unique 2',3' linkage produced by cGAS in the presence of exogenous double-stranded DNA (e.g. that released by invading bacteria, viruses or protozoa) or of self-DNA in mammals (Wu et al., 2013; Sun, L. et al. "Cyclic GMP-AMP Synthase Is a Cytosolic DNA Sensor That Activates the Type I Interferon Pathway" *Science,* 2013, vol. 339: 786-791; Bhat N and Fitzgerald K A. "Recognition of Cytosolic DNA by cGAS and other STING-dependent sensors". *Eur J Immunol.* 2014 March; 44(3): 634-40). STING activation can also occur through binding of exogenous (3',3) cyclic dinucleotides (c-di-GMP, c-di-AMP and 3'3'-cGAMP) that are released by invading bacteria (Zhang X, et al. "Cyclic GMP-AMP Containing Mixed Phosphodiester Linkages Is An Endogenous High-Affinity Ligand for STING" *Molecular Cell,* 2013, vol. 51: 226-235; Danilchanka, O and Mekalanos, J J. "Cyclic Dinucleotides and the Innate Immune Response" Cell. 2013. vol. 154: 962-970).

Activation of the STING pathway triggers an immune response that results in generation of specific killer T-cells that can shrink tumors and provide long lasting immunity so they do not recur. The striking antitumor activity obtained with STING agonists in preclinical models has generated a high level of excitement for this target and small molecule compounds that can modulate the STING pathway have potential to treat both cancer and reduce autoimmune diseases.

Activation of the STING pathway also contributes to an antiviral response. Loss-of-functional response, either at the cellular or organism level, demonstrates an inability to control viral load in the absence of STING. Activation of the STING pathway triggers an immune response that results in antiviral and proinflammatory cytokines that combat the virus and mobilize the innate and adaptive arms of the immune system. Ultimately, long-lasting immunity is developed against the pathogenic virus. The striking antiviral activity obtained with STING agonists in preclinical models has generated a high level of excitement for this target and small molecule compounds that can modulate the STING pathway have potential to treat chronic viral infections, such as hepatitis B.

Chronic hepatitis B virus (HBV) infection is a significant global health problem, affecting over 5% of the world population (over 350 million people worldwide and 1.25 million individuals in the U.S.). Despite the availability of certain HBV vaccines and therapies, the burden of chronic HBV infection continues to be a significant unmet worldwide medical problem due to suboptimal treatment options and sustained rates of new infections in most parts of the developing world. Current treatments are limited to only two classes of agents: interferon alpha and nucleoside analogues acting as inhibitors of the viral polymerase. Yet none of these therapies offer a cure to the disease, and drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma. There is, therefore, a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, may lead to significantly reduced virus burden, improved prognosis, diminished progression of the disease and enhanced seroconversion rates.

The potential therapeutic benefits of enhancing both innate and adaptive immunity make STING an attractive therapeutic target that demonstrates impressive activity by itself and can also be combined with other immunotherapies.

SUMMARY OF THE INVENTION

The present invention is directed to compounds of Formula (I):

Formula (I)

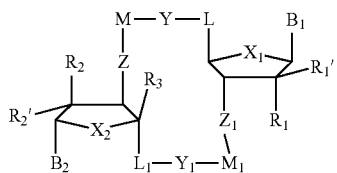

$B_1$ and $B_2$ are independently b1, b2, b3, b4, b5, b6, b7, b8, b9, b10, b11, b12, b13, b14, b15, b16, b17, b18, b19, b20, b21, b22, b23, b24, b25, b26, b27, b28, b29, or b30:

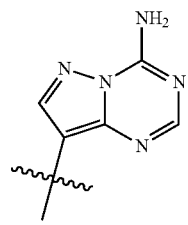
b1

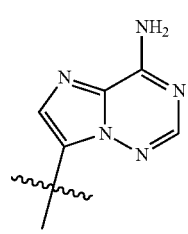
b2

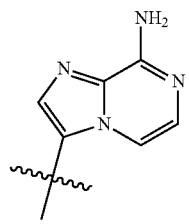
b3

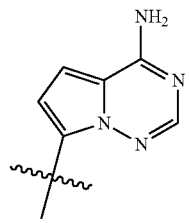
b4

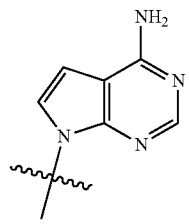
b5

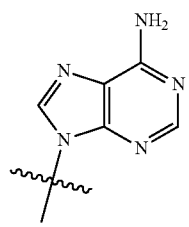
b6

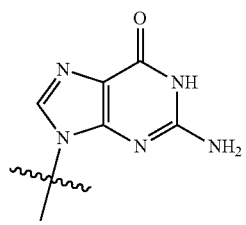
b7

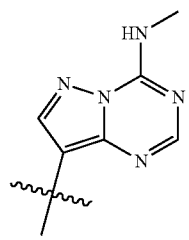
b8

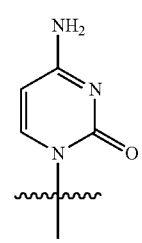
b9

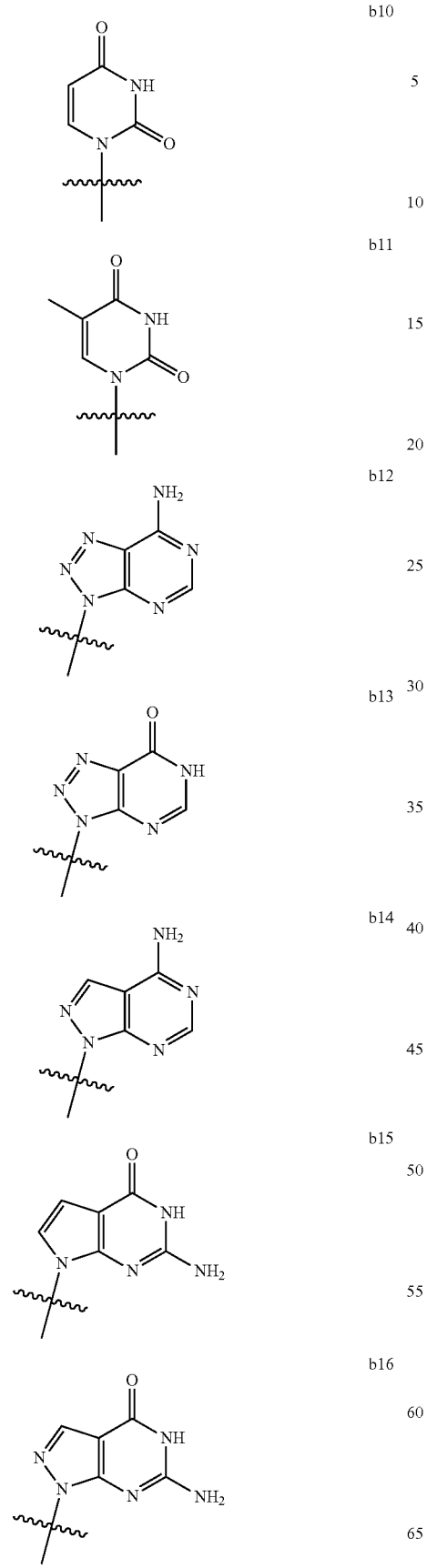
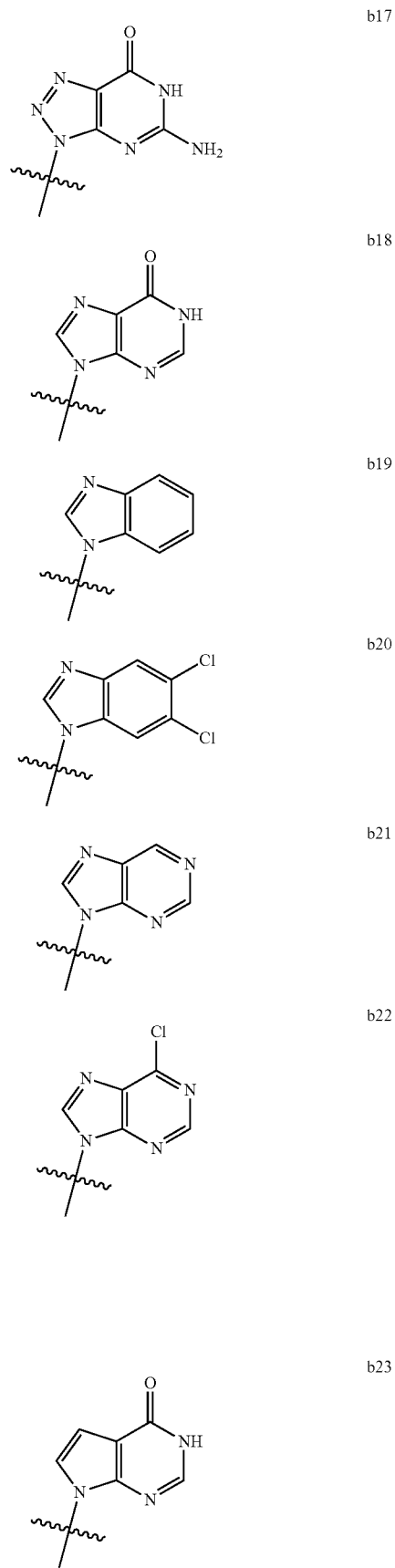

b24 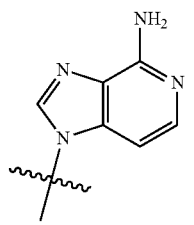

b25 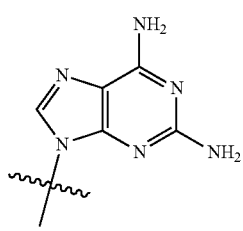

b26 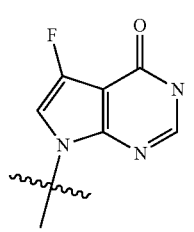

b27 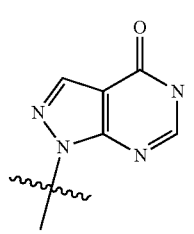

b28 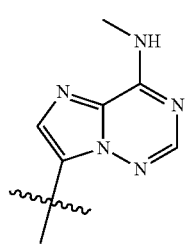

b29 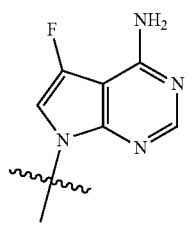

b30

$B_1$ and $B_2$ may be the same or differ. In some aspects, $B_1$ and $B_2$ are the same. In other aspects, $B_1$ and $B_2$ differ. In some embodiments, $B_1$ is b1. In other embodiments, $B_1$ is b2. In further embodiments, $B_1$ is b3. In yet other embodiments, $B_1$ is b4. In still further embodiments, $B_1$ is b5. In other embodiments, $B_1$ is b6. In further embodiments, $B_1$ is b7. In still other embodiments, $B_1$ is b8. In yet further embodiments, $B_1$ is b9. In other embodiments, $B_1$ is b10. In further embodiments, $B_1$ is b11. In yet other embodiments, $B_1$ is b12. In still further embodiments, $B_1$ is b13. In other embodiments, $B_1$ is b14. In further embodiments, $B_1$ is b15. In still other embodiments, $B_1$ is b16. In yet further embodiments, $B_1$ is b17. In other embodiments, $B_1$ is b18. In further embodiments, $B_1$ is b19. In yet other embodiments, $B_1$ is b20. In still further embodiments, $B_1$ is b21. In other embodiments, $B_1$ is b22. In further embodiments, $B_1$ is b23. In still other embodiments, $B_1$ is b24. In yet other embodiments, $B_1$ is b25. In still further embodiments, $B_1$ is b26. In other embodiments, $B_1$ is b27. In further embodiments, $B_1$ is b28. In still other embodiments, $B_1$ is b29. In yet further embodiments, $B_1$ is b30. In other embodiments, $B_1$ is b6, b7, b12-b14, b17, b18, b20, b21, or b26-b30. In further embodiments, $B_1$ is b6 or b7.

In some embodiments, $B_2$ is b1. In other embodiments, $B_2$ is b2. In further embodiments, $B_2$ is b3. In yet other embodiments, $B_2$ is b4. In still further embodiments, $B_2$ is b5. In other embodiments, $B_2$ is b6. In further embodiments, $B_2$ is b7. In still other embodiments, $B_2$ is b8. In yet further embodiments, $B_2$ is b9. In other embodiments, $B_2$ is b10. In further embodiments, $B_2$ is b11. In yet other embodiments, $B_2$ is b12. In still further embodiments, $B_2$ is b13. In other embodiments, $B_2$ is b14. In further embodiments, $B_2$ is b15. In still other embodiments, $B_2$ is b16. In yet further embodiments, $B_2$ is b17. In other embodiments, $B_2$ is b18. In further embodiments, $B_2$ is b19. In yet other embodiments, $B_2$ is b20. In still further embodiments, $B_2$ is b21. In other embodiments, $B_2$ is b22. In further embodiments, $B_2$ is b23. In still other embodiments, $B_2$ is b24. In yet other embodiments, $B_2$ is b25. In still further embodiments, $B_2$ is b26. In other embodiments, $B_2$ is b27. In further embodiments, $B_2$ is b28. In still other embodiments, $B_2$ is b29. In yet further embodiments, $B_2$ is b30. In other embodiments, $B_2$ is b6, b7, b12-b14, b17, b18, b20, b21, or b26-b30. In further embodiments, $B_2$ is b6 or b7.

$R_1$ is independently selected from hydrogen; hydroxy; fluoro; $C_{1-3}$alkoxy optionally independently substituted with one to seven halogen substituents, methoxy, or $C_{6-10}$aryl; wherein said $C_{6-10}$aryl is optionally independently substituted with one to two substituents independently selected from the group consisting of fluoro, chloro, bromo, iodo, $C_{1-3}$alkoxy, $C_{1-3}$alkyl, hydroxy, nitro and cyano; $C_{3-6}$alkenyloxy; $C_{2-6}$alkynyloxy; hydroxy($C_{1-3}$alkoxy); or $C_{1-3}$alkyl optionally independently substituted with one to three substituents selected from fluoro, chloro, bromo, iodo, or hydroxy. In some embodiments, $R_1$ is hydrogen. In other embodiments, $R_1$ is hydroxy. In further embodiments, $R_1$ is fluoro. In still other embodiments, $R_1$ is $C_{1-3}$alkoxy optionally substituted with one to seven halogen substituents, methoxy, or $C_{6-10}$aryl. In some aspects, the $C_{6-10}$aryl substituent is optionally substituted with one to two substituents that are, independently, fluoro, chloro, bromo, iodo, $C_{1-3}$alkoxy, $C_{1-3}$alkyl, hydroxy, nitro, or cyano. In yet other embodiments, $R_1$ is $C_{3-6}$alkenyloxy. In still further embodiments, $R_1$ is $C_{2-6}$alkynyloxy. In other embodiments, $R_1$ is hydroxy($C_{1-3}$alkoxy). In further embodiments, $R_1$ is $C_{1-3}$alkyl optionally substituted with one to three substituents that are fluoro, chloro, bromo, iodo, or hydroxy. In still other embodiments, $R_1$ is $C_{1-6}$alkoxy substituted with phenyl. In yet further embodiments, $R_1$ is $OCH_2$-phenyl. In other embodiments, $R_1$ is $OCH_2$-substituted phenyl. In further embodiments, $R_1$ is $OCH_2$-phenyl substituted with fluoro, chloro, bromo, iodo, $C_{1-3}$alkoxy, $C_{1-3}$alkyl, hydroxy, nitro, or cyano, preferably $C_{1-3}$alkoxy, more preferably methoxy. In yet other embodiments, $R_1$ is F, OH, or hydrogen.

$R_1'$ is independently selected from hydrogen, fluoro, hydroxy, or $C_{1-6}$alkyl; provided that when $R_1'$ is fluoro, $R_1$ is hydrogen or fluoro. In some embodiments, $R_1'$ is hydrogen. In other embodiments, $R_1'$ is fluoro. In further embodiments, $R_1'$ is hydroxy. In yet other embodiments, $R_1'$ is $C_{1-6}$alkyl, such as methyl, ethyl, propyl, butyl, pentyl, or hexyl. In still further embodiments, $R_1'$ is methyl. In other embodiments, when $R_1'$ is fluoro, $R_1$ is hydrogen or fluoro. In further embodiments, $R_1'$ is hydrogen, fluoro, or methyl.

$R_2$ is hydrogen; hydroxy; fluoro; $C_{1-3}$alkoxy optionally independently substituted with one to seven halogen, methoxy, or $C_{6-10}$aryl (wherein said $C_{6-10}$aryl is optionally independently substituted with one to two substituents that are, independently, fluoro, chloro, bromo, iodo, $C_{1-3}$alkoxy, $C_{1-3}$alkyl, hydroxy, nitro, or cyano); $C_{3-6}$alkenyloxy; $C_{2-6}$alkynyloxy; hydroxy($C_{1-3}$alkoxy); or $C_{1-3}$alkyl optionally independently substituted with one to three substituents that are fluoro, chloro, bromo, iodo, or hydroxy; and $R_3$ is hydrogen. In some embodiments, $R_2$ is H. In other embodiments, $R_2$ is hydroxy. In further embodiments, $R_2$ is fluoro. In still other embodiments, $R_2$ is $C_{1-3}$alkoxy optionally independently substituted with one to seven halogen, methoxy, or $C_{6-10}$aryl. In some aspects, $R_2$ is $C_{1-3}$ alkoxy substituted with one to two substituents that are, independently, fluoro, chloro, bromo, iodo, $C_{1-3}$alkoxy, $C_{1-3}$alkyl, hydroxy, nitro, or cyano. In yet further embodiments, $R_2$ is $C_{3-6}$alkenyloxy. In other embodiments, $R_2$ is $C_{2-6}$alkynyloxy. In further embodiments, $R_2$ is hydroxy($C_{1-3}$alkoxy). In still other embodiments, $R_2$ is $C_{1-3}$alkyl. In further embodiments, $R_2$ is $C_{1-3}$ alkyl independently substituted with one to three substituents that are fluoro, chloro, bromo, iodo, or hydroxy. In yet other embodiments, $R_2$ is F, hydrogen, or hydroxy. In still further embodiments, $R_2$ is F or H. In other embodiments, $R_2$ is H or hydroxy. In further embodiments, $R_2$ is F or hydroxy.

Alternatively, $R_3$ is —$CH_2$— or —$CH_2CH_2$—, and $R_2$ is —O—; such that $R_2$, $R_3$ and the atoms to which they are attached form a 5- or 6-membered ring. In some embodiments, $R_3$ is —$CH_2$— and $R_2$ is —O—; such that $R_2$, $R_3$ and the atoms to which they are attached form a 5-membered ring. In other embodiments, $R_3$ is —$CH_2CH_2$— and $R_2$ is —O—; such that $R_2$, $R_3$ and the atoms to which they are attached form a 6-membered ring.

$R_2'$ is independently selected from hydrogen, fluoro, or hydroxy; provided that when $R_2'$ is fluoro, $R_2$ is hydrogen or fluoro. In some embodiments, $R_2'$ is hydrogen. In other embodiments, $R_2'$ is fluoro. In further embodiments, $R_2'$ is hydroxy. In still other embodiments, when $R_2'$ is fluoro, $R_2$ is hydrogen or fluoro.

$R_3$ is independently selected from hydrogen, fluoro, $CH_3$, or $CH_2F$. In some embodiments, $R_3$ is hydrogen. In other embodiments, $R_3$ is fluoro. In further embodiments, $R_3$ is $CH_3$. In yet other embodiments, $R_3$ is $CH_2F$.

$X_1$ and $X_2$ are independently selected from the group consisting of O, S, and $CH_2$. In some aspects, $X_1$ and $X_2$ are the same. In other aspects, $X_1$ and $X_2$ differ. In some embodiments, $X_1$ is O, S, or $CH_2$. In other embodiments, $X_1$ is O. In further embodiments, $X_1$ is S. In further embodiments, $X_1$ is $CH_2$. In yet other embodiments, $X_2$ is O. In still further embodiments, $X_2$ is S. In other embodiments, $X_2$ is $CH_2$. In further embodiments, $X_1$ is O or $CH_2$. In further embodiments, $X_2$ is O or $CH_2$.

L and $L_1$ are independently selected from the group consisting of —$CH_2$— and —$CH_2CH_2$—. In some aspects, L and $L_1$ are the same. In other aspects, L and $L_1$ differ. In some embodiments, L is —$CH_2$—. In other embodiments, L is —$CH_2CH_2$—. In further embodiments, $L_1$ is —$CH_2$—. In yet other embodiments, $L_1$ is —$CH_2CH_2$—.

Y and $Y_1$ are each independently absent or selected from the group consisting of O, NH, or N($C_{1-6}$alkyl). Y and $Y_1$ are the same or may differ. In some aspects, Y and $Y_1$ are the same. In other aspects, Y and $Y_1$ differ. In some embodiments, Y is O. In other embodiments, Y is NH. In further embodiments, $Y_1$ is O. In yet other embodiments, $Y_1$ is NH. In still further embodiments, Y is N($C_{1-6}$alkyl) such as N($CH_3$). In other embodiments, $Y_1$ is N($C_{1-6}$alkyl) such as N($CH_3$).

Z and $Z_1$ are, independently, selected from the group consisting of O and NH. Z and $Z_1$ are the same or may differ. In some aspects, Z and $Z_1$ are the same. In other aspects, Z and $Z_1$ differ. In some embodiments, Z is O. In other embodiments, Z is NH. In further embodiments, $Z_1$ is O. In yet other embodiments, $Z_1$ is NH.

M and $M_1$ are, independently,

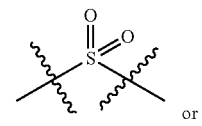

or

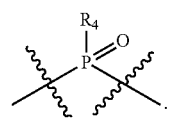

In some embodiments, M and $M_1$ are the same. In other embodiments, M and $M_1$ differ. In further embodiments, M is

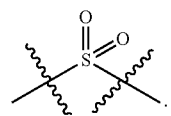

In yet other embodiments, $M_1$ is

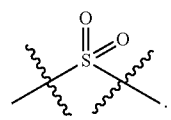

In still further embodiments, M is

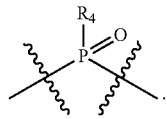

In other embodiments, $M_1$ is

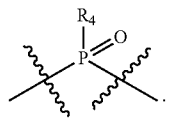

In further embodiments, M and $M_1$ are

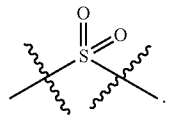

In still other embodiments, M is

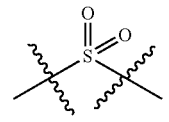

and $M_1$ is

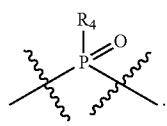

In yet further embodiments, M is

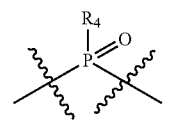

and $M_1$ is

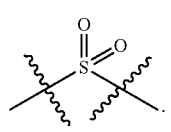

In still other embodiments, one of M and $M_1$ is

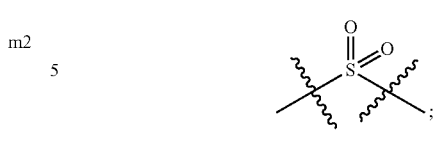

and the other of M and $M_1$ is independently selected from

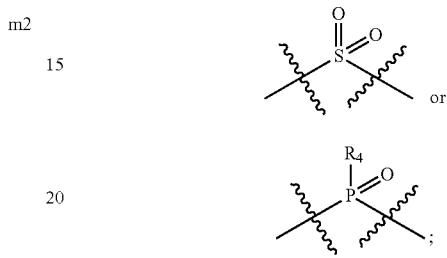

such that, when M is

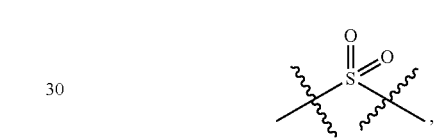

one of Y and Z is NH, and the other of Y and Z is O; and, such that $M_1$ is

one of $Y_1$ and $Z_1$ is NH, and the other of $Y_1$ and $Z_1$ is O; with the proviso when Y is absent, L is —CH$_2$CH$_2$, and M is

with the proviso when $Y_1$ is absent, $L_1$ is —CH$_2$CH$_2$, and $M_1$ is

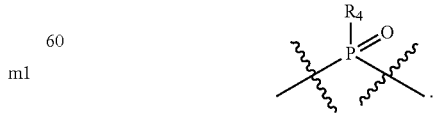

In some aspects, the combination of the Z, M, Y, and L groups form a Z-M-Y-L moiety. This Z-M-Y-L moiety may be OP(O)(OH)OCH$_2$, OP(O)(SH)OCH$_2$, OS(O)$_2$NHCH$_2$, NHS(O)$_2$OCH$_2$, OP(BH$_3$)(O)OCH$_2$. In other embodiments, Z-M-Y-L is OP(O)(OH)OCH$_2$, OP(O)(SH)OCH$_2$, or NHS(O)$_2$OCH$_2$. In further embodiments, Z-M-Y-L is OP(O)(OH)OCH$_2$. In yet other embodiments, Z-M-Y-L is OP(O)(SH)OCH$_2$. In still further embodiments, Z-M-Y-L is OS(O)$_2$NHCH$_2$. In other embodiments, Z-M-Y-L is NHS(O)$_2$OCH$_2$. In further embodiments, Z-M-Y-L is OP(BH$_3$)(O)OCH$_2$.

In other aspects, the combination of the L$_1$, Y$_1$, M$_1$, and Z$_1$ groups form a L$_1$-Y$_1$-M$_1$-Z$_1$ moiety. This L$_1$-Y$_1$-M$_1$-Z$_1$ moiety may be CH$_2$NHS(O)$_2$O, CH$_2$OP(O)(OH)O, CH$_2$CH$_2$OP(O)(OH)O, CH$_2$OP(O)(SH)O, CH$_2$OS(O)$_2$NH, CH$_2$N(CH$_3$)S(O)$_2$O, or CH$_2$CH$_2$OP(O)(SH)O. In some embodiments, L$_1$-Y$_1$-M$_1$-Z$_1$ is CH$_2$NHS(O)$_2$O. In other embodiments, L$_1$-Y$_1$-M$_1$-Z$_1$ is CH$_2$OP(O)(OH)O. In further embodiments, L$_1$-Y$_1$-M$_1$-Z$_1$ is CH$_2$CH$_2$OP(O)(OH)O. In yet other embodiments, L$_1$-Y$_1$-M$_1$-Z$_1$ is CH$_2$OP(O)(SH)O. In still further embodiments, L$_1$-Y$_1$-M$_1$-Z$_1$ is CH$_2$OS(O)$_2$NH. In other embodiments, L$_1$-Y$_1$-M$_1$-Z$_1$ is CH$_2$N(CH$_3$)S(O)$_2$O. In further embodiments, L$_1$-Y$_1$-M$_1$-Z$_1$ is CH$_2$CH$_2$OP(O)(SH)O.

R$_4$ is independently selected from the group consisting of hydroxy, methyl, BH$_3$, and —SR$_5$; wherein R$_5$ is independently selected from the group consisting of hydrogen, —CH$_2$OC(O)R$_6$, —CH$_2$OC(O)OR$_6$, —CH$_2$CH$_2$SC(O)R$_6$, and —CH$_2$CH$_2$S—SCH$_2$R$_6$. In some embodiments, R$_4$ is hydroxy. In other embodiments, R$_4$ is methyl. In further embodiments, R$_4$ is BH$_3$. In still other embodiments, R$_4$ is —SR$_5$. In some aspects, R$_5$ is hydrogen. In other aspects, R$_5$ is —CH$_2$OC(O)R$_6$. In further aspects, R$_5$ is —CH$_2$OC(O)OR$_6$. In yet other aspects, R$_5$ is —CH$_2$CH$_2$SC(O)R$_6$. In further aspects, R$_5$ is —CH$_2$CH$_2$S—SCH$_2$R$_6$.

R$_6$ is independently selected from the group consisting of C$_{6-10}$aryl, heteroaryl, heterocycloalkyl, C$_{3-12}$cycloalkyl, and C$_{1-20}$alkyl optionally independently substituted with one to five fluoro or hydroxy substituents, C$_{1-6}$alkyl, C$_{6-10}$aryl, or C$_{3-12}$cycloalkyl. In some embodiments, R$_6$ is C$_{6-10}$aryl. In other embodiments, R$_6$ is heteroaryl. In further embodiments, R$_6$ is heterocycloalkyl. In yet other embodiments, R$_6$ is C$_{3-12}$cycloalkyl. In still further embodiments, R$_6$ is C$_{1-20}$alkyl optionally independently substituted with one to five fluoro or hydroxy substituents, C$_{1-6}$alkyl, C$_{6-10}$aryl, or C$_{3-12}$cycloalkyl.

Also contemplated are enantiomers, diastereomers, or pharmaceutically acceptable salts of the compounds described herein.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or (Ia)-(Ir), or a pharmaceutically acceptable salt form thereof In some aspects, the disease or condition is hepatitis B.

Also provided are processes for making a pharmaceutical composition comprising, consisting of, and/or consisting essentially of admixing a compound of Formula (I) or (Ia)-(Ir), and a pharmaceutically acceptable carrier, a pharmaceutically acceptable excipient, and/or a pharmaceutically acceptable diluent. In some aspects, the disease or condition is hepatitis B.

The present invention further provides methods for treating or ameliorating a viral infection, disease, syndrome, or condition in a subject, including a mammal and/or human in which the viral infection, disease, syndrome, or condition is affected by the agonism of STING, using a compound of Formula (I) or (Ia)-(Ir).

The present invention further provides methods for treating or ameliorating a viral infection, disease, syndrome, or condition in a subject, including a mammal and/or human, using a compound of Formula (I) or (Ia)-(Ir).

The present invention further provides methods for treating or ameliorating a viral infection, disease, syndrome, or condition in a subject, including a mammal and/or human in which the viral infection, disease, syndrome, or condition is affected by the agonism of STING, selected from the group consisting of melanoma, colon cancer, breast cancer, prostate cancer, lung cancer, fibrosarcoma, and hepatitis B, using a compound of Formula (I) or (Ia)-(Ir). In some aspects, the disease or condition is hepatitis B.

The present invention further provides methods for treating or ameliorating a viral infection, disease, syndrome, or condition in a subject, including a mammal and/or human, selected from the group consisting of melanoma, colon cancer, breast cancer, prostate cancer, lung cancer, fibrosarcoma, and hepatitis B, using a compound of Formula (I) or (Ia)-(Ir). In some aspects, the disease or condition is hepatitis B.

The present invention is also directed to the use of any of the compounds described herein in the preparation of a medicament wherein the medicament is prepared for treating a viral infection, disease, syndrome, or condition that is affected by the agonism of STING, selected from the group consisting of melanoma, colon cancer, breast cancer, prostate cancer, lung cancer, fibrosarcoma, and hepatitis B, in a subject in need thereof. In some aspects, the disease or condition is hepatitis B.

The present invention is also directed to the use of any of the compounds described herein in the preparation of a medicament wherein the medicament is prepared for treating a viral infection, disease, syndrome, or condition selected from the group consisting of melanoma, colon cancer, breast cancer, prostate cancer, lung cancer, fibrosarcoma, and hepatitis B, in a subject in need thereof. In some aspects, the disease or condition is hepatitis B.

The present invention is also directed to the preparation of substituted cyclic dinucleotide derivatives that act as selective agonists of STING.

Exemplifying the invention are methods of treating a viral infection, disease, syndrome, or condition modulated by STING selected from the group consisting of melanoma, colon cancer, breast cancer, prostate cancer, lung cancer, fibrosarcoma, and hepatitis B, comprising administering to a subject in need thereof a therapeutically effective amount of any of the compounds or pharmaceutical compositions described above. In some aspects, the disease or condition is hepatitis B.

Exemplifying the invention are methods of treating a viral infection, disease, syndrome, or condition selected from the group consisting of melanoma, colon cancer, breast cancer, prostate cancer, lung cancer, fibrosarcoma, and hepatitis B, comprising administering to a subject in need thereof a therapeutically effective amount of any of the compounds or pharmaceutical compositions described above. In some aspects, the disease or condition is hepatitis B.

In another embodiment, the present invention is directed to a compound of Formula (I) or (Ia)-(Ir) for use in the treatment of a viral infection, disease, syndrome, or condition affected by the agonism of STING selected from the group consisting of melanoma, colon cancer, breast cancer, prostate cancer, lung cancer, fibrosarcoma, and hepatitis B. In some aspects, the disease or condition is hepatitis B.

In another embodiment, the present invention is directed to a composition comprising a compound of Formula (I) or (Ia)-(Ir) for the treatment of a viral infection, disease, syndrome, or condition selected from the group consisting of melanoma, colon cancer, breast cancer, prostate cancer, lung cancer, fibrosarcoma, and hepatitis B. In some aspects, the disease or condition is hepatitis B.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to about 20 carbon atoms. Therefore, designated numbers of carbon atoms (e.g., $C_{1-20}$) refer independently to the number of carbon atoms in an alkyl moiety or to the alkyl portion of a larger alkyl-containing substituent. In some embodiments, the alkyl is a $C_{1-20}$alkyl. In further embodiments, the alkyl is a $C_{1-3}$alkyl. In other embodiments, the alkyl is a $C_{1-6}$alkyl. In yet further embodiments, the alkyl is a $C_{1-3}$alkyl. In still other embodiments, the alkyl is methyl. In substituent groups with multiple alkyl groups such as, $(C_{1-6}alkyl)_2$amino-, the $C_{1-6}$alkyl groups of the dialkylamino may be the same or different.

The term "alkoxy" refers to an —O-alkyl group, wherein the term "alkyl" is as defined above. In some embodiments, the alkoxy is a $C_{1-6}$alkoxy. In further embodiments, the alkoxy is a $C_{1-3}$alkoxy. In further embodiments, the alkoxy is a $C_{1-6}$alkoxy. In other embodiments, the alkoxy is methoxy.

The terms "alkenyl" and "alkynyl" refer to straight and branched carbon chains having 2 to about 8 carbon atoms, wherein an alkenyl chain contains at least one double bond and an alkynyl chain contains at least one triple bond. In some embodiments, the alkenyl is a $C_{2-6}$alkenyl. In further embodiments, the alkenyl is a $C_{2-6}$alkenyl. In some embodiments, the alkynyl is a $C_{2-6}$alkynyl. In further embodiments, the alkynyl is a $C_{2-4}$alkynyl.

The terms "alkenyloxy" and "alkynyloxy" refer to O-alkenyl and O-alkynyl groups, wherein alkenyl and alkynyl are defined herein. In some embodiments, the alkenyloxy is a O—$C_{2-6}$alkenyl. In further embodiments, the alkenyloxy is a O—$C_{3-6}$alkenyl. In some embodiments, the alkynyloxy is a O—$C_{2-6}$alkynyl. In further embodiments, the alkynyloxy is a $C_{3-6}$alkynyl.

The term "hydroxy($C_{1-3}$alkoxy)" refers to a $C_{1-3}$alkoxy group as defined herein, wherein at least one carbon atom of the alkoxy moiety is substituted with at least OH group. In some embodiments, the $C_{1-3}$alkoxy group is substituted with one OH group.

The term "cycloalkyl" refers to saturated or partially saturated, monocyclic or polycyclic hydrocarbon rings of 3 to about 14 carbon atoms. Examples of such rings include cyclopropyl, cyclobutyl, cyclopentyl, cyclohexyl, cycloheptyl, and adamantyl. In some embodiments, the cycloalkyl is a $C_{3-12}$alkyl. In other embodiments, the cycloalkyl is a $C_{3-8}$alkyl. In further embodiments, the cycloalkyl is a $C_{3-6}$alkyl. In yet other embodiments, the cycloalkyl is a cyclopropyl, cyclobutyl, or cyclopentyl.

The terms "heterocyclyl" and "heterocycloalkyl" are interchangeable and refer to a nonaromatic monocyclic or bicyclic ring system having 3 to about 10 ring members that include at least 1 carbon atom and from 1 to 4 heteroatoms independently selected from N, O, and S. Included within the term heterocyclyl is a nonaromatic cyclic ring of about 5 to about 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated.

The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are nonaromatic and at least one of the rings contains a heteroatom ring member.

Examples of heterocyclyl groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic carbocyclic ring of about 6 to about 10 carbon members. In some embodiments, the aryl is a $C_{6-10}$aryl. In further embodiments, the aryl is a $C_{6-8}$aryl. Examples of aryl rings include phenyl and naphthalenyl. In some embodiments, the aryl is a phenyl.

The term "heteroaryl" refers to an aromatic monocyclic or bicyclic ring system having about 5 to about 10 ring members, which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms. In some embodiments, the halogen is a fluorine. In other embodiments, the halogen is a chlorine. In further embodiments, the halogen is a bromine. In yet other embodiments, the halogen is an iodine.

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example, $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

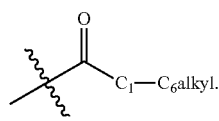

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "STING agonist" is intended to encompass a compound that interacts with STING by binding to it and inducing downstream signal transduction characterized by activation of the molecules associated with STING function. This includes direct phosphorylation of STING, IRF3 and/or NF-κB and could also include STAT6. STING pathway activation results in increased production of type I interferons (mainly IFN-α and IFN-β) and expression of interferon-stimulated genes (Chen H, et al. "Activation of STAT6 by STING Is Critical for Antiviral Innate Immunity". *Cell.* 2011, vol. 14: 433-446; and Liu S-Y, et al. "Systematic identification of type I and type II interferon-induced antiviral factors". *Proc. Natl. Acad. Sci.* 2012: vol. 109 4239-4244).

The term "STING-modulated" is used to refer to a condition affected by STING directly or via the STING pathway, including but not limited to, viral infections, diseases or conditions such as melanoma, colon cancer, breast cancer, prostate cancer, lung cancer, fibrosarcoma, and hepatitis B infection. In some embodiments, the STING-modulated condition is a viral infection. In other embodiments, the STING-modulated condition is melanoma. In further embodiments, the STING-modulated condition is colon cancer. In yet other embodiments, the STING-modulated condition is colon cancer. In still further embodiments, the STING-modulated condition is breast cancer. In other embodiments, the STING-modulated condition is prostate cancer. In further embodiments, the STING-modulated condition is lung cancer. In still other embodiments, the STING-modulated condition is fibrosarcoma. In yet further embodiments, the STING-modulated condition is hepatitis B.

As used herein, unless otherwise noted, the term "disorder modulated by STING" shall mean any viral infection, disease, disorder or condition characterized in that at least one of its characteristic symptoms is alleviated or eliminated upon treatment with a STING agonist. Suitable examples include, but are not limited to melanoma, colon cancer, breast cancer, prostate cancer, lung cancer, fibrosarcoma, and hepatitis B.

As used herein, unless otherwise noted, the term "affect" or "affected" (when referring to a viral infection, disease, syndrome, condition or disorder that is affected by agonism of STING) includes a reduction in the frequency and/or severity of one or more symptoms or manifestations of said viral infection, disease, syndrome, condition or disorder; and/or include the prevention of the development of one or more symptoms or manifestations of said viral infection, disease, syndrome, condition or disorder or the development of the viral infection, disease, condition, syndrome or disorder.

The compounds of the instant invention are useful in methods for treating or ameliorating a viral infection, disease, a syndrome, a condition or a disorder that is affected by the agonism of STING. Such methods comprise, consist of and/or consist essentially of administering to a subject, including an animal, a mammal, and a human in need of such treatment, amelioration and/or prevention, a therapeutically effective amount of a compound of Formula (I) or (Ia)-(Ir), or an enantiomer, diastereomer, solvate or pharmaceutically acceptable salt thereof.

In particular, the compounds of Formula (I) or (Ia)-(Ir), or an enantiomer, diastereomer, solvate or pharmaceutically acceptable salt form thereof are useful for treating or ameliorating diseases, syndromes, conditions, or disorders such as melanoma, colon cancer, breast cancer, prostate cancer, lung cancer, fibrosarcoma, and hepatitis B.

More particularly, the compounds of Formula (I) or (Ia)-(Ir), or an enantiomer, diastereomer, solvate or pharmaceutically acceptable salt form thereof are useful for treating or ameliorating melanoma, colon cancer, breast cancer, prostate cancer, lung cancer, fibrosarcoma, and hepatitis B, comprising administering to a subject in need thereof a therapeutically effective amount of a compound of Formula (I) or (Ia)-(Ir), or an enantiomer, diastereomer, solvate or pharmaceutically acceptable salt form thereof as herein defined.

Some embodiments disclosed herein relate to methods of ameliorating and/or treating a viral infection including infections caused by Hepadnaviridae such as hepatitis B virus or HBV. The methods can include administering to a subject identified as suffering from a viral infection an effective amount of one or more compounds of Formula (I) or (Ia)-(Ir), or a pharmaceutically acceptable salt form thereof, or a pharmaceutical composition that includes one or more compounds of Formula (I) or (Ia)-(Ir), or a pharmaceutically acceptable salt form thereof.

Other embodiments disclosed herein relate to a method of ameliorating and/or treating a viral infection that can include contacting a cell infected with the virus with an effective amount of one or more compounds described herein (for example, a compound of Formula (I) or (Ia)-(Ir), or a pharmaceutically acceptable salt form thereof), or a pharmaceutical composition that includes one or more compounds described herein, or a pharmaceutically acceptable salt thereof Still other embodiments described herein relate to using one or more compounds of Formula (I) or (Ia)-(Ir), or a pharmaceutically acceptable salt form thereof, in the manufacture of a medicament for ameliorating and/or treating a viral infection.

Yet still other embodiments described herein relate to one or more compounds of Formula (I) or (Ia)-(Ir), or a pharmaceutically acceptable salt form thereof, or a pharmaceutical composition that includes one or more compounds of Formula (I) or (Ia)-(Ir), or a pharmaceutically acceptable salt form thereof, that can be used for ameliorating and/or treating a viral infection. Some embodiments disclosed herein relate to a method of inhibiting replication of a virus that can include contacting a cell infected with the virus with an effective amount of one or more compounds of Formula (I) or (Ia)-(Ir), or a pharmaceutically acceptable salt form thereof, or a pharmaceutical composition that includes one or more compounds described herein, or a pharmaceutically acceptable salt form thereof.

Other embodiments described herein relate to using one or more compounds of Formula (I) or (Ia)-(Ir), or a pharmaceutically acceptable salt form thereof) in the manufacture of a medicament for inhibiting replication of a virus. Still other embodiments described herein relate to one or more compounds described herein (for example, a compound of Formula (I) or (Ia)-(Ir), or a pharmaceutically acceptable salt form thereof), or a pharmaceutical composition that includes one or more compounds described herein, or a pharmaceutically acceptable salt form thereof, that can be used for inhibiting replication of a virus.

In some embodiments, the viral infection can be a hepatitis B viral infection. The methods can include administering to a subject identified as suffering from HBV an effective amount of one or more compounds of Formula (I) or (Ia)-(Ir), or a pharmaceutically acceptable salt form thereof, or a pharmaceutical composition that includes one or more compounds of Formula (I) or (Ia)-(Ir), or a pharmaceutically acceptable salt form thereof.

Other embodiments disclosed herein relate to a method of ameliorating and/or treating a viral infection that can include contacting a cell infected with HBV with an effective amount of one or more compounds of Formula (I) or (Ia)-(Ir), or a pharmaceutically acceptable salt form thereof, or a pharmaceutical composition that includes one or more compounds of Formula (I) or (Ia)-(Ir), or a pharmaceutically acceptable salt form thereof Still other embodiments described herein relate to using one or more compounds of Formula (I) or (Ia)-(Ir), or a pharmaceutically acceptable salt form thereof, in the manufacture of a medicament for ameliorating and/or treating HBV.

Yet still other embodiments described herein relate to one or more compounds of Formula (I) or (Ia)-(Ir), or a pharmaceutically acceptable salt form thereof, or a pharmaceutical composition that includes one or more compounds of Formula (I) or (Ia)-(Ir), or a pharmaceutically acceptable salt form thereof, that can be used for ameliorating and/or treating HBV. Some embodiments disclosed herein relate to a method of inhibiting replication of HBV that can include contacting a cell infected with the virus with an effective amount of one or more compounds of Formula (I) or (Ia)-(Ir), or a pharmaceutically acceptable salt form thereof, or a pharmaceutical composition that includes one or more compounds of Formula (I) or (Ia)-(Ir), or a pharmaceutically acceptable salt thereof.

Other embodiments described herein relate to using one or more compounds of Formula (I) or (Ia)-(Ir), or a pharmaceutically acceptable salt thereof) in the manufacture of a medicament for inhibiting replication of HBV. Still other embodiments described herein relate to one or more compounds of Formula (I) or (Ia)-(Ir), or a pharmaceutically acceptable salt thereof, or a pharmaceutical composition that includes one or more compounds of Formula (I) or (Ia)-(Ir), or a pharmaceutically acceptable salt form thereof, that can be used for inhibiting replication of HBV.

Embodiments of the present invention include a compound of Formula (I) or (Ia)-(Ir) as herein defined, or an enantiomer, diastereomer, solvate, or a pharmaceutically acceptable salt form thereof, wherein the substituents selected from one or more of the variables defined herein (e.g. $B_2$, $X_2$, $R_2$, $R_2'$, $R_3$, Z-M-Y-L, $L_1$-$Y_1$-$M_1$-$Z_1$, $B_1$, $X_1$, $R_1'$, and $R_1$) are independently selected to be any individual substituent or any subset of substituents from those exemplified in the listing in Table 1.

TABLE 1

Formula (I)

| Compound No. | B₁ | X₂ | R₂ | R₂' | R₃ | Z-M-Y-L | L₁-Y₁-M₁-Z₁ | B₂ | X₁ | R₁ | R₁' |
|---|---|---|---|---|---|---|---|---|---|---|---|
| 1 | b6 | O | F | H | H | OP(O)(OH)OCH₂ | CH₂NHS(O)₂O | b6 | O | F | H |
| 2 | b6 | O | F | H | H | (*R)OP(O)(SH)OCH₂ | CH₂NHS(O)₂O | b6 | O | F | H |
| 3 | b6 | O | F | H | H | (*S)OP(O)(SH)OCH₂ | CH₂NHS(O)₂O | b6 | O | F | H |
| 4 | b6 | O | F | H | H | OP(O)(OH)OCH₂ | CH₂NHS(O)₂O | b7 | O | OCH₃ | H |
| 5 | b6 | O | F | H | H | OP(O)(OH)OCH₂ | CH₂NHS(O)₂O | b18 | O | F | H |
| 6 | b6 | O | H | H | H | OP(O)(OH)OCH₂ | CH₂NHS(O)₂O | b6 | O | F | H |
| 7 | b6 | O | F | H | H | OP(O)(OH)OCH₂ | CH₂NHS(O)₂O | b7 | O | OH | H |
| 8 | b6 | O | F | H | H | OP(O)(OH)OCH₂ | CH₂NHS(O)₂O | b6 | O | OH | H |
| 9 | b6 | O | OH | H | H | OP(O)(OH)OCH₂ | CH₂NHS(O)₂O | b7 | O | F | H |
| 10 | b6 | O | F | H | H | OP(O)(OH)OCH₂ | CH₂NHS(O)₂O | b7 | O | F | H |
| 11 | b6 | O | OH | H | H | OS(O)₂NHCH₂ | CH₂OP(O)(OH)O | b6 | O | OH | H |
| 12-R | b6 | O | OH | H | H | OS(O)₂NHCH₂ | CH₂OP(O)(SH)O | b6 | O | OH | H |
| 13 | b6 | O | F | H | H | OP(O)(OH)OCH₂ | CH₂NHS(O)₂O | b6 | O | OH | H |
| 14-R | b6 | O | OH | H | H | OP(O)(SH)OCH₂ | CH₂NHS(O)₂O | b7 | O | F | H |
| 14-S | b6 | O | OH | H | H | OP(O)(SH)OCH₂ | CH₂NHS(O)₂O | b6 | O | F | H |
| 15-R | b6 | O | F | H | H | OP(O)(SH)OCH₂ | CH₂NHS(O)₂O | b6 | O | OCH₂-(4-OMe-phenyl) | H |
| 15-S | b6 | O | F | H | H | OP(O)(SH)OCH₂ | CH₂NHS(O)₂O | b6 | O | OCH₂-(4-OMe-phenyl) | H |
| 16-S | b6 | O | F | H | H | OS(O)₂NHCH₂ | CH₂OP(O)(SH)O | b7 | O | F | H |
| 16-R | b6 | O | F | H | H | OS(O)₂NHCH₂ | CH₂OP(O)(SH)O | b7 | O | F | H |
| 17-R | b6 | O | F | H | H | OP(O)(SH)OCH₂ | CH₂NHS(O)₂O | B18 | O | F | H |
| 17-S | b6 | O | F | H | H | OP(O)(SH)OCH₂ | CH₂NHS(O)₂O | B18 | O | F | H |
| 18-R | b6 | O | F | H | H | OP(O)(SH)OCH₂ | CH₂NHS(O)₂O | b7 | O | F | H |
| 18-S | b6 | O | F | H | H | OP(O)(SH)OCH₂ | CH₂NHS(O)₂O | b7 | O | F | H |
| 19-R | b6 | O | F | H | H | OP(O)(SH)OCH₂ | CH₂NHS(O)₂O | b6 | O | OH | H |
| 19-S | b6 | O | F | H | H | OP(O)(SH)OCH₂ | CH₂NHS(O)₂O | b6 | O | OH | H |
| 20-R | b6 | O | H | H | H | OP(O)(SH)OCH₂ | CH₂NHS(O)₂O | b6 | O | F | H |
| 20-S | b6 | O | H | H | H | OP(O)(SH)OCH₂ | CH₂NHS(O)₂O | b6 | O | F | H |
| 21 | b6 | O | F | H | H | OP(O)(OH)OCH₂ | CH₂OS(O)₂NH | b6 | O | F | H |
| 22-S | b6 | O | F | H | H | NHS(O)₂OCH₂ | CH₂OP(O)(SH)O | b18 | O | F | H |
| 22-R | b6 | O | F | H | H | NHS(O)₂OCH₂ | CH₂OP(O)(SH)O | b18 | O | F | H |
| 23 | b6 | O | F | H | H | OP(O)(OH)OCH₂ | CH₂NHS(O)₂O | b7 | O | H | H |
| 24 | b6 | O | F | H | H | OS(O)₂NHCH₂ | CH₂OP(O)(OH)O | b18 | O | F | H |
| 25 | b6 | O | F | H | H | OP(O)(OH)OCH₂ | CH₂NHS(O)₂O | b13 | O | H | F |
| 26 | b6 | O | F | H | H | OP(O)(OH)OCH₂ | CH₂NHS(O)₂O | b7 | O | H | F |
| 27 | b6 | CH₂ | H | H | H | OS(O)₂NHCH₂ | CH₂OP(O)(OH)O | b6 | O | F | H |
| 28 | b6 | O | H | H | H | NHS(O)₂OCH₂ | CH₂OP(O)(OH)O | b18 | O | F | H |
| 29 | b6 | O | F | H | H | OP(O)(OH)OCH₂ | CH₂NHS(O)₂O | b30 | O | H | H |
| 30 | b6 | O | F | H | H | OP(O)(OH)OCH₂ | CH₂NHS(O)₂O | b7 | CH₂ | OH | H |
| 31-S | b6 | O | F | H | H | OS(O)₂NHCH₂ | CH₂OP(O)(SH)O | b18 | O | F | H |
| 31-R | b6 | O | F | H | H | OS(O)₂NHCH₂ | CH₂OP(O)(SH)O | b18 | O | F | H |
| 32 | b6 | O | F | H | H | OP(O)(OH)OCH₂ | CH₂NHS(O)₂O | b20 | O | H | H |
| 33 | b6 | O | F | H | H | OP(O)(OH)OCH₂ | CH₂NHS(O)₂O | b21 | O | H | H |
| 34-S | b6 | O | F | H | H | OP(O)(SH)OCH₂ | CH₂NHS(O)₂O | b7 | O | H | F |
| 34-R | b6 | O | F | H | H | OP(O)(SH)OCH₂ | CH₂NHS(O)₂O | b7 | O | H | F |
| 35 | b6 | O | F | H | H | OP(O)(OH)OCH₂ | CH₂NHS(O)₂O | b12 | O | H | H |
| 36 | b6 | O | F | H | H | OP(O)(OH)OCH₂ | CH₂NHS(O)₂O | b2 | O | OH | H |
| 37-S | b6 | O | O | H | CH₂ | OS(O)₂NHCH₂ | CH₂OP(O)(SH)O | b6 | O | F | H |
| 37-R | b6 | O | O | H | CH₂ | OS(O)₂NHCH₂ | CH₂OP(O)(SH)O | b6 | O | F | H |
| 38 | b6 | O | O | H | CH₂ | OS(O)₂NHCH₂ | CH₂OP(O)(OH)O | b6 | O | F | H |
| 39 | b6 | O | F | H | H | OP(O)(OH)OCH₂ | CH₂NHS(O)₂O | b28 | O | H | H |
| 40 | b6 | O | F | H | H | OP(O)(OH)OCH₂ | CH₂NHS(O)₂O | b17 | O | H | H |
| 41 | b6 | O | F | H | H | OP(O)(OH)OCH₂ | CH₂NHS(O)₂O | b27 | O | H | H |
| 42 | b6 | O | F | H | H | OP(O)(OH)OCH₂ | CH₂NHS(O)₂O | b13 | O | H | H |
| 43 | b6 | O | F | H | H | OP(O)(OH)OCH₂ | CH₂NHS(O)₂O | b25 | O | H | H |
| 44 | b6 | O | F | H | H | OP(O)(OH)OCH₂ | CH₂NHS(O)₂O | b26 | O | F | H |
| 45 | b6 | O | F | H | H | OP(O)(OH)OCH₂ | CH₂NHS(O)₂O | b14 | O | H | H |
| 46 | b6 | O | F | H | H | OP(O)(OH)OCH₂ | CH₂NHS(O)₂O | b7 | O | OCH-phenyl | H |
| 47 | b6 | O | F | H | H | OS(O)₂NHCH₂ | CH₂NHS(O)₂O | b6 | O | F | H |
| 48 | b6 | O | F | H | H | OP(O)(OH)OCH₂ | CH₂NHS(O)₂O | b14 | O | OH | H |
| 49 | b6 | O | OH | H | H | (*R)OP(O)(SH)OCH₂ | CH₂NHS(O)₂O | b6 | O | OH | H |
| 50 | b6 | O | OH | H | H | (*S)OP(O)(SH)OCH₂ | NHS(O)₂O | b6 | O | OH | H |
| 51 | b6 | CH₂ | OH | H | H | OP(O)(OH)OCH₂ | CH₂NHS(O)₂O | b6 | O | F | H |

TABLE 1-continued

Formula (I)

Compound structure with M—Y—L, B₁, X₁, R₁', R₂, Z, R₃, R₂', X₂, Z₁, R₁, B₂, L₁—Y₁—M₁

| Compound No. | B₁ | X₂ | R₂ | R₂' | R₃ | Z-M-Y-L | L₁-Y₁-M₁-Z₁ | B₁ | X₁ | R₁ | R₁' |
|---|---|---|---|---|---|---|---|---|---|---|---|
| 52 | b6 | O | F | H | H | NHS(O)₂OCH₂ | CH₂OP(O)(OH)O | b18 | O | F | H |
| 53 | b6 | O | H | H | H | OP(O)(OH)OCH₂ | CH₂NHS(O)₂O | b6 | O | OH | H |
| 54 | b6 | O | F | H | H | (*)OP(BH₃)(O)OCH₂ | CH₂NHS(O)₂O | b6 | O | F | H |
| 55 | b6 | O | F | H | H | OP(O)(OH)OCH₂ | CH₂NHS(O)₂O | b17 | S | OH | H |
| 56 | b6 | O | F | H | H | (*R)OP(O)(SH)OCH₂ | CH₂NHS(O)₂O | b17 | S | OH | H |
| 57 | b6 | O | F | H | H | (*S)OP(O)(SH)OCH₂ | CH₂NHS(O)₂O | b17 | S | OH | H |

An embodiment of the present invention is directed to a compound of Formula (Ia):

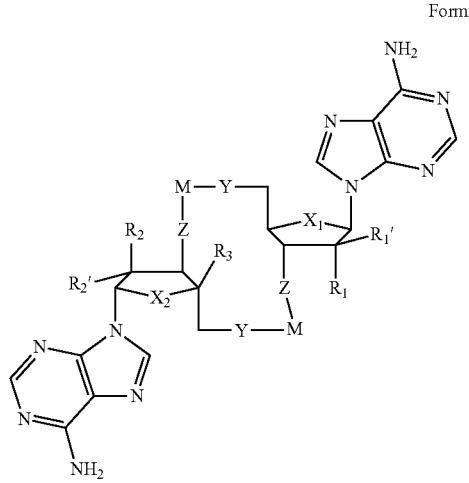

Formula (Ia)

wherein $R_1$ is independently selected from hydrogen; hydroxy; fluoro; $C_{1-3}$alkoxy optionally independently substituted with one to seven halogen substituents, methoxy, or $C_{6-10}$aryl; wherein said $C_{6-10}$aryl is optionally independently substituted with one to two substituents independently selected from the group consisting of fluoro, chloro, bromo, iodo, $C_{1-3}$alkoxy, $C_{1-3}$alkyl, hydroxy, nitro and cyano; $C_{3-6}$alkenyloxy; $C_{2-6}$alkynyloxy; hydroxy($C_{1-3}$alkoxy); or $C_{1-3}$alkyl optionally independently substituted with one to three substituents selected from fluoro, chloro, bromo, iodo, or hydroxy;

$R_1'$ is independently selected from hydrogen, fluoro, or hydroxy; provided that when $R_1'$ is fluoro, $R_1$ is hydrogen or fluoro;

$R_2$ is independently selected from hydrogen; hydroxy; fluoro; $C_{1-3}$alkoxy optionally independently substituted with one to seven halogen substituents, methoxy, or $C_{6-10}$aryl; wherein said $C_{6-10}$aryl is optionally independently substituted with one to two substituents independently selected from the group consisting of fluoro, chloro, bromo, iodo, $C_{1-3}$alkoxy, $C_{1-3}$alkyl, hydroxy, nitro and cyano; $C_{3-6}$alkenyloxy; $C_{2-6}$alkynyloxy; hydroxy($C_{1-3}$alkoxy); or $C_{1-3}$alkyl optionally independently substituted with one to three substituents selected from fluoro, chloro, bromo, iodo, or hydroxy; and $R_3$ is hydrogen;

or, $R_3$ is —CH₂—, and $R_2$ is —O—; such that $R_2$, $R_3$ and the atoms to which they are attached form a 5-membered ring;

$R_2'$ is independently selected from hydrogen, fluoro, or hydroxy; provided that when $R_2'$ is fluoro, $R_2$ is hydrogen or fluoro;

$R_3$ is independently selected from hydrogen, fluoro, CH₃, or CH₂F;

$X_1$ and $X_2$ are independently selected from the group consisting of O, S, and CH₂;

L and $L_1$ are independently selected from the group consisting of —CH₂— and —CH₂CH₂—;

Y and $Y_1$ are each independently absent or selected from the group consisting of O and NH;

Z and $Z_1$ are independently selected from the group consisting of O and NH;

one of M and $M_1$ is

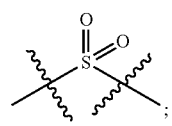

m1 and the other of M and $M_1$ is independently selected from

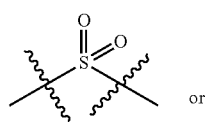

m1 or

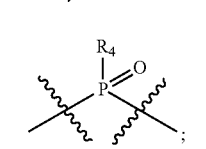

m2 such that, when M is

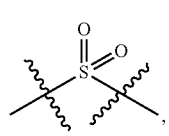
m1 one of Y and Z is NH, and the other of Y and Z is O;
and, such that $M_1$ is

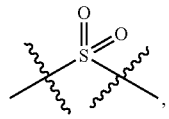
m1 one of $Y_1$ and $Z_1$ is NH, and the other of $Y_1$ and $Z_1$ is O;

with the proviso when Y is absent, L is —CH$_2$CH$_2$, and M is

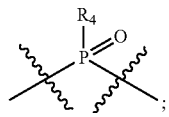
m2 with the proviso when $Y_1$ is absent, $L_1$ is absent, and $M_1$ is

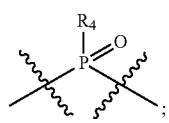
m2

$R_4$ is independently selected from the group consisting of hydroxy, methyl, BH$_3$, and —SR$_5$; wherein R$_5$ is independently selected from the group consisting of hydrogen, —CH$_2$OC(O)R$_6$, —CH$_2$OC(O)OR$_6$, —CH$_2$CH$_2$SC(O)R$_6$, and —CH$_2$CH$_2$S—SCH$_2$R$_6$;

$R_6$ is independently selected from the group consisting of $C_{6-10}$aryl, heteroaryl, heterocycloalkyl, $C_{3-12}$cycloalkyl, and $C_{1-20}$alkyl optionally independently substituted with one to five fluoro or hydroxy substituents, $C_{1-6}$alkyl, $C_{6-10}$aryl, or $C_{3-12}$cycloalkyl;

or an enantiomer, diastereomer, or pharmaceutically acceptable salt form thereof.

A further embodiment of the present invention is directed to a compound of Formula (Ib):

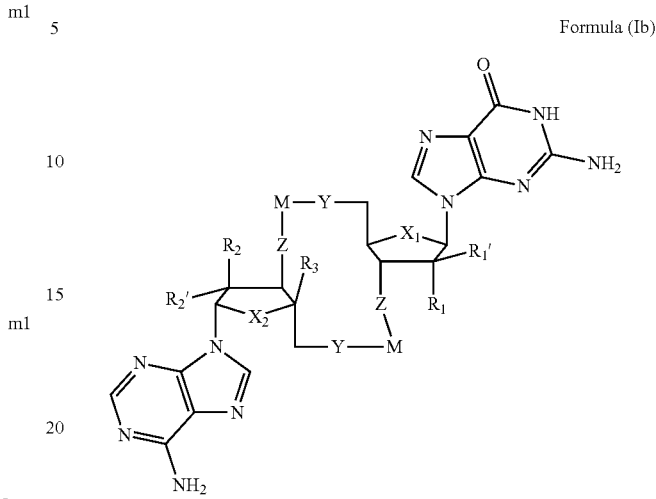
Formula (Ib)

wherein $R_1$ is independently selected from hydrogen; hydroxy; fluoro; $C_{1-3}$alkoxy optionally independently substituted with one to seven halogen substituents, methoxy, or $C_{6-10}$aryl; wherein said $C_{6-10}$aryl is optionally independently substituted with one to two substituents independently selected from the group consisting of fluoro, chloro, bromo, iodo, $C_{1-3}$alkoxy, $C_{1-3}$alkyl, hydroxy, nitro and cyano; $C_{3-6}$alkenyloxy; $C_{2-6}$alkynyloxy; hydroxy($C_{1-3}$alkoxy); or $C_{1-3}$alkyl optionally independently substituted with one to three substituents selected from fluoro, chloro, bromo, iodo, or hydroxy;

$R_1'$ is independently selected from hydrogen, fluoro, or hydroxy; provided that when $R_1'$ is fluoro, $R_1$ is hydrogen or fluoro;

$R_2$ is independently selected from hydrogen; hydroxy; fluoro; $C_{1-3}$alkoxy optionally independently substituted with one to seven halogen substituents, methoxy, or $C_{6-10}$aryl; wherein said $C_{6-10}$aryl is optionally independently substituted with one to two substituents independently selected from the group consisting of fluoro, chloro, bromo, iodo, $C_{1-3}$alkoxy, $C_{1-3}$alkyl, hydroxy, nitro and cyano; $C_{3-6}$alkenyloxy; $C_{2-6}$alkynyloxy; hydroxy($C_{1-3}$alkoxy); or $C_{1-3}$alkyl optionally independently substituted with one to three substituents selected from fluoro, chloro, bromo, iodo, or hydroxy; and $R_3$ is hydrogen;

or, $R_3$ is —CH$_2$—, and $R_2$ is —O—; such that $R_2$, $R_3$ and the atoms to which they are attached form a 5-membered ring;

$R_2'$ is independently selected from hydrogen, fluoro, or hydroxy; provided that when $R_2'$ is fluoro, $R_2$ is hydrogen or fluoro;

$R_3$ is independently selected from hydrogen, fluoro, CH$_3$, or CH$_2$F;

$X_1$ and $X_2$ are independently selected from the group consisting of O, S, and CH$_2$;

L and $L_1$ are independently selected from the group consisting of —CH$_2$— and —CH$_2$CH$_2$—;

Y and $Y_1$ are each independently absent or selected from the group consisting of O and NH;

Z and $Z_1$ are independently selected from the group consisting of O and NH;

one of M and $M_1$ is

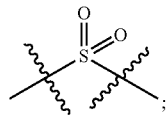   m1 and the other of M and $M_1$ is independently selected from

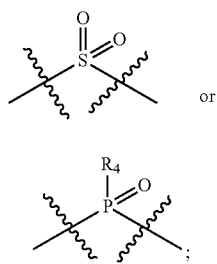   m1 or m2 such that, when M is

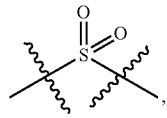   m1 one of Y and Z is NH, and the other of Y and Z is O; and, such that $M_1$ is

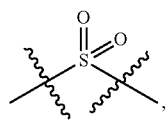   m1 one of $Y_1$ and $Z_1$ is NH, and the other of $Y_1$ and $Z_1$ is O;

with the proviso when Y is absent, L is —CH$_2$CH$_2$, and M is

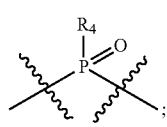   m2 with the proviso when $Y_1$ is absent, $L_1$ is absent, and $M_1$ is

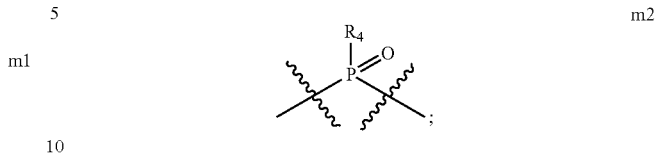   m2

$R_4$ is independently selected from the group consisting of hydroxy, methyl, BH$_3$, and —SR$_5$; wherein $R_5$ is independently selected from the group consisting of hydrogen, —CH$_2$OC(O)R$_6$, —CH$_2$OC(O)OR$_6$, —CH$_2$CH$_2$SC(O)R$_6$, and —CH$_2$CH$_2$S—SCH$_2$R$_6$, $R_6$ is independently selected from the group consisting of $C_{6-10}$aryl, heteroaryl, heterocycloalkyl, $C_{3-12}$cycloalkyl, and $C_{1-20}$alkyl optionally independently substituted with one to five fluoro or hydroxy substituents, $C_{1-6}$alkyl, $C_{6-10}$aryl, or $C_{3-12}$cycloalkyl;

or an enantiomer, diastereomer, or pharmaceutically acceptable salt form thereof.

In further embodiments, the compound is of formula (Ic), wherein $R_1$, $R_2$, L, $L_1$, Y, $Y_1$, M, $M_1$, and $B_1$ are defined herein.

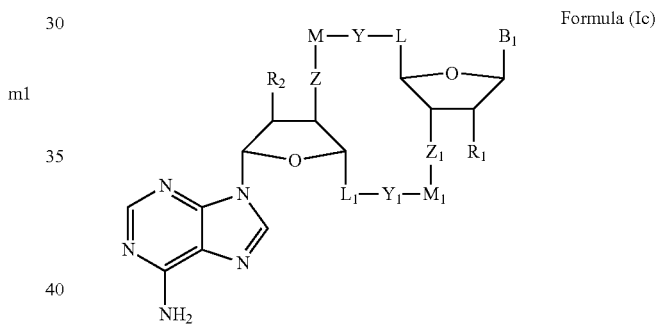

Formula (Ic)

In other embodiments, the compound is of formula (Id), wherein $R_1$, $R_2$, L, $L_1$, Y, $Y_1$, M, $M_1$, Z, and $Z_1$ are defined herein.

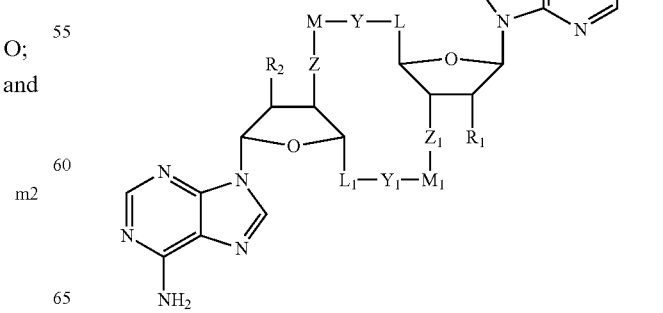

Formula (Id)

In further embodiments, the compound is of formula (Ie), wherein $R_1$, $R_2$, L, $L_1$, Y, $Y_1$, M, $M_1$, Z, and $Z_1$ are defined herein.

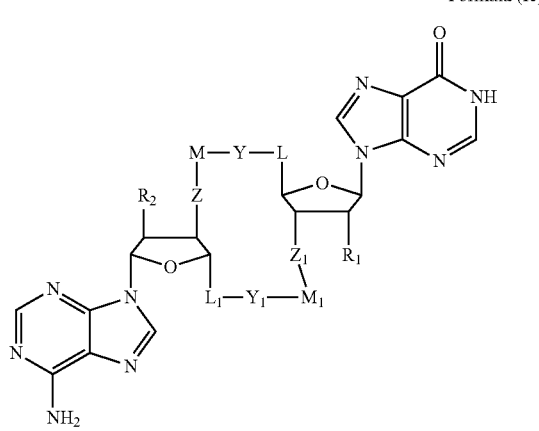

Formula (Ie)

In yet other embodiments, the compound is of formula (If), wherein $R_1$, $R_2$, L, $L_1$, Y, $Y_1$, M, $M_1$, Z, and $Z_1$ are defined herein.

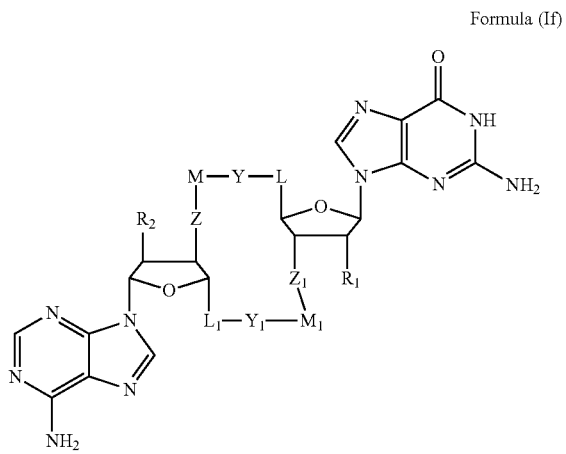

Formula (If)

In still further embodiments, the compound is of formula (Ig), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

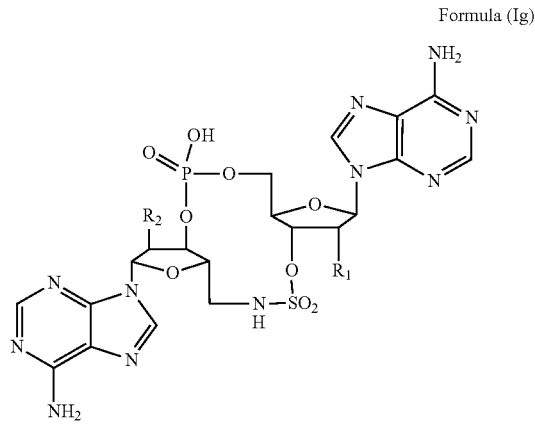

Formula (Ig)

In other embodiments, the compound is of formula (Ih), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

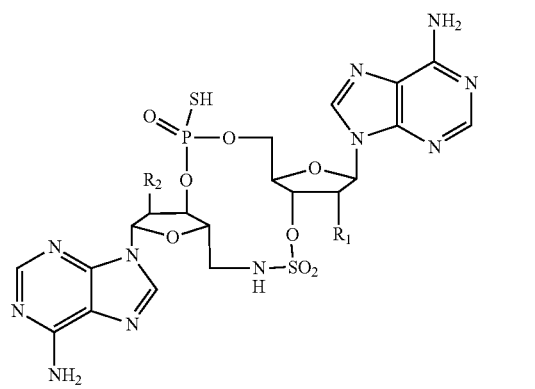

Formula (Ih)

In further embodiments, the compound is of formula (Ij), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

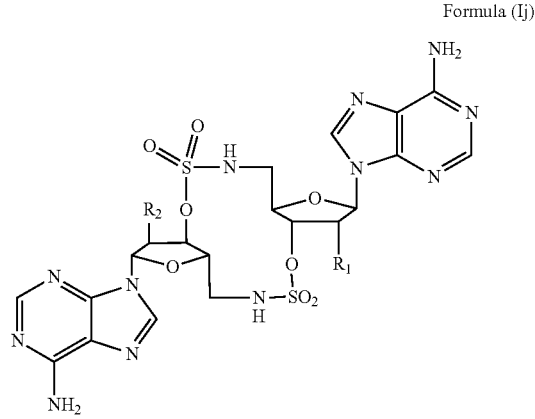

Formula (Ij)

In still other embodiments, the compound is of formula (Ik), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

Formula (Ik)

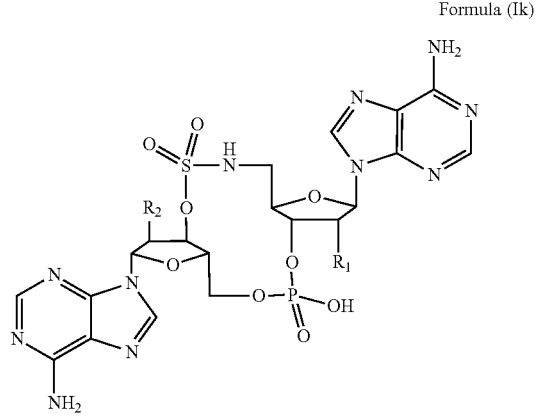

In yet further embodiments, the compound is of formula (Im), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

Formula (Im)

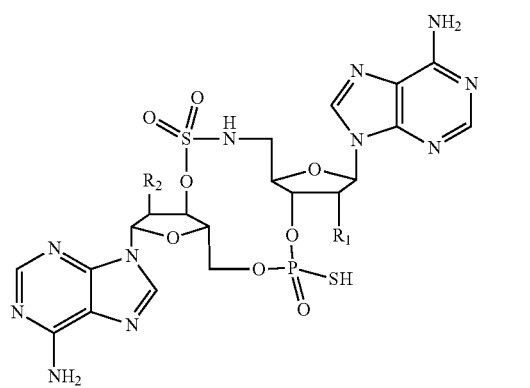

In other embodiments, the compound is of formula (In), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

Formula (In)

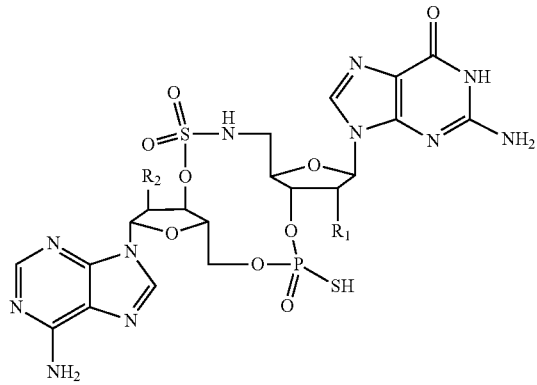

In further embodiments, the compound is of formula (Ip), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

Formula (Ip)

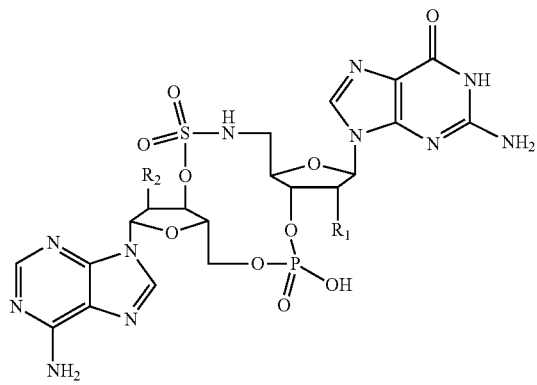

In other embodiments, the compound is of formula (Iq), wherein $R_1$ and $R_2$ are defined herein. In some aspects, $R_1$ and $R_2$ are F. In other aspects, $R_1$ is F and $R_2$ is H. In further aspects, $R_1$ and $R_2$ are H. In still other aspects, $R_1$ is H and $R_2$ is F.

Formula (Iq)

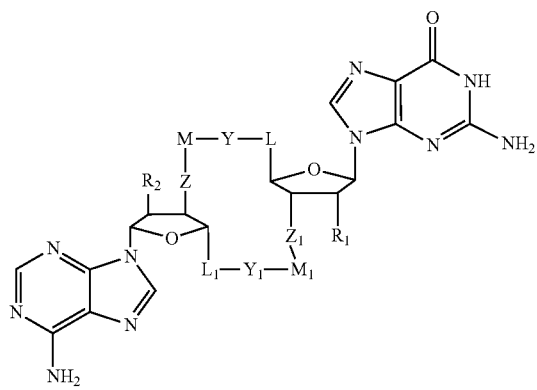

In still further aspects, the compound is of formula (Ir), wherein $R_1$ and $R_2$ are defined herein. In some embodiments, Z-M-Y-L is $OP(O)(OH)OCH_2$ and $L_1-Y_1-M_1-Z_1-R_2$ is $CH_2NHS(O)_2O$. In other embodiments, Z-M-Y-L is $CH_2NHS(O)_2O$ and $L_1-Y_1-M_1-Z_1-$ is $OP(O)(OH)OCH_2$. In further embodiments, Z-M-Y-L is $OS(O)_2NHCH_2$ and $L_1-Y_1-M_1-Z_1-$ is $CH_2OP(O)(SH)O$. In still other embodiments, Z-M-Y-L is $NHS(O)_2OCH_2$ and $L_1-Y_1-M_1-Z_1-$ is $CH_2OP(O)(OH)O$. In yet other embodiments, Z-M-Y-L is $OS(O)_2NHCH_2$ and $L_1-Y_1-M_1-Z_1-$ is $CH_2OP(O)(OH)O$. In further embodiments, Z-M-Y-L is $NHS(O)_2OCH_2$ and $L_1-Y_1-M_1-Z_1-$ is $CH_2OP(O)(SH)O$. In some aspects, $R_1$ and $R_2$ are F. In other aspects, $R_1$ is H and $R_2$ is F. In further aspects, $R_1$ is F and $R_2$ is H.

Formula (Ir)

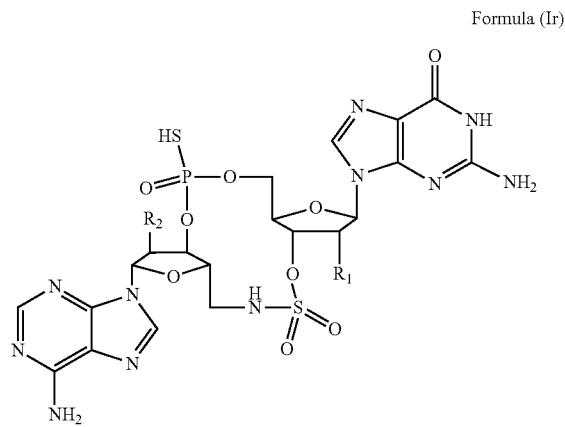

A further embodiment of the present invention is directed to a compound of Formula (I) or (Ia)-(Ir), selected from the group consisting of one of more of the individual compounds discussed herein.

For use in medicine, salts of compounds of Formula (I) or (Ia)-(Ir) refer to non-toxic "pharmaceutically acceptable salts." Other salts may, however, be useful in the preparation of compounds of Formula (I) or (Ia)-(Ir) or of their pharmaceutically acceptable salt forms thereof. Suitable pharmaceutically acceptable salts of compounds of Formula (I) or (Ia)-(Ir) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) or (Ia)-(Ir) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2(diethylamino)-ethanol, ethanolamine, ethylenediamine, N-methyl-glucamine, hydrabamine, 1Himidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I) or (Ia)-(Ir). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorph and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I) or (Ia)-(Ir).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) or (Ia)-(Ir) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100.$$

Another embodiment of the present invention is a composition, including a pharmaceutical composition, comprising, consisting of, and consisting essentially of the (−)-enantiomer of a compound of Formula (I) or (Ia)-(Ir) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(+) - \text{enantiomer} = \frac{(\text{mass}(-) - \text{enantiomer})}{(\text{mass}(+) - \text{enantiomer}) + (\text{mass}(-) - \text{enantiomer})} \times 100.$$

It is intended that within the scope of the present invention, any one or more element(s), in particular when mentioned in relation to a compound of Formula (I) or (Ia)-(Ir), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) or (Ia)-(Ir) may comprise one or more radioactive isotope(s) selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$.

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) or (Ia)-(Ir) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) or (Ia)-(Ir) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) or (Ia)-(Ir) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) or (Ia)-(Ir) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or (Ia)-(Ir) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) or (Ia)-(Ir) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I) or (Ia)-(Ir).

An embodiment of the present invention is directed to a pharmaceutical composition for oral administration, comprising a compound of Formula (I) or (Ia)-(Ir) in an amount of from about 25 mg to about 500 mg.

Advantageously, a compound of Formula (I) or (Ia)-(Ir) may be administered in a single daily dose, or the total daily dosage may be administered in divided doses of two, three and four times daily.

Optimal dosages of a compound of Formula (I) or (Ia)-(Ir) to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) or (Ia)-(Ir) may be administered in any of the foregoing compositions and dosage regimens or by means of those compositions and dosage regimens established in the art whenever use of a compound of Formula (I) or (Ia)-(Ir) is required for a subject in need thereof.

As STING protein agonists, the compounds of Formula (I) or (Ia)-(Ir) are useful in methods for treating or preventing a viral infection, disease, a syndrome, a condition or a disorder in a subject, including an animal, a mammal and a human in which the viral infection, disease, the syndrome, the condition or the disorder is affected by the modulation, including agonism, of the STING protein. Such methods comprise, consist of and/or consist essentially of administering to a subject, including an animal, a mammal, and a human, in need of such treatment or prevention, a therapeutically effective amount of a compound, salt or solvate of Formula (I) or (Ia)-(Ir).

In one embodiment, the present invention is directed to a compound of Formula (I) or (Ia)-(Ir), or a pharmaceutically acceptable salt form thereof, for the use in the treatment of cancer, and cancer diseases and conditions, or a viral infection.

Examples of cancer diseases and conditions for which compounds of Formula (I) or (Ia)-(Ir), or pharmaceutically acceptable salts or solvates thereof, may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hamartoma; inesothelioma; Hodgkin's Disease or a combination of one or more of the foregoing cancers. Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal madenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, pro myelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulvar cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, GIST (gastrointestinal stromal tumor) and testicular cancer.

In another embodiment, the present invention is directed to a compound of Formula (I) or (Ia)-(Ir), or a pharmaceutically acceptable salt form thereof, for use in the treatment of a disorder affected by the agonism of STING selected from the group consisting of melanoma, colon cancer, breast cancer, prostate cancer, lung cancer, fibrosarcoma, and hepatitis B.

The disclosed compounds of Formula (I) or (Ia)-(Ir) may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature described capsid assembly modulators, reverse transcriptase inhibitors, immunomodulatory agents, TLR-agonists, and other agents with distinct or unknown mechanisms that affect the HBV life cycle or that affect the consequences of HBV infection.

In non-limiting examples, the disclosed compounds may be used in combination with one or more drugs (or a salt thereof) selected from the group comprising:

HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA); interferons including, but not limited to, interferon alpha (IFN-α), interferon beta (IFN-β), interferon lambda (IFN-λ), and interferon gamma (IFN-γ); viral entry inhibitors; viral maturation inhibitors; capsid assembly modulators, such as, but not limited to, BAY 41-4109; reverse transcriptase inhibitors; immunomodulatory agents such as TLR-agonists; and agents of distinct or unknown mechanisms, such as, but not limited to, AT-61 ((E)-N-(1-chloro-3-oxo-1-phenyl-3-(piperidin-1-yl)prop-1-en-2-yl)benzamide), AT-130 (E)-N-(1-bromo-1-(2-methoxyphenyl)-3-oxo-3-(piperidin-1-yl)prop-1-en-2-yl)-4-nitrobenzamide), and analogs thereof.

In one embodiment, the additional therapeutic agent is an interferon. The term "interferon" or "IFN" refers to any member of the family of highly homologous species-specific proteins that inhibit viral replication and cellular proliferation and modulate immune response. For example, human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferonalpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula (I) or (Ia)-(Ir) can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferonalpha-n1.

In another specific embodiment, the interferon-alpha-2a or interferon-alpha-2b is pegylated. In a preferred embodiment, the interferon-alpha-2a is pegylated interferon-alpha-2a (PEGASYS). In another embodiment, the additional therapeutic agent is selected from immune modulator or immune stimulator therapies, which includes biological agents belonging to the interferon class.

Further, the additional therapeutic agent may be an agent that disrupts the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or nonnucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can affect maturation of antigen presenting cells, proliferation of T-cells and cytokine release (e.g., IL-12, IL-18, IFN-alpha, beta, and -gamma and TNF-alpha among others).

In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8hydroxy-2-(2-methoxy-ethoxy)adenine) and AZD 8848 (methyl [3-({[3-(6-amino-2-butoxy-8oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine. The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with an antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the target HBV nucleic acids to inhibit replication of the viral genome, transcription of viral RNAs, or translation of viral proteins.

In another embodiment, the disclosed compound and at least one additional therapeutic agent are co-formulated. In yet another embodiment, the disclosed compound and at least one additional therapeutic agent are co-administered. For any combination therapy described herein, synergistic effect may be calculated, for example, using suitable methods such as the Sigmoid-$E_{max}$ equation (Holford & Schemer, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 2755). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Abbreviations used in the instant specification, particularly the schemes and examples, are as follows:
AcOH glacial acetic acid
aq. aqueous
Bn or Bzl benzyl
Boc tert-butyloxycarbonyl
conc. concentrated
DBU 1,8-diazabicyclo[5.4.0]undec-7-ene
DCE 1,2-dichloroethane
DCM dichloromethane
DIPEA or DIEA diisopropyl-ethyl amine
DMAP 4-dimethylaminopyridine
DMF N,N-dimethylformamide
DMSO dimethylsulfoxide
DMTr 4,4'-dimethoxytrityl
DDTT 3-[(dimethylaminomethylene)amino]-3H-1,2,4-dithiazole-5-thione
ESI electrospray ionization
EtOAc or EA ethyl acetate
EtOH ethanol
h or hr(s) hour or hours
HEK human embryonic kidney
HPLC high performance liquid chromatography
MeOH methanol
MHz megahertz
min minute or minutes
MS mass spectrometry
Ms methanesulfonyl
NMR nuclear magnetic resonance
PADS phenylacetyldisulfide
PE petroleum ether
PMB paramethoxybenzyl
$PPh_3$ triphenylphosphine
RP reverse-phase
rt or RT room temperature
Rt retention time
Sec second or seconds
TBAF tetrabutylammonium fluoride
TBAI tetrabutylammonium iodide
TBS t-butyldimethylsilyl
tBuOOH t-butyl hydroperoxide
TEA or $Et_3N$ triethylamine
TFA trifluoroacetic acid
THF tetrahydrofuran
TIPS triisopropylsilyl
TLC thin layer chromatography
TMS tetramethylsilane
Ts 4-toluenesulfonyl Certain compounds of Formula (I) or (Ia)-(Ir) may be prepared according to the process outlined in Scheme 1, below.

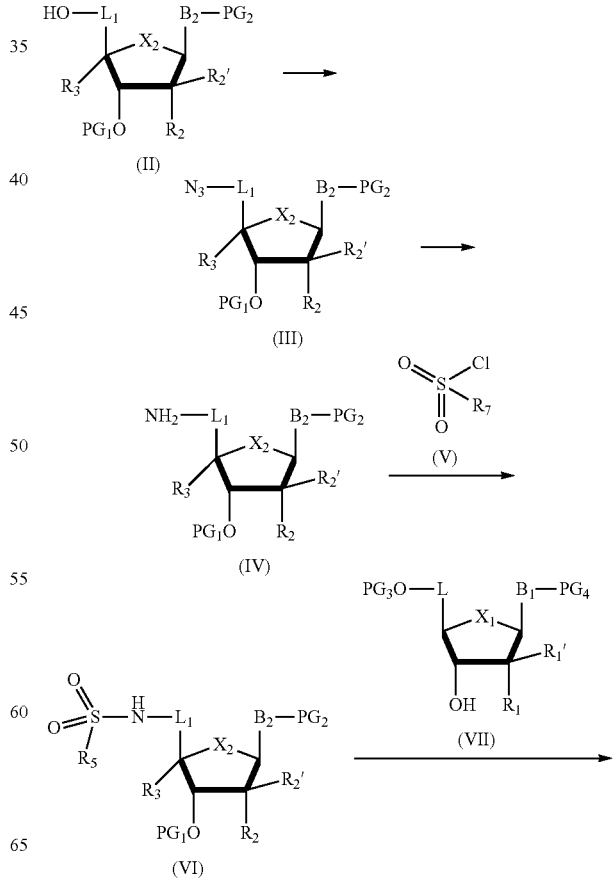

General Scheme 1

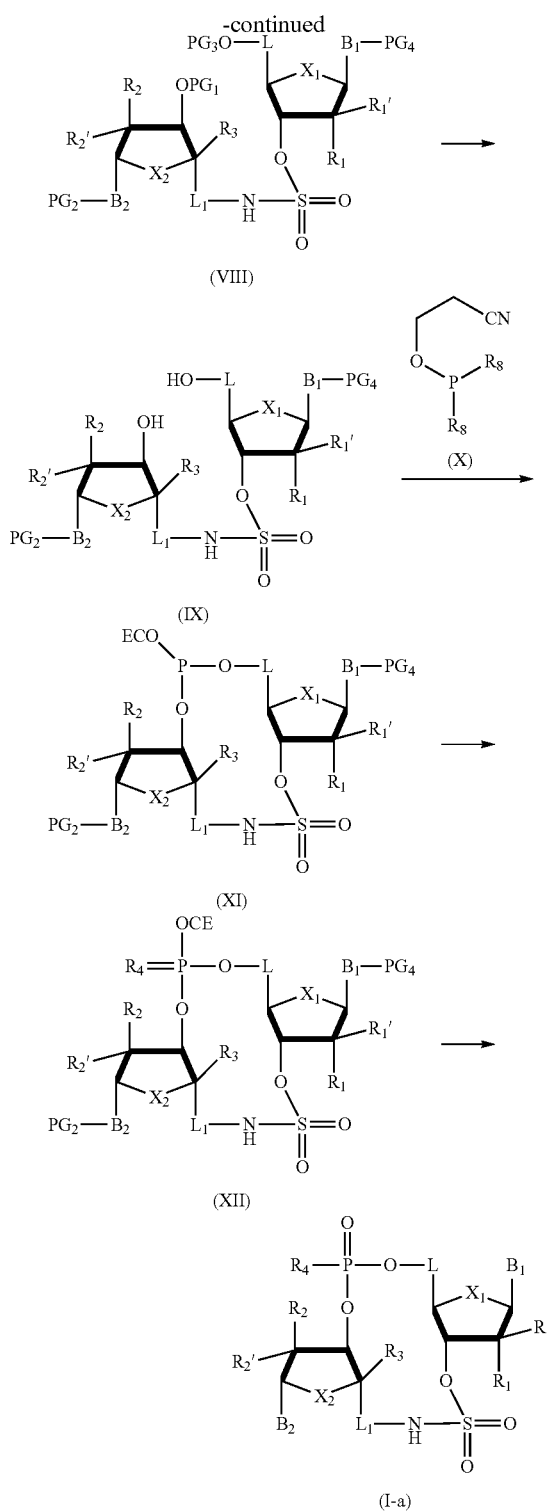

(VIII)

(IX)

(XI)

(XII)

(I-a)

Accordingly, a suitably substituted compound of formula (II) in which $L_1$ is $(CH_2)_{n=1-2}$, $PG_1$ and $PG_2$ are protecting groups known to one of skill in the art, wherein $PG_1$ may be selected from acetyl, trimethylsilyl, tert-butyldimethyl silyl, benzyl, trityl, dimethoxytrityl or the like, and $PG_2$ may be selected from acyl, benzoyl, isobutyryl, or the like, a known compound or compound prepared by known methods, may be reacted with triphenylphosphine, sodium azide, in the presence of tetrabutylammonium iodide and carbon tetra-bromide, in a suitably selected solvent or mixture of solvents such as DMF, THF, toluene, and the like, at a temperature ranging from about 0° C. to about 130° C., to yield the corresponding compound of formula (III). Alternatively, a suitably substituted compound of formula (II), a known compound or compound prepared by known methods, may be reacted with methanesulfonyl chloride, trifluoromethylsulfonyl chloride or the like, in the presence of a suitably selected base such as $Et_3N$, DIPEA, DMAP, and the like, in a suitably selected solvent or mixture of solvents such as $CHCl_3$, $CH_2Cl_2$, THF, pyridine, and the like, at a temperature ranging from about 0° C. to about 130° C., to yield the corresponding mesyl or triflyl analogue, which may be further reacted with sodium azide in a suitably selected solvent or mixture of solvents such as DMF, THF, toluene, and the like, at a temperature ranging from about 0° C. to about 130° C., to yield the corresponding compound of formula (III).

Yet another method may involve treating a suitably substituted compound of formula (II), with a combination of iodine, triphenyl phosphine and imidazole, in a suitable solvent such as pyridine, DMF, or the like; at a temperature ranging from about 0° C. to about 30° C., to yield the corresponding iodo analogue, which may be further reacted with sodium azide in a suitably selected solvent or mixture of solvents such as DMF, THF, toluene, and the like, at a temperature ranging from about 0° C. to about 130° C., to yield the corresponding compound of formula (III).

The compound of formula (III) may then be reacted with a source of hydrogen, under hydrogenation conditions, in the presence of a suitably selected catalyst or catalyst system, such as Pd/C, Pt, and the like, in a solvent such as MeOH, EtOH, EtOAc, and the like, to yield the corresponding compound of formula (IV). Alternatively, the compound of formula (III) may be reacted with triphenyl phosphine, in a suitable solvent such as THF, DMF, or the like; at a temperature ranging from about 20° C. to about 60° C., followed by treatment with water at the same temperature to yield the corresponding compound of formula (IV).

The compound of formula (IV) may be reacted with a compound of formula (V) such as sulfuryl chloride, 4-nitrophenyl chlorosulfate, or the like, in the presence of a suitably selected base such as $Et_3N$, DIPEA, and the like, in a suitably selected solvent or mixture of solvents such as $CHCl_3$, $CH_2Cl_2$, THF, pyridine, and the like, at a temperature ranging from about −78° C. to about 50° C., to yield the corresponding compound of formula (VI).

The compound of formula (VI) may then be reacted with a suitably substituted compound of formula (VII) in which L is $(CH_2)_{n=1-2}$, $PG_3$ and $PG_4$ are protecting groups known to one of skill in the art, in which $PG_3$ might be selected from acetyl, trimethylsilyl, tert-butyldimethyl silyl, benzyl, trityl, dimethoxytrityl or the like, and $PG_2$ might be selected from acyl, benzoyl, isobutyryl, or the like, a known compound or compound prepared by known methods, in the presence of a suitably selected base such as $Et_3N$, DIPEA, DMAP, $Cs_2CO_3$ or the like, in a suitably selected solvent or mixture of solvents such as $CHCl_3$, $CH_2Cl_2$, THF, MeCN, pyridine, and the like, at a temperature ranging from about −10° C. to about 80° C., to yield the corresponding compound of formula (VIII).

The alcohol protecting groups $PG_1$ and $PG_3$ of a compound of formula (VIII) may then be cleaved by methods well within the skill of persons versed in the art, in the presence of basic or acidic conditions, to yield the corresponding compound of formula (IX).

The compound of formula (IX) may then be reacted with a suitably substituted compound of formula (X) in which $R_8$ is halogen, diisopropylamino, or the like, a known compound or compound prepared by known methods, in the presence of a suitably activator such as tetrazole, DMAP, 5-ethylthio-1H-tetrazole, or the like, in a suitably selected solvent or mixture of solvents such as MeCN, $CH_2Cl_2$, THF, dioxane, and the like, at a temperature ranging from about −10° C. to about 60° C., to yield the corresponding phosphite compound of formula (XI).

The compound of formula (XI) may then be reacted with an oxidant such as iodine, hydrogen peroxide, tert-butylperoxide, Beaucage reagent, DDTT, 3-amino-1,2,4-dithiazole-5-thione, PADS, and the like, or a $BH_3.SMe_2$, $BH_3.THF$ complex, or the like, in a suitably selected solvent or mixture of solvents such as $CHCl_3$, $CH_2Cl_2$, THF, MeCN, dioxane, and the like, at a temperature ranging from about −10° C. to about 80° C., to generate the compound of formula (XII) wherein $R_4$ is O, S or $BH_3$.

The compound of formula (XII) may then be deprotected using conditions basic conditions such as $MeNH_2$, $tBuNH_2$, ammonium hydroxide, $Et_3N.3HF$ and the like, in a suitably selected solvent or mixture of solvents such as EtOH, $H_2O$, iPrOH, and the like, at a temperature ranging from about −10° C. to about 120° C., or by methods well within the skill of persons versed in the art, in the presence of basic or acidic conditions, to yield the corresponding compound of formula (I-a).

Alternatively, compounds of Formula (I) or (Ia)-(Ir) may be prepared according to the process outlined in General Scheme 2, below.

General Scheme 2

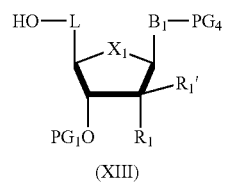

(XIII)

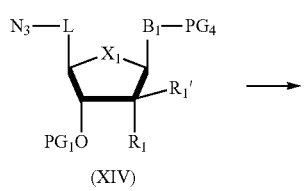

(XIV)

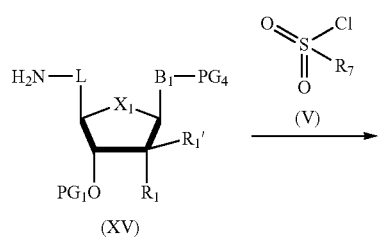

(XV)

-continued

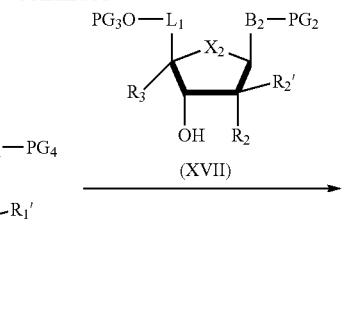

(XVII)

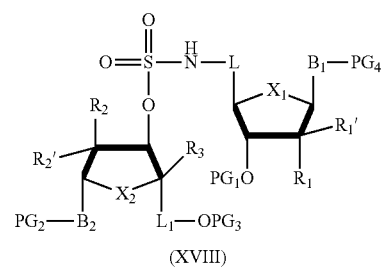

(XVI)

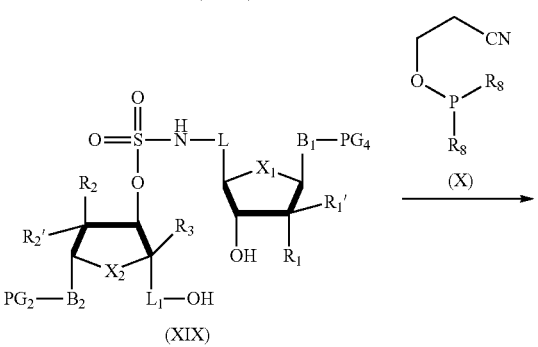

(XVIII)

(XIX)

(X)

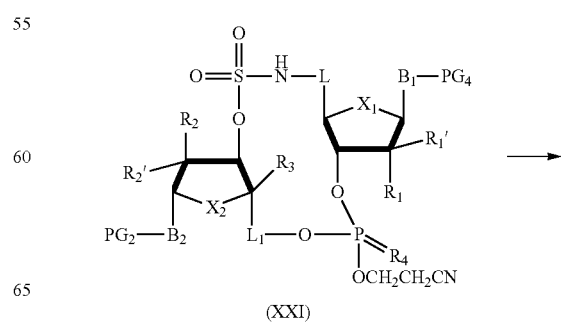

(XX)

(XXI)

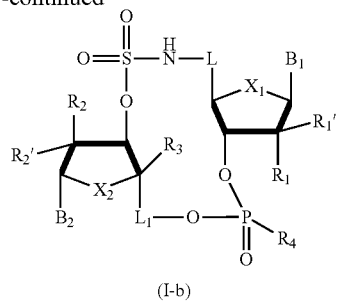

(I-b)

Accordingly, a suitably substituted compound of formula (XIII) in which L is $(CH_2)_{n=1-2}$, $PG_1$ and $PG_4$ are protecting groups known to one of skill in the art, $PG_1$ may be selected from acetyl, trimethylsilyl, tert-butyldimethyl silyl, benzyl, trityl, dimethoxytrityl, or the like, and $PG_4$ might be selected from acyl, benzoyl, isobutyryl, or the like, a known compound or compound prepared by known methods, may be reacted with triphenylphosphine, sodium azide, in the presence of tetrabutylammonium iodide and carbon tetrabromide in a suitably selected solvent or mixture of solvents such as DMF, THF, toluene, and the like, at a temperature ranging from about 0° C. to about 130° C., to yield the corresponding compound of formula (XIV). Alternatively, a suitably substituted compound of formula (XIII), a known compound or compound prepared by known methods, may be reacted with methanesulfonyl chloride, trifluoromethylsulfonyl chloride, or the like, in the presence of a suitably selected base such as $Et_3N$, DIPEA, DMAP, or the like, in a suitably selected solvent or mixture of solvents such as $CHCl_3$, $CH_2Cl_2$, THF, pyridine, and the like, at a temperature ranging from about 0° C. to about 130° C., to yield the corresponding mesyl or triflyl analogue, which may then be further reacted with sodium azide, in a suitably selected solvent or mixture of solvents such as DMF, THF, toluene, and the like, at a temperature ranging from about 0° C. to about 130° C., to yield the corresponding compound of formula (XIV). Yet another method may involve treating a suitably substituted compound of formula (XIII), with a combination of iodine, triphenyl phosphine and imidazole, in a suitable solvent such as pyridine, DMF, or the like, at a temperature ranging from about 0° C. to about 30° C., to yield the corresponding iodo analogue, which may be further reacted with sodium azide in a suitably selected solvent or mixture of solvents such as DMF, THF, toluene, and the like, at a temperature ranging from about 0° C. to about 130° C., to yield the corresponding compound of formula (XIV).

The compound of formula (XIV) may then be reacted with a source of hydrogen, under hydrogenation conditions, in the presence of a suitably selected catalyst or catalyst system, such as Pd/C, Pt, and the like, in a solvent such as MeOH, EtOH, EtOAc, and the like, to yield the corresponding compound of formula (XV). Alternatively, the compound of formula (XIV) may be reacted with triphenyl phosphine, in a suitable solvent such as THF, DMF, or the like, at a temperature ranging from about 20° C. to about 60° C., followed by treatment with water at the same temperature to yield the corresponding compound of formula (XV).

The compound of formula (XV) may be reacted with a compound of formula (V) such as sulfuryl chloride, 4-nitrophenyl chlorosulfate, or the like, in the presence of a suitably selected base such as $Et_3N$, DIPEA, or the like, in a suitably selected solvent or mixture of solvents such as $CHCl_3$, $CH_2Cl_2$, THF, pyridine, and the like, at a temperature ranging from about −78° C. to about 50° C., to yield the corresponding compound of formula (XVI).

The compound of formula (XVI) may then be reacted with a suitably substituted compound of formula (XVII) in which $L_1$ is $(CH_2)_{n=1-2}$, $PG_2$ and $PG_3$ are protecting groups known to one of skill in the art, in which $PG_3$ may be selected from acetyl, trimethylsilyl, tert-butyldimethyl silyl, benzyl, trityl, dimethoxytrityl, or the like, and $PG_2$ may be selected from acyl, benzoyl, isobutyryl, or the like, a known compound or compound prepared by known methods, in the presence of a suitably selected base such as $Et_3N$, DIPEA, DMAP, $Cs_2CO_3$ or the like, in a suitably selected solvent or mixture of solvents such as $CHCl_3$, $CH_2Cl_2$, THF, MeCN, pyridine, and the like, at a temperature ranging from about −10° C. to about 80° C., to yield the corresponding compound of formula (XVIII). The alcohol protecting groups $PG_1$ and $PG_3$ in compound of formula (XVIII) may then be cleaved by methods well within the skill of persons versed in the art in the presence of basic or acidic conditions to yield the corresponding compound of formula (XIX).

The compound of formula (XIX) may then be reacted with a suitably substituted compound of formula (X) in which $R_8$ is halogen, diisopropylamino and the like, a known compound or compound prepared by known methods, in the presence of a suitably activator such as tetrazole, DMAP, 5-ethylthio-1H-tetrazole, or the like, in a suitably selected solvent or mixture of solvents such as MeCN, $CH_2Cl_2$, THF, dioxane, and the like, at a temperature ranging from about −10° C. to about 60° C., to yield the corresponding phosphite compound of formula (XX).

The compound of formula (XX) may then be reacted with an oxidant such as iodine, hydrogen peroxide, tert-butylperoxide, Beaucage reagent, DDTT, 3-amino-1,2,4-dithiazole-5-thione, PADS and the like, or a $BH_3.SMe_2$, $BH_3.THF$ complex, or the like, in a suitably selected solvent or mixture of solvents such as $CHCl_3$, $CH_2Cl_2$, THF, MeCN, dioxane, and the like, at a temperature ranging from about −10° C. to about 80° C., to generate the compound of formula (XXI) wherein $R_4$ is O, S or $BH_3$.

The compound of formula (XXI) may then be deprotected using conditions basic conditions such as $MeNH_2$, $tBuNH_2$, ammonium hydroxide, $Et_3N.3HF$ and the like, in a suitably selected solvent or mixture of solvents such as EtOH, $H_2O$, iPrOH, and the like, at a temperature ranging from about −10° C. to about 120° C., or by methods well within the skill of persons versed in the art, in the presence of basic or acidic conditions, to yield the corresponding compound of formula (I-b).

Alternatively, compounds of Formula (I) or (Ia)-(Ir) may be prepared according to the process outlined in General Scheme 3, below.

General Scheme 3

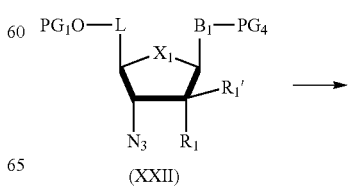

(XXII)

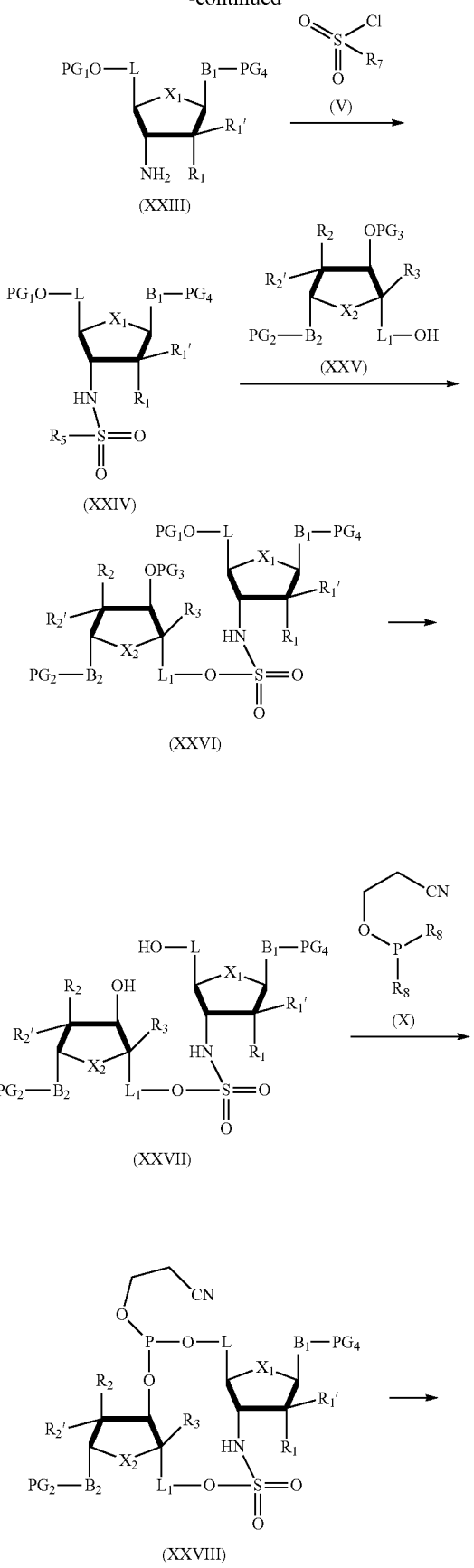
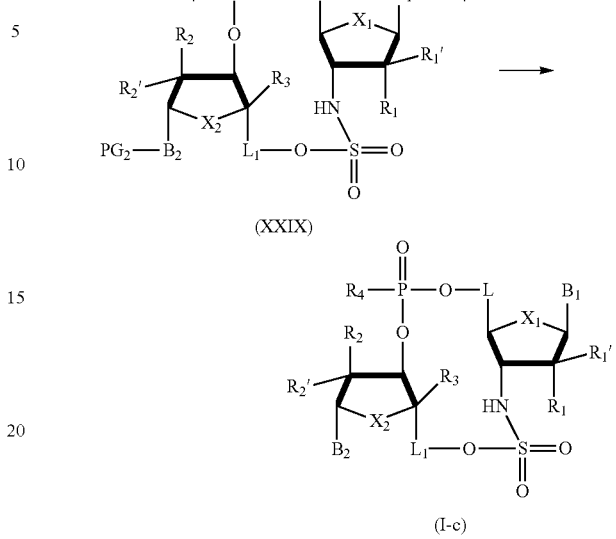

Accordingly, a suitably substituted compound of formula (XXII) in which L is $(CH_2)_{n=1-2}$, $PG_1$ and $PG_4$ are protecting groups known to one of skill in the art, $PG_1$ may be selected from acetyl, trimethylsilyl, tert-butyldimethyl silyl, benzyl, trityl, dimethoxytrityl or the like, and $PG_4$ may be selected from acyl, benzoyl, isobutyryl, or the like, a known compound or compound prepared by known methods, may be reacted with a source of hydrogen, under hydrogenation conditions, in the presence of a suitably selected catalyst or catalyst system, such as Pd/C, Pt, and the like, in a solvent such as MeOH, EtOH, EtOAc, and the like, to yield the corresponding compound of formula (XXIII). Alternatively, the compound of formula (XXII) may be reacted with triphenyl phosphine, in a suitable solvent such as THF, DMF, or the like, at a temperature ranging from about 20° C. to about 60° C., followed by treatment with water at the same temperature to yield the corresponding compound of formula (XXIII).

The compound of formula (XXIII) may be reacted with a compound of formula (V) such as sulfuryl chloride, 4-nitrophenyl chlorosulfate, or the like, in the presence of a suitably selected base such as $Et_3N$, DIPEA, or the like, in a suitably selected solvent or mixture of solvents such as $CHCl_3$, $CH_2Cl_2$, THF, pyridine, and the like, at a temperature ranging from about −78° C. to about 50° C., to yield the corresponding compound of formula (XXIV).

The compound of formula (XXIV) may then be reacted with a suitably substituted compound of formula (XXV) in which $L_1$ is $(CH_2)_{n=1-2}$, $PG_2$ and $PG_3$ are protecting groups known to one of skill in the art, in which $PG_3$ may be selected from acetyl, trimethylsilyl, tert-butyldimethyl silyl, benzyl, trityl, dimethoxytrityl, or the like, and $PG_2$ may be selected from acyl, benzoyl, isobutyryl, or the like, a known compound or compound prepared by known methods, in the presence of a suitably selected base such as $Et_3N$, DIPEA, DMAP, $Cs_2CO_3$, or the like, in a suitably selected solvent or mixture of solvents such as $CHCl_3$, $CH_2Cl_2$, THF, MeCN, pyridine, and the like, at a temperature ranging from about −10° C. to about 80° C., to yield the corresponding compound of formula (XXVI).

The alcohol protecting groups PG₁ and PG₃ in a compound of formula (XXVI) may then be cleaved by methods well within the skill of persons versed in the art, in the presence of basic or acidic conditions, to yield the corresponding compound of formula (XXVII).

The compound of formula (XXVII) may then be reacted with a suitably substituted compound of formula (X) in which R₈ is halogen, diisopropylamino or the like, a known compound or compound prepared by known methods, in the presence of a suitable activator such as tetrazole, DMAP, 5-ethylthio-1H-tetrazole, or the like, in a suitably selected solvent or mixture of solvents such as MeCN, CH₂Cl₂, THF, dioxane, and the like, at a temperature ranging from about −10° C. to about 60° C., to yield the corresponding phosphite compound of formula (XXVIII).

The compound of formula (XXVIII) may then be reacted with an oxidant such as iodine, hydrogen peroxide, tert-butylperoxide, Beaucage reagent, DDTT, 3-amino-1,2,4-dithiazole-5-thione, PADS or the like, or a BH₃.SMe₂, BH₃.THF complex, or the like, in a suitably selected solvent or mixture of solvents such as CHCl₃, CH₂Cl₂, THF, MeCN, dioxane, and the like, at a temperature ranging from about −10° C. to about 80° C., to generate the compound of formula (XXIX) wherein R₄ is O, S or BH₃.

The compound of formula (XXIX) may then be deprotected using basic conditions such as MeNH₂, tBuNH₂, ammonium hydroxide, Et₃N.3HF, or the like, in a suitably selected solvent or mixture of solvents such as EtOH, H₂O, iPrOH, and the like, at a temperature ranging from about −10° C. to about 120° C., or by methods well within the skill of persons versed in the art, in the presence of basic or acidic conditions, to yield the corresponding compound of formula (I-c).

Alternatively, compounds of Formula (I) or (Ia)-(Ir) may be prepared according to the process outlined in General Scheme 4, below.

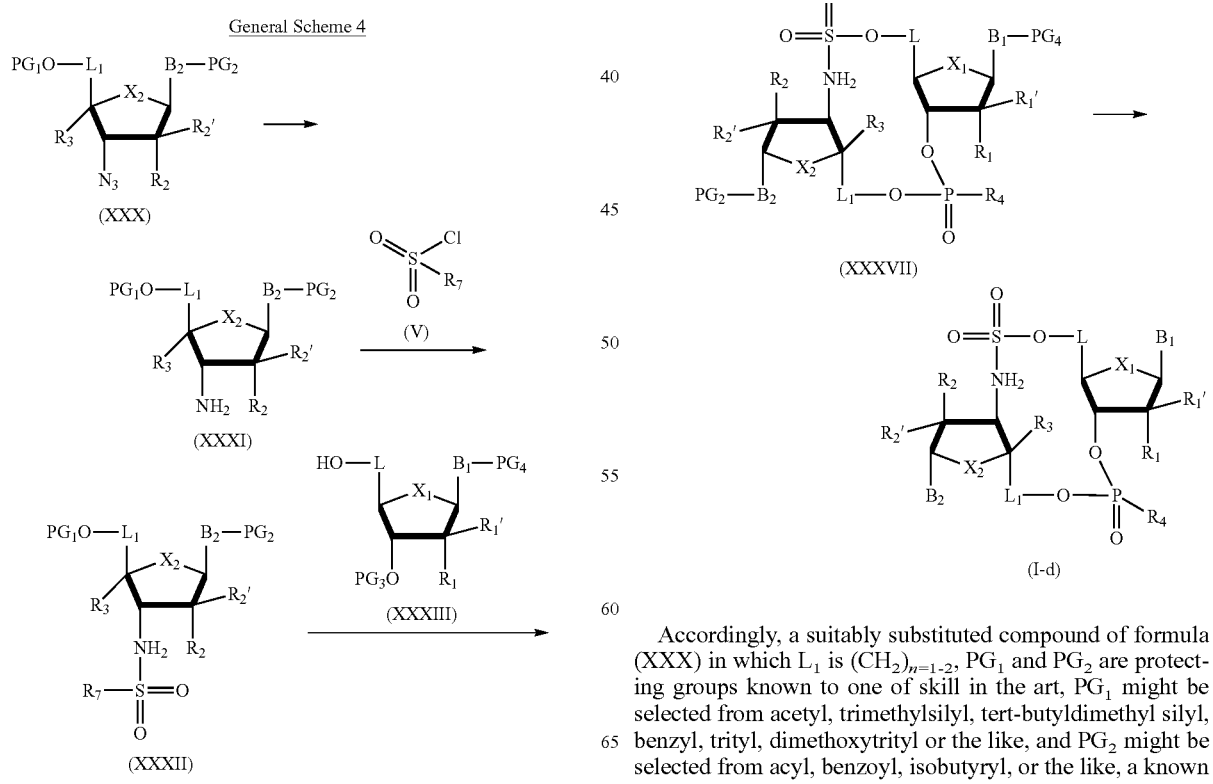
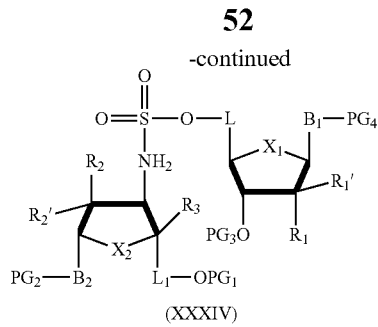
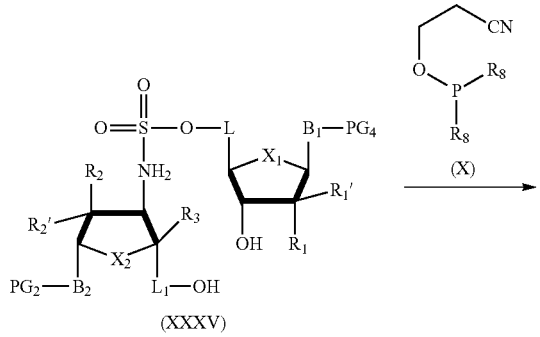
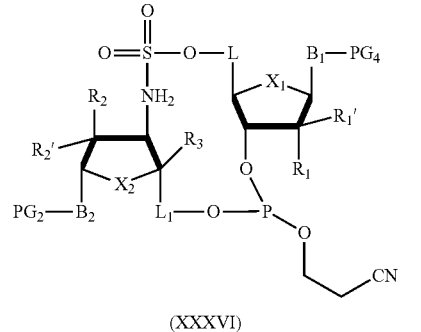

Accordingly, a suitably substituted compound of formula (XXX) in which L₁ is (CH₂)ₙ₌₁₋₂, PG₁ and PG₂ are protecting groups known to one of skill in the art, PG₁ might be selected from acetyl, trimethylsilyl, tert-butyldimethyl silyl, benzyl, trityl, dimethoxytrityl or the like, and PG₂ might be selected from acyl, benzoyl, isobutyryl, or the like, a known compound or compound prepared by known methods, may be reacted with a source of hydrogen, under hydrogenation conditions, in the presence of a suitably selected catalyst or catalyst system, such as Pd/C, Pt, and the like, in a solvent such as MeOH, EtOH, EtOAc, and the like, to yield the corresponding compound of formula (XXXI). Alternatively, the compound of formula (XXX) may be reacted with triphenyl phosphine, in a suitable solvent such as THF, DMF, or the like, at a temperature ranging from about 20° C. to about 60° C., followed by treatment with water at the same temperature to yield the corresponding compound of formula (XXXI).

The compound of formula (XXXI) may be reacted with a compound of formula (V) such as sulfuryl chloride, 4-nitrophenyl chlorosulfate, or the like, in the presence of a suitably selected base such as $Et_3N$, DIPEA, or the like, in a suitably selected solvent or mixture of solvents such as $CHCl_3$, $CH_2Cl_2$, THF, pyridine, and the like, at a temperature ranging from about −78° C. to about 50° C., to yield the corresponding compound of formula (XXXII).

The compound of formula (XXXII) may then be reacted with a suitably substituted compound of formula (XXXIII) in which L is $(CH_2)_{n=1-2}$, $PG_3$ and $PG_4$ are protecting groups known to one of skill in the art, in which $PG_3$ may be selected from acetyl, trimethylsilyl, tert-butyldimethyl silyl, benzyl, trityl, dimethoxytrityl or the like, and $PG_2$ may be selected from acyl, benzoyl, isobutyryl, or the like, a known compound or compound prepared by known methods, in the presence of a suitably selected base such as $Et_3N$, DIPEA, DMAP, $Cs_2CO_3$, or the like, in a suitably selected solvent or mixture of solvents such as $CHCl_3$, $CH_2Cl_2$, THF, MeCN, pyridine, and the like, at a temperature ranging from about −10° C. to about 80° C., to yield the corresponding compound of formula (XXXIV).

The alcohol protecting groups $PG_1$ and $PG_3$ in a compound of formula (XXXIV) may then be cleaved by methods well within the skill of persons versed in the art, in the presence of basic or acidic conditions, to yield the corresponding compound of formula (XXXV).

The compound of formula (XXXV) may then be reacted with a suitably substituted compound of formula (X) in which $R_8$ is halogen, diisopropylamino and the like, a known compound or compound prepared by known methods, in the presence of a suitably activator such as tetrazole, DMAP, 5-ethylthio-1H-tetrazole, or the like, in a suitably selected solvent or mixture of solvents such as MeCN, $CH_2Cl_2$, THF, dioxane, and the like, at a temperature ranging from about −10° C. to about 60° C., to yield the corresponding phosphite compound of formula (XXXVI).

The compound of formula (XXXVI) may then be reacted with an oxidant such as iodine, hydrogen peroxide, tert-butylperoxide, Beaucage reagent, DDTT, 3-amino-1,2,4-dithiazole-5-thione, PADS, or the like, or a $BH_3.SMe_2$, $BH_3.THF$ complex, or the like, in a suitably selected solvent or mixture of solvents such as $CHCl_3$, $CH_2Cl_2$, THF, MeCN, dioxane, and the like, at a temperature ranging from about −10° C. to about 80° C., to generate the compound of formula (XXXVII) wherein $R_4$ is O, S or $BH_3$.

The compound of formula (XXXVII) may then be deprotected using basic conditions such as $MeNH_2$, $tBuNH_2$, ammonium hydroxide, $Et_3N.3HF$, or the like, in a suitably selected solvent or mixture of solvents such as EtOH, $H_2O$, iPrOH, and the like, at a temperature ranging from about −10° C. to about 120° C., or by methods well within the skill of persons versed in the art, in the presence of basic or acidic conditions, to yield the corresponding compound of formula (I-d).

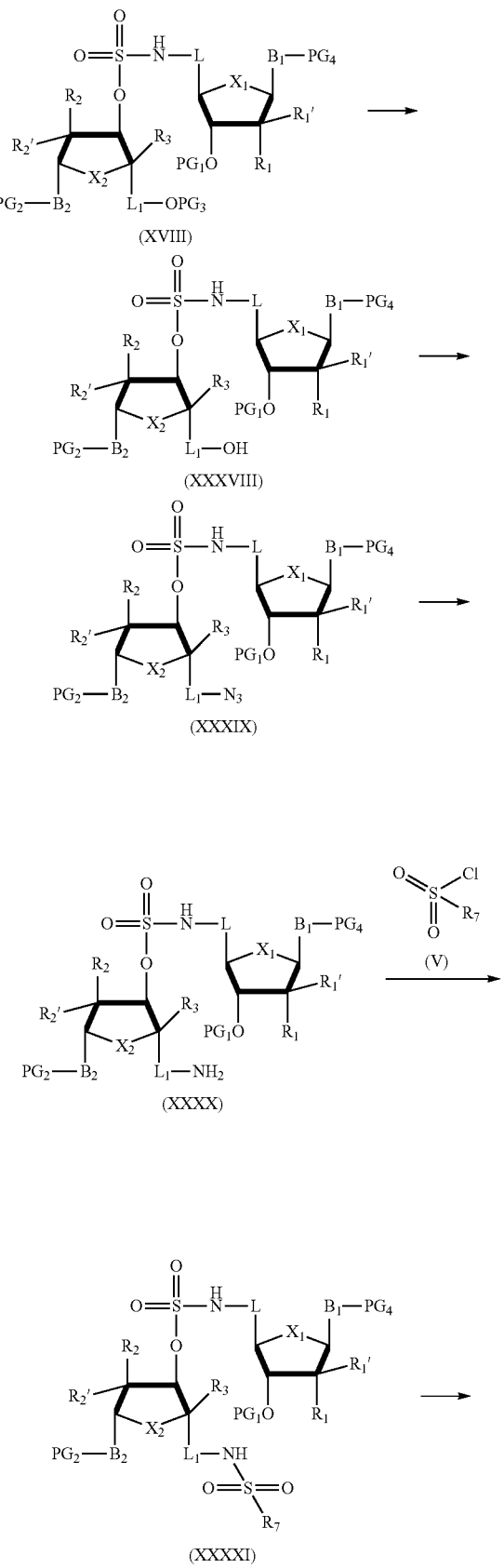

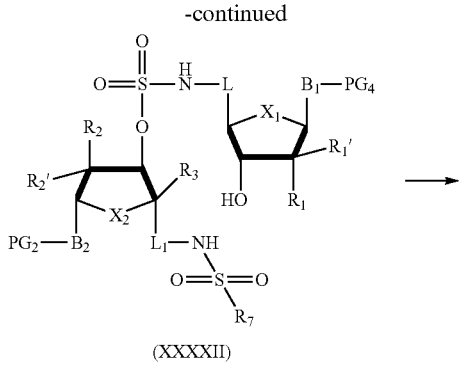

(XXXXII)

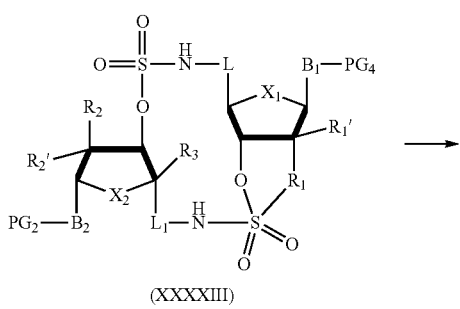

(XXXXIII)

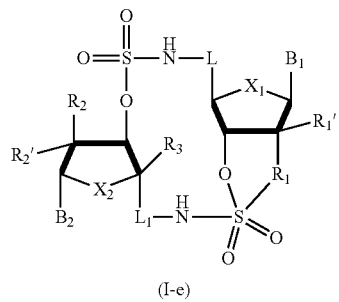

(I-e)

Accordingly, the alcohol protecting group PG$_3$ in a compound of formula (XVIII) in which A$_2$ is (CH$_2$)$_{n=1-2}$, PG$_1$, PG$_2$, PG$_3$ and PG$_4$ are protecting groups known to one of skill in the art, PG$_1$ and PG$_3$ may be selected from acetyl, trimethylsilyl, tert-butyldimethyl silyl, benzyl, trityl, dimethoxytrityl, or the like, and PG$_2$ and PG$_4$ may be selected from acyl, benzoyl, isobutyryl, or the like, a known compound or compound prepared by known methods, may be cleaved selectively in the presence of the alcohol protecting group PG$_1$ by methods well within the skill of persons versed in the art, in the presence of basic or acidic conditions, to yield the corresponding compound of formula (XXXVIII).

The compound of formula (XXXVIII) may be reacted with triphenylphosphine, sodium azide, in the presence of tetrabutylammonium iodide and carbon tetrabromide, in a suitably selected solvent or mixture of solvents such as DMF, THF, toluene, and the like, at a temperature ranging from about 0° C. to about 130° C., to yield the corresponding compound of formula (XXXIX). Alternatively, a suitably substituted compound of formula (XVIII), a known compound or compound prepared by known methods, may be reacted with methanesulfonyl chloride, trifluoromethylsulfonyl chloride or the like, in the presence of a suitably selected base such as Et$_3$N, DIPEA, DMAP, or the like, in a suitably selected solvent or mixture of solvents such as CHCl$_3$, CH$_2$Cl$_2$, THF, pyridine, and the like, at a temperature ranging from about 0° C. to about 130° C., to yield the corresponding mesyl or triflyl analogue, which may be further reacted with sodium azide in a suitably selected solvent or mixture of solvents such as DMF, THF, toluene, and the like, at a temperature ranging from about 0° C. to about 130° C., to yield the corresponding compound of formula (XXXIX).

Yet another method may involve treating a suitably substituted compound of formula (XVIII), with a combination of iodine, triphenyl phosphine and imidazole, in a suitable solvent like pyridine or DMF, or the like, at a temperature ranging from about 0° C. to about 30° C., to yield the corresponding iodo analogue, which may be further reacted with sodium azide in a suitably selected solvent or mixture of solvents such as DMF, THF, toluene, and the like, at a temperature ranging from about 0° C. to about 130° C., to yield the corresponding compound of formula (XXXIX).

The compound of formula (XXXIX) may then be reacted with a source of hydrogen, under hydrogenation conditions, in the presence of a suitably selected catalyst or catalyst system, such as Pd/C, Pt, and the like, in a solvent such as MeOH, EtOH, EtOAc, or the like, to yield the corresponding compound of formula (XXXX). Alternatively, the compound of formula (XXXIX) may be reacted with triphenyl phosphine, in a suitable solvent such as THF, DMF, or the like, at a temperature ranging from about 20° C. to about 60° C., followed by treatment with water at the same temperature to yield the corresponding compound of formula (XXXX).

The compound of formula (XXXX) may be reacted with a compound of formula (V) such as sulfuryl chloride, 4-nitrophenyl chlorosulfate, or the like, in the presence of a suitably selected base such as Et$_3$N, DIPEA, or the like, in a suitably selected solvent or mixture of solvents such as CHCl$_3$, CH$_2$Cl$_2$, THF, pyridine, and the like, at a temperature ranging from about −78° C. to about 50° C., to yield the corresponding compound of formula (XXXXI). The alcohol protecting group PG$_1$ in a compound of formula (XXXIV) may then be cleaved by methods well within the skill of persons versed in the art, in the presence of basic or acidic conditions, to yield the corresponding compound of formula (XXXXII).

The compound of formula (XXXXII) may be reacted in the presence of a suitably selected base such as Et$_3$N, DIPEA, DMAP, Cs$_2$CO$_3$, or the like, in a suitably selected solvent or mixture of solvents such as CHCl$_3$, CH$_2$Cl$_2$, THF, MeCN, pyridine, and the like, at a temperature ranging from about −10° C. to about 80° C., to yield the corresponding compound of formula (XXXXIII).

The compound of formula (XXXXIII) may then be deprotected using basic conditions such as MeNH$_2$, tBuNH$_2$, ammonium hydroxide, Et$_3$N.3HF and the like, in a suitably selected solvent or mixture of solvents such as EtOH, H$_2$O, iPrOH, and the like, at a temperature ranging from about −10° C. to about 120° C., or by methods well within the skill of persons versed in the art, in the presence of basic or acidic conditions, to yield the corresponding compound of formula (I-e).

Aspects of the Invention
Non-limiting aspects of the invention include the following:
Aspect 1: A compound of Formula (I):
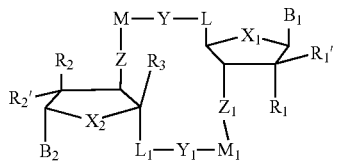
Formula (I)
wherein
B$_1$ and B$_2$ are independently selected from the group consisting of b1, b2, b3, b4, b5, b6, b7, b8, b9, b10, b11, b12, b13, b14, b15, b16, b17, b18, b19, b20, b21, b22, b23, b24 and b25
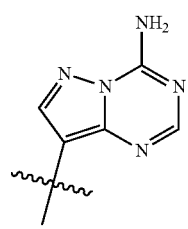
b1
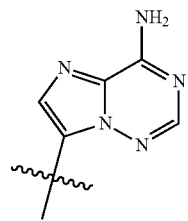
b2
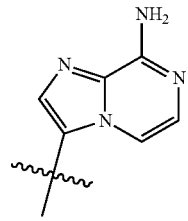
b3
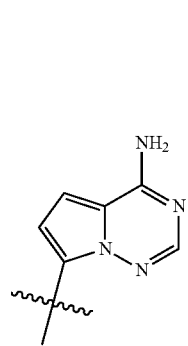
b4
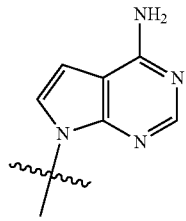
b5
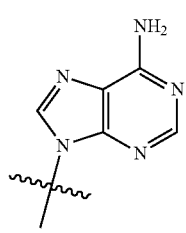
b6
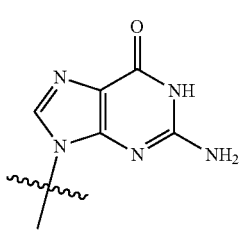
b7
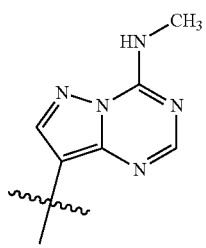
b8
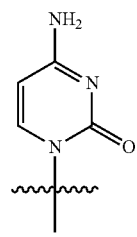
b9
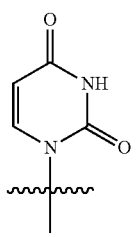
b10
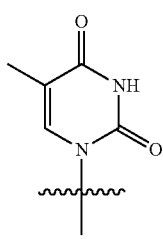
b11

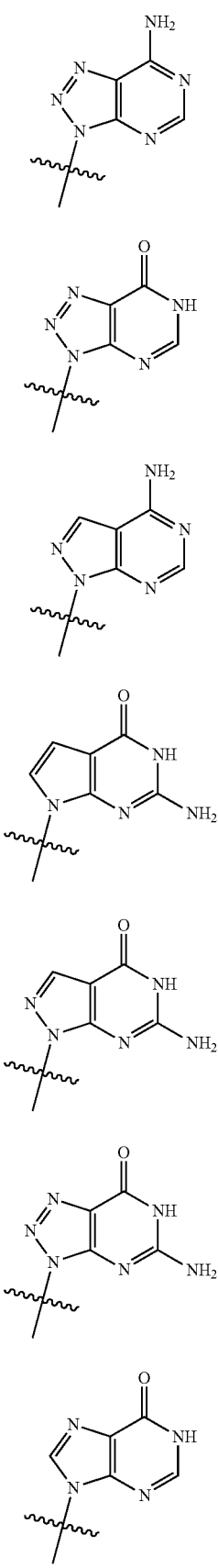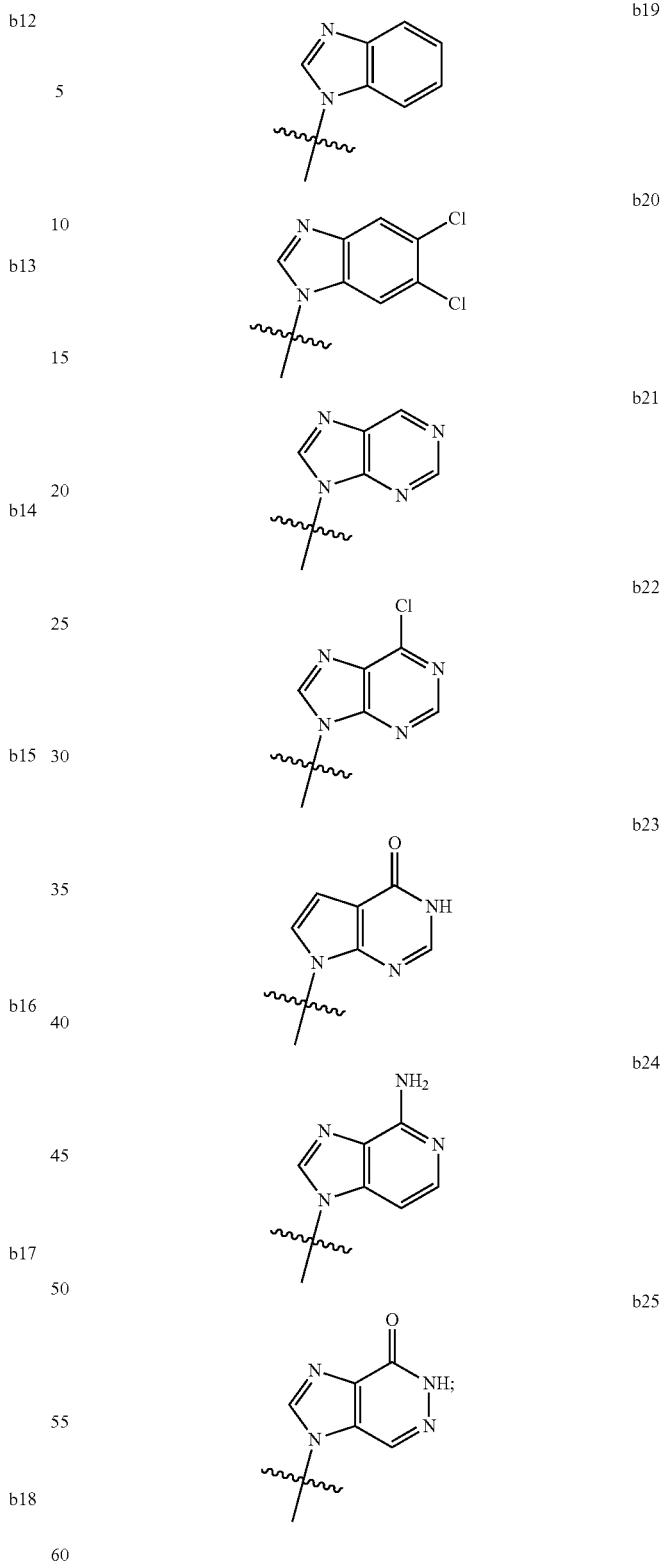

$R_1$ is independently selected from hydrogen; hydroxy; fluoro; $C_{1-3}$alkoxy optionally independently substituted with one to seven halogen substituents, methoxy, or $C_{6-10}$aryl; wherein said $C_{6-10}$aryl is optionally independently substituted with one to two substituents independently selected from the group consisting of fluoro, chloro, bromo, iodo, $C_{1-3}$alkoxy, $C_{1-3}$alkyl, hydroxy, nitro and cyano; $C_{3-6}$alkenyloxy; C$_{2-6}$alkynyloxy; hydroxy(C$_{1-3}$)alkoxy; or C$_{1-3}$alkyl optionally independently substituted with one to three substituents selected from fluoro, chloro, bromo, iodo, or hydroxy;

R$_1$' is independently selected from hydrogen, fluoro, or hydroxy; provided that when R$_1$' is fluoro, R$_1$ is hydrogen or fluoro;

R$_2$ is independently selected from hydrogen; hydroxy; fluoro; C$_{1-3}$alkoxy optionally independently substituted with one to seven halogen substituents, methoxy, or C$_{6-10}$aryl; wherein said C$_{6-10}$aryl is optionally independently substituted with one to two substituents independently selected from the group consisting of fluoro, chloro, bromo, iodo, C$_{1-3}$alkoxy, C$_{1-3}$alkyl, hydroxy, nitro and cyano; C$_{3-6}$alkenyloxy; C$_{2-6}$alkynyloxy; hydroxy(C$_{1-3}$)alkoxy; or C$_{1-3}$alkyl optionally independently substituted with one to three substituents selected from fluoro, chloro, bromo, iodo, or hydroxy; and R$_3$ is hydrogen;

or, R$_3$ is —CH$_2$—, and R$_2$ is —O—; such that R$_2$, R$_3$ and the atoms to which they are attached form a 5-membered ring;

R$_2$' is independently selected from hydrogen, fluoro, or hydroxy; provided that when R$_2$' is fluoro, R$_2$ is hydrogen or fluoro;

R$_3$ is independently selected from hydrogen, fluoro, CH$_3$, or CH$_2$F;

X$_1$ and X$_2$ are independently selected from the group consisting of O, S, and CH$_2$;

L and L$_1$ are independently selected from the group consisting of —CH$_2$— and —CH$_2$CH$_2$—;

Y and Y$_1$ are each independently absent or selected from the group consisting of O and NH;

Z and Z$_1$ are independently selected from the group consisting of O and NH;

one of M and M$_1$ is

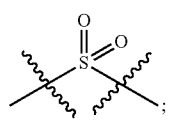

and the other of M and M$_1$ is independently selected from

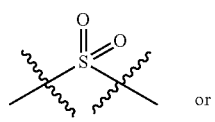

such that, when M is

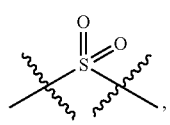

one of Y and Z is NH, and the other of Y and Z is O;

and, such that M$_1$ is

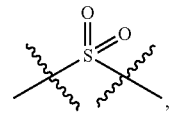

one of Y$_1$ and Z$_1$ is NH, and the other of Y$_1$ and Z$_1$ is O;

with the proviso when Y is absent, L is —CH$_2$CH$_2$—, and M is

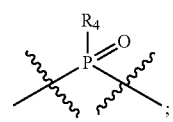

with the proviso when Y$_1$ is absent, L$_1$ is absent, and M$_1$ is

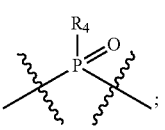

R$_4$ is independently selected from the group consisting of hydroxy, methyl, BH$_3$, and —SR$_5$; wherein R$_5$ is independently selected from the group consisting of hydrogen, —CH$_2$OC(O)R$_6$, —CH$_2$OC(O)OR$_6$, —CH$_2$CH$_2$SC(O)R$_6$, and —CH$_2$CH$_2$S—SCH$_2$R$_6$;

R$_6$ is independently selected from the group consisting of C$_{6-10}$aryl, heteroaryl, heterocycloalkyl, C$_{3-12}$cycloalkyl, and C$_{1-20}$alkyl optionally independently substituted with one to five fluoro or hydroxy substituents, C$_{1-6}$alkyl, C$_{6-10}$aryl, or C$_{3-12}$cycloalkyl;

or an enantiomer, diastereomer, or pharmaceutically acceptable salt form thereof.

Aspect 2: The compound of aspect 1 wherein B$_1$ and B$_2$ are each b6

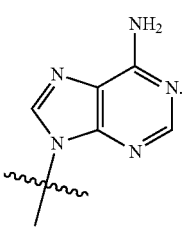

Aspect 3: The compound of aspect 1 wherein $B_1$ is b7 and $B_2$ is b6

and
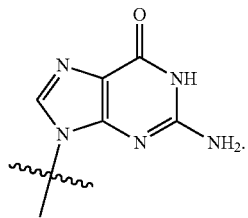
Aspect 4: A compound of aspect 1 that is:
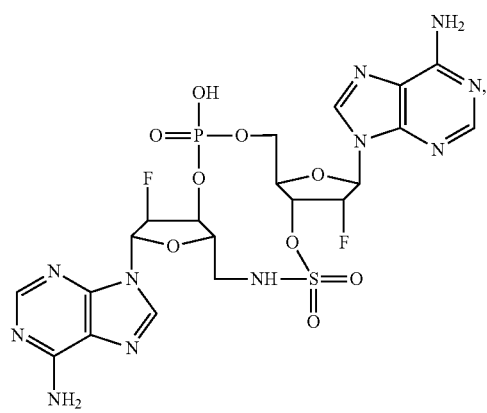
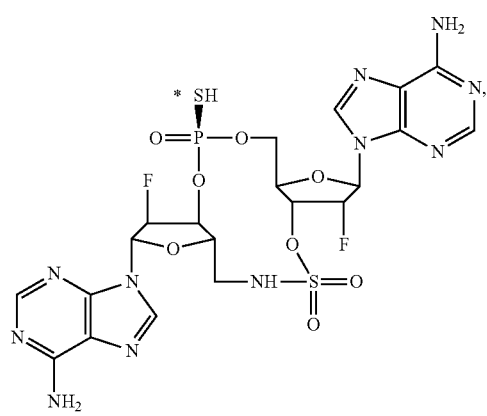
-continued
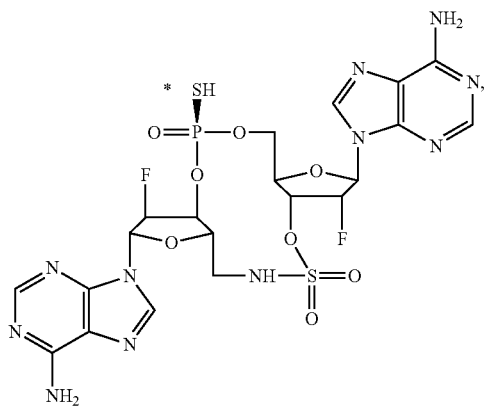
b6
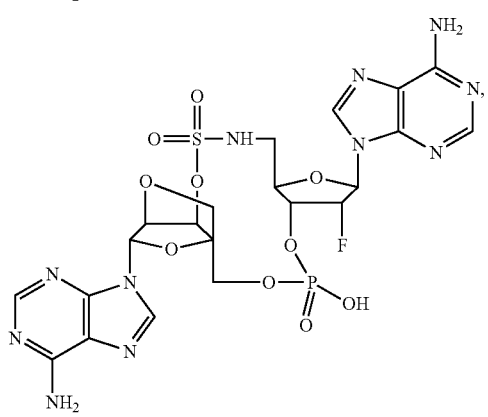
b7
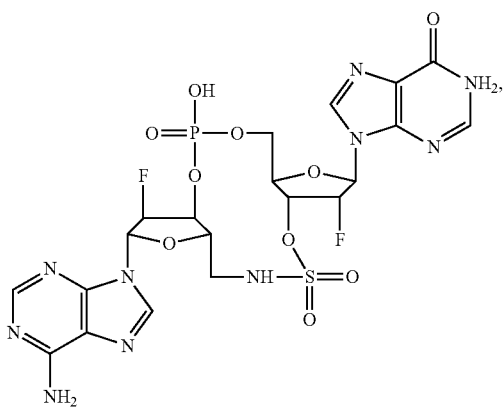
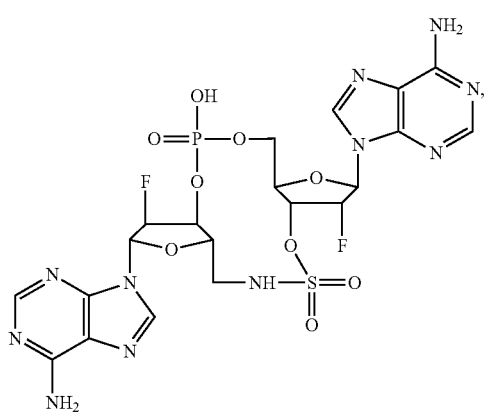

65
-continued
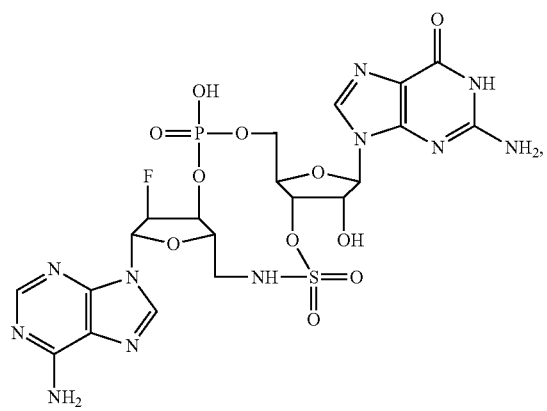 [SMILES: Nc1nc2c(nnn2C2SC3CO[P@](=O)(S)OC4C(CNS(=O)(=O)OC3C2O)OC(n2cnc3c(N)ncnc32)C4F)c(=O)[nH]1]
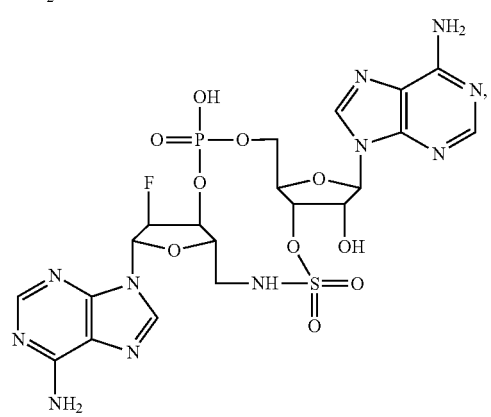
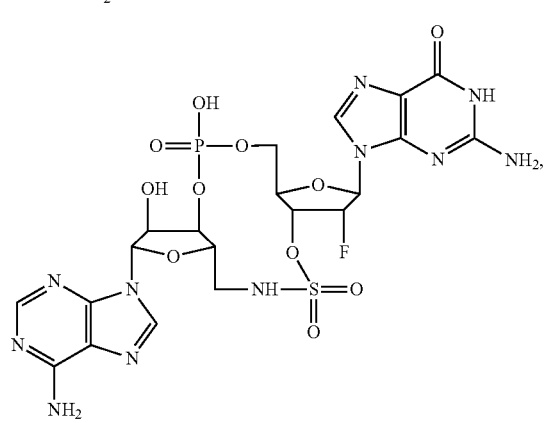
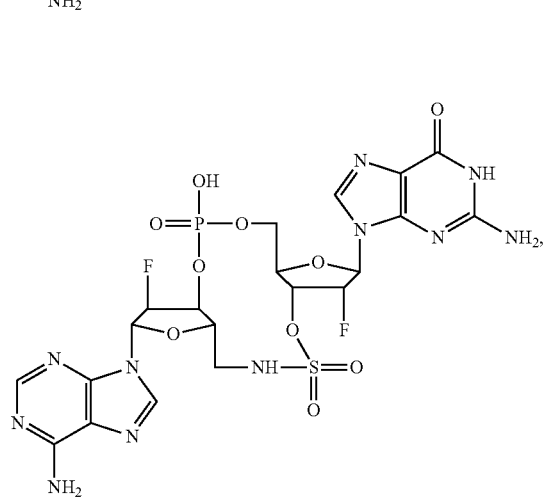
66
-continued
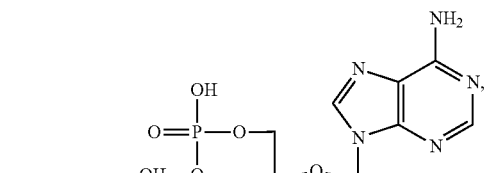
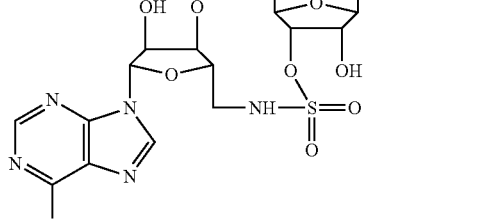
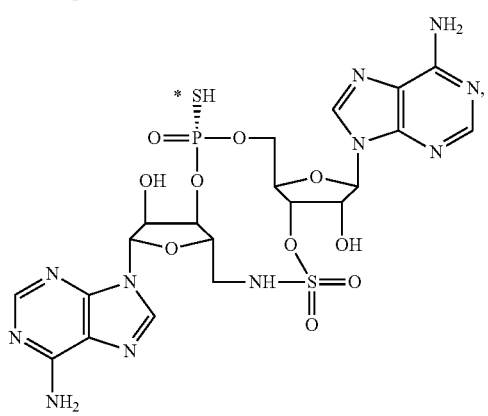
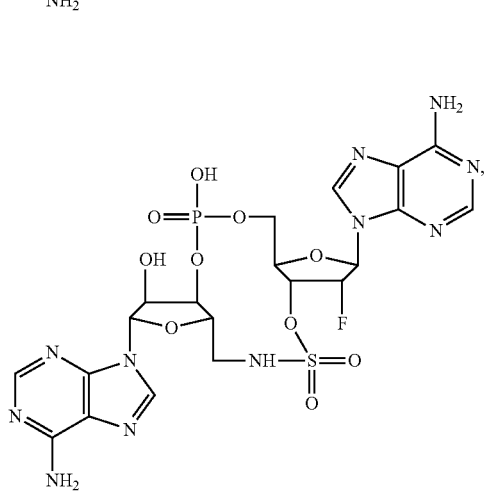

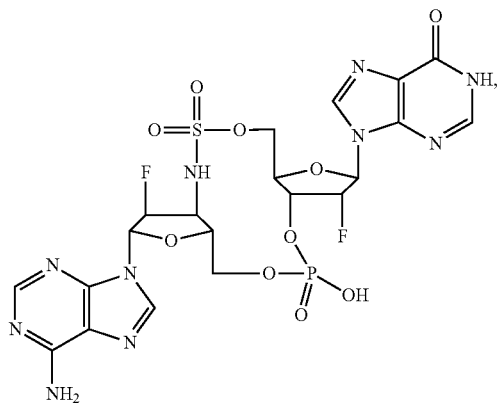

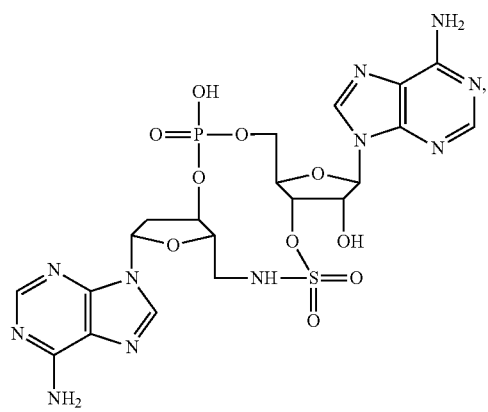

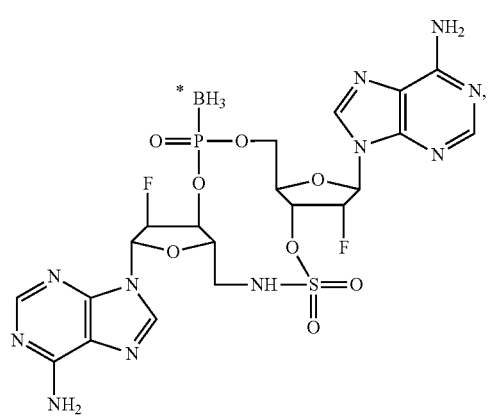

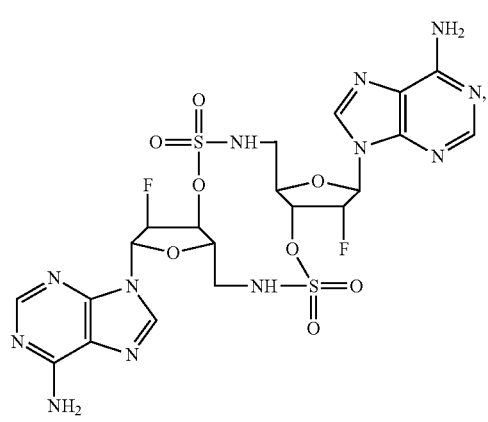

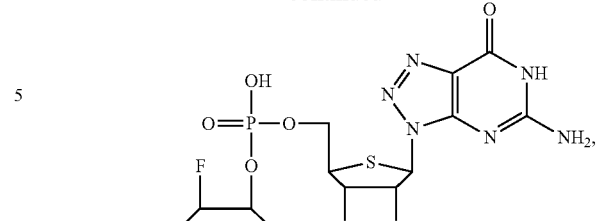

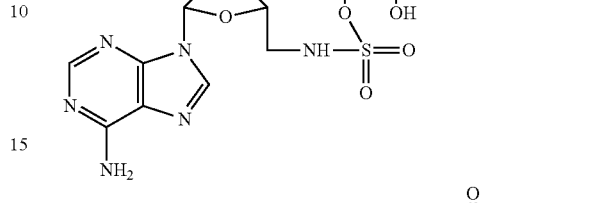

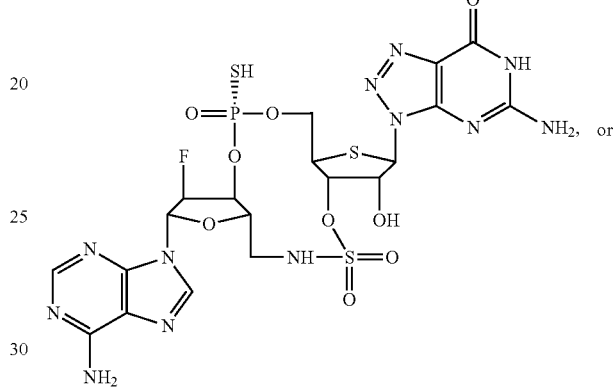

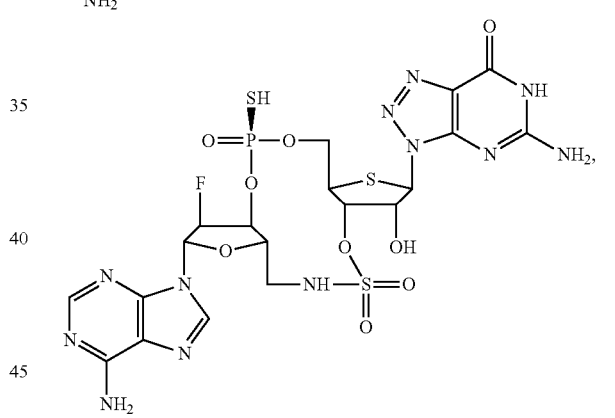

or a pharmaceutically acceptable salt form thereof.

Aspect 5: A pharmaceutical composition comprising a compound of any one of aspects 1 to 4 and at least one of a pharmaceutically acceptable carrier, a pharmaceutically acceptable excipient, and a pharmaceutically acceptable diluent.

Aspect 6: The pharmaceutical composition of aspect 5, wherein the composition is a solid oral dosage form.

Aspect 7: The pharmaceutical composition of aspect 5, wherein the composition is a syrup, an elixir or a suspension.

Aspect 8: A pharmaceutical composition comprising a compound of aspect 4 and at least one of a pharmaceutically acceptable carrier, a pharmaceutically acceptable excipient, and a pharmaceutically acceptable diluent.

Aspect 9: A method of treating a disease, syndrome, or condition modulated by STING, comprising administering to a subject in need thereof a therapeutically effective amount of the compound of aspect 1.

Aspect 10: A method of treating a disease, syndrome, or condition, wherein said disease, syndrome, or condition is affected by the agonism of STING, comprising administering to a subject in need thereof a therapeutically effective amount of the compound of aspect 1.

Aspect 11: The method of aspect 10 wherein said disease, syndrome, or condition is cancer.

Aspect 12: The method of aspect 11 wherein said cancer is selected from the group consisting of melanoma, colon cancer, breast cancer, prostate cancer, lung cancer, and fibrosarcoma.

Aspect 13: The method of aspect 10, wherein said disease, syndrome, or condition is a viral infection.

Aspect 14: The method of aspect 13, wherein the viral infection is hepatitis B.

Aspect 15: A method of treating a disease, syndrome, or condition selected from the group consisting of viral infection, melanoma, colon cancer, breast cancer, prostate cancer, lung cancer, and fibrosarcoma, comprising administering to a subject in need thereof a therapeutically effective amount of the composition of aspect 5.

Aspect 16: The method of aspect 15, wherein the viral infection is hepatitis B.

Aspect 17: The use of a compound as defined in aspect 1 for the preparation of a medicament for treating a disease, syndrome, or condition selected from the group consisting of viral infection, melanoma, colon cancer, breast cancer, prostate cancer, lung cancer, and fibrosarcoma, in a subject in need thereof.

Aspect 18: The use of a compound as defined in aspect 1, for use in a method for treating a disease, syndrome, or condition selected from the group consisting of viral infection, melanoma, colon cancer, breast cancer, prostate cancer, lung cancer, and fibrosarcoma, in a subject in need thereof.

Example 1: Compound 1

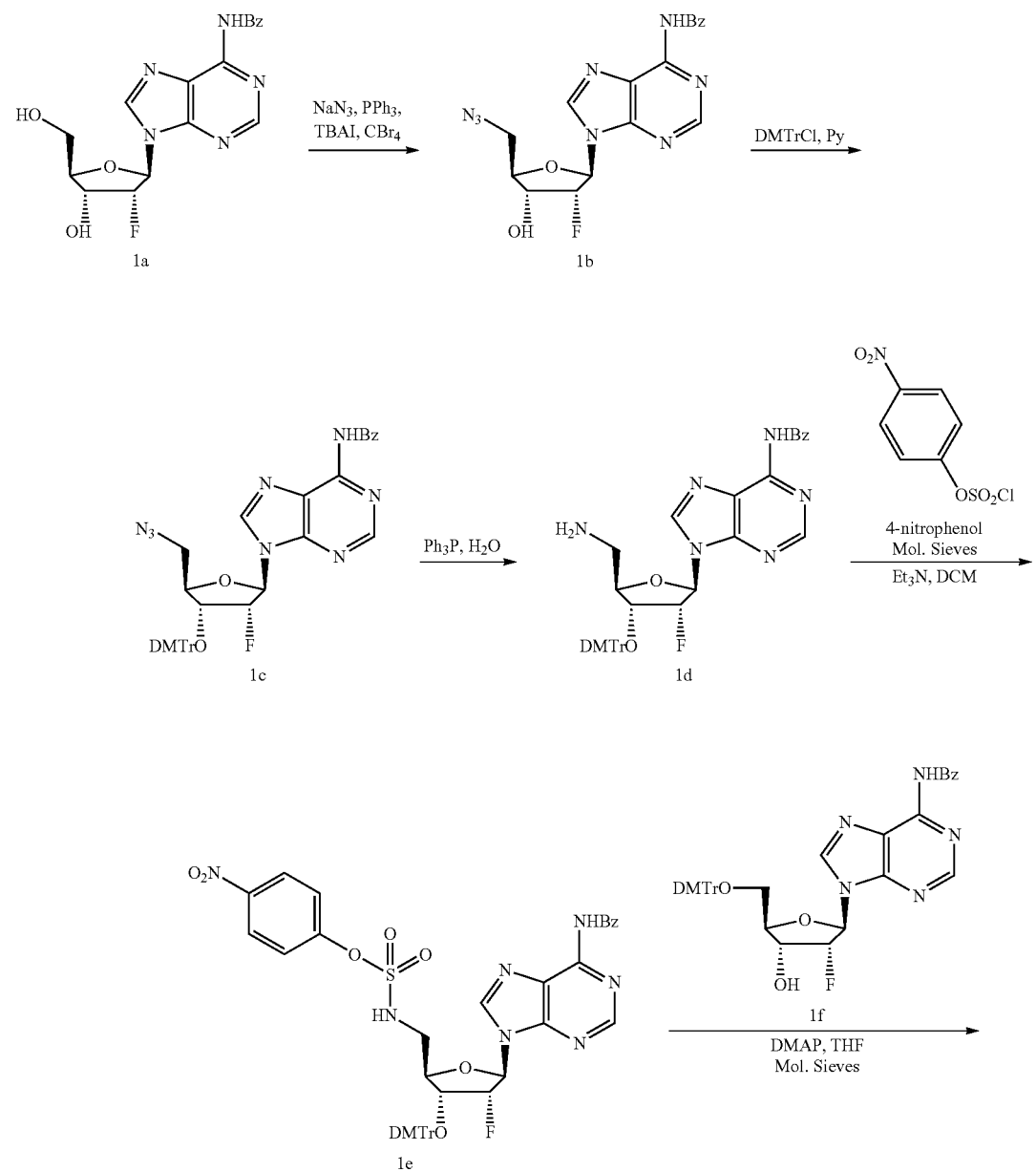

-continued
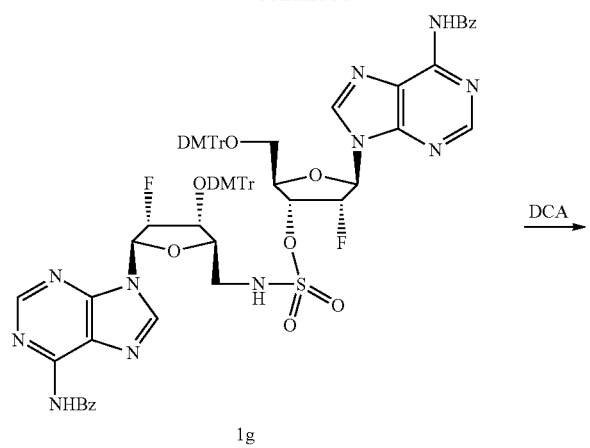
1g
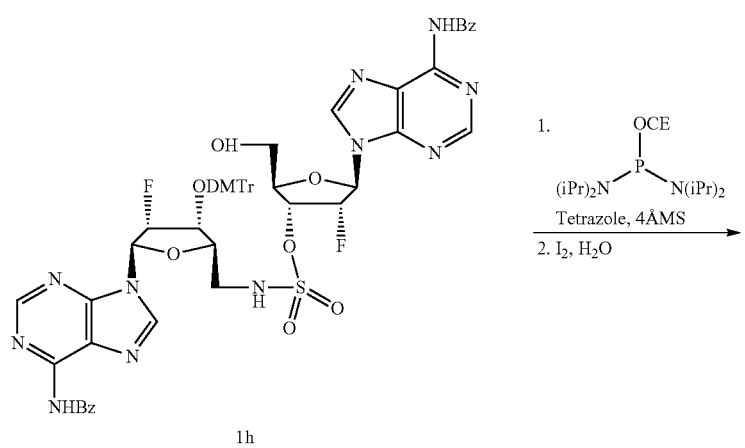
1h
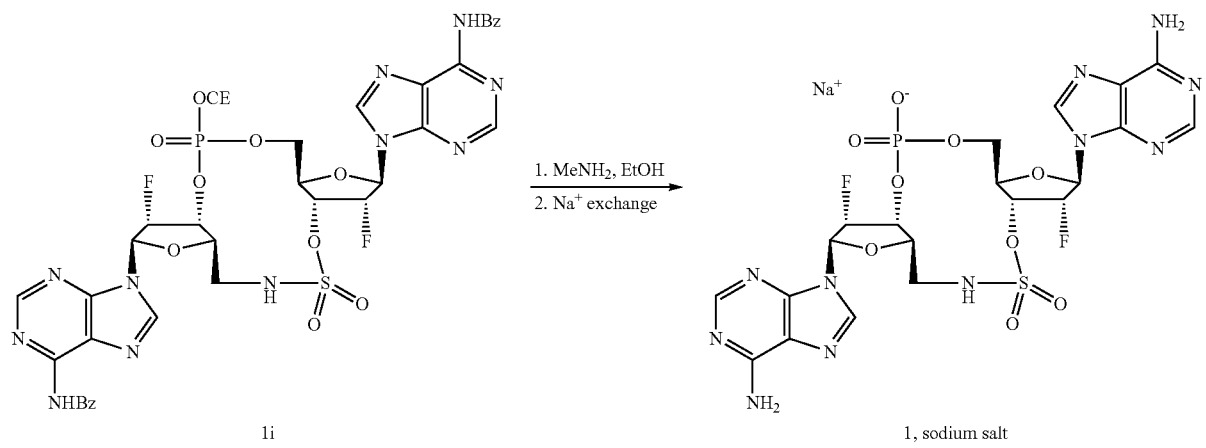
1i          1, sodium salt

Step 1: To a stirred suspension of intermediate 1a (7.5 g, 20.08 mmol), triphenylphosphine (7.90 g, 30.13 mmol), TBAI (1.48 g, 4.01 mmol) and NaN$_3$ (5.22 g, 80.35 mmol) in DMF (80 mL) was added CBr$_4$ (9.99 g, 30.13 mmol) portionwise at 0° C. resulting in a yellow suspension. After stirring at room temperature for 2 hr and heated at 35° C. for 48 h, the reaction mixture was combined with another batch (same scale) and added slowly to a mixture of 600 mL of saturated aqueous NaHCO$_3$, 500 mL of MTBE and 40 mL of EtOAc (3 phases) under vigorous stirring. Precipitate formed was collected by filtration; the filter cake was transferred into a 100 mL flask, to which was added 40 mL of DCM and 8 mL of EtOH; the resulting suspension was sonicated and stirred for 30 min. The solid was then collected by filtration and dried under vacuum to give intermediate 1b as a white solid (12.9 g). $^1$H NMR (400 MHz, DMSO-d$_6$) 11.28 (br d, J=1.7 Hz, 1H), 8.82-8.69 (m, 1H), 8.62 (s, 1H), 8.05 (br d, J=7.3 Hz, 2H), 7.69-7.59 (m, 1H), 7.59-7.48 (m, 1H), 6.41 (br d, J=19.8 Hz, 1H), 5.95 (br s, 1H), 5.78-5.55 (m, 1H), 4.86-4.70 (m, 1H), 4.12 (br s, 1H), 3.81-3.69 (m, 1H), 3.57 (br dd, J=5.7, 13.6 Hz, 1H), 3.34 (s, 4H); $^{19}$F NMR (376 MHz, DMSO-d$_6$) −201.61 (td, J=20.5, 52.8 Hz), ESI-MS: m/z=398.9 [M+H]$^+$.

Step 2: Intermediate 1b was co-evaporated with pyridine (60 mL) twice before use. To a solution of intermediate 1b (6 g, 15.06 mmol) in Py. (60 mL) was added DMTrCl (10.2 g, 30.12 mmol) and DMAP (920 mg, 7.53 mmol) at 5 C. The reaction mixture was stirred for 18 hr at 80° C. resulting in a yellow solution. The reaction mixture was combined with another batch (same scale) and concentrated under reduced pressure; the residue was dissolved in DCM (150 mL) and slowly poured into saturated aqueous NaHCO$_3$ (100 mL) under vigorous stirring. Aqueous layer was extracted with DCM (100 mL×2). Organic layers were then combined, dried over anhydrous Na$_2$SO$_4$, filtered and concentrated to give a yellow residue. Purification by flash column chromatography over silica gel (gradient 0-100% EtOAc in Petroleum ether) gave intermediate 1c as a yellow solid (12.6 g, 88%). ESI-MS: m/z=701.1 [M+H]f.

Step 3: PPh$_3$ was added to a solution of intermediate 1c (12.6 g, 17.98 mmol) in THF (100 mL) (6.6 g, 25.1 mmol) in one portion at RT; after stirring at 40° C. for 2 h under N$_2$, of H$_2$O (50 mL) was added and the resulting mixture was stirred for another 12 h, resulting in a colorless solution. The reaction mixture was then concentrated under reduced pressure and the residual aqueous layer was partitioned between DCNMH$_2$O (80/30 mL). Aqueous layer was extracted with DCM (40 mL×2). Organic layers were then combined, dried over anhydrous Na$_2$SO$_4$, filtered and concentrated to give a white solid. Purification by flash column chromatography over silica gel (gradient 0-5% MeOH in DCM) afforded intermediate 1d as a white solid (11.6 g). $^1$H NMR (400 MHz, CDCl$_3$) 8.93 (br s, 1H), 8.71 (s, 1H), 8.31 (s, 1H), 8.01 (br d, J=7.3 Hz, 2H), 7.33-7.19 (m, 4H), 6.82 (dd, J=6.9, 8.9 Hz, 4H), 6.17 (dd, J=1.5, 17.6 Hz, 1H), 4.64 (ddd, J=4.4, 7.6, 19.4 Hz, 1H), 4.57-4.36 (m, 1H), 4.18-4.08 (m, 1H), 3.77 (d, J=5.3 Hz, 6H), 2.94 (dd, J=2.4, 14.2 Hz, 1H), 2.64 (dd, J=4.3, 14.3 Hz, 1H); $^{19}$F NMR (376 MHz, CDCl$_3$) −197.03 (br s, 1F), ESI-MS: m/z=675.1 [M+H]$^+$.

Step 4: A solution of 4-nitrophenyl chlorosulfate (768 mg, 3.23 mmol) in dry CH$_2$Cl$_2$ (5 mL) was added rapidly to a mixture of intermediate 1d (727 mg, 1.07 mmol), 4-nitrophenol (449 mg, 3.23 mmol), Et$_3$N (654 mg, 6.46 mmol) and activated 4 Å molecular sieves (~1 g) in dry CH$_2$Cl$_2$ (15 mL) under N$_2$ at −78° C. The reaction mixture was then warmed to room temperature gradually over 1.5 h. The reaction mixture was combined with other batches and filtered through a pad of diatomaceous earth. The filtrate was washed with saturated aqueous NaHCO$_3$ (200 mL×4). Organic layers were then combined, dried over anhydrous Na$_2$SO$_4$, filtered and concentrated to give a yellow residue, which was purified by flash column chromatography over silica gel (gradient 0-100% EtOAc in petroleum ether) to give intermediate 1e (16 g, 70%) as a light yellow solid. $^1$H NMR (400 MHz, CDCl$_3$) 8.93-8.81 (m, 2H), 8.41 (s, 1H), 8.11-7.92 (m, 5H), 7.67-7.58 (m, 1H), 6.86 (br t, J=7.7 Hz, 4H), 6.20 (br dd, J=5.1, 13.7 Hz, 1H), 5.34-5.23 (m, 2H), 5.16 (br t, J=5.1 Hz, 1H), 4.73 (br s, 1H), 3.90 (br s, 1H), 3.79 (d, J=6.4 Hz, 6H), 3.23 (br d, J=13.2 Hz, 1H), 2.89 (br dd, J=8.7, 12.6 Hz, 1H); $^{19}$F NMR (376 MHz, CDCl$_3$) −199.28-−205.90 (m, 1F). ESI-MS: m/z=876.1 [M+H]$^+$.

Intermediate 1e (750 mg, 0.857 mmol) and intermediate 1f (482 mg, 0.714 mmol) were dissolved in dry THF (8 mL). Activated molecular sieve powder (2 g, 4 Å) was added to the mixture. After stirring at RT for 1 h, DMAP (435 mg, 7.4 mmol) was added to the mixture. After stirring the reaction mixture for 40 h at RT, the molecular sieve powder was removed by filtration, washed thoroughly with EtOAc (100 mL). The organic layer was successively washed with saturated aqueous NaHCO$_3$ (1×20 mL), saturated aqueous NaCl (1×20 mL) and deionized H$_2$O (1×20 mL). The organic layer was dried with anhydrous Na$_2$SO$_4$, filtered and the filtrate concentrated under reduced pressure. The crude residue was purified by silica column chromatography over silica gel (gradient elution: 0 to 15% MeOH in DCM) to give intermediate 1g (880 mg, yield: 72%) as a solid. ESI-MS: m/z 1412 [M+H]$^+$. Step 6: To a solution of intermediate 1g (800 mg, 0.566 mmol) in DCM (10 mL) was added triethylsilane (5 mL) and 6% DCA in DCM (10 mL). After stirring the reaction mixture for 40 min at RT, it was diluted with EtOAc (50 mL) and washed with saturated aqueous NaHCO$_3$ (1×20 mL) and saturated aqueous NaCl (1×20 mL). The aqueous phase was extracted with EtOAc (1×35 mL) and combined organic layers were successively dried over anhydrous Na$_2$SO$_4$, filtered and concentrated to dryness. The resulting crude residue was purified by flash column chromatography over silica gel (gradient elution: 0-15% MeOH in EtOAc) to give intermediate 1h (408 mg, yield: 89%) as a white solid. ESI-MS: m/z 808 [M+H]$^+$.

Step 7: Intermediate 1h (84 mg, 0.104 mmol) was co-evaporated with a mixture of dry toluene:acetonitrile (1:1, v/v, 3×10 mL) and then dissolved in anhydrous THF (5 mL), and sonicated for 5 min for complete solubility of 1h. To the mixture was then added 4 Å molecular sieves powder (0.5 g) and 0.45 M tetrazole in acetonitrile (1.15 mL, 0.52 mmol). The resulting heterogeneous mixture was bubbled with Argon for 4 min. After stirring this mixture at rt for 10 min, 2-cyanoethyl-N,N,N',N'-tetra(isopropyl)phosphorodiamidite (47 mg, 0.156 mmol, 1.5 eq, in 2 mL of CH$_3$CN) was added to this over 30 min at rt. After stirring the reaction mixture for 1.5 h, the mixture was filtered, and the solids were washed with EtOAc. The combined filtrate was concentrated under reduced pressure to afford the phosphite intermediate. MS: m/z 907 [M+H]$^+$. The resulting mixture was used directly into the next step. Iodine (0.5 M in THF:H$_2$O:Py 8:1:1, v/v/v) was added. After stirring the reaction mixture at rt for 30 min, it was then diluted with EtOAc (30 mL). Excess iodine was quenched with saturated aqueous Na$_2$S$_2$O$_3$. The organic and aqueous phases were separated. The organic layer was successively washed with saturated aqueous NaHCO$_3$ (1×20 mL), saturated aqueous NaCl (1×20 mL). The aqueous layer was extracted with EtOAc (1×20 mL). The combined organic layers were concentrated under reduced pressure to dryness. The resulting crude material was purified by flash column chromatography over silica gel (gradient 0-10% MeOH in dichloromethane) to get intermediate 1i (45 mg). ESI-MS: m/z 923 [M+H]+.

Step 8: A saturated solution of methylamine in ethanol (6 mL) was mixed with intermediate 1i (45 mg) at rt. After stirring for 2 h at rt, the reaction mixture was concentrated under reduced pressure. The resulting crude solid was washed with DCM (15 mL) and the precipitate was collected by filtration and purified by preparative reverse phase HPLC (column: Synergi 4 μm, Hydro RP, 250 mm×30 mm, Mobile Phase: Buffer A: 50 mM triethylammonium acetate in $H_2O$; Buffer B: 50 mM triethylammonium acetate in $CH_3CN$, gradient: 0-40% of B over 30 min, flow rate 24 mL/min) to get Compound 1 (9.1 mg) as a triethylammonium acetate salt. ESI-MS: m/z: 660 [M-1]−.

Dowex 50W×8, 200-400 (5 mL, H form) was added to a beaker and washed with deionized water (30 mL). Then to the resin was added 15% $H_2SO_4$ in deionized water, the mixture was gently stirred for 5 min, and decanted (30 mL). The resin was transferred to a column with 15% $H_2SO_4$ in deionized water and washed with 15% $H_2SO_4$ (at least 4 Column Volume [CV]), and then with deionized water until the column was pH neutral. The resin was transferred back into the beaker, 15% NaOH in deionized water solution was added, and mixture was gently stirred for 5 min, and decanted (1×). The resin was transferred to the column and washed with 15% NaOH in water (at least 4 CV), and then with deionized water until the column was pH neutral. Compound 1 TEAA salt (9.1 mg) were dissolved in a minimum amount of deionized water, added to the top of the column, and eluted with deionized water. Appropriate fractions of CDN based on UV were pooled together and lyophilized to give Compound 1 as a white flocculent solid (8.45 mg). $^1$H NMR (400 MHz, $D_2O$): δ 7.85-7.95 (m, 3H), 6.89 (br. s, 1H), 6.10-6.20 (m, 2H), 5.71 (d, J=3.2 Hz, 0.5H), 5.58 (d, J=3.2 Hz, 0.5H), 5.20-5.30 (m, 1.5H), 5.10-5.16 (m, 0.5H), 4.80-4.90 (m, 1H), 4.56 (d, J=8.4 Hz, 1H), 4.35-4.43 (m, 2H), 4.01-4.07 (m, 1H), 3.71 (d, J=13.2 Hz, 1H), 3.41 (d, J=13.2 Hz, 1H). $^{31}$P NMR (162 MHz, $D_2O$): δ −1.67; $^{19}$F NMR (379 MHz, $D_2O$): δ two broad peaks −197.03, −200.48 ppm. ESI-MS: m/z: 660 [M−H]−.

Example 2: Compounds (*R) 2 and (*S) 3

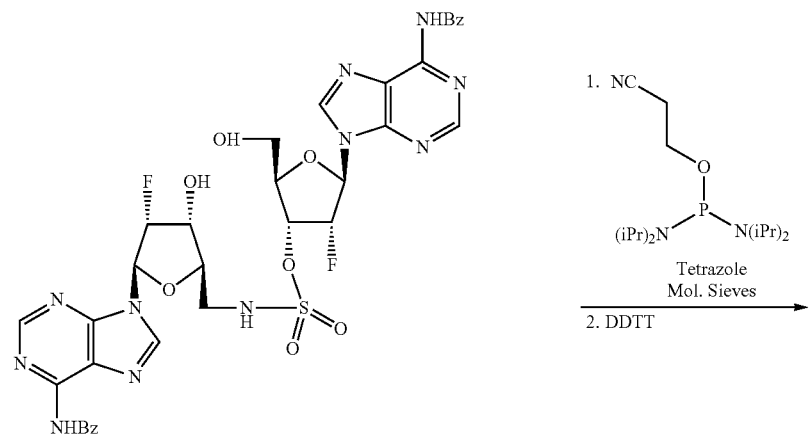

1h

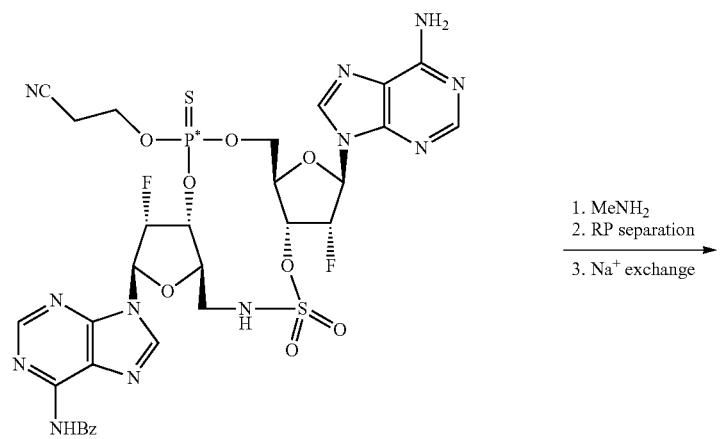

2a

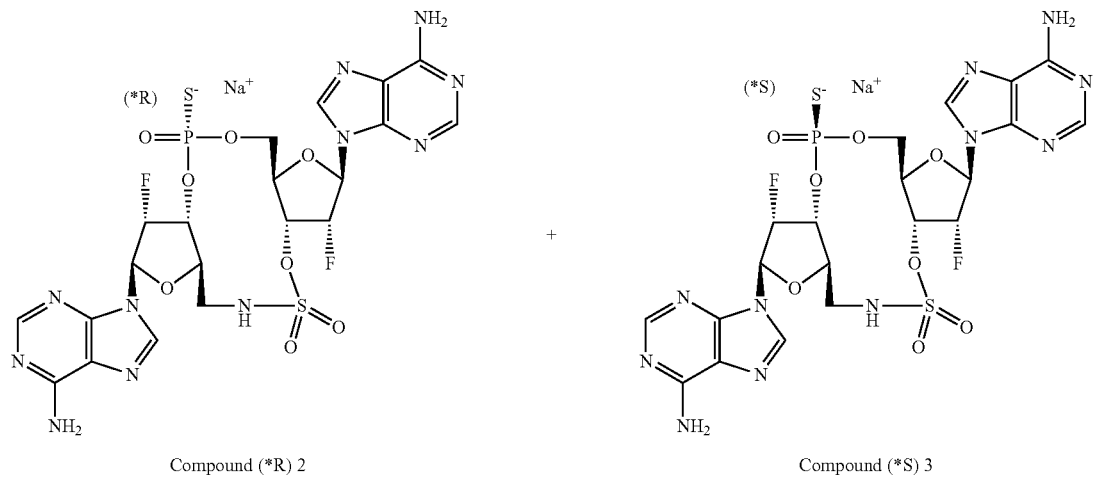

Compound (*R) 2                                   Compound (*S) 3

Step 1: Intermediate 1h (140 mg, 0.173 mmol) was co-evaporated with a dry toluene/acetonitrile solvent mixture (1:1, v/v, 3×30 mL) then dissolved in anhydrous THF (8 mL), and sonicated for 5 min until complete solubility of intermediate 1h. To the mixture was then added 4 Å molecular sieves powder (1 g) and 0.45 M tetrazole in acetonitrile (3.0 mL, 1.38 mmol). The resulting heterogeneous mixture was bubbled with argon for 4 min. After stirring the mixture at rt for 10 min, 2-cyanoethyl-N,N,N',N'-tetra(isopropyl) phosphorodiamidite (84 mg in 3.08 mL of $CH_3CN$, 0.277 mmol) was added to this over 30 min at rt. After stirring for 90 min, the reaction mixture was filtered, and the solids were washed with THF (15 mL). The combined filtrate was concentrated under reduced pressure. A solution of DDTT (177 mg, 0.865 mmol) in pyridine (5 mL) was added to the obtained residue. After stirring at room temperature for 30 min, the reaction mixture was diluted with EtOAc (30 mL) and washed with saturated aqueous $NaHCO_3$ (1×20 mL) and brine (1×20 mL). The aqueous phase was extracted with EtOAc (1×40 mL). The combined organic layers were concentrated to dryness and the obtained residue was purified by flash column chromatography over silica gel (gradient elution: 0-10% MeOH in DCM) to give intermediate 2a (220 mg) as a mixture of P-isomers. ESI-MS: m/z 939 $[M+H]^+$.

Step 2: Intermediate 2a (220 mg) was subjected to concentrated solution of methylamine in ethanol (10 mL) at rt. After stirring for 2.5 h, the reaction mixture was concentrated under reduced pressure. The resulting crude solid was washed with DCM (15 mL) and the precipitate was collected by filtration and purified by preparative reversed phase HPLC (stationary phase: Synergi 4 μm, Hydro RP, 250 mm×30 mm, mobile phase: Buffer A: 50 mM triethylammonium acetate in $H_2O$; Buffer B: 50 mM triethylammonium acetate in $CH_3CN$, gradient: 0-40% of B over 30 min, flow rate 24 mL/min) to afford Compound (*R) 2 (11.2 mg) as the second eluting isomer and Compound (*S) 3 (12.8 mg) as the first eluting isomer.

Dowex 50W×8, 200-400 (5 mL, H form) was added to a beaker and washed with deionized water (30 mL). Then to the resin was added 15% $H_2SO_4$ in deionized water, the mixture was gently stirred for 5 min, and decanted (30 mL). The resin was transferred to a column with 15% $H_2SO_4$ in deionized water and washed with 15% $H_2SO_4$ (at least 4 Column Volume [CV]), and then with deionized water until it was pH neutral. The resin was transferred back into the beaker, 15% NaOH in deionized water solution was added, and mixture was gently stirred for 5 min, and decanted (1×). The resin was transferred to the column and washed with 15% NaOH in $H_2O$ (at least 4 CV), and then with deionized water until it was pH neutral. Triethylammonium analogues 2 (11.2 mg) and 3 (12.8 mg) were dissolved in a minimum amount of deionized water, added to the top of the column, and eluted with deionized water. Appropriate fractions were pooled together and lyophilized to give Compound (*R) 2, sodium salt (10.9 mg) as a white fluffy solid. $^1$H NMR (400 MHz, $D_2O$): δ ppm 8.22 (s, 1H), 7.97 (s, 1H), 7.68 (s, 1H), 7.27 (s, 1H), 6.20-6.33 (m, 2H), 5.68 (d, J=4.4 Hz, 0.5H), 5.55 (d, J=4.4 Hz, 0.5H), 5.51 (d, J=4.4 Hz, 0.5H), 5.38 (d, J=4.4 Hz, 0.5H), 5.20-5.32 (m, 1H), 4.90-4.99 (m, 1H), 4.50 (d, J=8.8 Hz, 1H), 4.38 (d, J=9.6 Hz, 1H), 4.31 (d, J=12 Hz, 1H), 4.01 (dd, J=4.4 and 12 Hz, 1H), 3.66 (d, J=12 Hz, 1H), 3.33 (d, J=12 Hz, 1H); $^{31}$P NMR (162 MHz, $D_2O$): δ ppm 54.368; $^{19}$F NMR (379 MHz, $D_2O$): δ ppm two broad peaks −198.08, −200.09; ESI-MS: m/z: 676 $[M−H]^−$.

Using a similar protocol, Compound (*S) 3 was converted into its sodium salt (12.1 mg). $^1$H NMR (400 MHz, $D_2O$): δ ppm 7.90 (m. 3H), 6.92 (br. s, 1H), 6.10-6.15 (m, 2H), 5.69 (d, J=3.6 Hz, 0.5H), 5.57 (d, J=3.6 Hz, 0.5H), 5.20-5.28 (m, 1.5H), 5.14 (br.s, 0.5H), 4.90-4.97 (m, 1H), 4.52-4.60 (m, 1H), 4.47 (d, J=12 Hz, 1H), 4.39 (d, J=9.6 Hz, 1H), 3.98 (dd, J=6.4 and 12 Hz, 1H), 3.69 (d, J=12 Hz, 1H), 3.35 (d, J=12 Hz, 1H); $^{31}$P NMR (162 MHz, $D_2O$): δ ppm 55.136; $^{19}$F NMR (379 MHz, $D_2O$): δ two broad peaks −196.439, −200.613 ppm; ESI-MS m/z: 676 $[M−H]^−$.

Compounds (*S) 15, (*R) 15, (*R) 16, (*S) 16, (*S) 18, (*R) 18, (*S) 20, (*R) 20, (*R) 22, (*S) 22, (*R) 31, (*S) 31, (*S) 34 and (*R) 34 were prepared in a similar way starting from the appropriate intermediates selected from intermediates S1-S7 and A1-A27 and the analytical data is shown in Table 2.

15-S
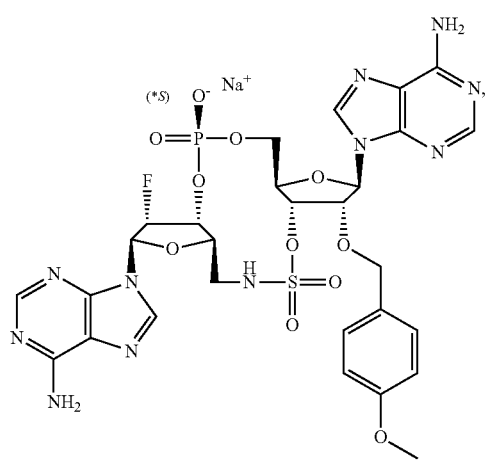
16-S
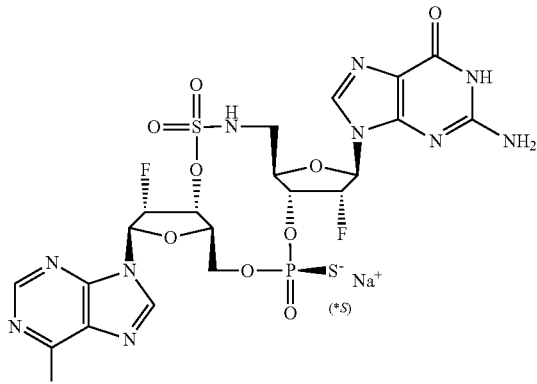
15-R
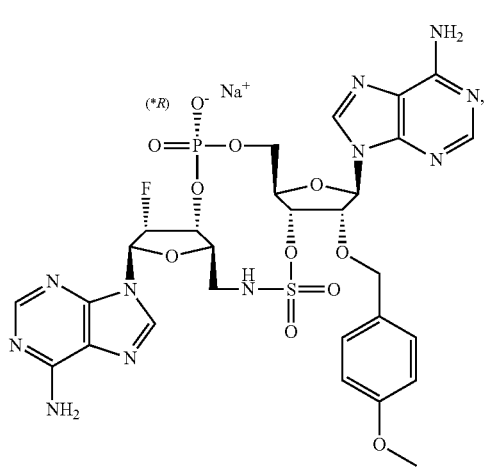
18-S
16-R
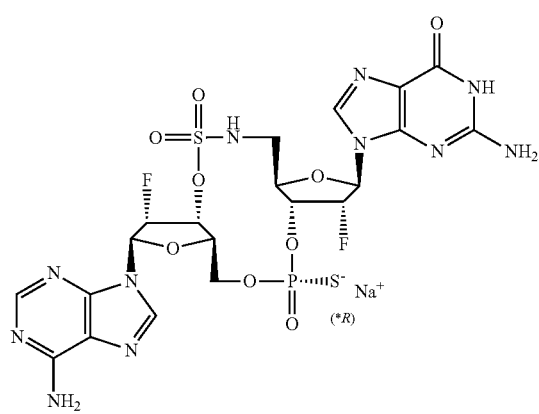
18-R
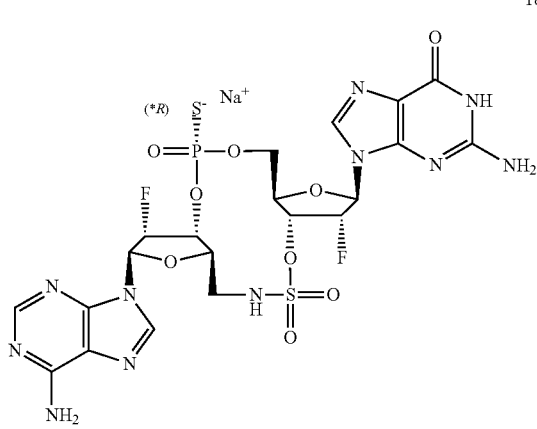

20-S
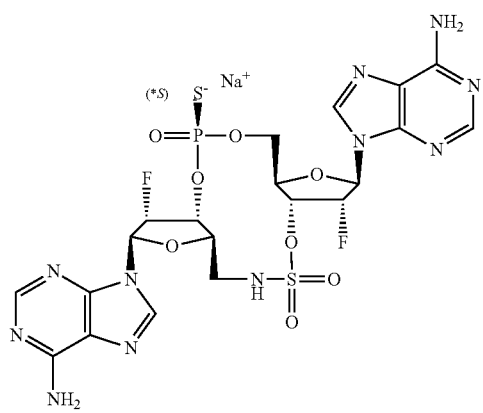
22-S
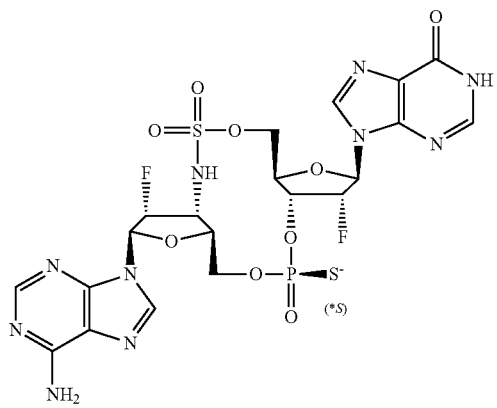
20-R
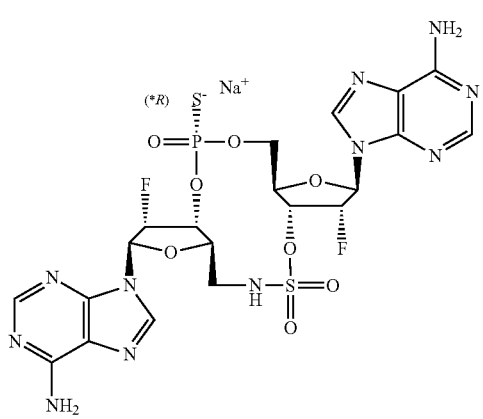
31-R
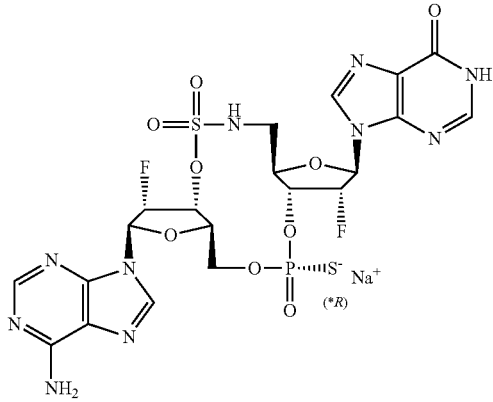
22-R
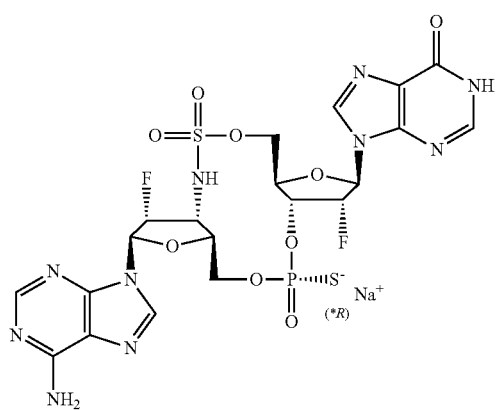
31-S
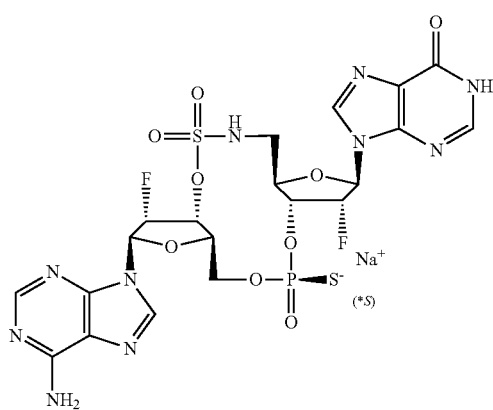

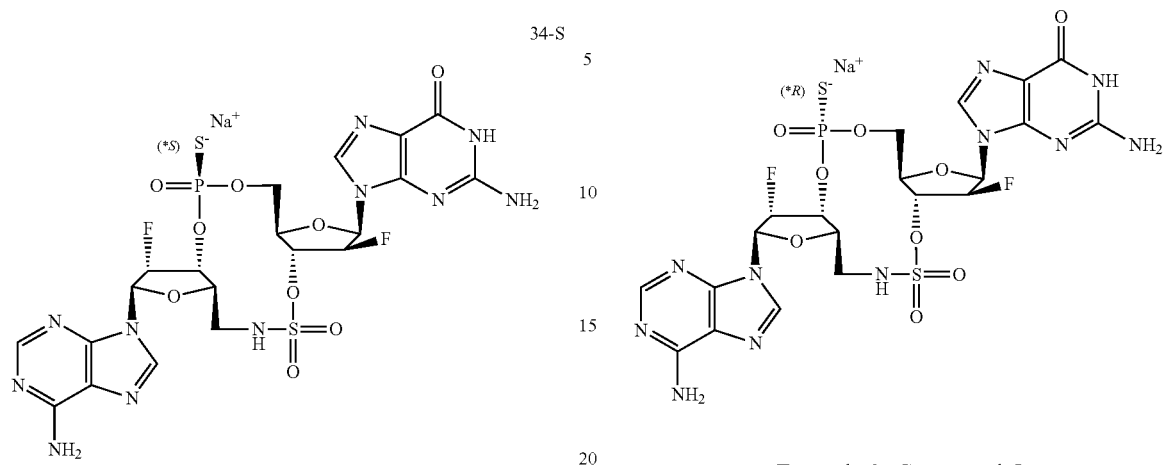
Example 3: Compound 5
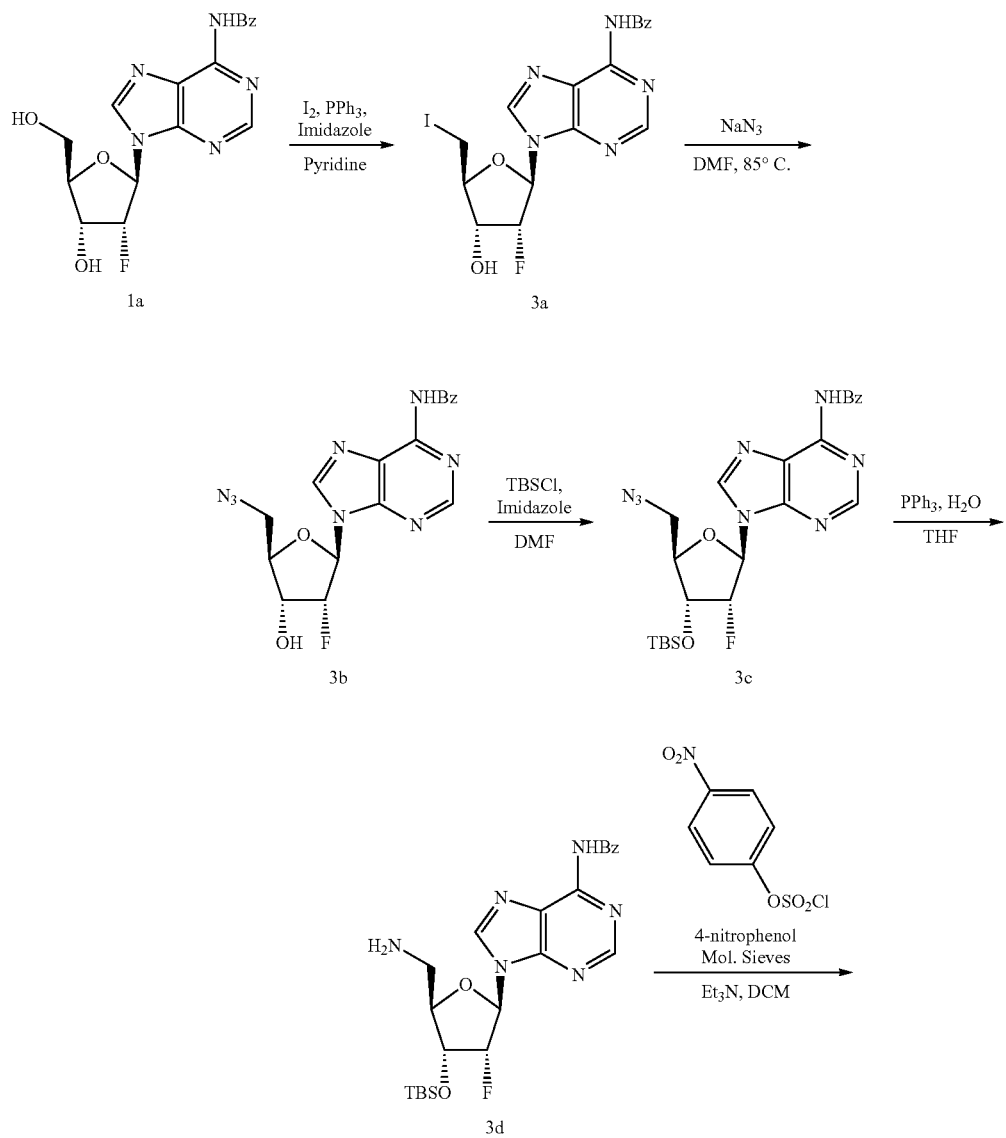

-continued
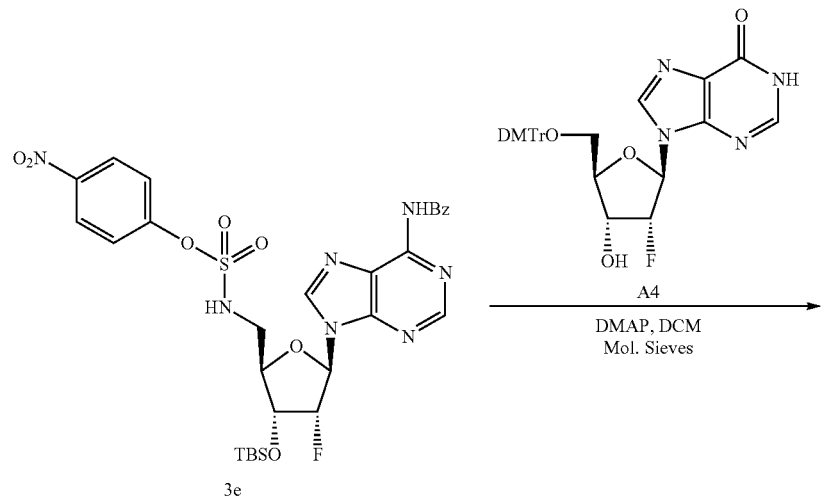
3e
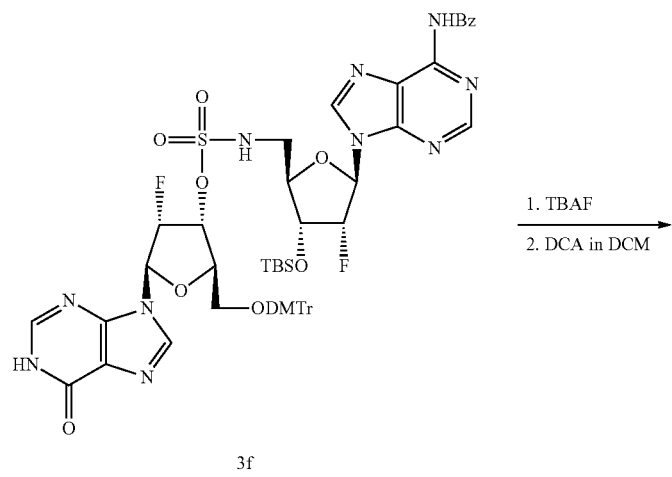
3f
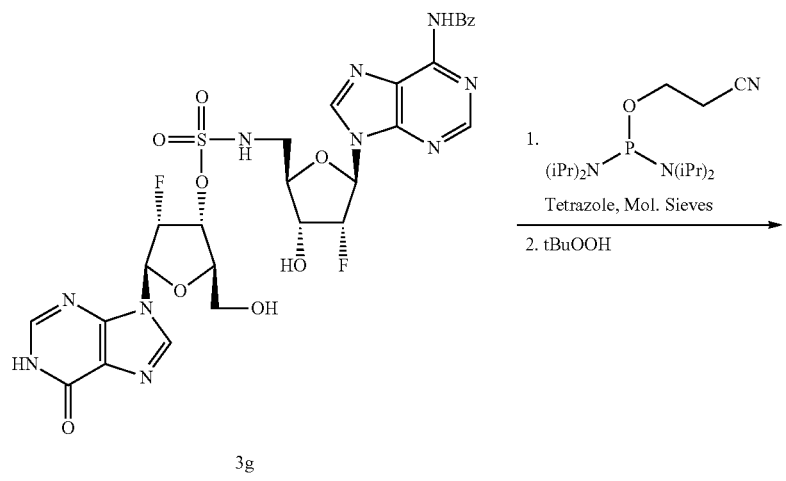
3g

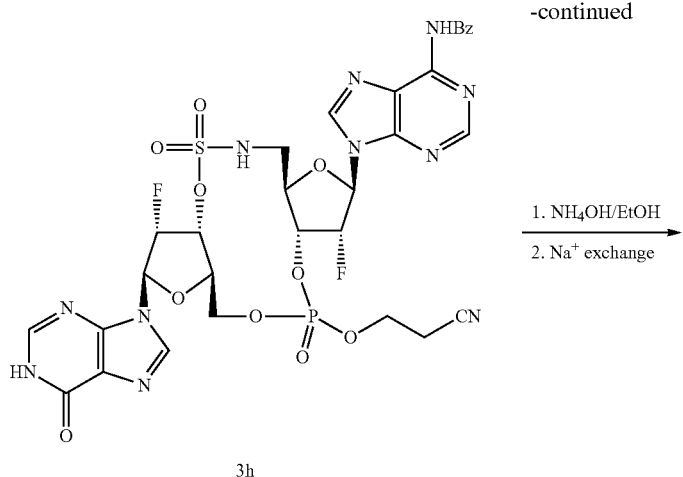

3h

1. NH₄OH/EtOH
2. Na⁺ exchange

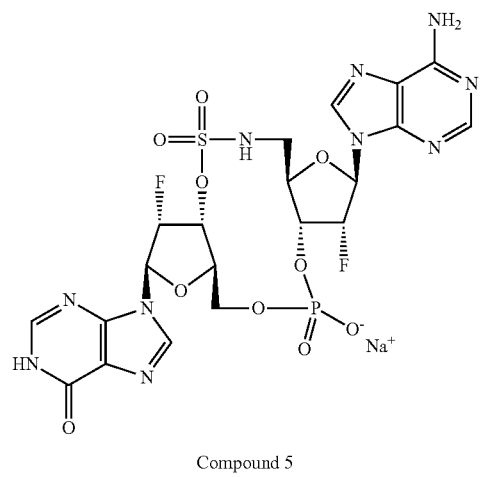

Compound 5

Step 1: Imidazole (18.2 g, 267.9 mmol), triphenylphosphine (52.7 g, 200.9 mmol) and iodine (51.0 g, 201.6 mmol) were added to a solution of N₆-benzoyl-2'-deoxy-2'-fluoroadenosine (1a, 50 g, 113.9 mmol) in anhydrous pyridine. The reaction mixture was stirred at 0~-5C for 12 h under N₂ after which it was concentrated to dryness. The obtained residue was dissolved in DCM (500 mL) followed by the addition of a saturated aqueous sodium bicarbonate (500 mL). The resulting suspension was stirred for 30 min, after which the precipitate was collected by filtration. The filter cake was recrystallized from MeCN/H₂O (8/1, 400 mL) to give intermediate 3a (42 g, yield: 65%). ¹H NMR (500 MHz, DMSO-d₆) δ ppm 11.26 (br s, 1H), 8.77 (s, 1H), 8.65 (s, 1H), 8.06 (d, J=7.5 Hz, 2H), 7.64 (t, J=7.5 Hz, 1H), 7.55 (t, J=7.5 Hz, 2H), 6.42 (dd, J=19.5, 1.5 Hz, 1H), 6.01 (br s, 1H), 5.74 (dd, J=52.5, 2.5 Hz), 4.57 (dt, J=20, 6.5 Hz, 1H), 3.96 (dd, J=10.5, 6 Hz, 1H), 3.67 (dd, J=11.3, 3.8 Hz, 1H), 3.50 (dd, J=11, 6.5 Hz, 1H); ESI-MS: m/z 484.4 [M+H]⁺.

Step 2: Sodium azide (8.07 g, 124.2 mmol) was added to a solution of intermediate 3a (20 g, 41.4 mmol) in anhydrous DMF. The reaction mixture was stirred at 85° C. for 2 h under N₂. The reaction solution was cooled down to room temperature, poured into water (2 L) and stirred for 30 min. The precipitate was collected by filtration and dried to give intermediate 3b (15 g, yield: 90%). ¹H NMR (500 MHz, DMSO-d₆) δ ppm 11.22 (s, 1H), 8.79 (s, 1H), 8.66 (s, 1H), 8.06 (d, J=7.5 Hz, 2H), 7.65 (t, J=7.3 Hz, 1H), 7.56 (t, J=7.5 Hz, 2H), 6.43 (d, J=19.5 Hz, 1H), 5.93 (d, J=6 Hz, 1H), 5.68 (dd, J=52.8, 2.8 Hz), 4.80-4.75 (m, 1H), 4.14 (br s, 1H), 3.76 (dd, J=13.5, 2.5 Hz, 1H), 3.59 (dd, J=13.8, 5.8 Hz, 1H); ESI-MS: m/z 399.0 [M+H]⁺.

Step 3: TBSCl (6.81 g, 45.2 mmol) and imidazole (3.84 g, 56.5 mmol) were added to a solution of intermediate 3b (15 g, 37.7 mmol) in anhydrous DMF. The reaction mixture was stirred at room temperature for 24 h under N₂ protection, after which it was concentrated under vacuum at 55° C. The resulting residue was dissolved in EtOAc and washed with water. The organic phase was dried with Na₂SO₄, filtered and evaporated to dryness at 45° C. under reduced pressure. The crude product was purified by silica column chromatography (gradient elution: 20 to 40% EtOAc in heptane) to give intermediate 3c (16 g, yield: 83%). ¹H NMR (400 MHz, CHLOROFORM-d) δ ppm 0.18 (s, 6H), 0.95 (s, 9H), 3.52 (dd, J=13.6, 4.3 Hz, 1H), 3.78 (dd, J=13.6, 3.0 Hz, 1H), 4.25 (m, J=7.2, 3.5, 3.5 Hz, 1H), 4.85 (ddd, J=18.8, 7.5, 4.5 Hz, 1H), 5.53 (ddd, J=53.0, 4.5, 1.8 Hz, 1H), 6.24 (dd, J=18.2, 1.9 Hz, 1H), 7.50-7.58 (m, 2H), 7.59-7.67 (m, 1H), 7.99-8.08 (m, 2H), 8.23 (s, 1H), 8.80 (s, 1H), 9.04 (br s, 1H); ESI-MS: m/z 513.1 [M+H]⁺.

Step 4: Triphenylphosphine (12.28 g, 46.8 mmol) was added to a solution of intermediate 3c (16 g, 31.2 mmol) in THF. The reaction mixture was stirred at room temperature for 10 min after which water (2.25 g, 124.9 mmol) was added dropwise over 30 min. Stirring was continued until complete conversion. pTSA (5.4 g) was added and stirring was continued for an extra 10 min. The reaction solution was evaporated to dryness under reduced pressure, the resulting residue was dissolved in DCM and washed with water. The organic phase was dried with Na₂SO₄, filtered and concentrated under reduced pressure. The crude material was purified by silica column chromatography (gradient elution: 1 to 5% MeOH in DCM) to give intermediate 3d as its pTSA salt (12 g, yield: 58%). ¹H NMR (400 MHz, DMSO-d₆) δ ppm 0.18 (s, 3H), 0.17 (s, 3H), 0.95 (s, 9H), 2.29 (s, 3H), 3.26-3.28 (br m, 2H), 4.24 (br m, 1H), 4.86-4.93 (m, 1H), 5.82 (dt, J=52, 3.6 Hz, 1H), 6.51 (dd, J=18.2, 2.6 Hz, 1H), 7.13 (d, J=7.6 Hz, 2H), 7.49 (d, J=8.4 Hz, 2H), 7.56 (t, J=7.6 Hz, 1H), 7.67 (t, J=7.4 Hz, 1H), 8.00 (br s, 2H), 8.06 (d, J=7.6 Hz, 1H), 8.82 (d, J=7.6 Hz, 1H); ESI-MS: m/z 487.2 [M+H]⁺.

Step 5: Intermediate 3d (16 g of pTSA salt, 24.3 mmol), 4-nitrophenol (33.8 g, 242.9 mmol) and Et₃N (29.5 g, 6.98 mmol) were dissolved in DCM (320 ml). The reaction mixture was cooled to −78° C., followed by the dropwise addition of 4-nitrophenyl chlorosulfate (12.7 g, 53.5 mmol) in DCM (80 mL). The reaction solution was allowed to warm to 0° C., diluted with DCM and washed with 1.0 M aq. NaH₂PO₄. The organic phase was dried with Na₂SO₄, filtered and concentrated under reduced pressure. The crude material was purified by silica column chromatography (gradient elution: 1 to 5% DCM in MTBE) to give pure intermediate 3e (9.5 g, yield: 87%). ¹H NMR (500 MHz, CHLOROFORM-d) S ppm: 9.30 (br s, 1H), 8.89 (br s, 1H), 8.52 (s, 1H), 8.27 (d, J=7.5 Hz, 2H), 8.15-8.11 (m, 1H), 8.02 (d, J=7.5 Hz, 2H), 7.64 (t, J=7.5 Hz, 1H), 7.54 (t, J=8 Hz, 2H), 7.41-7.38 (m, 2H), 6.14 (q, J=5 and 13 Hz, 1H), 5.55-5.43 (m, 1H), 4.72-4.69 (m, 1H), 4.41 (s, 1H), 3.69 (t, J=11 Hz, 2H), 0.93 (s, 9H), 0.16 (s, 6H); ESI-MS: m/z 688.6 [M+H]⁺.

Step 6: Intermediate 3e (0.70 g, 1.02 mmol), 5'-O-DMT-2'-F-deoxyinosine (1f, 0.87 g, 1.53 mmol) and DMAP (0.62 g, 5.1 mmol) were separately dissolved in dry DCM (3×4.0 mL, dried on an appropriate drying agent before use), to each solution a large amount of activated molecular sieves were added, followed by shaking for at least 1.5 h under inert atmosphere. To the flask containing the DMAP solution was added the 5'-O-DMT-2'-F-deoxyinosine solution followed by the addition of the intermediate 3e solution (in both cases the transfer was done by pouring whole mixture, including molecular sieves). The resulting reaction mixture was stirred overnight. The molecular sieves were removed by filtration and thoroughly washed with dichloromethane. The filtrate was washed with a saturated aqueous NaHCO$_3$, and the aqueous phase was then extracted with DCM (2×50 mL). The combined organic phases were dried over Na$_2$SO$_4$, filtered, and concentrated under reduced pressure. The residue was purified by silica column chromatography (gradient elution: 1 to 10% MeOH in DCM) to give pure intermediate 3f (540 mg, yield: 47%). $^1$H NMR (300 MHz, chloroform-d) δ ppm 12.09 (br s, 1H), 9.42 (br s, 1H), 9.23 (br d, J=7.8 Hz, 1H), 8.78 (s, 1H), 8.15 (s, 1H), 8.06 (d, J=7.2 Hz, 2H), 7.98 (s, 1H), 7.89 (s, 1H), 7.53-7.14 (m, 13H), 6.82 (d, J=8.7 Hz, 4H), 6.15-6.04 (m, 2H), 5.63-5.36 (m, 3H), 4.70-4.63 (br m, 1H), 4.41-4.36 (m, 2H), 3.73 (s, 6H), 3.64-3.45 (m, 4H), 0.94 (s, 9H), 0.17 (s, 3H), 0.15 (s, 3H); ESI-MS: m/z 1121.9 [M+H]+; 1143.9 [M+Na]+.

Step 7: TBAF (1.07 mL, 1 M in THF, 1.07 mmol) was added to a solution of intermediate 3f (598 mg, 0.53 mmol) in THF (9.4 mL). The reaction mixture was stirred at room temperature overnight, after which it was diluted with EtOAc and washed with saturated aqueous NH$_4$Cl. The organic phase was dried over Na$_2$SO$_4$, filtered and evaporated under reduced pressure. The resulting residue was dissolved in DCM (24 mL) to which water (48 μL, 2.6 mmol) and dichloroacetic acid (170 μL, 2.4 mmol) were added. The reaction mixture was stirred at room temperature for 1 h after which pyridine (220 μL, 2.7 mmol) and some methanol were added. The resulting mixture was partially concentrated under reduced pressure and transferred to a silica column for purification (gradient elution: 7 to 15% methanol in dichloromethane) to give intermediate 3g (360 mg, yield: 96%). $^1$H NMR (300 MHz, DMSO-d$_6$) δ ppm 12.48 (br s, 1H), 11.26 (s, 1H), 8.76 (s, 1H), 8.67 (br s, 1H), 8.64 (s, 1H), 8.34 (s, 1H), 8.10 (d, J=3.6 Hz, 1H), 8.05 (d, J=7.2 Hz, 2H), 7.68-7.63 (m, 1H), 7.58-7.53 (m, 2H), 6.43-6.36 (dd, J=20.1, 2.1 Hz, 1H), 6.34-6.28 (dd, J=16.5, 3.0 Hz, 1H), 5.94 (d, J=6 Hz, 1H), 5.79-5.70 (m, 1H), 5.62-5.52 (m, 1H), 5.36 (t, J=5.3 Hz, 1H), 5.26-5.18 (m, 1H), 4.69-4.56 (br m, 1H), 4.29-4.27 (m, 1H), 4.13-4.05 (m, 1H), 3.78-3.73 (m, 1H), 3.62-3.34 (m, 4H); ESI-MS: m/z 705.5 [M+H]$^+$; 727.5 [M+Na]$^+$; 806.7 [M+TEA]$^+$.

Step 8: A solution of intermediate 3g (180 mg, 0.255 mmol) and 1H-tetrazole (0.45 M in MeCN (pre-dried on 4A molecular sieves (beads)), 1.13 mL, 0.51 mmol) in 1:1:1 MeCN/THF/DCM (6.9 mL) was treated with 4A molecular sieves (beads) for at least 2 h before the addition of 2-cyanoethyl-N,N,N',N'-tetra(isopropyl)phosphorodiamidite (77 mg, 0.255 mmol). The resulting reaction mixture was stirred at room temperature overnight. Additional 2-cyanoethyl-N, N,N'N-tetra(isopropyl)phosphorodiamidite (115.3 mg, 0.383 mmol) was added to the reaction mixture in three equal portions until reaction completion. Next, tBuOOH (120 μL, 5.5 M in decane, 0.64 mmol) was added and the reaction mixture was stirred at room temperature for 30 min. The reaction mixture was diluted with DCM and washed with saturated aqueous NaHCO$_3$. The aqueous phase was re-extracted with EtOAc and DCM. The combined organic phases were dried over Na$_2$SO$_4$, filtered and concentrated under reduced pressure. The residue was purified by silica column chromatography (gradient elution: 2 to 15% MeOH in DCM) to afford intermediate 3h (22.7 mg, yield: 11%) which was used as such in the subsequent deprotection step. ESI-MS: m/z 818.6 [M−H]$^-$.

Step 9: Intermediate 3h (22.7 mg, 27 μmol) was stirred in a mixture of 28% aqueous ammonium hydroxide and ethanol (3/1, 2.5 mL) at room temperature overnight. The resulting crude product obtained after concentration under vacuum was purified by preparative reversed phase HPLC (Stationary phase: XBridge C18 OBD, 5 μm, 250×30 mm; Mobile phase: aqueous 0.25% ammonia bicarbonate (A)-MeOH (B)) to give compound 5 as the ammonium salt. Compound 5 was converted into the sodium salt by elution of an aqueous solution over a column packed with a cationic sodium ion-exchange resin affording 7.5 mg (yield: 35%) of Compound 5 as a white fluffy solid after lyophilization. $^1$H NMR (400 MHz, DMSO-d$_6$, 100° C.) δ ppm 8.72 (br s, 1H), 8.24 (s, 1 H), 8.07 (s, 1H), 7.88 (s, 1H), 6.87 (br s, 2H), 6.28 (d, J=18.7 Hz, 1H), 6.29 (d, J=17.9 Hz, 1H), 5.38-5.65 (m, 1H), 5.31 (br s, 1H), 5.25 (dd, J=52.1, 3.7 Hz, 1H), 5.08 (dtd, J=24.5, 8.5, 8.5, 4.1 Hz, 1H), 4.26 (br d, J=7.7 Hz, 1H), 4.19 (br d, J=9.0 Hz, 1H), 4.12 (dt, J=12.2, 2.0 Hz, 1H), 3.81 (ddd, J=12.4, 4.3, 1.2 Hz, 1H), 3.53 (br dd, J=13.6, 3.5 Hz, 1H), 3.24 (br d, J=13.4 Hz, 1H); $^{31}$P NMR (162 MHz, DMSO-d$_6$, 100° C.) δ ppm −2.28 (s, 1P); ESI-MS: m/z 663.3 [M+H]$^+$.

Example 4: Compound (*R) 17 and Compound (*S) 17

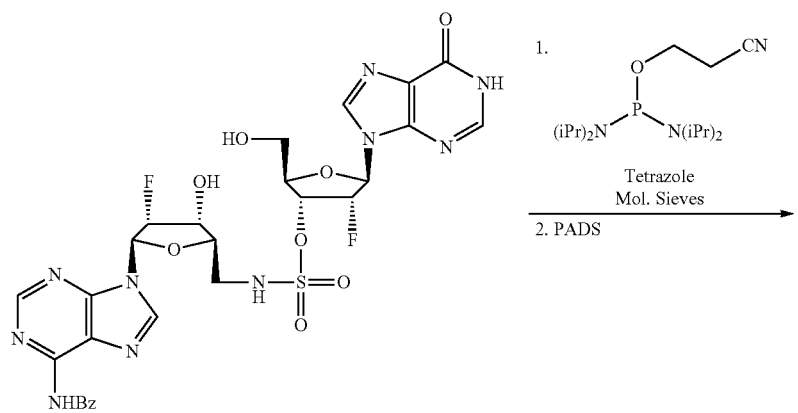

3g

-continued
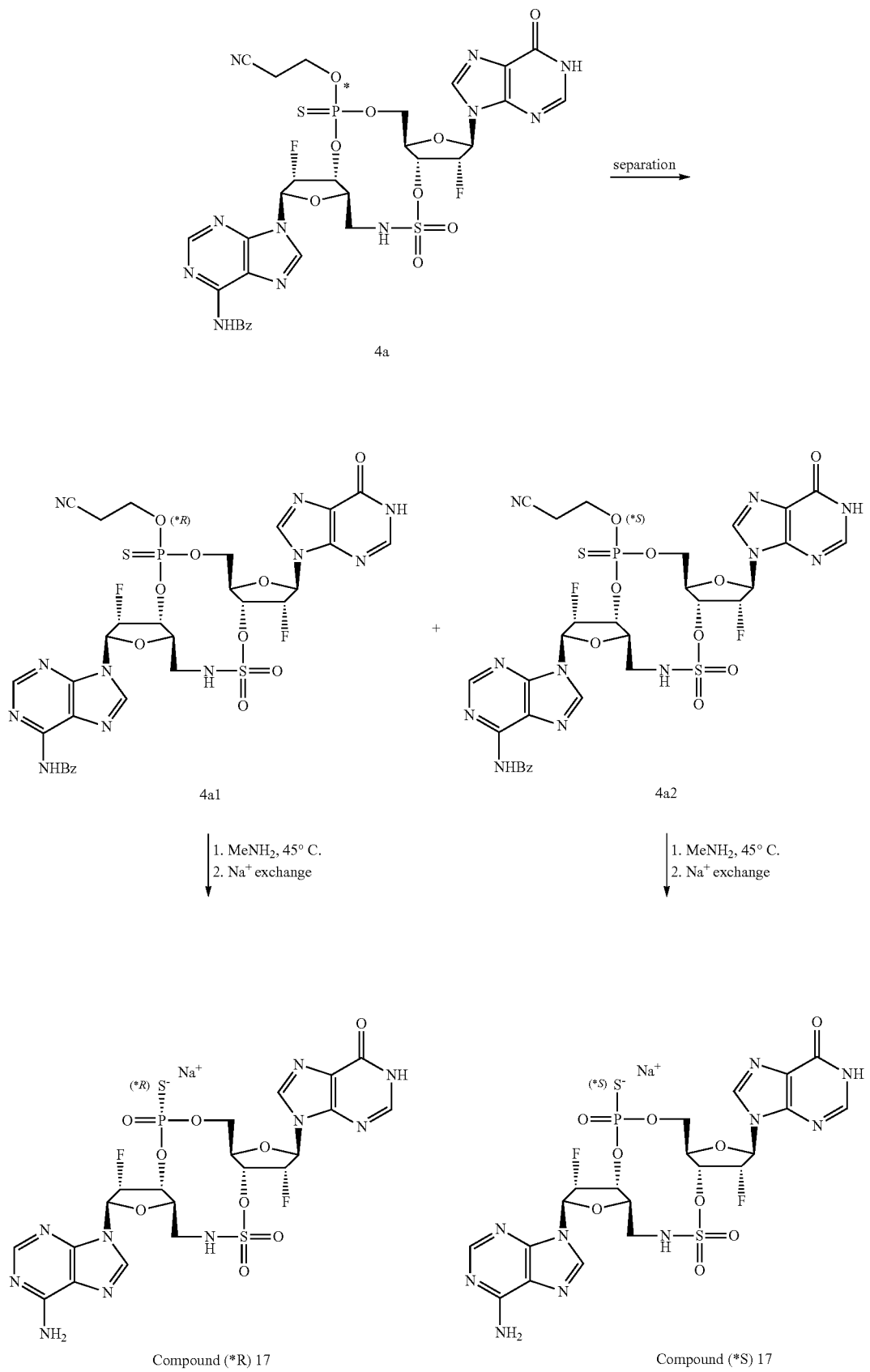

Step 1: (Note: reaction solvents were dried on an appropriate drying agent before use.) A solution of intermediate 3g (0.5 g, 0.71 mmol) and 1H-tetrazole (8.28 mL of a 3-4% in MeCN, dried on molecular sieves before use) in dry THF/MeCN (1:1, 100 mL) was treated with activated 3A molecular sieves for 1 h under $N_2$. 2-Cyanoethyl-N,N,N',N'-tetra(isopropyl)phosphorodiamidite (230 μL, 0.71 mmol) was added in one portion, the reaction mixture was shaken for 5 h. An additional amount of 2-cyanoethyl-N,N,N',N'-tetra(isopropyl)phosphorodiamidite (110 μL, 0.35 mmol) was added and shaking was continued for 2 h. Next, PADS (0.43 g, 1.42 mmol) was added, the reaction mixture was shaken for 18 h. The molecular sieves were removed by filtration and rinsed with dichloromethane. The filtrate was washed with saturated aqueous $NaHCO_3$ and brine, dried with $MgSO_4$, filtered and concentrated under reduced pressure to give intermediate 4a as the P-epimeric mixture. The isomers were separated by column chromatography over silica (gradient elution: 0 to 10% MeOH in DCM) to give intermediate 4a1 (77 g, yield: 11%, purity: 85%) as the first eluting isomer and intermediate 4a2 (62 mg, yield: 3%, purity: 62%) as the second eluting isomer. Intermediate 4a1: ESI-MS: m/z 836.4 [M+H]$^+$; intermediate 4a2: ESI-MS: m/z 836.4 [M+H]$^+$.

Step 2: The above intermediate 4a1 was stirred in a concentrated solution of methylamine in ethanol (4 mL) at 45° C. for 1 h. The reaction mixture was evaporated to dryness under reduced pressure. The residue was triturated in acetonitrile (3 mL). The precipitate was filtered off and purified by preparative reversed phase HPLC (Stationary phase: XBridge C18 OBD, 10 μm, 150×50 mm; Mobile phase: aqueous 0.25% ammonia bicarbonate (A)-MeOH (B); gradient elution) to give Compound (*R) 17 as a white solid after lyophilization. Conversion into the sodium salt was done by elution of an aqueous solution over a column packed with a cationic sodium ion-exchange resin to give a white fluffy solid after lyophilization (26 mg, yield: 46%). $^1$H NMR (400 MHz, DMSO-d$_6$, 80° C.) δ ppm 3.15-3.34 (m, 1H) 3.51-3.62 (m, 1H) 3.71-3.82 (m, 1H) 4.16-4.40 (m, 3H) 5.14-5.76 (m, 4H) 6.30 (s, 1H) 6.35 (s, 1H) 7.05 (br s, 1H) 7.83 (br s, 1H) 8.07 (s, 1H) 8.22 (s, 1H); $^{31}$P NMR (162 MHz, DMSO-d$_6$, 80° C.) δ ppm 52.85 (s, 1P); ESI-MS: m/z 679.3 [M+H]$^+$.

Using a similar protocol, Compound (*S) 17, sodium salt was prepared from intermediate 4a2 (yield: 24% from intermediate 4a2). $^1$H NMR (400 MHz, Deuterium oxide) δ ppm 8.39 (s, 1H), 8.39 (br s, 1H), 7.89 (br s, 1H), 7.75 (br s, 1H), 6.48 (d, J=18.7 Hz, 1H), 6.41 (d, J=20.3 Hz, 1H), 5.68 (dd, J=51.7, 4.5 Hz, 1H), 5.74 (dd, J=50.9, 4.5 Hz, 1H), 5.48-5.60 (m, 1H), 5.08-5.21 (m, 1H), 4.54 (br d, J=9.4 Hz, 1H), 4.46 (br d, J=9.4 Hz, 1H), 4.34 (br d, J=11.8 Hz, 1H), 4.09 (dd, J=11.2, 5.1 Hz, 1H), 3.73 (dd, J=13.8, 2.4 Hz, 1H), 3.39 (br d, J=13.4 Hz, 1H); $^{31}$P NMR (162 MHz, D$_2$O) δ ppm 54.84 (s, 1P); ESI-MS: m/z 679.3 [M+H]$^+$.

Example 5: Compound 40

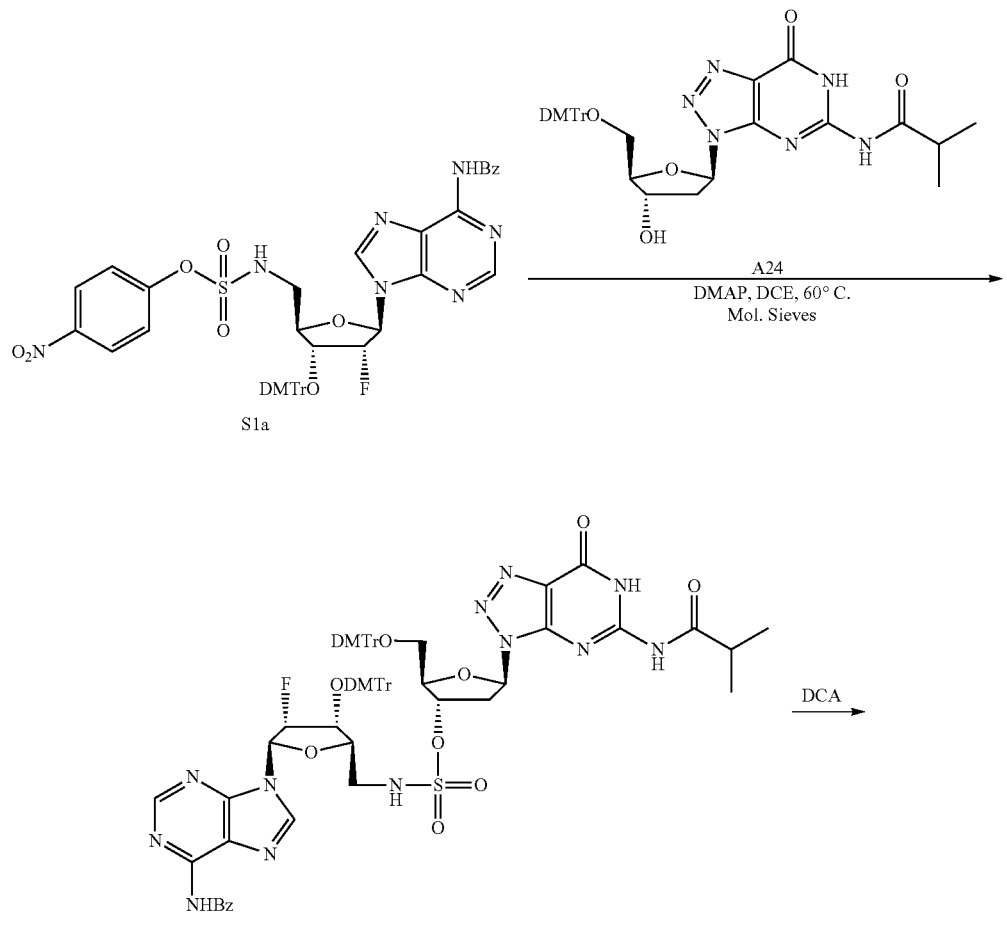

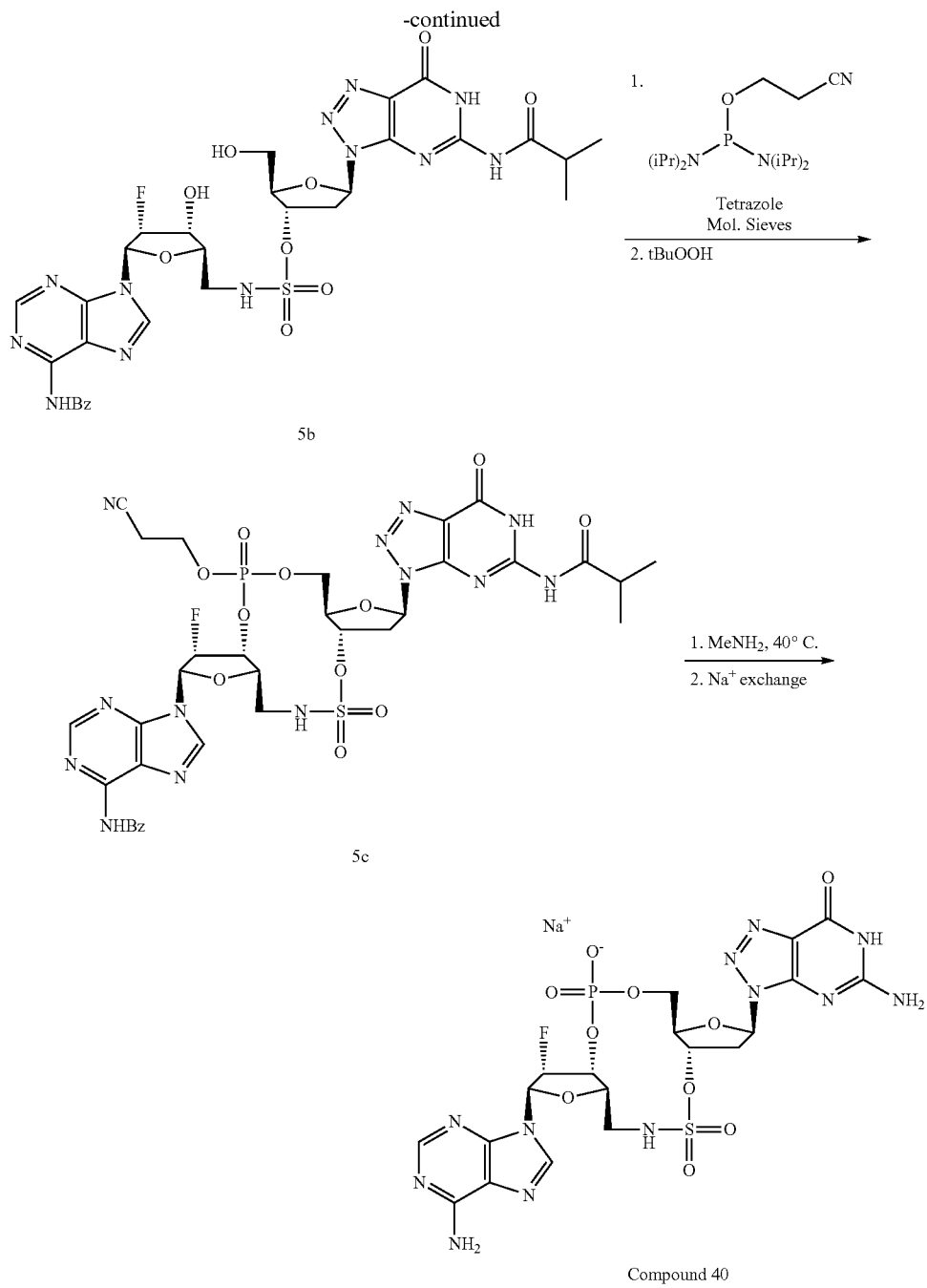

5b

5c

Compound 40

Step 1: (Note: reaction solvents were dried on an appropriate drying agent before use.) A solution of intermediate S1a (1.65 g, 1.88 mmol) and intermediate A24 (1.57 g, 2.45 mmol) in dry DCE (30 mL), and a solution of DMAP (1.15 g, 9.42 mmol) in dry DCE (10 mL), were dried on activated molecular sieves overnight. The two solutions were mixed and stirred at 60° C. under $N_2$ for 6 h. The resulting reaction mixture was cooled to room temperature and washed with water. The organic phase was concentrated to give crude intermediate 5a which was used directly in the next step.

Step 2: A solution of the above intermediate 5a in DCM (100 mL) was treated with water (169 mg, 9.40 mmol) and DCA (1.21 g, 9.40 mmol), and stirred at room temperature for 2 h. The resulting reaction mixture was washed with 5% aqueous $NaHCO_3$ and concentrated under reduced pressure. The residue was purified by reversed phase flash chromatography (gradient elution: 0 to 50% MeCN in water) to give intermediate 5b (0.6 g, yield: 41% from S1a). $^1$H NMR (600 MHz, DMSO-$d_6$) δ (ppm): 12.11 (br s, 2H), 11.26 (s, 1H), 8.75 (s, 1H), 8.65 (s, 1H), 8.53 (brs, 1H), 8.04 (d, J=7.2 Hz, 2H), 7.65 (t, J=7.2 Hz, 1H), 7.55 (t, J=7.8 Hz, 2H), 6.44-6.40 (m, 2H), 5.92 (brs, 1H), 5.63 (ddd, J=1.8, 3.5, 52.8 Hz, 1H), 5.27-5.25 (m, 1H), 4.92 (s, not resolved, 1H), 4.65-4.60 (m, 1H), 4.19-4.17 (m, 1H), 4.12-4.09 (m, 1H), 3.51-3.34 (m, 5H), 2.83-2.75 (m, 2H), 1.12 (d, J=7.2 Hz, 3H), 1.11 (d, J=7.2 Hz, 3H); ESI-MS: m/z 773.2 [M+H]$^+$.

Step 3: (Note: reaction solvents were dried on an appropriate drying agent before use.) A solution of intermediate 5b (200 mg, 0.259 mmol) and 1H-tetrazole (4.6 mL, 0.45 M in MeCN, 2.07 mmol, dried on molecular sieves before use) in dry THF (4 mL) was treated with activated molecular sieves for 30 min under $N_2$ after which a solution of 2-cyanoethyl-N,N,N',N'-tetra(isopropyl)phosphorodiamidite (140 mg, 0.466 mmol) in THF (1.6 mL) was added dropwise over 25 min. The resulting reaction mixture was stirred for 2 h. tBuOOH (414 µL, 5.0 M in decane, 2.07 mmol) was added and stirring was continued for 30 min. The reaction mixture was diluted with a DCM/MeOH solvent mixture (10/1) and filtered through a pad of diatomaceous earth. The filtrate was concentrated and the residue purified by column chromatography over silica (gradient elution: 0 to 5% MeOH in DCM) to give intermediate 5c as a white solid (142 mg, yield: 62%). ESI-MS: m/z 888.2 [M+H]+.

Step 4: Intermediate 5c (142 mg, 0.16 mmol) was stirred in a concentrated methylamine solution in ethanol (10 mL) at 40° C. for 2 h. The reaction mixture was evaporated to dryness under reduced pressure. The residue was dissolved in water and washed with DCM. The crude product obtained after lyophilization was purified by reversed phase HPLC (stationary phase: XBridge C18 OBD, 10 µm, 150×40 mm; mobile phase: 10 mM ammonia bicarbonate (A)-MeCN (B); gradient elution) to give pure Compound 40 as a white solid after lyophilization. Conversion into the sodium salt was done by elution of an aqueous solution over a column packed with a cationic sodium ion-exchange resin to give a white fluffy solid after lyophilization (82.5 mg, yield: 46%). $^1$H NMR (400 MHz, $D_2O$): δ ppm 8.25-8.06 (m, 2H), 6.55 (br dd, J=3.4, 7.4 Hz, 1H), 6.48-6.36 (m, 1H), 5.59 (br d, J=7.8 Hz, 1H), 5.53-5.22 (m, 2H), 4.50 (br d, J=9.3 Hz, 1H), 4.37 (br d, J=5.3 Hz, 1H), 4.25-4.04 (m, 2H), 3.85-3.72 (m, 1H), 3.49 (br d, J=12.8 Hz, 1H), 3.43-3.29 (m, 1H), 3.11-2.95 (m, 1H); $^{19}$F NMR (376 MHz, $D_2O$): δ ppm −198.05 (br s, 1F); $^{31}$P NMR (162 MHz, $D_2O$): δ ppm −1.64 (s, 1P); ESI-MS: m/z 661.0 [M+H]+.

Compounds 6, 29, 32, 35, 39, 41, 44 and 46 were prepared in a similar way starting from the appropriate intermediates selected from S1-S7 and A1-A27 and the analytical data is shown in Table 2.

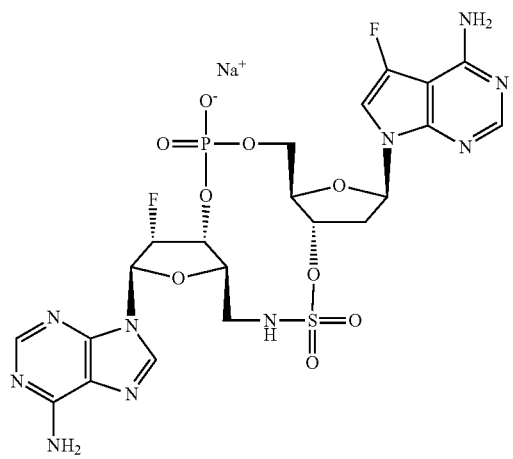

29

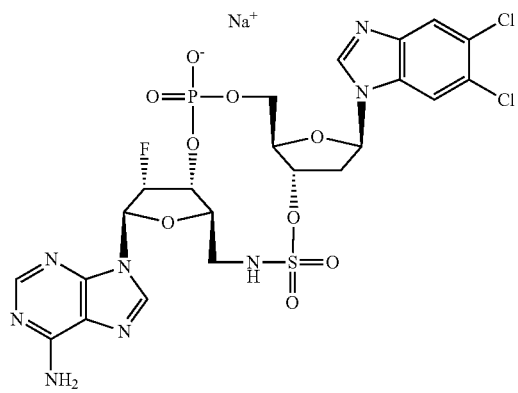

32

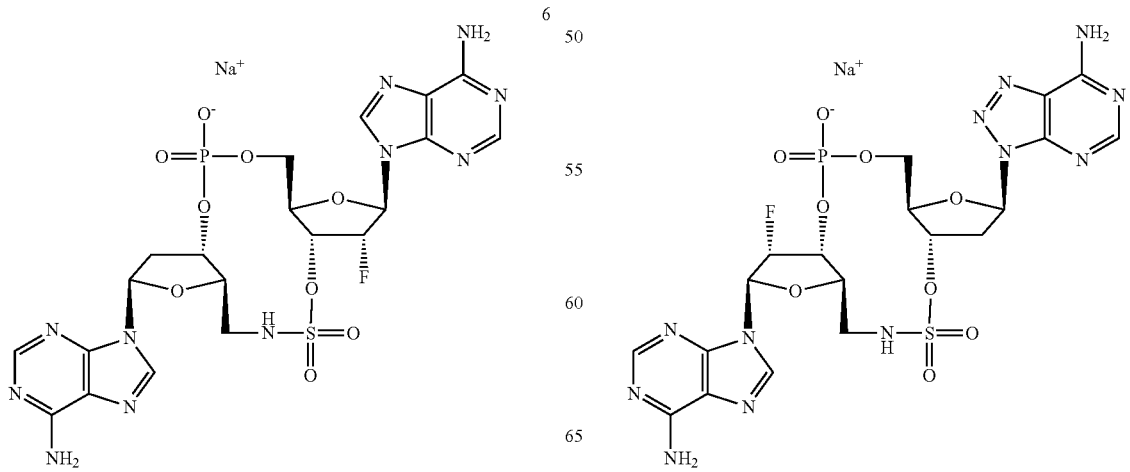

6

35

99
-continued
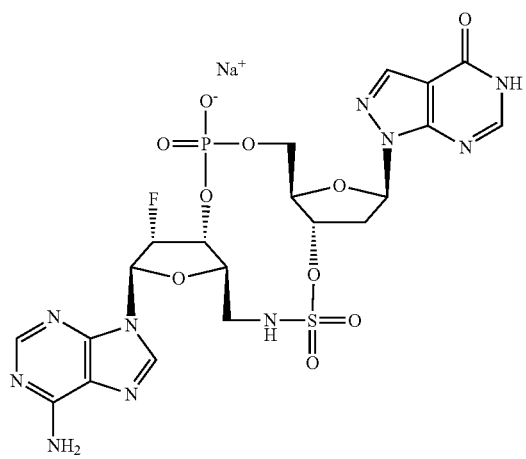
39
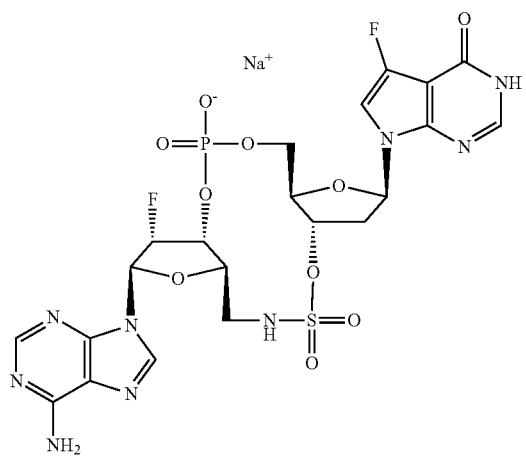
41
100
-continued
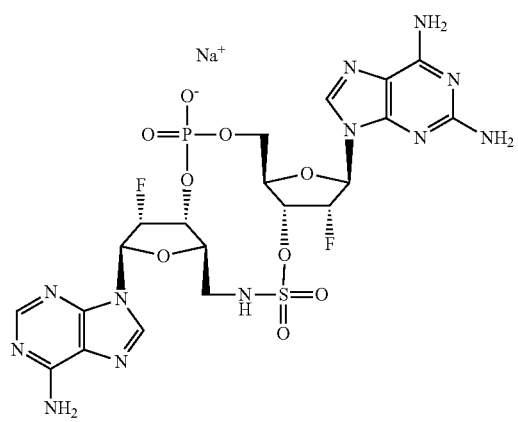
44
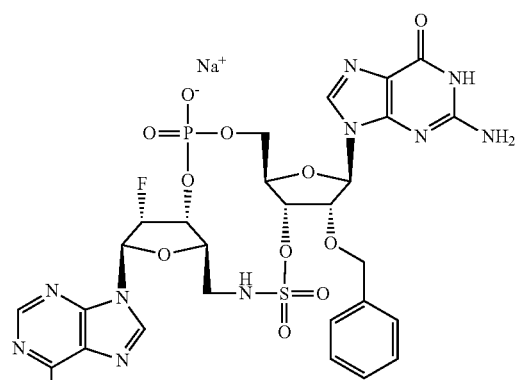
46
Example 6: Compound 9
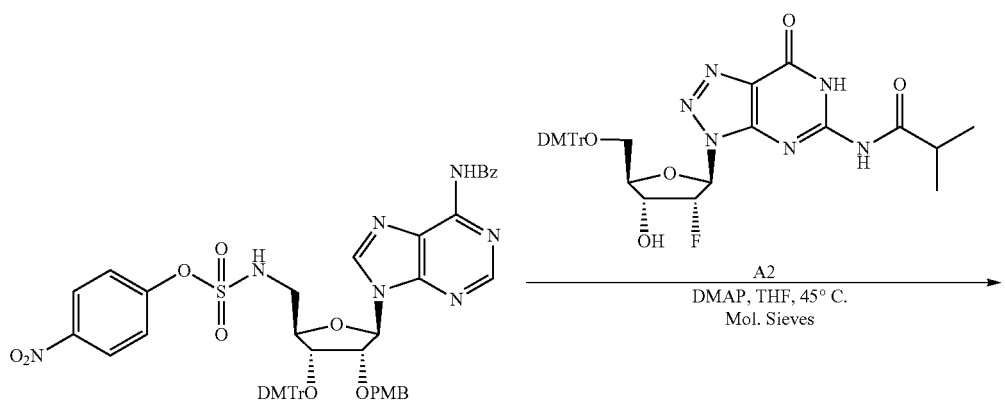

-continued
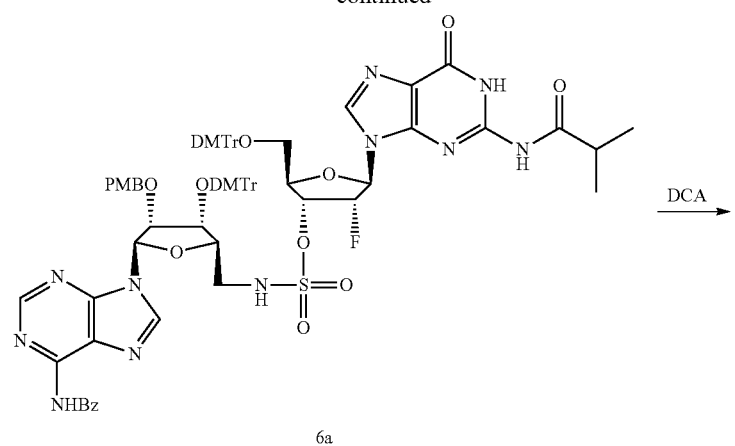
6a
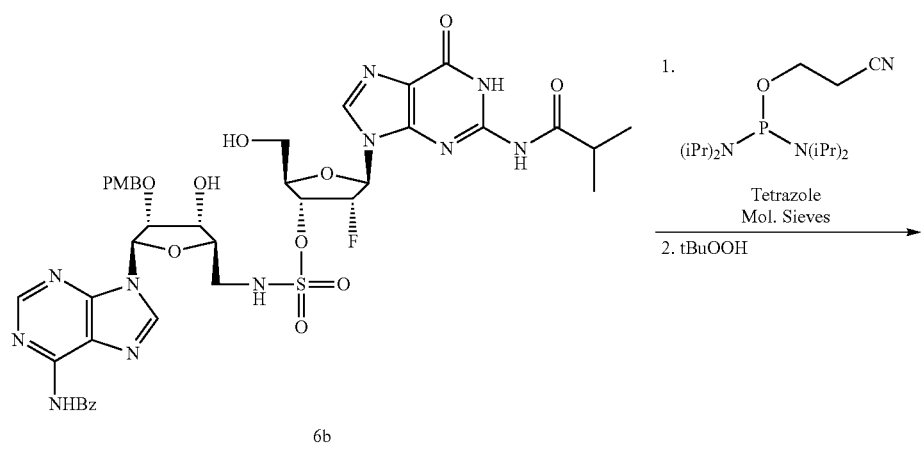
6b
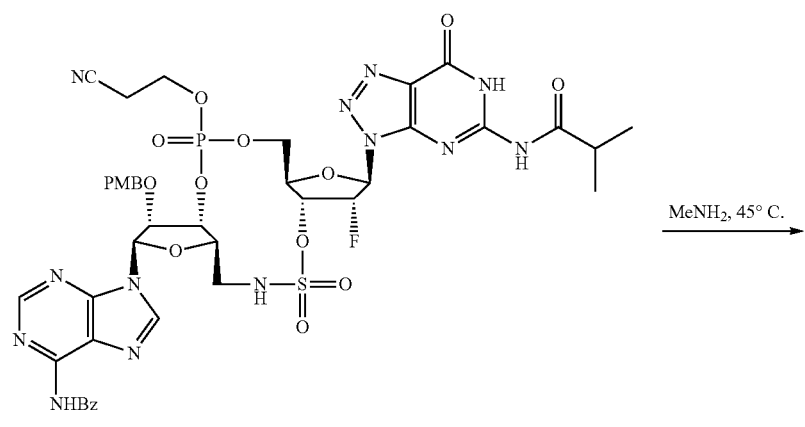
6c

-continued

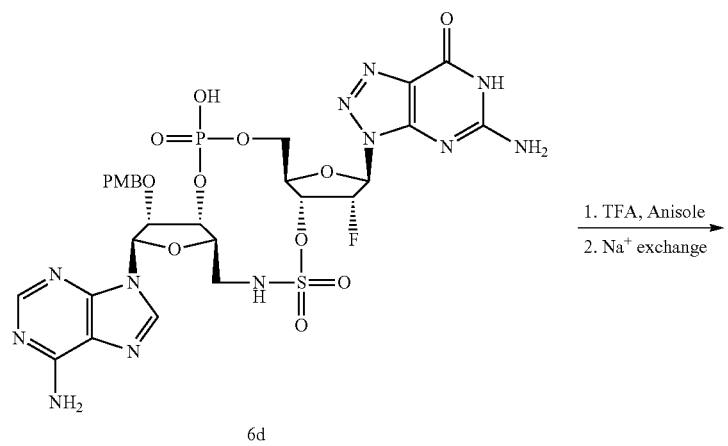

6d

1. TFA, Anisole
2. Na+ exchange

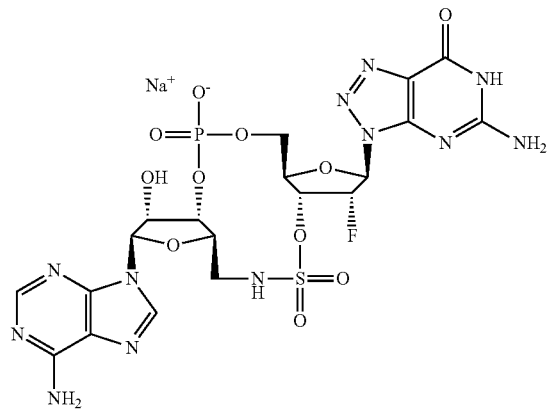

Compound 9

Step 1: (Note: reaction solvents were dried on an appropriate drying agent before use.) A solution of intermediate S5 (7.03 g, 7.07 mmol) and intermediate A2 (3.1 g, 4.71 mmol) in dry THF (100 mL) was stirred for 30 min in the presence of an excess of activated molecular sieves. Next, DMAP (2.88 g, 23.57 mmol) was added, the reaction mixture was stirred at 45° C. for 12 h. The resulting reaction solution was cooled to room temperature and diluted with EtOAc after which the molecular sieves were removed by filtration. The filtrate was washed with saturated aqueous $NaHCO_3$ and brine, dried with $Na_2SO_4$, filtered, and concentrated under reduced pressure. The resulting residue was purified by silica column chromatography (gradient elution: 0 to 2% MeOH in DCM) to give pure intermediate 6a (5.3 g, yield: 75%). ESI-MS: m/z 756.7 [M/2+H]+.

Step 2: Intermediate 6a (4.4 g, 2.91 mmol) was dissolved in DCM (30 mL), followed by the addition of water (524 μL, 29.09 mmol) and DCA (490 μL in DCM (10 mL), 5.98 mmol). The reaction mixture was stirred at room temperature for 4 h, after which pyridine (936 μL, 11.64 mmol) and MeOH (5 mL) were added. The resulting reaction solution was concentrated under reduced pressure, the crude product was purified by column chromatography over silica (gradient elution: 0 to 5.3% MeOH in DCM) to give intermediate 6b (2.2, yield: 83%). ESI-MS: m/z 908.3 [M+H]+.

Step 3: (Note: reaction solvents were dried on an appropriate drying agent before use.) A solution of intermediate 6b (0.60 g, 0.66 mmol) and 1H-tetrazole (5.79 mL, 3-4% in MeCN, dried on 3A molecular sieves before use) in a dry THF/MeCN solvent mixture (1:1, 100 mL) was treated with activated molecular sieves for 1 h under $N_2$ after which 2-cyanoethyl-N,N,N',N'-tetra(isopropyl)phosphorodiamidite (210 μL, 0.66 mmol) was added in one portion. The reaction mixture was shaken for 2 h. An additional amount of 2-cyanoethyl-N,N,N',N'-tetra(isopropyl)phosphorodiamidite (210 mg, 0.66 mmol) was added and shaking was continued for 2 h. Next, a solution of tBuOOH (160 μL, 5.5 M in decane, 0.86 mmol) was added, the reaction mixture was shaken overnight. An additional amount of tBuOOH (160 μL, 5.5 M in decane, 0.86 mmol) was added and the reaction mixture was shaken for an extra hour. The molecular sieves were removed by filtration and rinsed with dichloromethane. The filtrate was washed with a mixture of a saturated aqueous $Na_2S203$ and saturated aqueous $NaHCO_3$, brine, dried with $MgSO_4$, filtered and concentrated under reduced pressure. The residue was purified by column chromatography over silica (gradient elution: 0 to 10% MeOH in DCM) to give intermediate 6c (0.12 g, yield: 11%). $^1$H NMR (400 MHz, DMSO-$d_6$) δ ppm 12.12 (s, 1H), 11.73 (s, 1H), 11.22 (s, 1H), 8.71 (br t, J=5.9 Hz, 1H), 8.66

(s, 1H), 8.63 (s, 1H), 8.28 (s, 1H), 8.05 (d, J=7.3 Hz, 2H), 7.62-7.69 (m, 1H), 7.53-7.60 (m, 2H), 7.08 (d, J=8.8 Hz, 2H), 6.72 (d, J=8.5 Hz, 2H), 0.00 (d, J=5.8 Hz, 1H), 6.19 (dd, J=14.1, 3.8 Hz, 1H), 5.55-5.58 (m, 1H), 5.64 (dt, J=50.7, 4.0 Hz, 1H), 5.48 (t, J=4.9 Hz, 1H), 5.14 (dt, J=12.5, 4.8 Hz, 1H), 4.72 (t, J=5.5 Hz, 1H), 4.63 (d, J=11.5 Hz, 1H), 4.36-4.44 (m, 1H), 4.42 (d, J=11.5 Hz, 1H), 4.31 (br d, J=3.0 Hz, 1H), 4.07-4.13 (m, 1H), 3.71-3.77 (m, 1H), 3.67 (s, 3H), 3.58-3.65 (m, 1H), 3.40-3.51 (m, 1H), 3.28-3.35 (m, 1H), 2.75 (spt, J=6.8 Hz, 1H), 1.11 (d, J=6.5 Hz, 6H); ESI-MS: m/z 1023.5 [M+H]$^+$.

Step 4: Intermediate 6c (0.12 g, 0.072 mmol) was stirred in a concentrated methylamine solution in ethanol (10 mL) at 45° C. for 1 h. The reaction mixture was evaporated to dryness under reduced pressure. The residue was triturated in acetonitrile (3 mL). The precipitate was filtered off, washed with acetonitrile and dried to give intermediate 6d which was used as such in the next step. ESI-MS: m/z 794.3 [M−H]$^−$.

Step 5: A solution of anisole (0.16 mL, 1.48 mmol) in TFA (1.13 mL, 14.78 mmol) at 0° C. was added to the above intermediate 6d. The reaction mixture was stirred at 0° C. for 75 min after which the majority of the TFA was removed by a constant stream of $N_2$. The partially concentrated reaction mixture was basified by the addition of concentrated methylamine (33% solution in EtOH, 1.83 mL, 14.8 mmol) at 0° C., after which it was further concentrated to dryness by $N_2$ blowing. The resulting residue was triturated in MeCN. The precipitate was filtered off and purified by preparative reversed phase HPLC (Stationary phase: XBridge C18 OBD, 10 μm, 150×50 mm; Mobile phase: aqueous 0.25% ammonia bicarbonate (A)-MeOH (B); gradient elution) to give pure Compound 6 as a white solid after lyophilization. Conversion into the sodium salt was done by elution of an aqueous solution over a column packed with a cationic sodium ion-exchange resin to give a white fluffy solid after lyophilization (30 mg, yield: 58% from intermediate 6c). $^1$H NMR (400 MHz, DMSO-$d_6$, 80° C.) δ ppm 8.39 (br s, 1H), 8.11 (s, 1H), 7.90 (s, 1H), 6.91 (br s, 2H), 6.42 (br s, 2H), 6.37 (br s, 1H), 6.11 (d, J=17.1 Hz, 1H), 5.92 (d, J=6.1 Hz, 1H), 5.35-5.58 (m, 1H), 5.25 (br d, J=19.1 Hz, 1H), 4.77-4.89 (m, 2H), 4.25-4.33 (m, 1H), 4.07-4.19 (m, 2H), 3.88 (ddd, J=12.2, 5.9, 1.8 Hz, 1H), 3.37-3.51 (m, 1H), 3.28 (br dd, J=14.2, 4.1 Hz, 1H); $^{31}$P NMR (162 MHz, DMSO-$d_6$) δ ppm 0.92 (s, 1P); ESI-MS: m/z 676.3 [M+H]$^+$.

Compounds 7, 8, 11 and 36 were prepared in a similar way starting from the appropriate intermediates selected from S1-S7 and A1-A27 and the analytical data is shown in Table 2.

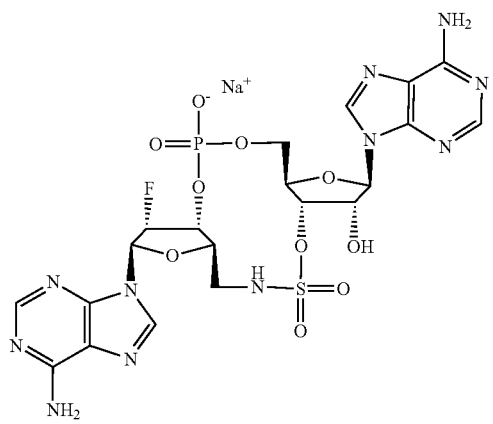

8

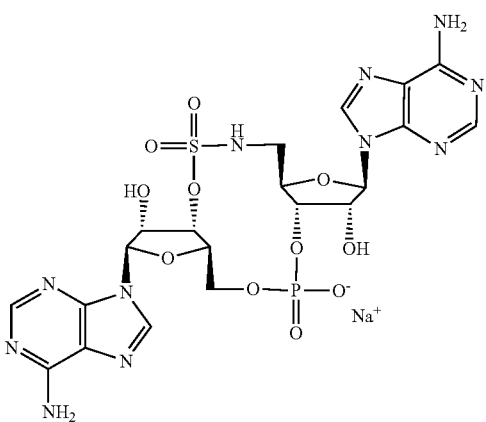

11

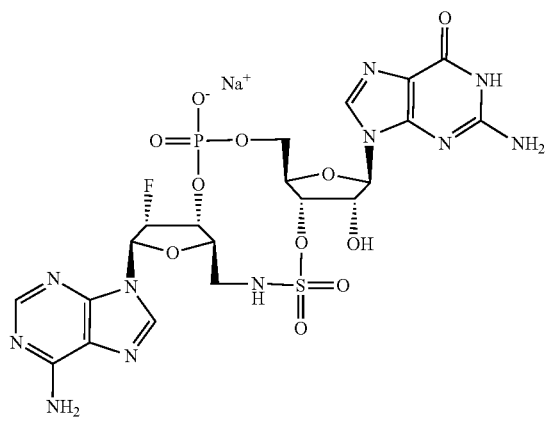

7

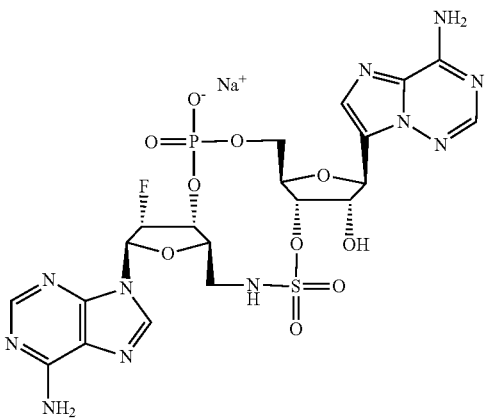

36

Example 7: Compounds (*R) 14 and (*S) 14
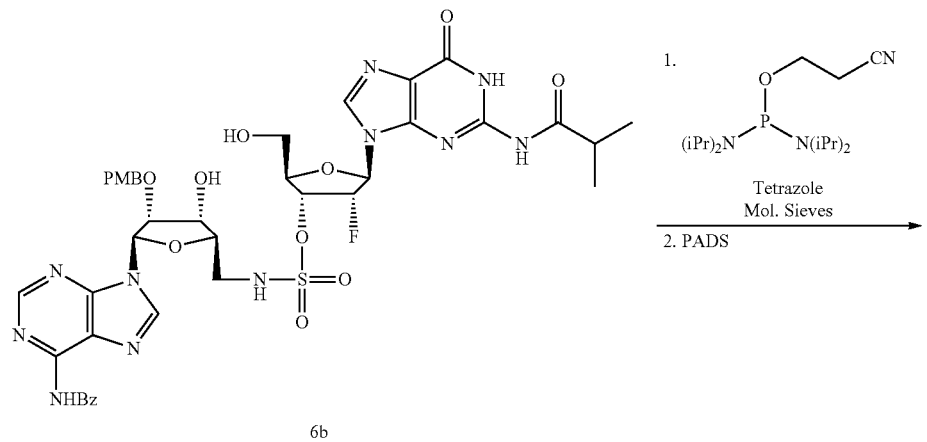
6b
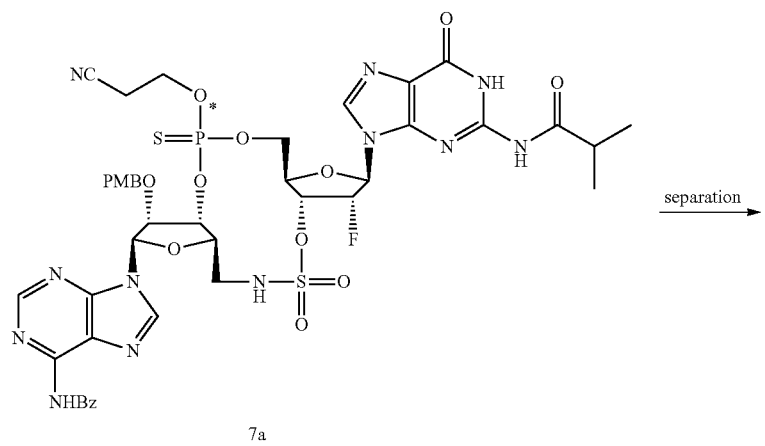
7a
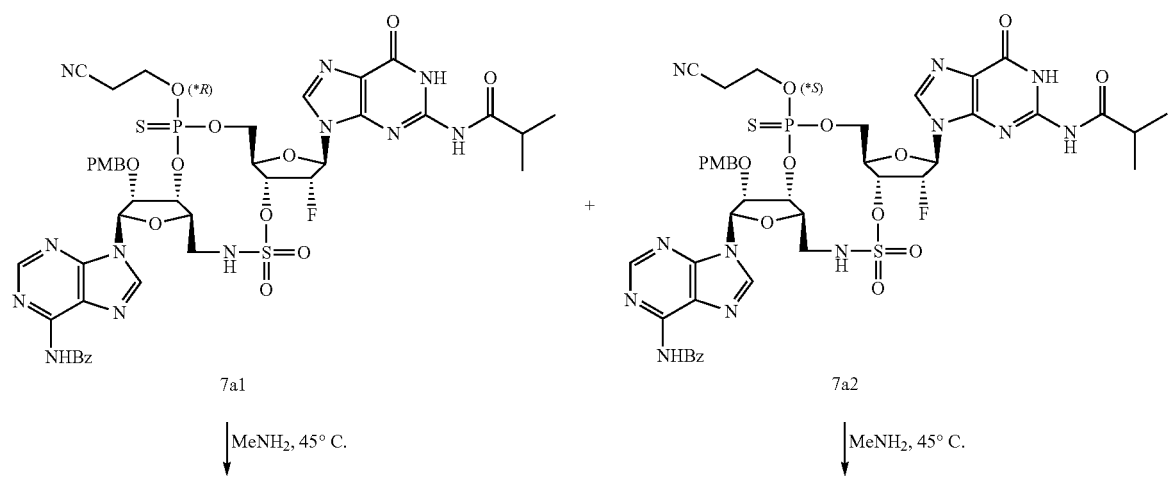
7a1 + 7a2
↓ MeNH₂, 45° C.          ↓ MeNH₂, 45° C.

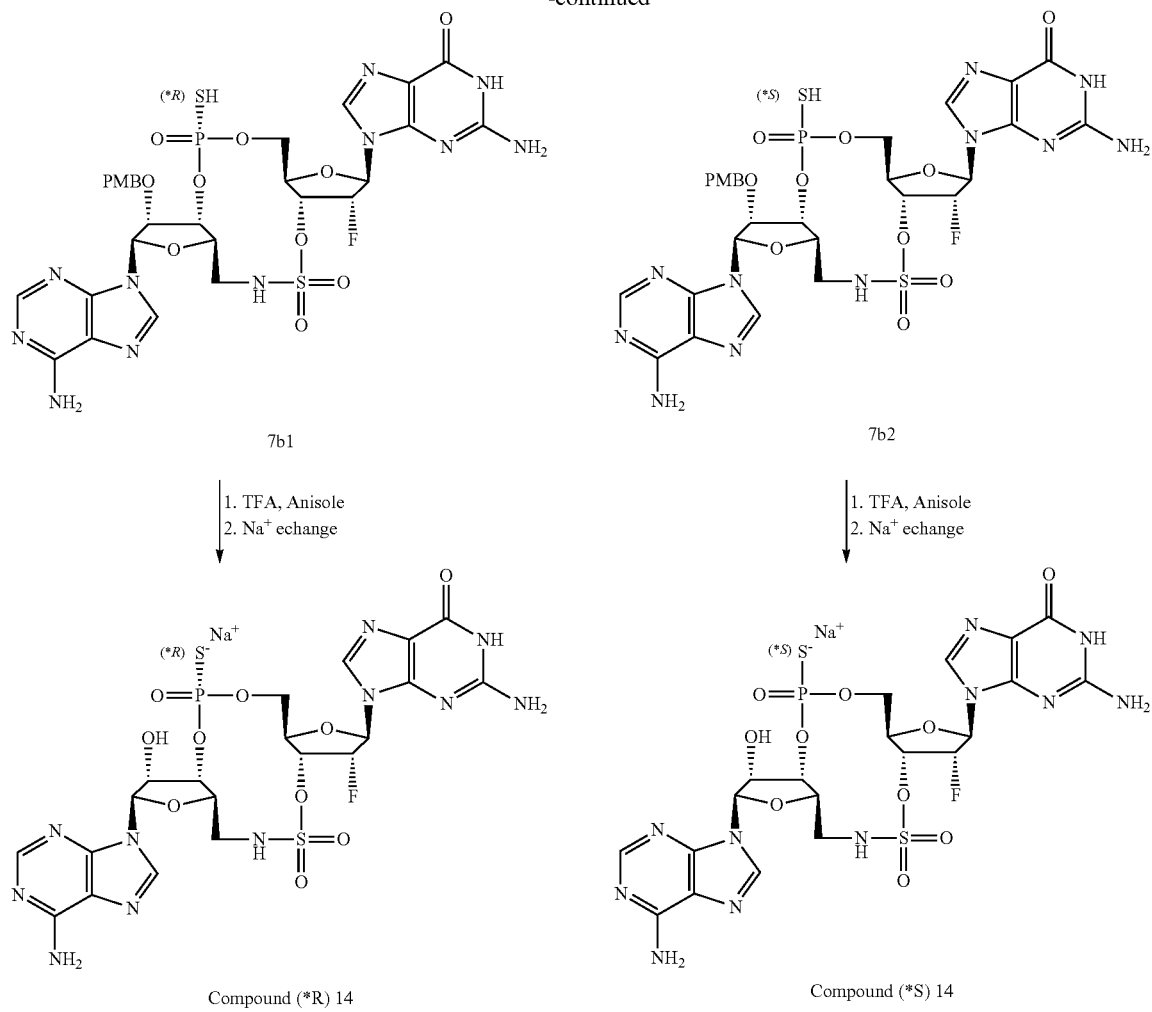

Step 1: (Note: reaction solvents were dried on an appropriate drying agent before use.) A solution of intermediate 6b (1.0 g, 1.1 mmol) and 1H-tetrazole (9.65 mL, 3-4% in MeCN, dried on activated molecular sieves before use) in dry THF/MeCN solvent mixture (1:1, 160 mL) was treated with activated molecular sieves for 1 h under $N_2$. 2-Cyanoethyl-N,N,N',N'-tetra(isopropyl)phosphorodiamidite (350 μL, 1.1 mmol) was added in one portion, the reaction mixture was shaken for 2 h. An additional amount of 2-cyanoethyl-N,N,N',N'-tetra(isopropyl)phosphorodiamidite (350 μL, 1.1 mmol) was added and shaking was continued for 2 h. PADS (0.67 g, 2.2 mmol) was added and the reaction mixture was shaken for 18 h. The molecular sieves were removed by filtration and rinsed with dichloromethane. The filtrate was washed with saturated aqueous $NaHCO_3$ and brine, dried with $MgSO_4$, filtered and concentrated under reduced pressure to give intermediate 7a as the P-epimeric mixture. Both isomers were separated by column chromatography over silica (gradient elution: 0 to 10% MeOH in DCM) to give intermediate xa1 (0.175 g, yield: 11%, purity: 71%) as the first eluting isomer and intermediate 7a2 (0.278 g, yield: 19%, purity: 79%) as the second eluting isomer. Intermediate 7a1: ESI-MS: m/z 1039.4 [M+H]$^+$; intermediate 7a2: ESI-MS: m/z 1039.5 [M+H]$^+$.

Step 2: Intermediate 7a1 (0.175 g, 0.12 mmol) was stirred in a concentrated methylamine solution in ethanol (10 mL) at 45° C. for 1 h. The reaction mixture was evaporated to dryness under reduced pressure. The residue was triturated in MeCN (3 mL). The precipitate was isolated by filtration and dried to give intermediate 7b1 which was used as such in the next step. ESI-MS: m/z 812.4 [M+H]$^+$. Using a similar protocol, intermediate 7b2 was prepared from intermediate 7a2. ESI-MS: m/z 812.4 [M+H]$^+$.

Step 3: A solution of anisole (0.13 mL, 1.19 mmol) in TFA (0.91 mL, 11.8 mmol) at 0° C. was added to the above intermediate 7b1 (147 mg, 0.15 mmol). The reaction mixture was stirred at 0° C. for 75 min after which the majority of the TFA was removed by a constant stream of $N_2$. The partially concentrated reaction mixture was basified by the addition of methylamine (33% solution in EtOH, 1.47 mL, 11.8 mmol) at 0° C., after which it was further concentrated to dryness by $N_2$ blowing. The resulting residue was triturated in MeCN. The precipitate was filtered isolated by filtration and purified by preparative reversed phase HPLC (stationary phase: XBridge C18 OBD, 10 μm, 150×50 mm; mobile phase: aqueous 0.25% ammonia bicarbonate (A)-MeOH (B); gradient elution) to give pure Compound (*R) 14 as a white solid after lyophilization. Conversion into the sodium salt was done by elution of an aqueous solution over a column packed with a cationic sodium ion-exchange resin to give a white fluffy solid after lyophilization (5 mg, yield:

6% from 7a1). $^1$H NMR (400 MHz, DMSO-d$_6$) δ ppm 10.65 (br s, 1H), 8.77 (br s, 1H), 8.13 (s, 1H), 7.97 (s, 1H), 7.19 (br s, 2H), 6.60 (br s, 2H), 6.05 (m, J=16.7 Hz, 2H), 5.87 (d, J=5.7 Hz, 1H), 5.09-5.37 (m, 1H), 4.99 (m, J=9.2, 4.7 Hz, 2H), 4.55-4.74 (m, 1H), 4.22 (m, J=12.2 Hz, 2H), 3.92-4.01 (m, 1H), 3.64-3.76 (m, 1H); $^{31}$P NMR (162 MHz, DMSO-d$_6$) δ ppm 55.98 (s, 1P); ESI-MS: m/z 692.1 [M+H]$^+$.

Using a similar protocol, compound (*S) 14, sodium salt was prepared from intermediate 7b2 (yield: 20% from intermediate 7a2). $^1$H NMR (400 MHz, DMSO-d$_6$, 80° C.) δ ppm 8.44 (br s, 1H), 8.11 (s, 1H), 8.00 (s, 1H), 6.93 (br s, 2H), 6.33 (br s, 2H), 6.12 (d, J=17.5 Hz, 1H), 5.95 (d, J=4.9 Hz, 1H), 0.00 (br d, J=52.5 Hz, 1H), 5.14-5.28 (m, 1H), 5.10 (dt, J=11.7, 4.7 Hz, 1H), 4.82-4.93 (m, 2H), 4.29 (br d, J=6.5 Hz, 1H), 4.22 (dt, J=12.2, 3.7 Hz, 1H), 4.13-4.19 (m, 1H), 3.87 (ddd, J=11.8, 5.3, 2.0 Hz, 1H), 3.40-3.55 (m, 1H), 3.27 (dd, J=14.0, 3.1 Hz, 1H); $^{31}$P NMR (162 MHz, DMSO-d$_6$) δ ppm 53.23 (s, 1P); ESI-MS: m/z 692.1 [M+H]$^+$.

Compounds (*R) 12, (*S) 19 and (*R) 19 were prepared in a similar way starting from the appropriate intermediates selected from S1-S7 and A1-A27 and the analytical data is shown in Table 2.

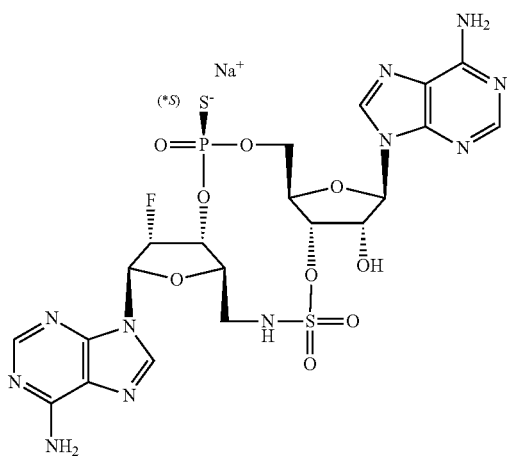

19-S

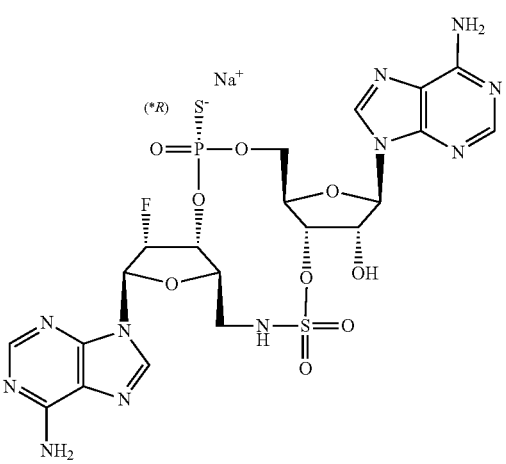

19-R

Example 8: Compound 13

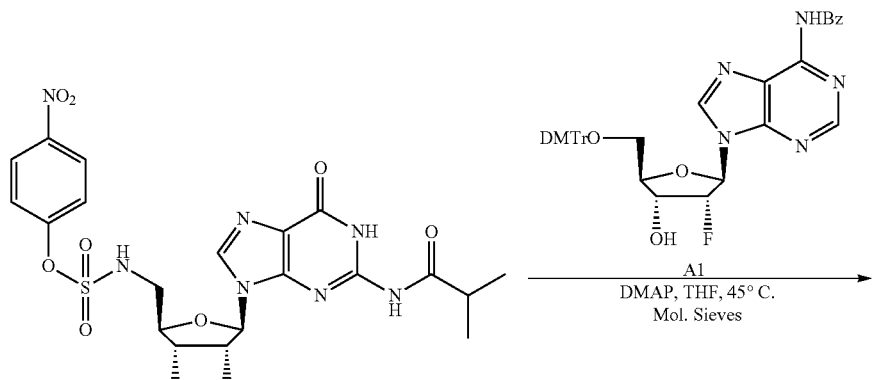

-continued
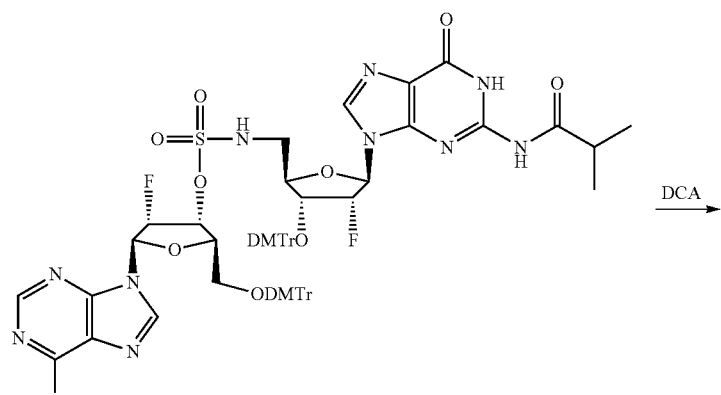
8a
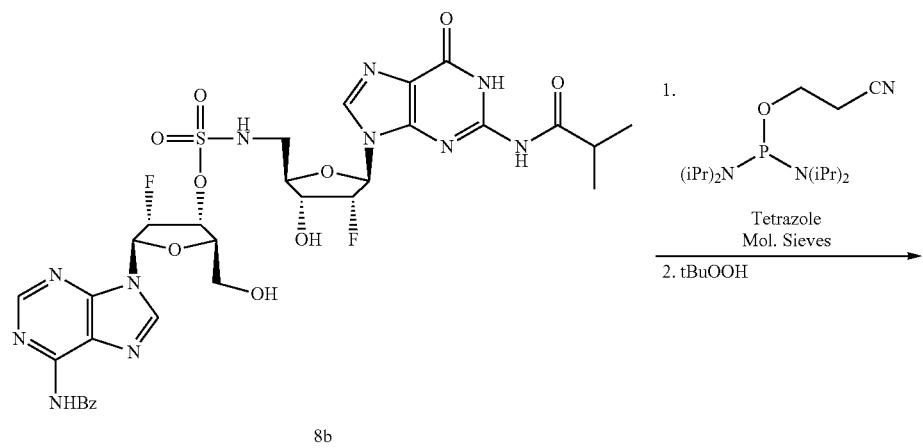
8b
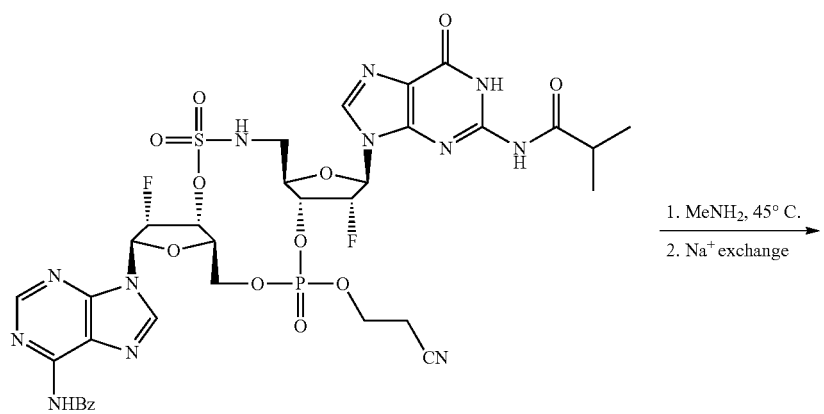
8c

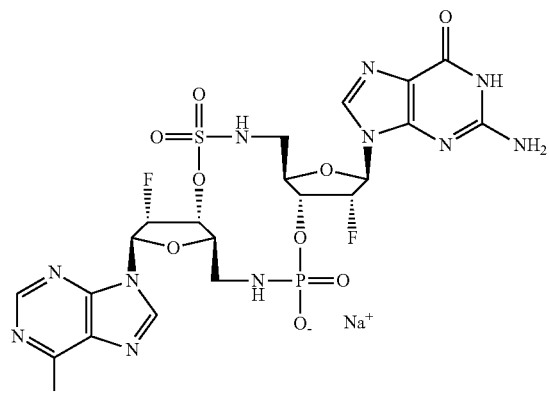

Compound 13

Step 1: (Note: reaction solvents were dried on an appropriate drying agent before use.) A solution of sulfamate S2 (3.0 g, 3.50 mmol) and alcohol A1 (1.82 g, 2.69 mmol) in dry THF (50 mL) was stirred for 30 min in the presence of an excess of activated molecular sieves. Next, DMAP (1.64 g, 13.45 mmol) was added, the reaction mixture was stirred at 45° C. for 18 h. The resulting reaction solution was cooled to room temperature and filtered through a pad of diatomaceous earth. The filtrate was concentrated, the resulting residue re-dissolved in EtOAc, washed with saturated aqueous NaHCO$_3$ and brine, dried with Na$_2$SO$_4$, filtered, and concentrated under reduced pressure. The resulting residue was purified by silica column chromatography (gradient elution: 0 to 2% MeOH in DCM) to give intermediate 8a (3.06 g, yield: 81%). ESI-MS: m/z 1394.7 [M+H]$^+$.

Step 2: Intermediate 8a (3.06 g, 2.19 mmol) was dissolved in DCM (100 mL), followed by the addition of water (395 µL, 21.94 mmol) and DCA (566 mg, 4.39 mmol). The reaction mixture was stirred at room temperature overnight, after which pyridine (707 µL, 8.77 mmol) and MeOH were added. The resulting reaction solution was concentrated under reduced pressure, the crude product was purified by column chromatography over silica (gradient elution: 0 to 5% MeOH in DCM) to give intermediate 8b (1.44, yield: 83%). $^1$H NMR (400 MHz, DMSO-d$_6$) δ ppm 12.13 (s, 1H), 11.60 (s, 1H), 11.27 (s, 1H), 8.76 (s, 1H), 8.70 (s, 1H), 8.68 (br t, J=6.0 Hz, 1H), 8.19 (s, 1H), 8.05 (d, J=7.3 Hz, 2H), 7.63-7.68 (m, 1H), 7.56 (t, J=7.7 Hz, 2H), 6.48 (dd, J=16.4, 2.9 Hz, 1H), 6.16 (dd, J=18.7, 2.1 Hz, 1H), 5.88 (dm, J=51.4 Hz, 1H), 5.87 (d, J=6.3 Hz, 1H), 5.31-5.47 (m, 3H), 4.40-4.51 (m, 1H), 4.30-4.35 (m, 1H), 4.02-4.09 (m, 1H), 3.74-3.82 (m, 1H), 3.57-3.67 (m, 1H), 3.51 (dd, 1H), 3.38-3.43 (m, 1H), 2.77 (spt, J=6.8 Hz, 1H), 1.12 (d, J=6.8 Hz, 3H), 1.13 (d, J=6.8 Hz, 3H); ESI-MS: m/z 790.3 [M+H]$^+$.

Step 3: (Note: reaction solvents were dried on an appropriate drying agent before use.) A solution of intermediate 8b (200 mg, 0.253 mmol) and 1H-tetrazole (4.5 mL of a 0.45 M solution in MeCN, dried on activated molecular sieves before use) in dry THF/MeCN (1:1, 10 mL) was treated with activated molecular sieves for 30 min under N$_2$. Next, a solution of 2-cyanoethyl-N,N,N',N'-tetra(isopropyl)-phosphorodiamidite (121 mg, 0.405 mmol) in MeCN (3.9 mL) was added dropwise, the resulting reaction mixture was stirred for 3 h. A solution of tBuOOH (253 µL, 5.5 M in decane, 1.39 mmol) was added and stirring was continued for 35 min. The reaction mixture was diluted with DCM and filtered through a pad of diatomaceous earth. The filtrate was concentrated under reduced pressure. The same reaction procedure was repeated on the same scale. The crude product from both reactions were combined for purification by column chromatography over silica (gradient elution: 0 to 6% MeOH in DCM) to give intermediate 8c (248 mg, yield: 54%). ESI-MS: m/z 905.3 [M+H]$^+$.

Step 4: Intermediate 8c (220 mg, 0.243 mmol) was stirred in a concentrated solution of methylamine in ethanol (20 mL) at ca. 45° C. until complete conversion (ca. 2 h). The reaction mixture was evaporated to dryness under reduced pressure. The residue was purified by preparative reversed phase HPLC (stationary phase: XBridge C18 OBD, 10 μm, 150×30 mm; mobile phase: 10 mM ammonia bicarbonate (A)-MeCN (B); gradient elution) to give pure Compound 13 as a white solid after lyophilization. Conversion into the sodium salt was done by elution of an aqueous solution over a column packed with a cationic sodium ion-exchange resin to give a white fluffy solid after lyophilization (124 mg, yield: 73%). $^1$H NMR (400 MHz, D$_2$O) δ=7.96 (br, s, 1H), 7.93 (s, 1H), 7.71 (s, 1H), 6.08-5.59 (m, 5H), 5.17-5.11 (m, 1H), 4.68 (br, d, J=8.8 Hz, 1H), 4.51 (br, d, J=11.3 Hz, 2H), 4.19 (br, dd, J=5.6, 11.9 Hz, 1H), 3.81 (d, J=12.0 Hz, 1H), 3.50 (d, J=13.6 Hz, 1H); $^{19}$F NMR (376 MHz, D$_2$O) δ=−201.43 (s, 1F), −200.81 (s, 1F); $^{31}$P NMR (162 MHz, D$_2$O) δ=−1.44 (s, 1P); ESI-MS: m/z 678.1 [M+H]$^+$.

Compounds 10, 25 and 27 were prepared in a similar way starting from the appropriate intermediates selected from S1-S7 and A1-A27 and the analytical data is shown in Table 2.

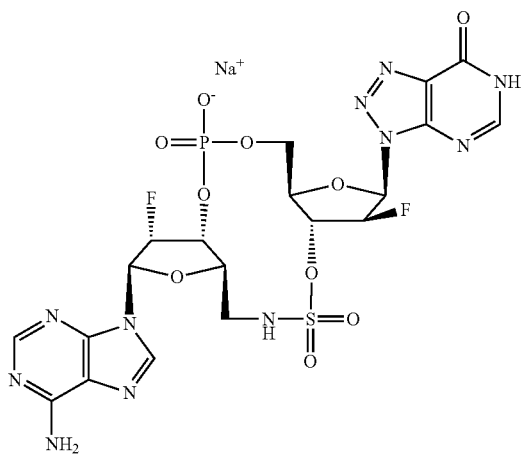

10

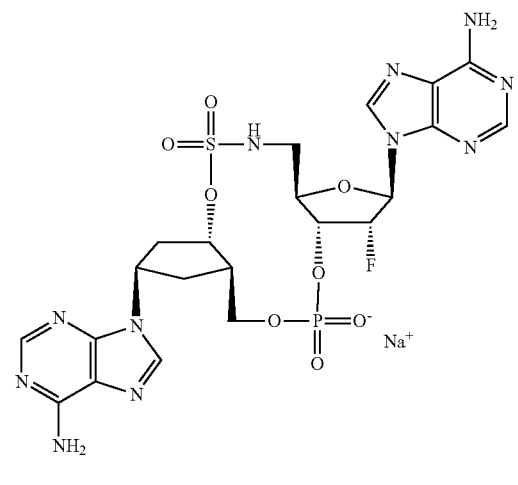

25

27

Example 9: Compound 24

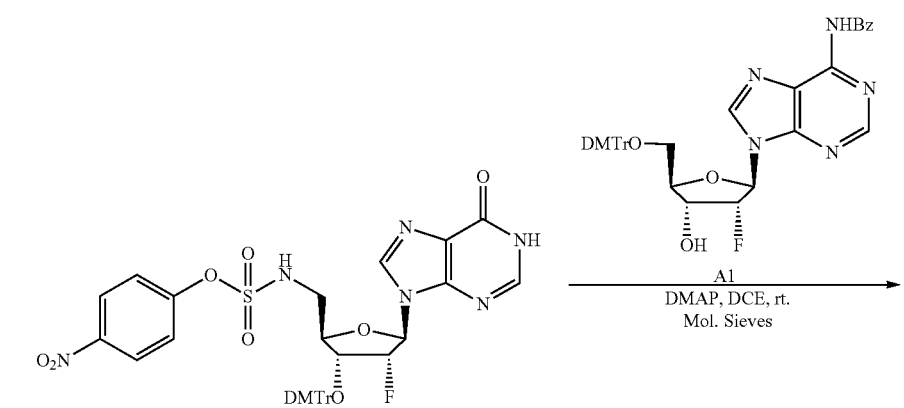

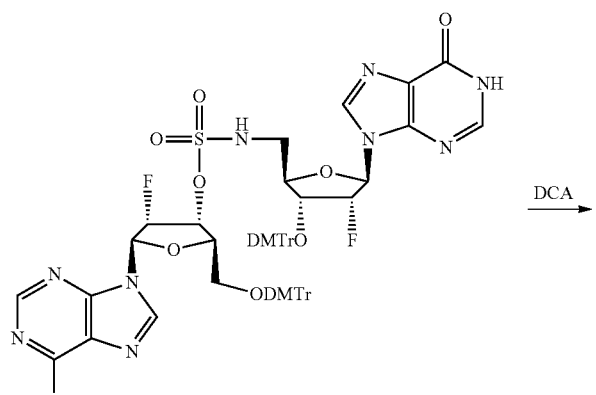
9a
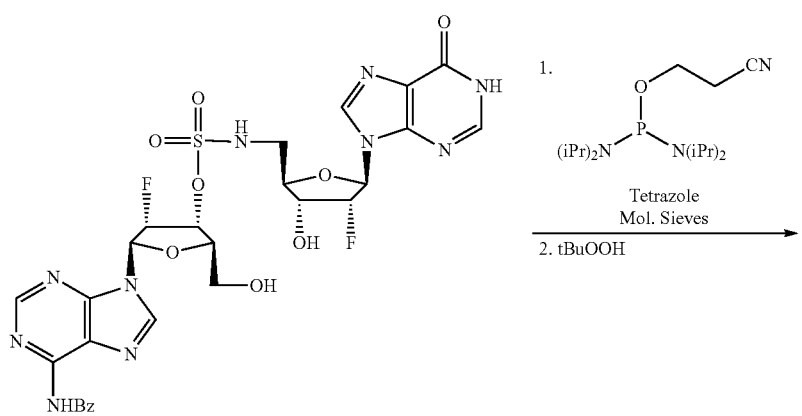
9b
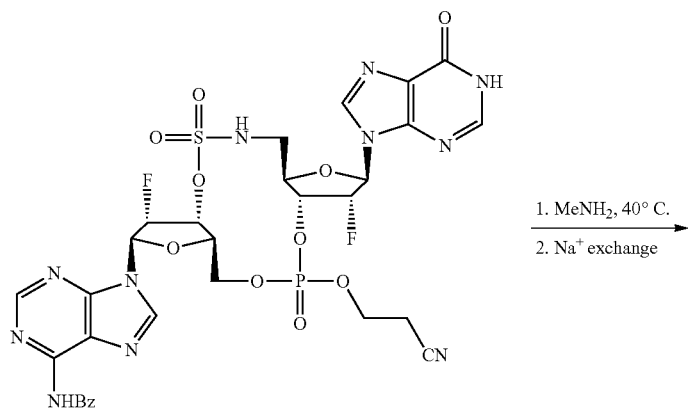
9c

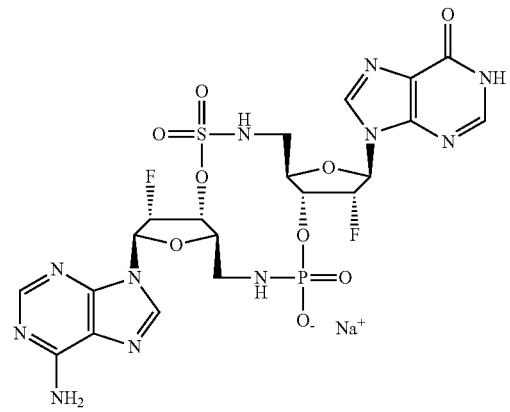

Compound 24

Step 1: (Note: reaction solvents were dried on an appropriate drying agent before use.) A reaction flask was charged with DMAP (1.77 g, 14.5 mmol), dry DCE (9.7 mL) and activated molecular sieves. The resulting mixture was shaken for 2 h under inert atmosphere. Simultaneously, a solution of alcohol A1 (1.94 g, 2.88 mmol) and a solution of sulfamate S3 (2.44 g, 3.16 mmol), each in dry DCE (2×9.7 mL), were dried on activated molecular sieves (ca. 2 h). Both solutions were successively transferred to the reaction flask. The resulting reaction mixture was stirred at room temperature overnight. The molecular sieves were removed by filtration and thoroughly rinsed with DCM. The filtrate was washed with saturated aqueous $NaHCO_3$, the aqueous phase was extracted with DCM. The combined organic layers were dried over $Na_2SO_4$, filtered, and concentrated under reduced pressure. The residue was purified by silica column chromatography (gradient elution: 1 to 4% MeOH in DCM) to give pure intermediate 9a (2.27 g, yield: 55%). ESI-MS: m/z 1310.5 $[M+H]^+$.

Step 2: Intermediate 9a (2.27 g, 1.73 mmol) was dissolved in DCM (87 mL), followed by the addition of water (160 μL, 8.65 mmol) and DCA (560 μL, 6.76 mmol). The reaction mixture was stirred at room temperature for 1 h, after which pyridine (700 μL, 8.65 mmol) and MeOH were added. The resulting reaction solution was partially concentrated under reduced pressure and transferred to a silica column for purification (gradient elution: 5 to 15% MeOH in DCM) to give intermediate 9b (1.19 g, yield: 97.5%). $^1$H NMR (300 MHz, DMSO-$d_6$) δ ppm 12.39-12.55 (m, 1H), 11.26 (s, 1H), 8.76 (s, 1H), 8.70 (s, 1H), 8.67 (br s, 1H), 8.28 (s, 1H), 8.02-8.09 (m, 3H), 7.66 (t, J=7.3 Hz, 1H), 7.56 (t, J=7.3 Hz, 2H), 6.48 (dd, J=16.7, 2.6 Hz, 1H), 6.25 (dd, J=19.0, 2.1 Hz, 1H), 5.90 (d, J=5.9 Hz, 1H), 5.88 (dm, J=51.6 Hz, 1H), 5.30-5.59 (m, 3H), 4.39-4.56 (m, 1H), 4.32 (br s, 1H), 4.01-4.11 (m, 1H), 3.72-3.84 (m, 1H), 3.56-3.69 (m, 1H), 3.44-3.55 (m, 1H); ESI-MS: m/z 728.0 $[M+Na]^+$.

Step 3: (Note: reaction solvents were dried on an appropriate drying agent before use.) A solution of intermediate 9b (200 mg, 0.284 mmol) and 1H-tetrazole (5.05 mL of a 0.45 M solution in MeCN, dried on activated molecular sieves before use) in dry DMF/MeCN (1:3, 4 mL) was treated with activated molecular sieves for 30 min under $N_2$. Next, a solution of 2-cyanoethyl-N,N,N',N'-tetra(isopropyl)phosphorodiamidite (154 mg, 0.511 mmol) in THF (2 mL) was added dropwise, the resulting reaction mixture was stirred for 2 h. Next, a solution of tBuOOH (454 μL, 5 M in decane, 2.27 mmol) was added and stirring was continued for 30 min. The molecular sieves were removed by filtration, the filtrate was concentrated under reduced pressure and transferred to a silica column for purification (gradient elution: 0 to 10% MeOH in DCM) to give crude intermediate 9c (175 mg, yield: 75%). ESI-MS: m/z 820.3 $[M+H]^+$.

Step 4: Intermediate 9c (175 mg, 0.214 mmol) was stirred in a concentrated methylamine solution in ethanol (5 mL) at ca. 40° C. until complete conversion (ca. 2.5 h). The reaction mixture was evaporated to dryness under reduced pressure. The residue was dissolved in water and washed with DCM. The aqueous layer was lyophilized, the resulting residue was purified by preparative reversed phase HPLC (stationary phase: XBridge C18 OBD, 5 μm, 150×30 mm; mobile phase: 10 mM ammonia bicarbonate (A)-MeCN (B); gradient elution) to give pure Compound 24 as a white solid after lyophilization. Conversion into the sodium salt was done by elution of an aqueous solution over a column packed with a cationic sodium ion-exchange resin to give a white fluffy solid after lyophilization (50 mg, yield: 34%). $^1$H NMR (400 MHz, D$_2$O) δ ppm 7.98 (s, 1H), 7.86 (s, 1H), 7.66 (s, 1H), 6.04-6.23 (m, 2H), 5.72 (br d, J=51.8 Hz, 1H), 5.39-5.52 (m, 1H), 5.46 (dd, J=50.4, 2.5 Hz, 1H), 4.86-5.05 (m, 1H), 4.56 (br d, J=9.3 Hz, 1H), 4.32-4.48 (m, 2H), 4.07 (br dd, J=11.9, 5.4 Hz, 1H), 3.69 (dd, J=13.3, 2.5 Hz, 1H), 3.41 (br d, J=13.1 Hz, 1H); $^{31}$P NMR (162 MHz, D$_2$O) δ ppm −1.82 (s, 1P); ESI-MS: m/z 663.2 [M+H]$^+$.

Compounds 4, 23, 26, 33, 38, 42, 43, 45, and 61 were prepared in a similar way starting from the appropriate intermediates selected from S1-S7 and A1-A28 and analytical data is shown in Table 2.

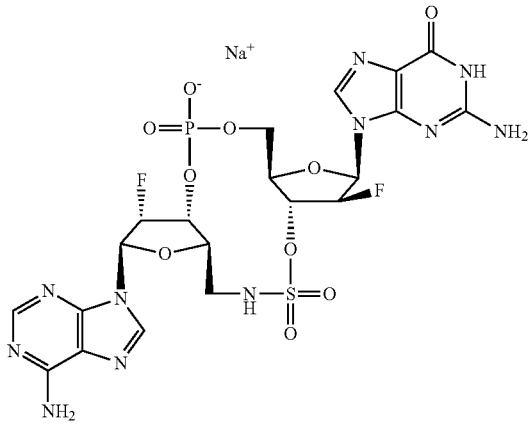

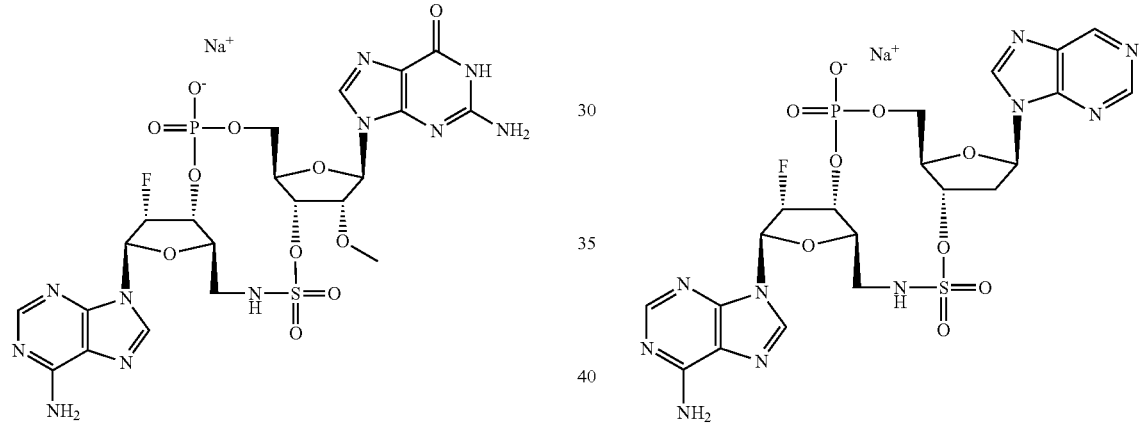

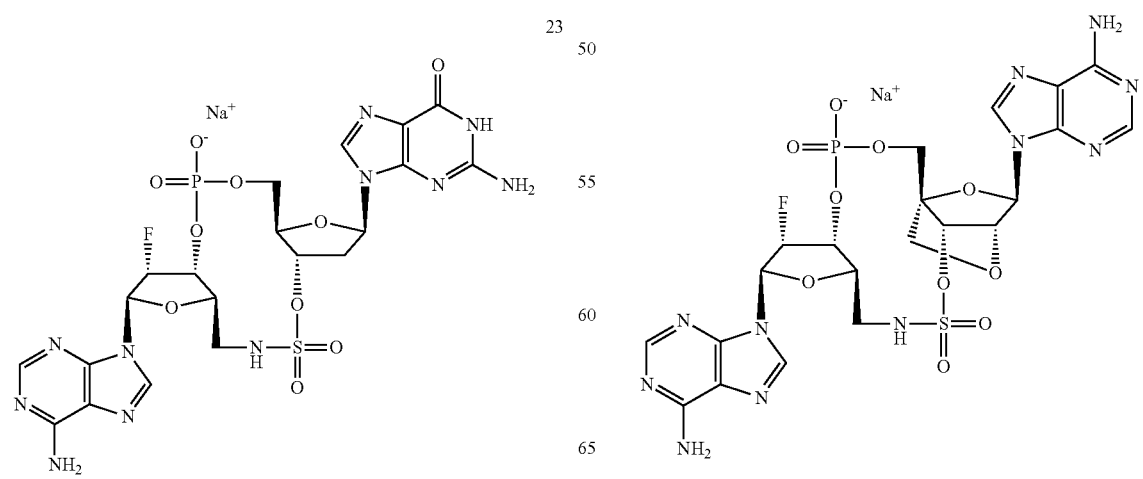

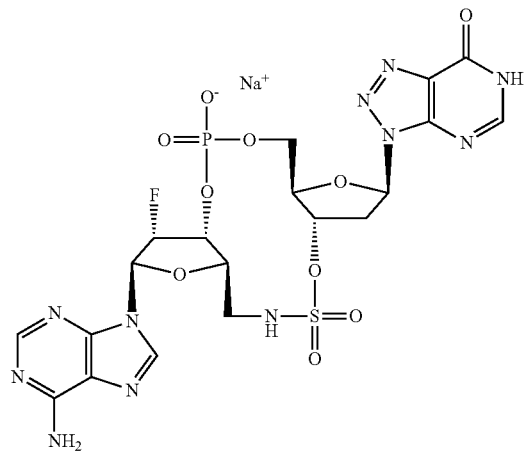
42
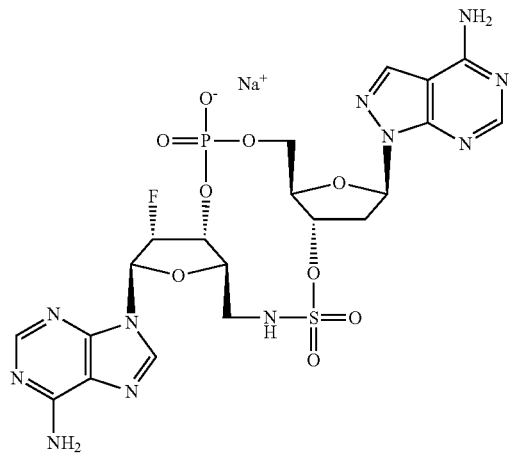
45
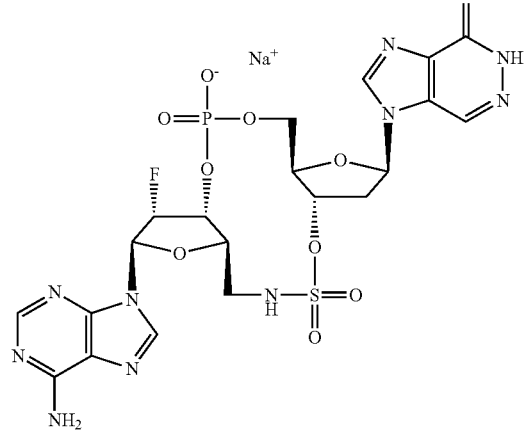
43
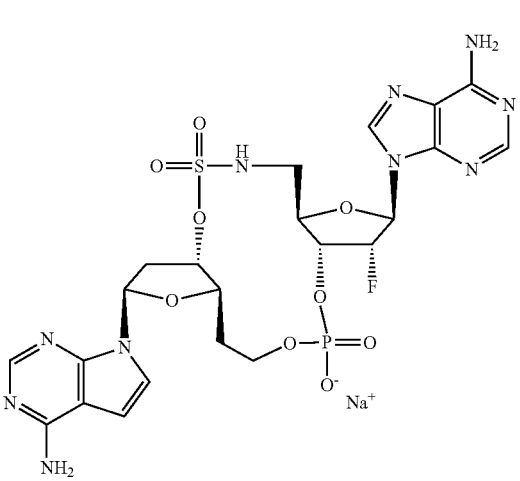
61
Example 10: Compounds (*R) 37 and (*S) 37
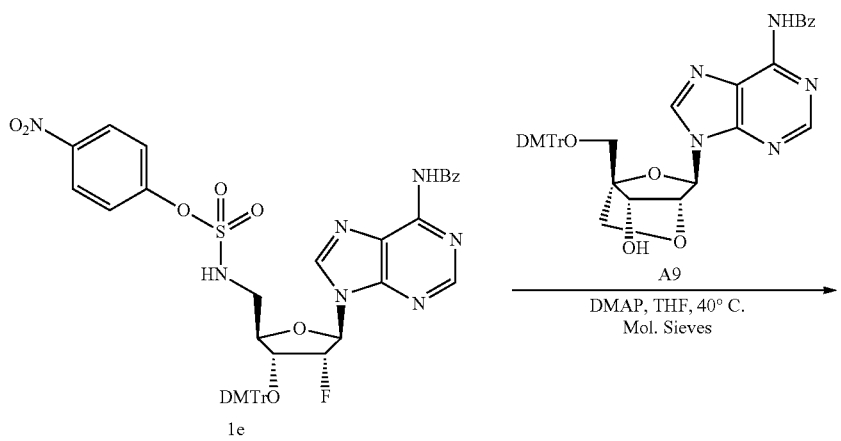

-continued
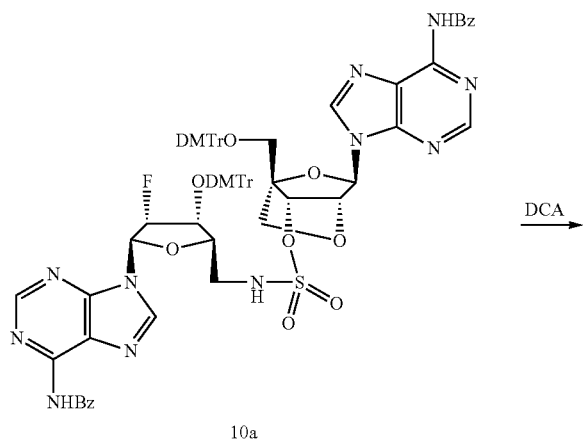
10a
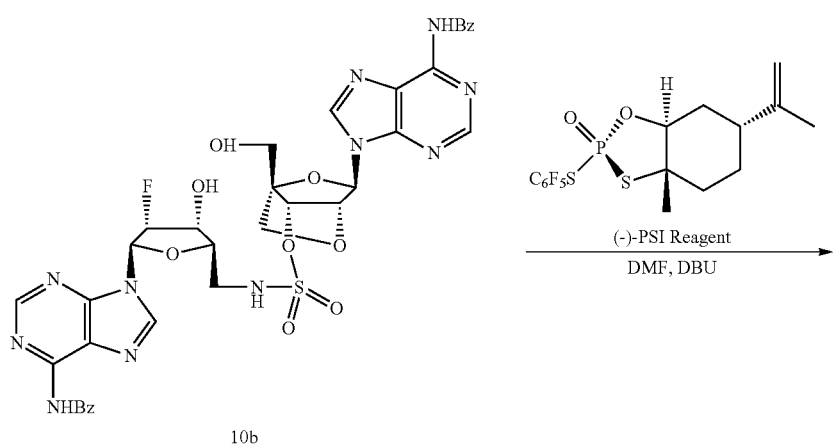
10b
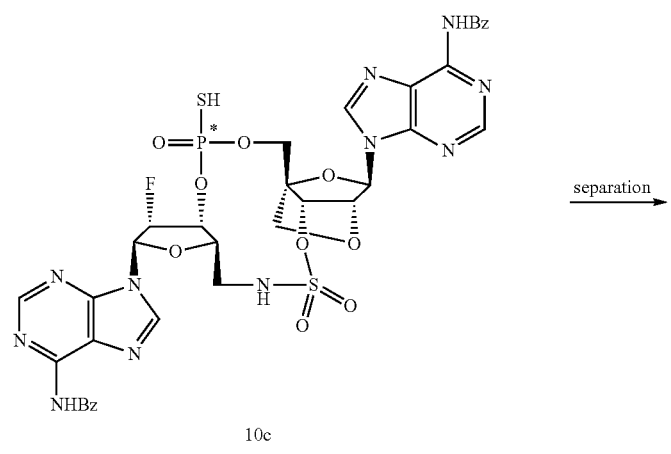
10c

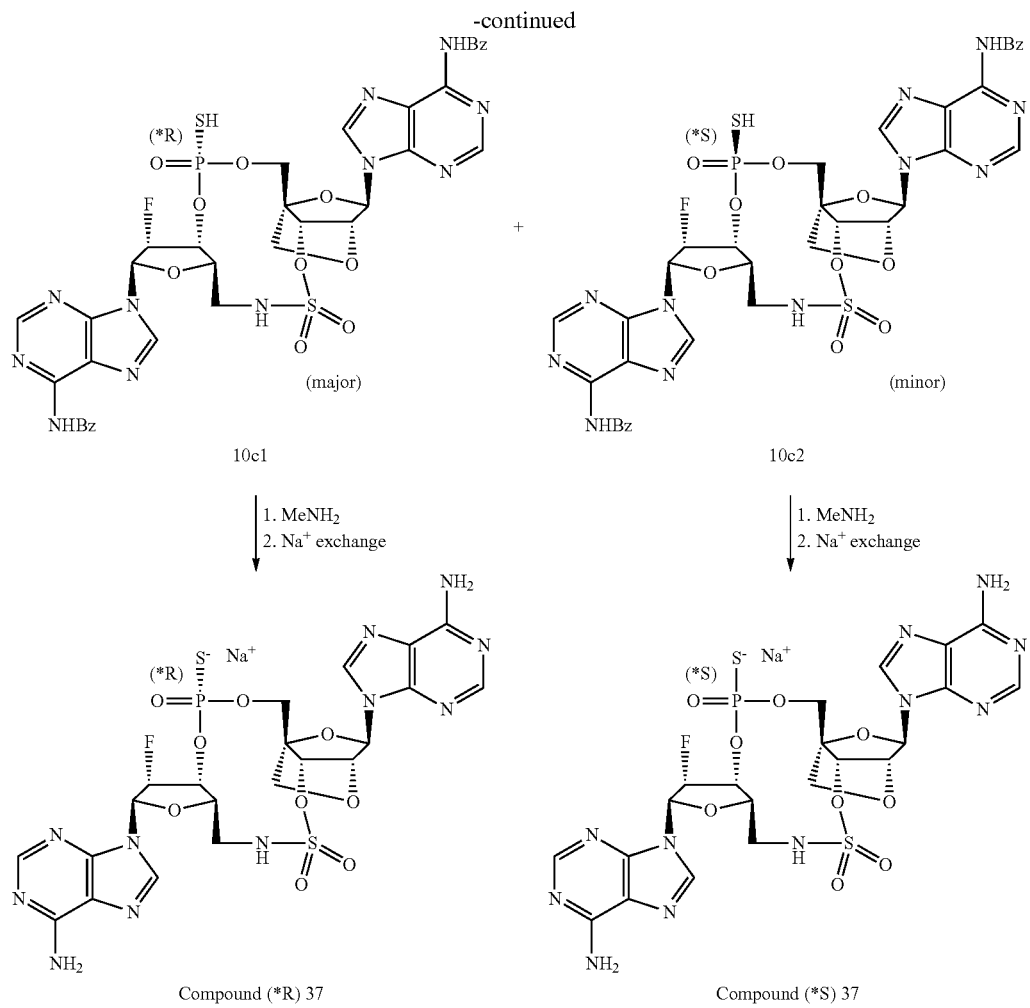

10c1 (major)     10c2 (minor)

↓ 1. MeNH$_2$  2. Na$^+$ exchange     ↓ 1. MeNH$_2$  2. Na$^+$ exchange

Compound (*R) 37     Compound (*S) 37

Step 1: A mixture of intermediate 1e (2.9 g, 3.3 mmol), intermediate A9 (1.5 g, 2.2 mmol) and activated molecular sieves in dry THF (25 mL, freshly distilled over Na/benzophenone) was stirred at room temperature for 30 min under N$_2$. DMAP (1.34 g, 10.9 mmol) was added and stirring was continued for 12 h at 40° C. The reaction solution was cooled to room temperature after which it was diluted with DCM and filtered through a pad of diatomaceous earth. The filtrate was concentrated under reduced pressure. Intermediate 10a was obtained as a white solid (yield: 58%) after two rounds of purification by silica column chromatography (gradient elution: 0 to 2% MeOH in DCM). ESI-MS: m/z 712.7 [[M+2H]/2]$^+$.

Step 2: Intermediate 10a (1.0 g, 0.7 mmol) was dissolved in DCM (10 mL), followed by the addition of water (127 mg, 7.0 mmol) and DCA (181 mg, 1.41 mmol) (formation of gum-like residue was observed). The reaction solution was stirred at room temperature overnight. MeOH (7 mL) and pyridine (222 mg, 2.81 mmol) were added, the resulting suspension was stirred for 15 min. The precipitate was isolated by filtration and washed with DCM. The filtrate was partially concentrated under reduced pressure resulting in a second crop of precipitate which was collected by filtration and washed with DCM. Both precipitates were dissolved in water and lyophilized to give compound 10b as a white solid (yield: 83%). $^1$H NMR (400 MHz, DMSO-d$_6$) δ ppm 11.24 (s, 2H), 8.76 (s, 1H), 8.75 (s, 1H), 8.70 (t, J=6.1 Hz, 1H), 8.63 (s, 1H), 8.53 (s, 1H), 8.01-8.07 (m, 4H), 7.61-7.68 (m, 2H), 7.52-7.61 (m, 4H), 6.39 (dd, J=19.4, 1.9 Hz, 1H), 6.21 (s, 1H), 5.93 (d, J=6.3 Hz, 1H), 5.62 (ddd, J=52.6, 4.4, 2.0 Hz, 1H), 5.32 (t, J=5.9 Hz, 1H), 5.07 (s, 1H), 5.01 (s, 1H), 4.56-4.66 (m, 1H), 4.02-4.09 (m, 1H), 3.99 (d, J=8.5 Hz, 1H), 3.95 (d, J=8.5 Hz, 1H), 3.83-3.89 (m, 2H), 3.45-3.52 (m, 1H), 3.26-3.31 (m, 1H), 2.53-2.58 (m, 1H). ESI-MS: m/z 818.3 [M+H]$^+$.

Step 3: A solution of intermediate 10b (100 mg, 0.122 mmol) and DBU (279 mg, 1.83 mmol) in DMF (10 mL) was cooled at 0° C. (−)-PSI reagent ((2S,3aS,6R,7aS)-3a-methyl-2-((perfluorophenyl)thio)-6-(prop-1-en-2-yl)hexahydrobenzo[d][1,3,2]oxathiaphosphole 2-sulfide, CAS: 102691-36-1, 82 mg, 0.18 mmol in 2 mL DMF) was added over 25 min. The reaction mixture was stirred for 2.5 h at 10° C. after which an extra amount of (−)-PSI reagent (40 mg, 0.089 mmol) was added in one portion, stirring was continued overnight. An additional amount of (−)-PSI reagent (80 mg, 0.18 mmol) and stirring for 12 h was needed to obtain full conversion (P-isomers were observed in a 2/3 ratio). The solvent was removed under reduced pressure to give a yellow gum which was purified by preparative reversed phase HPLC (stationary phase: XBridge C18 OBD, 5 μm, 150×30 mm; mobile phase: 10 mM ammonia bicarbonate (A)-MeCN (B); gradient elution) to give intermediate 10c (40 mg, yield: 20%, purity: 78%) as the first eluting isomer and intermediate 10c2 (23 mg, yield: 11.5%, purity: 68%) as the second eluting isomer. (Note: Based on literature the P(R)-isomer was expected to be the major isomer.) Intermediate 10c1: ESI-MS: m/z 896.2 [M+H]+; intermediate 10c2: ESI-MS: m/z 896.2 [M+H]+.

Step 4: Intermediate 10c (40 mg, 0.045 mmol) was stirred in a concentrated methylamine solution in ethanol at room temperature until complete conversion (ca. 2 h). The reaction mixture was evaporated to dryness under reduced pressure and the residue was dissolved in water. The aqueous solution was washed with DCM and lyophilized, the resulting crude product was purified by preparative reversed phase HPLC (stationary phase: XBridge C18 OBD, 5 μm, 150×30 mm; mobile phase: 10 mM ammonia bicarbonate (A)-MeCN (B); gradient elution) to give Compound (*R) 37. Final conversion into the corresponding sodium salt was done by elution of an aqueous solution over a column packed with a cationic sodium ion-exchange resin to give a white fluffy solid after lyophilization (29 mg, yield: 30% from 10c). $^{1}$H NMR (400 MHz, D$_2$O): 8.63 (s, 1H), 8.26 (d, J=2.8 Hz, 2H), 7.15 (s, 1H), 6.63-6.45 (m, 1H), 6.23 (s, 1H), 5.95-5.68 (m, 1H), 5.29-4.99 (m, 3H), 4.70-4.54 (m, 2H), 4.38 (dd, J=4.1, 12.2 Hz, 1H), 4.31-4.15 (m, 2H), 3.88 (dd, J=2.6, 12.9 Hz, 1H), 3.70 (br d, J=13.1 Hz, 1H); $^{19}$F NMR (376 MHz, deuterium oxide): −196.62 (br s, 1F); $^{31}$P NMR (162 MHz, D$_2$O): 54.30 (s, 1P); ESI-MS: m/z 688.0 [M+H]+.

Using a similar protocol, Compound (*S) 37, sodium salt was prepared from intermediate 10c2 (yield: 15% from intermediate 10c). $^{1}$H NMR (400 MHz, D$_2$O): 8.06-7.81 (m, 3H), 6.83 (s, 1H), 6.34-6.17 (m, 1H), 5.93 (s, 1H), 5.39-5.15 (m, 1H), 4.96-4.75 (m, 3H), 4.33 (d, J=11.5 Hz, 2H), 4.13 (dd, J=7.3, 12.0 Hz, 1H), 4.01 (s, 2H), 3.63 (br dd, J=2.5, 13.1 Hz, 1H), 3.47 (br d, J=12.8 Hz, 1H); $^{19}$F NMR (376 MHz, D$_2$O): −196.37 (br s, 1F); $^{31}$P NMR (162 MHz, D$_2$O): 54.18 (s, 1P); ESI-MS: m/z 688.0 [M+H]+.

Example 11: Compound 30

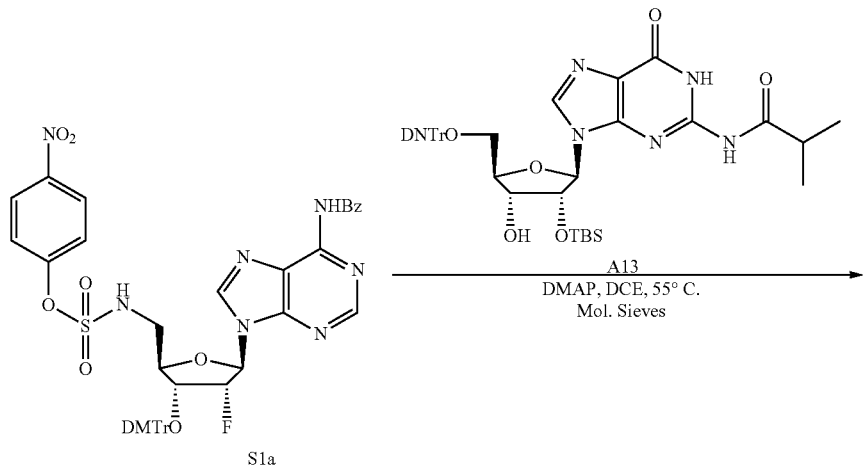

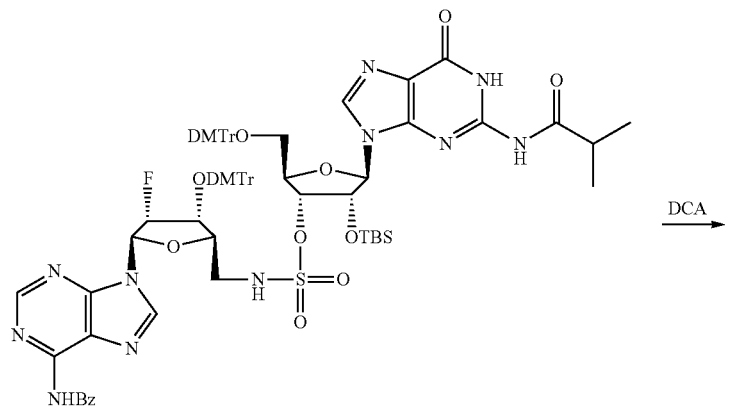

-continued
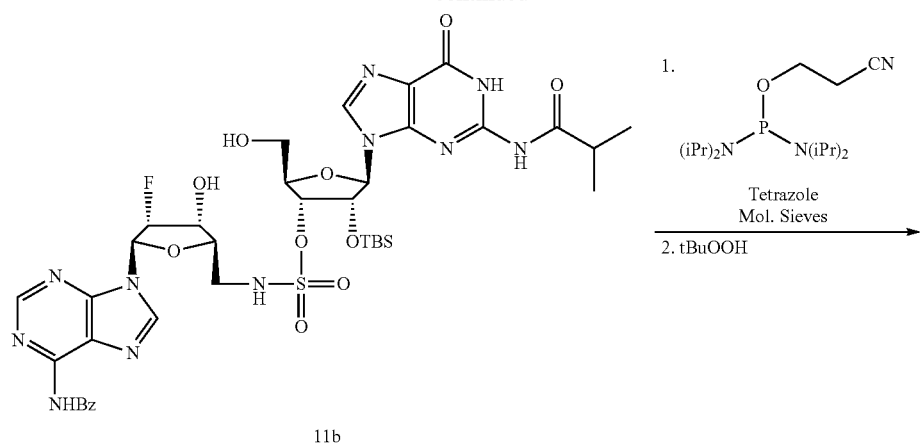
11b
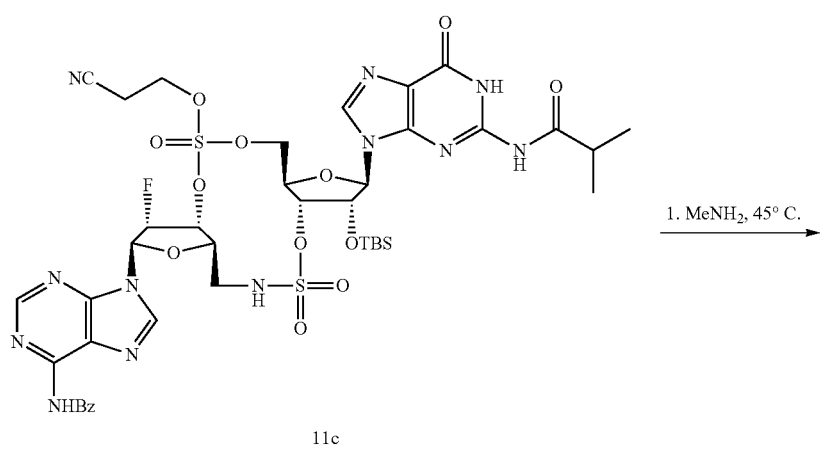
11c
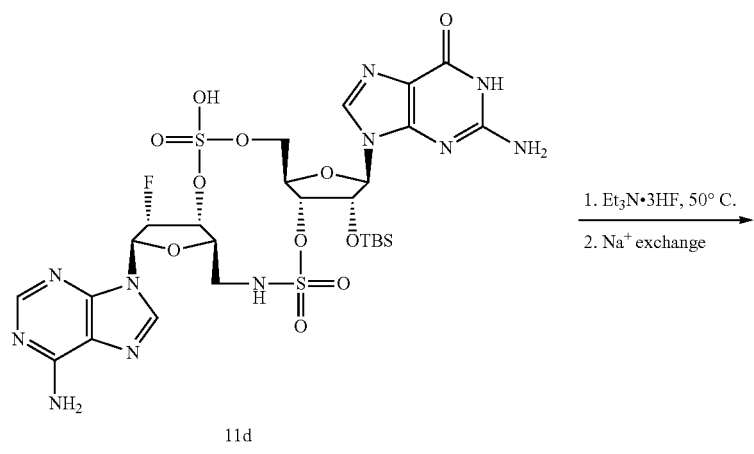
11d

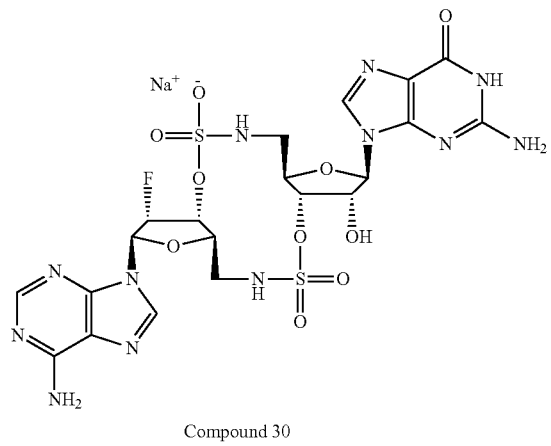

Compound 30

Step 1: A mixture of intermediate S1a (741 mg, 0.846 mmol), intermediate A13 (500 mg, 0.651 mmol) and molecular sieves in DCE (20 mL) was stirred under $N_2$ for 30 min at room temperature. DMAP (398 mg, 3.26 mmol) was added and stirring was continued for 12 h at 55° C. The reaction solution was cooled to room temperature and filtered. The filtrate was diluted with DCM, washed with brine and saturated aqueous $NaHCO_3$, dried over anhydrous $Na_2SO_4$, filtered and concentrated under reduced pressure. The crude product was purified silica column chromatography (gradient elution: 0 to 5% MeOH in DCM) followed by preparative reversed phase HPLC (stationary phase: Phenomenex Synergi Max-RP, 10 μm, 250×50 mm; mobile phase: water (A)-MeCN (B), gradient elution) to give intermediate 11a (yield: 45%) as a white solid. ESI-MS: m/z 753.2 [(M+2H)/2]$^+$.

Step 2: A solution of intermediate 11a (800 mg, 0.48 mmol) in DCM (20 mL) was treated with water (86 mg, 4.79 mmol) and DCA (123 mg, 0.96 mmol). The reaction mixture was stirred at room temperature until complete conversion (ca. 5 h). MeOH (5 mL) and pyridine (378 mg, 4.79 mmol) were added, and stirring was continued for an additional 2 h. The solution was next concentrated under pressure. The crude product was purified by silica column chromatography (gradient elution: 0 to 8% MeOH in DCM) to give intermediate 11b as a white solid (yield: 81%). $^1$H NMR (400 MHz, DMSO-$d_6$) δ ppm 12.05 (s, 1H), 11.78 (s, 1H), 11.26 (s, 1H), 8.77 (s, 1H), 8.66 (s, 1H), 8.57 (br d, J=4.3 Hz, 1H), 8.24-8.20 (m, 1H), 8.02 (br d, J=7.5 Hz, 2H), 7.69-7.60 (m, 1H), 7.56-7.52 (m, 1H), 7.38 (dd, J=5.8, 7.5 Hz, 1H), 6.53-6.33 (m, 1H), 6.06-5.89 (m, 1H), 5.72-5.54 (m, 1H), 5.05 (br s, 1H), 4.80-4.72 (m, 1H), 4.71-4.60 (m, 1H), 4.55 (d, J=4.8 Hz, 1H), 4.39 (dd, J=4.8, 10.0 Hz, 1H), 4.13-4.06 (m, 1H), 3.57-3.46 (m, 1H), 3.31-3.24 (m, 1H), 3.17 (s, 1H), 2.77 (sept, J=6.8 Hz, 1H), 2.42-2.30 (m, 1H), 2.21 (td, J=9.2, 12.8 Hz, 1H), 1.86-1.74 (m, 1H), 1.11 (d, J=6.9 Hz, 6H), 1.09 (s, 3H), 0.60 (s, 9H), −0.12 (s, 3H), −0.43 (s, 3H); ESI-MS: m/z 900.5 [M+H]$^+$.

Step 3: (Note: reaction solvents were dried on an appropriate drying agent before use.) A solution of intermediate 11b (200 mg, 0.222 mmol) in THF (4 ml) was treated with activated molecular sieves for 20 min under $N_2$. Next, a solution of 1H-tetrazole (3.95 mL, 0.45 M in MeCN, 1.78 mmol) was added, followed by the addition of 2-cyanoethyl-N,N,N',N'-tetra(isopropyl)phosphorodiamidite (134 mg, 0.444 mmol) in THF (1 mL). The resulting reaction mixture was stirred for 1.5 h. Next, a solution of tBuOOH (204 μL, 5.5 M in decane, 1.12 mmol) was added and stirring was continued for 1.5 h. The molecular sieves were removed by filtration, the filtrate was concentrated under reduced pressure and transferred to a silica column for purification (gradient elution: 0 to 15% MeOH in DCM) affording intermediate 11c (151 mg, yield: 54%). ESI-MS: m/z 1015.4 [M+H]$^+$.

Step 4: Intermediate 11c (151 mg, 0.149 mmol) was stirred in a concentrated methylamine solution in ethanol (5 mL) at 45° C. until complete conversion. The reaction mixture was concentrated under pressure. The residue was purified by preparative reversed phase HPLC (stationary phase: XBridge C18 OBD, 10 μm, 150×30 mm; mobile phase: 10 mM ammonia bicarbonate (A)-MeCN (B); gradient elution) to give intermediate 11d (55 mg, yield: 45%). ESI-MS: m/z=788.1 [M+H]$^+$.

Step 5: A solution of intermediate 11d (55 mg, 0.070 mmol) in pyridine (1.5 mL) to which Et$_3$N (424 mg, 4.19 mmol) and Et$_3$N.3HF (337 mg, 2.09 mmol) were added was stirred at 50° C. for 4 h. The reaction mixture was cooled to room temperature, THF (3 mL) and isopropoxytrimethylsilane (831 mg, 6.28 mmol) were added and stirring was continued for 2 h. The solvent was removed under reduced pressure, the resulting residue was purified by preparative reversed phase HPLC (stationary phase: XBridge C18 OBD, 10 μm, 150×30 mm; mobile phase: 10 mM ammonia bicarbonate (A)-MeCN (B); gradient elution) to give Compound 30. Final conversion into the corresponding sodium salt was done by elution of an aqueous solution over a column packed with a cationic sodium ion-exchange resin to give a white fluffy solid after lyophilization (18 mg, yield: 37% from 11d). $^1$H NMR (400 MHz, D$_2$O) δ ppm 8.61 (br s, 1H), 8.24 (s, 1H), 8.13 (br s, 1H), 6.91-6.77 (m, 1H), 5.84-5.64 (m, 1H), 5.63-5.51 (m, 1H), 5.47 (br s, 1H), 5.11 (br d, J=6.8 Hz, 1H), 4.89 (br d, J=9.5 Hz, 2H), 4.53-4.41 (m, 2H), 4.16 (br d, J=12.0 Hz, 1H), 3.96 (br d, J=13.2 Hz, 1H), 3.06 (br s, 2H), 2.88-2.74 (m, 1H); $^{19}$F NMR (376 MHz, D$_2$O) δ ppm −195.112 (s, 1F); $^{31}$P NMR (162 MHz, D$_2$O) δ ppm 0.931 (s, 1P); ESI-MS: m/z 674.1 [M+H]$^+$.

Compound 48 was prepared in an analogous way starting from intermediates A19 and S1a and the analytical data is shown in Table 2.

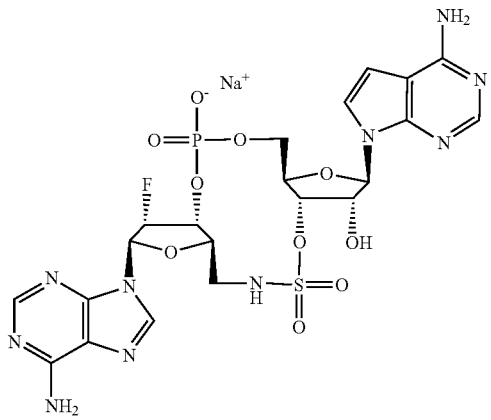

48

Example 12: Compound 28

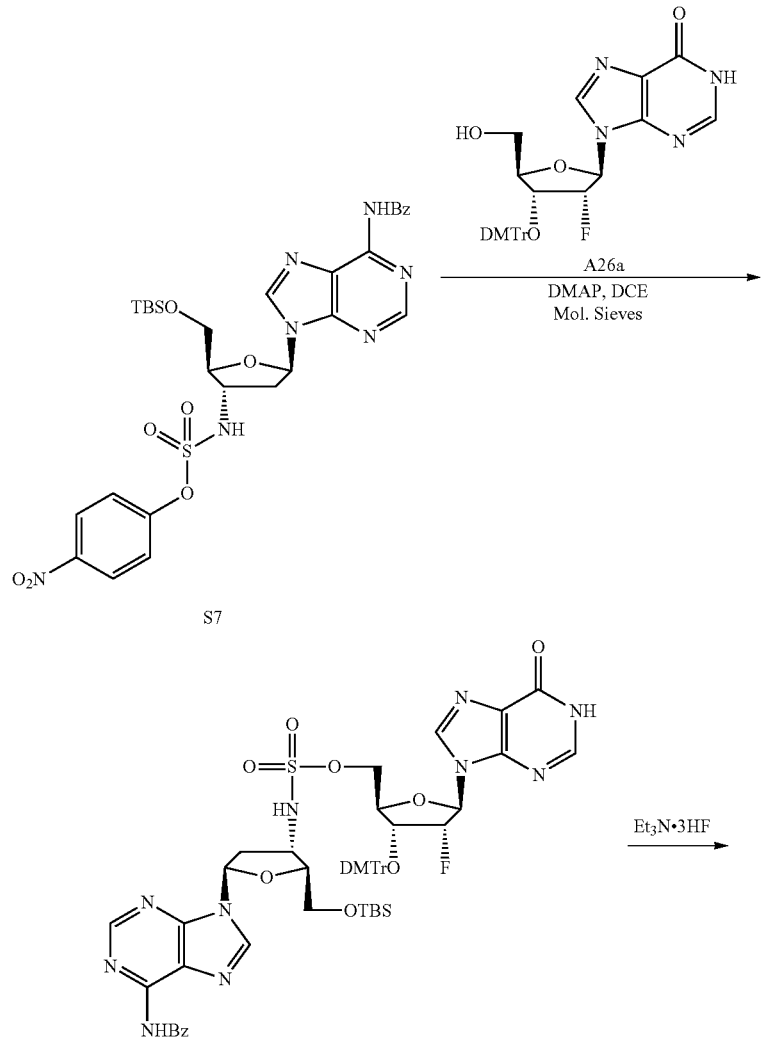

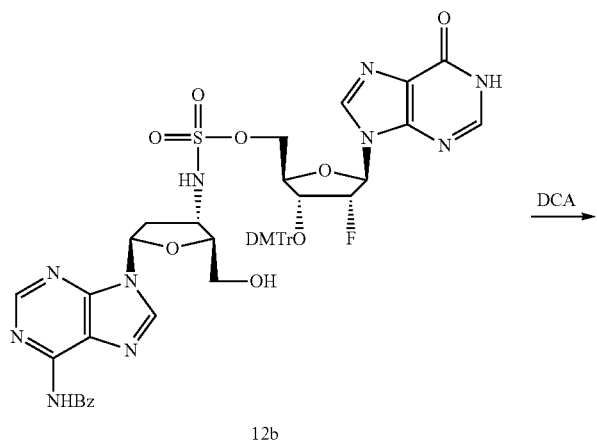
12b
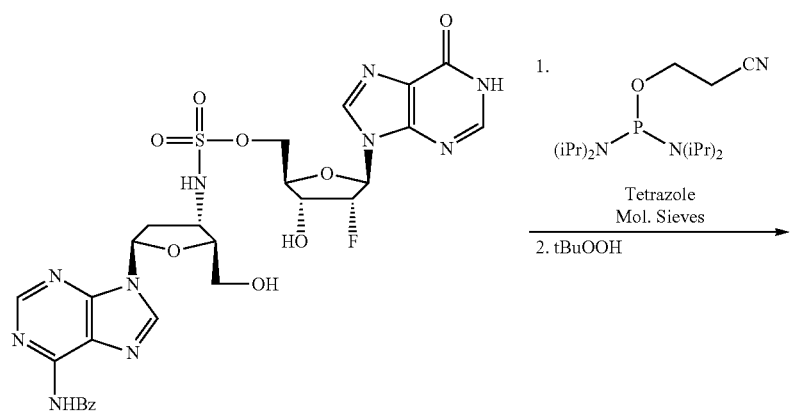
11b
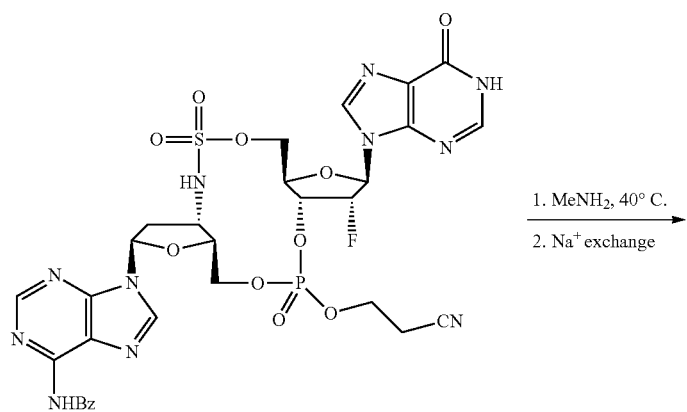
12d

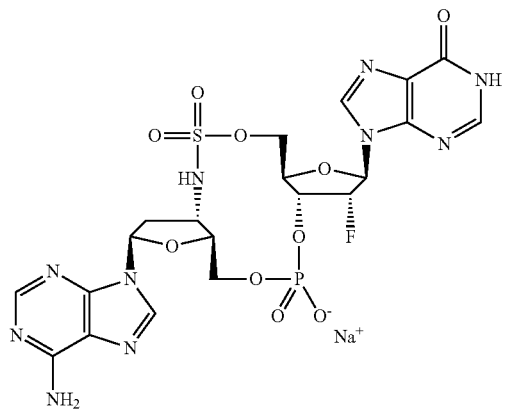

Compound 28

Step 1: (Note: reaction solvents were dried on an appropriate drying agent before use.) A reaction flask was charged with DMAP (2.44 g, 20 mmol), dry DCE (11 mL) and activated molecular sieves. The resulting mixture was stirred at room temperature for 2 h under inert atmosphere. Simultaneously, a solution of intermediate A26a (2.50 g, 4.40 mmol) and a solution of intermediate S7 (2.68 g, 4.0 mmol), each in dry DCE (2×11 mL), were dried on activated molecular sieves (ca. 2 h). Both solutions were successively transferred to the reaction flask. The resulting reaction mixture was stirred overnight. The molecular sieves were removed by filtration and thoroughly rinsed with DCM. The filtrate was washed with saturated aqueous NaHCO$_3$, the aqueous phase was extracted with DCM. The combined organic phases were dried over Na$_2$SO$_4$, filtered, and concentrated under reduced pressure. The residue was purified by column chromatography over silica (gradient elution: 1 to 5% MeOH in DCM) to give pure intermediate 12a (3.45 g, yield: 78%). ESI-MS: m/z 1103.4 [M+H]$^+$.

Step 2: A solution of intermediate 12a (3.35 g, 3.04 mmol) in pyridine (60.8 mL) to which Et$_3$N (21.2 mL, 153 mmol) and Et$_3$N.3HF (4.95 mL, 30.4 mmol) were added, was stirred at 45° C. until complete conversion (ca. 1.5 h). The reaction mixture was cooled to room temperature, isopropoxytrimethylsilane (32.4 mL, 182.4 mmol) was added and stirring was continued for 2 h. The solvent was removed under reduced pressure, the resulting residue was purified by column chromatography over silica (gradient elution: 0 to 4% MeOH in DCM) to obtain intermediate 12b as a yellow solid (1.41 g, yield: 47%). ESI-MS: m/z 989.1 [M+H]$^+$.

Step 3: Intermediate 12b (1.41 g, 1.43 mmol) was dissolved in DCM (71.5 mL), followed by the addition of H$_2$O (130 μL, 7.49 mmol) and DCA (833 mg, 6.5 mmol). The reaction mixture was stirred at room temperature until complete conversion (ca.1 h). Pyridine (0.58 mL, 7.15 mmol) and MeOH (27 mL) were added with stirring. The mixture was partially concentrated and transferred to a silica gel column for purification (gradient elution: 10 to 18% MeOH in DCM) to obtain pure intermediate 12c (0.46 g, yield: 46%). $^1$H NMR (300 MHz, DMSO-d$_6$) δ ppm 12.47 (br s, 1H), 11.21 (s, 1H), 8.74 (s, 1H), 8.70 (br d, J=7.6 Hz, 1H), 8.65 (s, 1H), 8.20 (s, 1H), 8.03-8.09 (m, 3H), 7.62-7.68 (m, 1H), 7.53-7.59 (m, 2H), 6.47 (t, J=6.4 Hz, 1H), 6.26 (d, J=19.3 Hz, 1H), 6.01 (d, J=6.4 Hz, 1H), 5.43 (dd, J=52.5, 3.2 Hz, 1H), 5.10 (t, J=5.3 Hz, 1H), 4.50-4.67 (m, 1H), 4.40-4.50 (m, 1H), 4.15-4.33 (m, 3H), 3.92-3.97 (m, 1H), 3.54-3.61 (m, 1H), 3.40-3.52 (m, 1H), 2.77-2.92 (m, 1H), 2.41-2.60 (m, 1H); ESI-MS: m/z 687.2 [M+H]$^+$.

Step 4: (Note: reaction solvents were dried on an appropriate drying agent before use.) To a solution of intermediate 12c (200 mg, 0.291 mmol) in dry DMF (4 mL) were added molecular sieves and 1H-tetrazole (5.1 mL, 0.45 M in MeCN, dried on molecular sieves before use). The resulting heterogeneous mixture was stirred for 30 min under N$_2$. Next, a solution of 2-cyanoethyl-N,N,N',N'-tetra(isopropyl) phosphorodiamidite in dry MeCN (158 mg in 1.5 mL MeCN, 0.52 mmol) was added dropwise over 35 min after which the reaction mixture was stirred for an additional 2 h at room temperature. Next, a solution of tBuOOH (466 μL, 5.0 M in decane, 2.33 mmol) was added and stirring was continued for 30 min. The reaction mixture was filtered through a pad of diatomaceous earth and concentrated under vacuum. The resulting residue was purified by column chromatography over silica (gradient elution: 0 to 16% MeOH in DCM) to give intermediate 12d (145 mg, yield: 62%). ESI-MS: m/z 802.3 [M+H]$^+$.

Step 5: Intermediate 12d (145 mg, 0.18 mmol) was stirred in a concentrated methylamine solution in ethanol at room temperature until complete conversion (ca. 2 h). The reaction mixture was evaporated to dryness under reduced pressure after which the residue was dissolved in water. The resulting aqueous solution was washed with DCM and lyophilized. The crude product was purified by preparative reversed phase HPLC (stationary phase: XBridge C18 OBD, 5 μm, 150×30 mm; mobile phase: 10 mM ammonia bicarbonate (A)-MeCN (B); gradient elution) to give Compound 28 as a white solid after lyophilization. Final conversion into the sodium salt was done by elution of an aqueous solution over a column packed with a cationic sodium ion-exchange resin to give a white fluffy solid after lyophilization (41 mg, yield: 35% from 12d). $^1$H NMR (400 MHz, D$_2$O): δ ppm 8.05 (s, 1H), 7.85 (s, 1H), 7.65 (s, 1H), 7.47 (s, 1H), 6.12-5.97 (m, 2H), 5.91-5.67 (m, 1H), 5.31-5.09 (m, 1H), 4.58 (d, J=9.0 Hz, 1H), 4.48-4.29 (m, 3H), 4.28-4.18 (m, 1H), 4.03 (dd, J=6.0, 11.8 Hz, 1H), 3.07 (dd, J=7.0, 13.8 Hz, 1H), 2.51 (ddd, J=6.8, 10.9, 13.7 Hz, 1H); $^{19}$F NMR (376 MHz, D$_2$O) δ ppm −204.12 (s, 1F); $^{31}$P NMR (162 MHz, D$_2$O) δ ppm −2.00 (s, 1P); ESI-MS. m/z 645.1 [M+H]$^+$.

Compound 21 was prepared in a similar way starting from intermediates S6 and A27 and the analytical data is shown in Table 2.

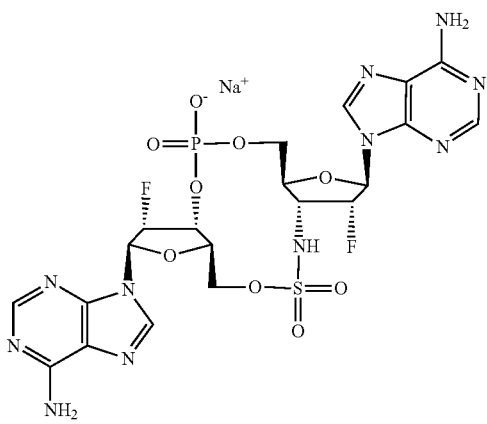

21

Example 13: Compound 47

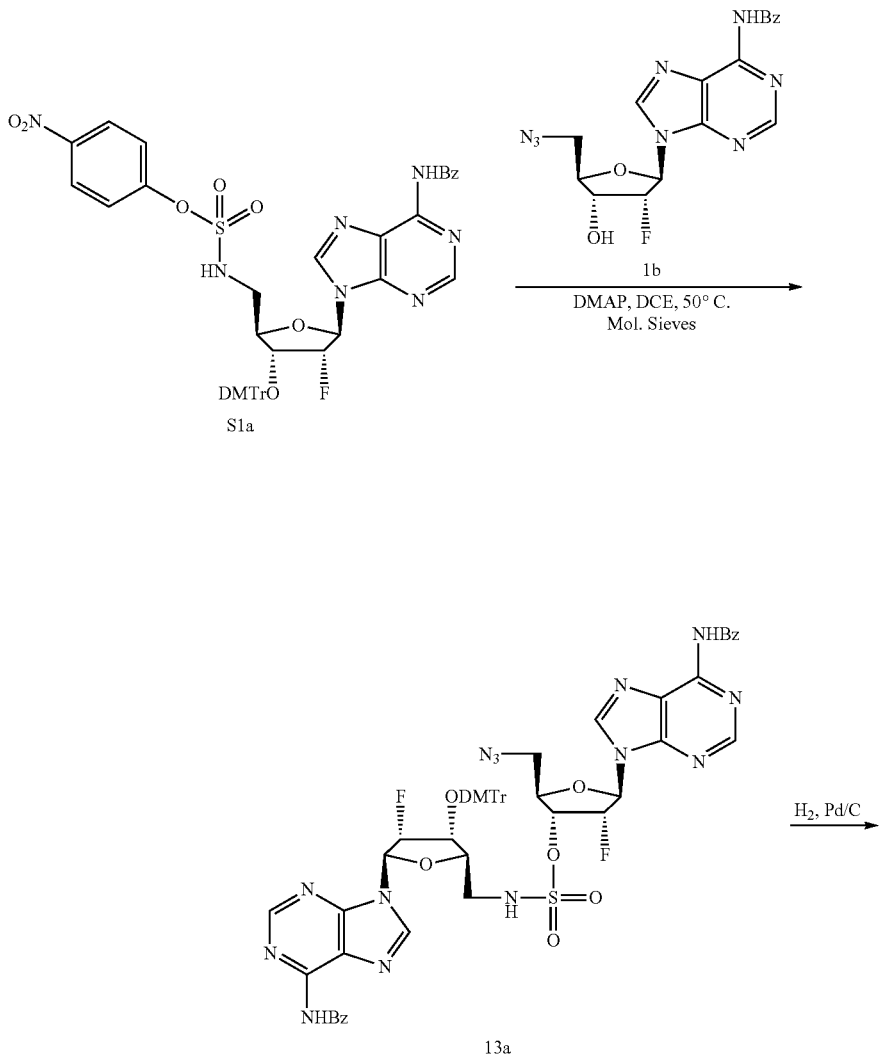

-continued
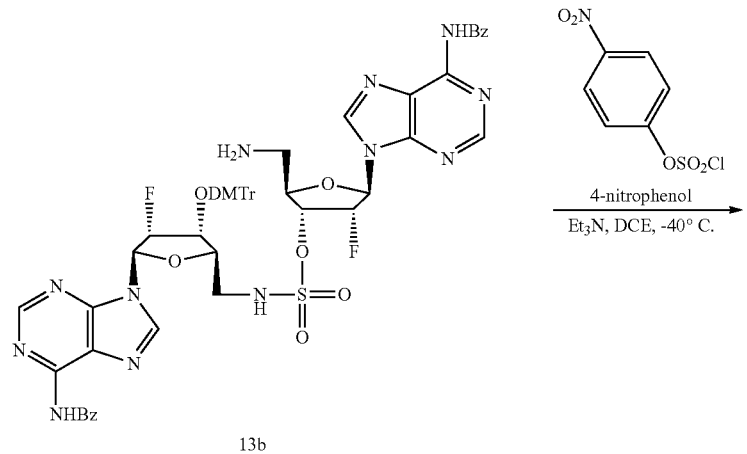
13b
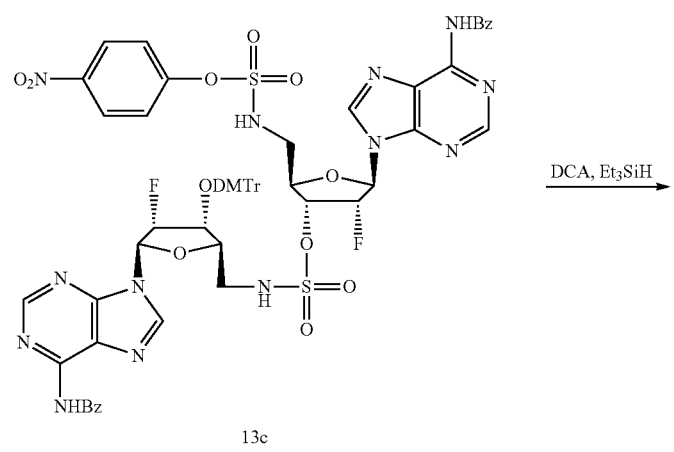
13c
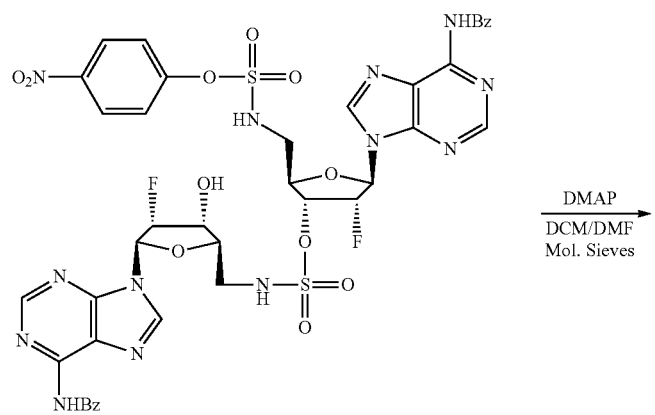
13d

-continued

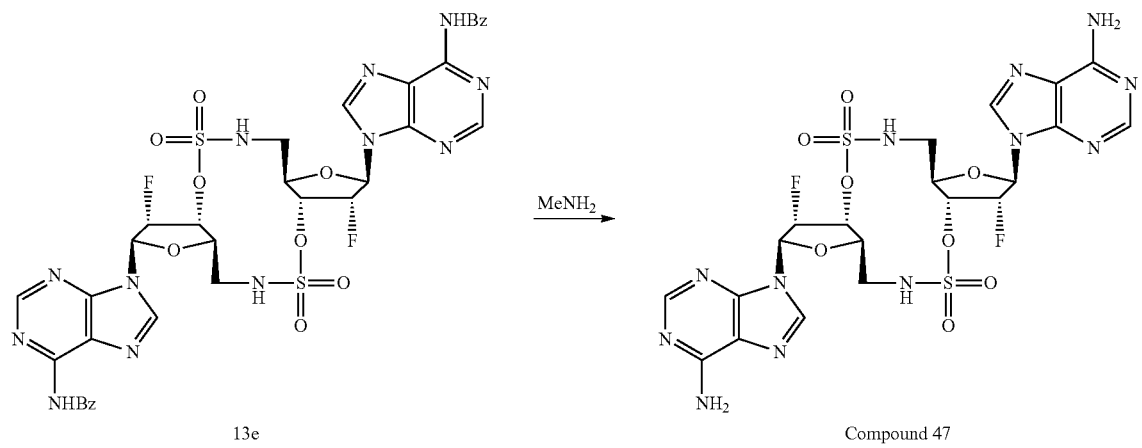

13e → (MeNH₂) → Compound 47

Step 1: (Note: reaction solvents were dried on an appropriate drying agent before use.) A mixture of intermediate S1a (3.29 g, 3.77 mmol) and intermediate 1b (1.00 g, 2.51 mmol) in dry DCE (70 mL) was treated with activated molecular sieves and stirred at room temperature for 30 min under $N_2$. DMAP (1.23 g, 10.04 mmol) was added and the resulting suspension was stirred at 50° C. for 3 h. The molecular sieves were removed by filtration through a pad of diatomaceous earth and the filtrate concentrated under reduced pressure. The resulting residue was dissolved in DCM and washed with saturated aqueous $NH_4Cl$ and $NaHCO_3$. The organic phase was dried with $Na_2SO_4$, filtered and concentrated. The crude product was purified by column chromatography over silica (gradient elution: 0 to 100% EtOAc in petroleum ether) to give intermediate 13a (1.14 g, yield: 40%). ESI-MS: m/z 1136.4 [M+H]$^+$.

Step 2: A solution of intermediate 13a (1.3 g, 1.15 mmol) in THF (70 mL) was hydrogenated at 15 psi on Pd/C (10%, 3.65 g, 3.44 mmol) for 2 h. The catalyst was removed by filtration through a pad of diatomaceous earth and rinsed with THF/MeOH (10/1). The filtrate was concentrated under reduced pressure to give intermediate 13b (835 mg). The crude product was used in the next step without purification. ESI-MS: m/z 1110.1 [M+H]$^+$.

Step 3: A mixture of the above intermediate 13b (835 mg), 4-nitrophenol (628 mg, 4.52 mmol) and $Et_3N$ (1.25 mL, 9.03 mmol) in DCE (20 ml) was treated with activated molecular sieves and stirred for 2 h under $N_2$. The reaction mixture was cooled to −40° C. after which a solution of 4-nitrophenyl chlorosulfate (1.07 g, 4.52 mmol) in DCE (5 mL) was added. The reaction mixture was then slowly warmed to room temperature and stirred for an additional 2 h. Next, the reaction solution was diluted with DCM, filtered and concentrated. The residue was re-dissolved in DCM and washed with saturated aqueous $NaHCO_3$. The organic phase was dried with $Na_2SO_4$, filtered, and concentrated. The residue was purified by flash column chromatography over silica (gradient elution: 0 to 10% MeOH in DCM) to give intermediate 13c (490 mg, impure). ESI-MS: m/z 1310.2 [M+H]$^+$.

Step 4: Triethylsilane (130 mg, 1.122 mmol) and DCA (28 mg, 0.224 mmol) were added to a solution of the above intermediate 13c (490 mg) in DCM (15 mL). The reaction mixture was stirred at room temperature for 12 h after which it was concentrated under reduced pressure. The residue was purified by silica column chromatography (gradient elution: 0-10% MeOH in DCM) to give intermediate 13d (227 mg, yield: 20% from intermediate 13a). ESI-MS: m/z 1008.1 [M+H]$^+$.

Step 5: A solution of intermediate 13d (227 mg, 0.225 mmol) in a DCM/DMF solvent mixture (75/25, 13 mL) was treated with activated molecular sieves and stirred at room temperature for 1 h. DMAP (138 mg, 1.13 mmol) was added and the resulting reaction solution was stirred at room temperature for 2 days. The molecular sieves were removed by filtration and rinsed with DCM. The filtrate was concentrated under reduced pressure. The residue was purified by silica column chromatography (gradient elution: 0 to 5% MeOH in DCM) to give intermediate 13e (50 mg, yield: 25%). ESI-MS: m/z 869.1 [M+H]$^+$.

Step 6: Intermediate 13e (55 mg, 0.063 mmol) was stirred in a concentrated methylamine solution in ethanol (5 mL) at room temperature for 90 min. The resulting reaction mixture was evaporated to dryness under reduced pressure. The residue was dissolved in water and washed with DCM. The crude product obtained after lyophilization was purified by reversed phase HPLC (stationary phase: XBridge C18 OBD, 10 μm, 150×40 mm; mobile phase: 10 mM ammonia bicarbonate (A)-MeCN (B); gradient elution) to give compound 46 (6.9 mg, yield: 16%). $^1$H NMR (400 MHz, $D_2O/CD_3CN$ 1/1) δ ppm 8.77 (br s, 2H), 8.25 (br s, 2H), 7.07 (br d, J=21.8 Hz, 2H), 6.30-6.47 (m, 2H), 6.20 (br d, J=52.2 Hz, 2H), 5.22 (br d, J=9.0 Hz, 2H), 4.42 (br d, J=13.1 Hz, 2H), 4.15 (br d, J=13.3 Hz, 2H); $^{19}$F NMR (376 MHz, $D_2O/CD_3CN$ 1/1) δ ppm −196.05 (br s, 2F); ESI-MS: m/z 661.2 [M+H]$^+$.

The 4-nitrophenyl-sulfamates derivatized nucleosides depicted below were used as intermediates representing examples of formula VI, XVI, XXIV and XXXII as defined hereinbefore. These can be synthesized according through procedures described in Examples 1 (S1a=1e), 3 (S1b=3e), and 14-19.

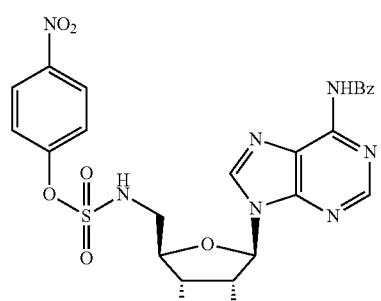
S1a: P = DMTr
S1b: P = TBS
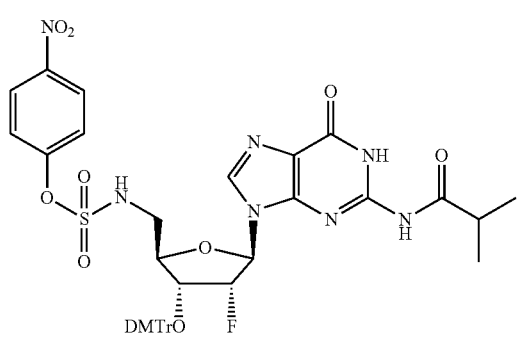
S2
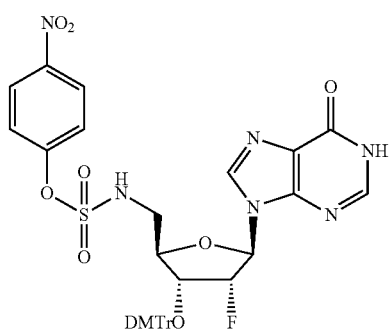
S3
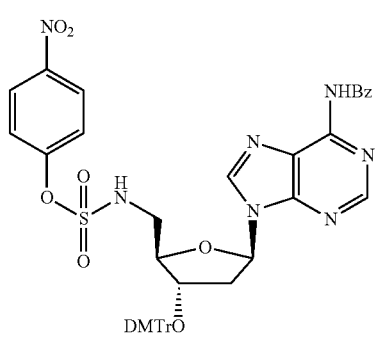
S4
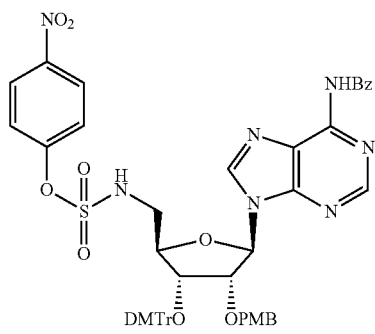
S5
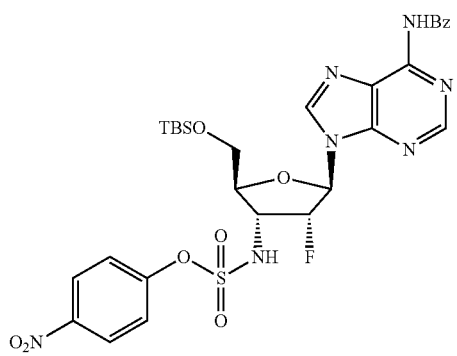
S6
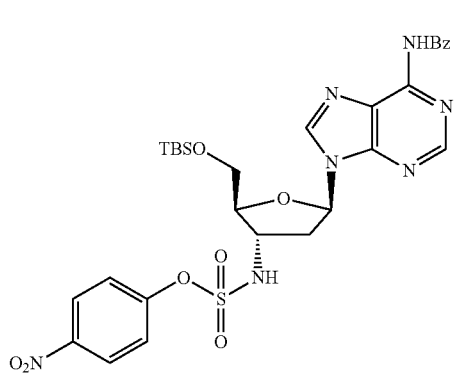
S7
Example 14: Synthesis of Intermediate S2
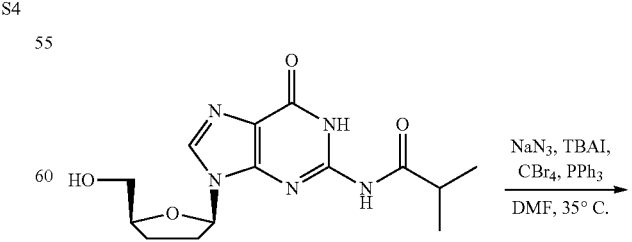
14a

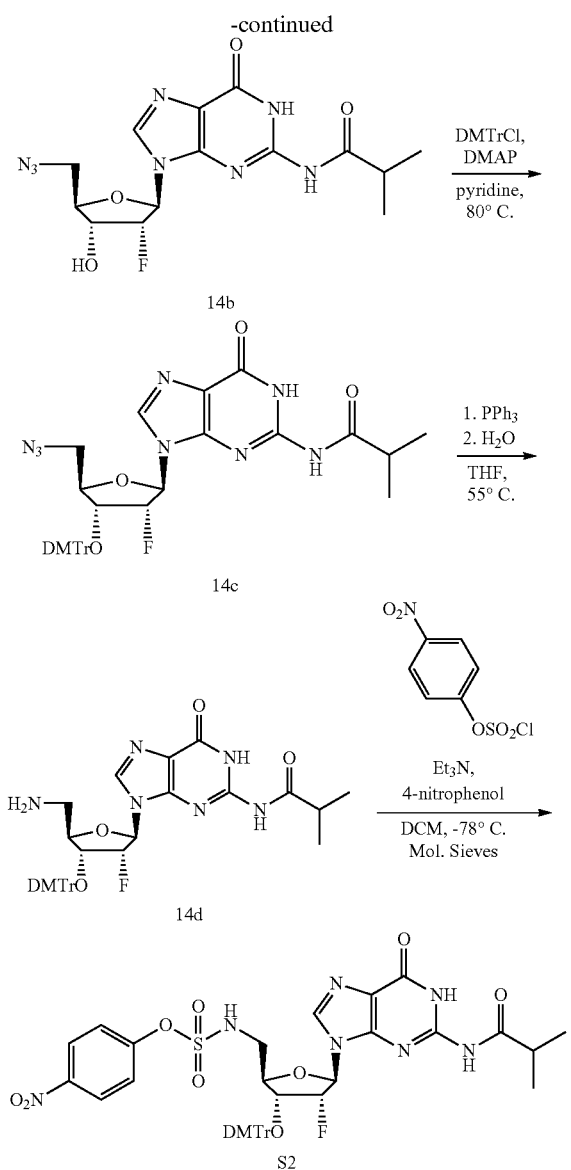

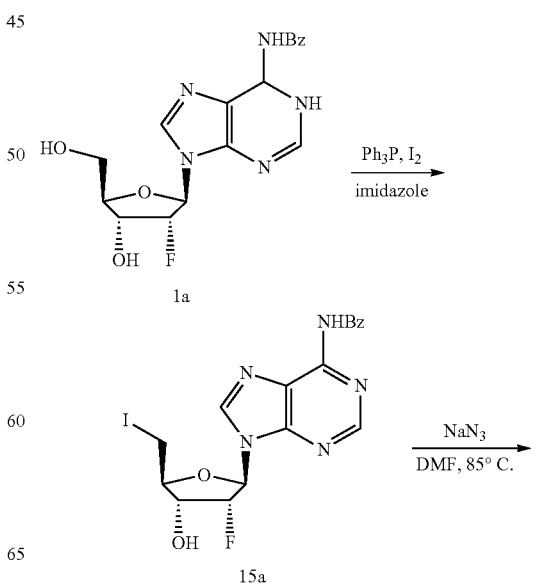

Step 1: CBr₄ (14.0 g, 42.22 mmol) was added portionwise to a stirred suspension of 2'-fluoro-N₂-isobutyryl-2'-deoxyguanosine (14a, 10.0 g, 28.14 mmol, CAS: 80681-25-0), triphenylphosphine (11.07 g, 42.22 mmol), TBAI (2.08 g, 5.63 mmol) and NaN₃ (7.38 g, 113.52 mmol) in DMF (100 mL) at 0° C. The reaction mixture was stirred for 2 h at room temperature, followed by stirring for 48 h at 35° C. Next, the reaction mixture was cooled to room temperature, poured into saturated aqueous NaHCO₃ (500 mL) and successively extracted with EtOAc (3×), 2-Me-THF (2×) and DCM/MeOH (10:1, 3×). The combined organic layers were dried on Na₂SO₄, filtered and concentrated under reduced pressure. The resulting residue was purified by column chromatography over silica (gradient elution: 0 to 10% MeOH in DCM) to give intermediate 14b (8.26 g, yield: 77%) as a white foam. ESI-MS: m/z 381.1 [M+H]⁺.

Step 2: A solution of intermediate 14b (7.0 g, 18.405 mmol) in dry pyridine (70 mL), to which DMAP (1.12 g, 9.20 mmol) and DMTrCl (12.47 g, 36.81 mmol) were added, was stirred at 80° C. for 15 h. The reaction mixture was concentrated under reduced pressure. The residue was re- dissolved in EtOAc, the resulting organic phase was washed with water and brine, dried over anhydrous Na₂SO₄, filtered and evaporated under reduced pressure. The crude product was purified by column chromatography over silica (gradient elution: 0 to 80% EtOAc/DCM 1/1 in petroleum ether to give intermediate 14c (10.1 g, yield: 80%) as a yellow foam. ESI-MS: m/z 683.3 [M+H]⁺.

Step 3: Triphenylphosphine (5.65 g, 21.53 mmol) was added to a solution of intermediate 14c (10.5 g, 15.38 mmol) in THF (100 mL). The reaction mixture was stirred at 55° C. for 2 h under N₂. Water (50 mL) was added and stirring was continued for 12 h at 55° C. The reaction solution was concentrated under reduced pressure. The resulting residue was further purified by column chromatography over silica (gradient elution: 0 to 10% MeOH in DCM) to give compound 14d (8.36 g, yield: 83%) as a white foam. ESI-MS: m/z 657.1 [M+H]⁺.

Step 4: Intermediate 14d (4 g, 6.09 mmol), 4-nitrophenol (2.54 g, 18.27 mmol) and Et₃N (3.7 g, 36.55 mmol) were dissolved in dry DCM (150 mL), followed by the addition of activated molecular sieves. The resulting mixture was cooled to −78° C. under N₂. A solution of 4-nitrophenyl chlorosulfate (4.34 g, 18.27 mmol) in dry DCM (50 mL) was added, after which the reaction mixture was allowed to warm to room temperature over 1.5 h. The reaction mixture was filtered through a pad of diatomaceous earth, the filtrate was transferred to a separatory funnel and washed with saturated aqueous NaHCO₃. The organic layer was dried over Na₂SO₄, filtered and concentrated. The residue was purified by column chromatography over silica (gradient elution: 10 to 100% EtOAc in petroleum ether) to give intermediate S2 (yield: 79%). ¹H NMR (400 MHz, CD₃CN) δ ppm 11.76-12.13 (m, 1H), 9.05 (s, 1H), 8.12-8.22 (m, 2H), 7.73 (s, 1H), 7.50-7.57 (m, 2H), 7.29-7.44 (m, 8H), 7.22-7.29 (m, 1H), 7.06 (dd, J=7.0, 4.0 Hz, 1H), 6.81-6.90 (m, 4H), 6.12 (dd, J=14.3, 5.0 Hz, 1H), 4.97 (dt, J=50.9, 5.2 Hz, 1H), 4.36-4.43 (m, 1H), 3.84-3.89 (m, 1H), 3.75 (s, 3H), 3.74 (s, 3H), 3.23 (dt, J=14.2, 3.3 Hz, 1H), 2.98 (ddd, J=13.9, 7.4, 5.0 Hz, 1H), 2.55 (spt, J=6.9 Hz, 1H), 1.16 (d, J=6.8 Hz, 3H), 1.14 (d, J=6.8 Hz, 3H); ¹⁹F NMR (376 MHz, CD₃CN) δ=−204.23 (s, 1F); ESI-MS: m/z 858.2 [M+H]⁺.

Example 15: Synthesis of Intermediate S3

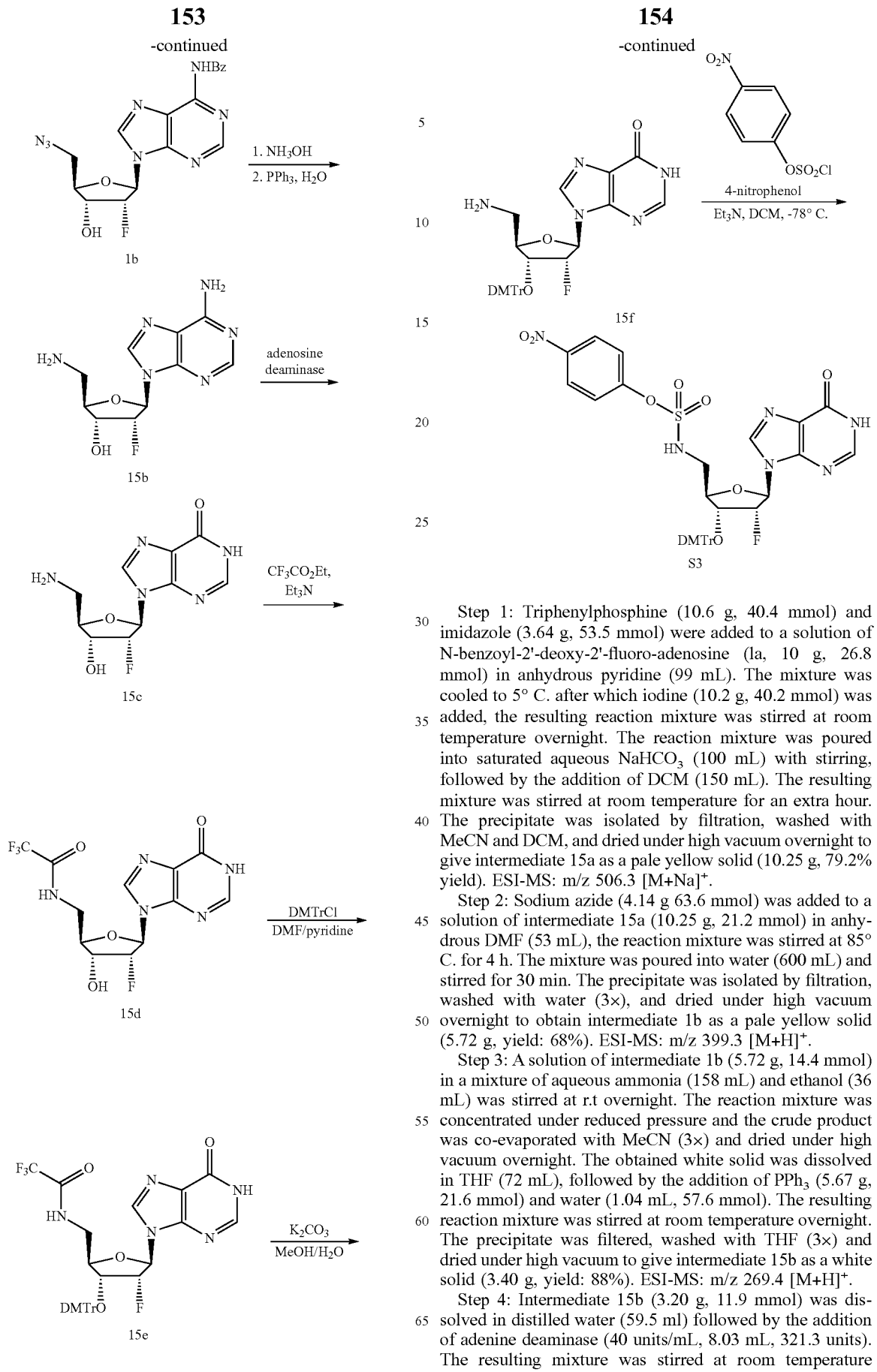

Step 1: Triphenylphosphine (10.6 g, 40.4 mmol) and imidazole (3.64 g, 53.5 mmol) were added to a solution of N-benzoyl-2'-deoxy-2'-fluoro-adenosine (1a, 10 g, 26.8 mmol) in anhydrous pyridine (99 mL). The mixture was cooled to 5° C. after which iodine (10.2 g, 40.2 mmol) was added, the resulting reaction mixture was stirred at room temperature overnight. The reaction mixture was poured into saturated aqueous NaHCO$_3$ (100 mL) with stirring, followed by the addition of DCM (150 mL). The resulting mixture was stirred at room temperature for an extra hour. The precipitate was isolated by filtration, washed with MeCN and DCM, and dried under high vacuum overnight to give intermediate 15a as a pale yellow solid (10.25 g, 79.2% yield). ESI-MS: m/z 506.3 [M+Na]$^+$.

Step 2: Sodium azide (4.14 g, 63.6 mmol) was added to a solution of intermediate 15a (10.25 g, 21.2 mmol) in anhydrous DMF (53 mL), the reaction mixture was stirred at 85° C. for 4 h. The mixture was poured into water (600 mL) and stirred for 30 min. The precipitate was isolated by filtration, washed with water (3×), and dried under high vacuum overnight to obtain intermediate 1b as a pale yellow solid (5.72 g, yield: 68%). ESI-MS: m/z 399.3 [M+H]$^+$.

Step 3: A solution of intermediate 1b (5.72 g, 14.4 mmol) in a mixture of aqueous ammonia (158 mL) and ethanol (36 mL) was stirred at r.t overnight. The reaction mixture was concentrated under reduced pressure and the crude product was co-evaporated with MeCN (3×) and dried under high vacuum overnight. The obtained white solid was dissolved in THF (72 mL), followed by the addition of PPh$_3$ (5.67 g, 21.6 mmol) and water (1.04 mL, 57.6 mmol). The resulting reaction mixture was stirred at room temperature overnight. The precipitate was filtered, washed with THF (3×) and dried under high vacuum to give intermediate 15b as a white solid (3.40 g, yield: 88%). ESI-MS: m/z 269.4 [M+H]$^+$.

Step 4: Intermediate 15b (3.20 g, 11.9 mmol) was dissolved in distilled water (59.5 ml) followed by the addition of adenine deaminase (40 units/mL, 8.03 mL, 321.3 units). The resulting mixture was stirred at room temperature overnight. Upon reaction completion, the mixture was concentrated and aqueous MeCN (5%) was added. The residue was sonicated, the precipitates were isolated by filtration, washed with aqueous MeCN (10%) (3×), and dried under high vacuum to give intermediate 15c as a white solid (2.98 g, yield: 93%). ESI-MS: m/z 292.3 [M+Na]$^+$.

Step 5: Ethyl trifluoroacetate (3.27 mL, 27.5 mmol) was added to a suspension of intermediate 15c (2.98 g, 11.1 mmol) in EtOH (56 mL), followed by the addition of TEA (1.55 mL, 11.1 mmol). The reaction mixture was stirred at 50° C. overnight, after which it was concentrated to dryness. The resulting residue was dissolved in 7% MeOH in DCM (50 mL) and sonicated for 10 min. The solid was isolated by filtration, washed with aqueous MeCN (5%) (3×) and dried under high vacuum overnight to give intermediate 15d as a white solid (3.58 g, 88% yield). ESI-MS: m/z 388.3 [M+Na]$^+$.

Step 6: A solution of intermediate 15d (3.58 g, 9.80 mmol) in a mixture of DMF (32.7 mL) and pyridine (16.3 mL) was stirred at room temperature for 1 h in the presence of a large amount of activated molecular sieves. DMTrCl (6.64 g, 19.6 mmol) was added in two portions (6.64 g+1.66 g, 19.6 mmol+4.9 mmol) with a time interval of 2 h, after which the reaction mixture was heated to 40° C. and stirred for 2 h. Next, the reaction mixture was cooled to room temperature, quenched by the addition of MeOH (10 mL) and poured into water (200 mL). Extraction was done with DCM and EtOAc. The combined organic layers were dried over Na$_2$SO$_4$, filtered, and concentrated to dryness. The crude product was purified by silica gel column chromatography (gradient elution: 2 to 7% MeOH in DCM) to give intermediate 15e as a yellow solid (6.79 g, yield: >99%, residual DMF present). ESI-MS: m/z 668.7 [M+H]$^+$.

Step 7: Aqueous K$_2$CO$_3$ (2.81 g in 17 mL water, 20.3 mmol) was added to a solution of intermediate 15e (6.79 g, 10.2 mmol) in MeOH (34 mL), the reaction mixture was stirred at room temperature overnight. The solvent was then partially concentrated under reduced pressure (until 1/3 volume remained) after which intermediate 15f was precipitated by adding saturated aqueous NaHCO$_3$ (200 mL). The solid was filtered, washed with water, and dried under high vacuum overnight (5.02 g, 86% yield). ESI-MS: m/z 572.8 [M+H]$^+$.

Step 8: Intermediate 15f (5.02 g, 8.78 mmol), 4-nitrophenol (12.2 g, 87.8 mmol) and Et$_3$N (14.7 mL, 105 mmol) were dissolved in DCM (40 mL). The reaction mixture was cooled to −78° C., followed by the dropwise addition of 4-nitrophenyl chlorosulfate (4.59 g, 19.3 mmol) in DCM (4.0 mL). The reaction solution was allowed to warm to room temperature overnight, after which it was diluted with DCM and washed with aqueous 1.0 M NaH$_2$PO$_4$. The organic phase was dried with Na$_2$SO$_4$, filtered and concentrated under reduced pressure. The crude material was purified by silica gel column chromatography to give pure intermediate S3 (2.44 g, yield: 36%). $^1$H NMR (300 MHz, DMSO-d$_6$) δ ppm 12.45 (br d, J=3.5 Hz, 1H), 8.88 (br t, J=5.6 Hz, 1H), 8.27 (d, J=9.4 Hz, 2H), 8.17 (s, 1H), 7.94 (d, J=4.1 Hz, 1H), 7.17-7.57 (m, 11H), 6.90 (dd, J=9.1, 2.6 Hz, 4H), 6.29 (dd, J=18.2, 2.3 Hz, 1H), 4.52-4.87 (m, 2H), 3.93 (br t, J=6.4 Hz, 1H), 3.71 (s, 6H), 2.93-3.05 (m, 1H), 2.78-2.92 (m, 1H); ESI-MS: m/z 773.9 [M+H]$^+$.

Example 16: Synthesis of Intermediate S4

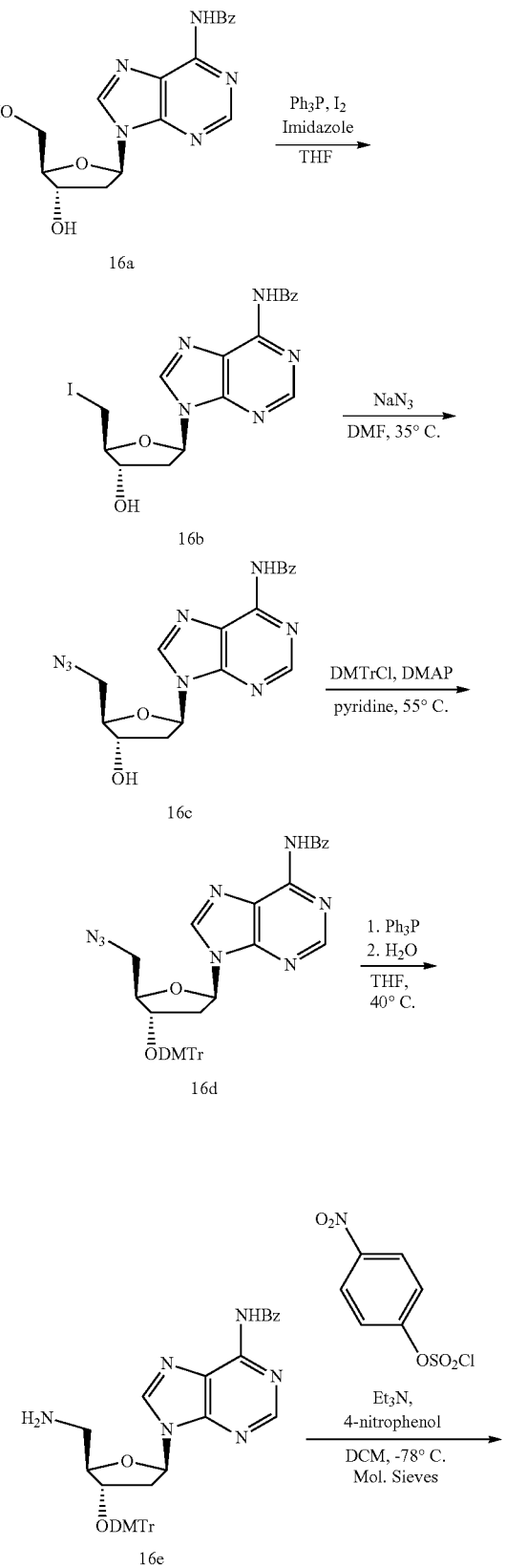

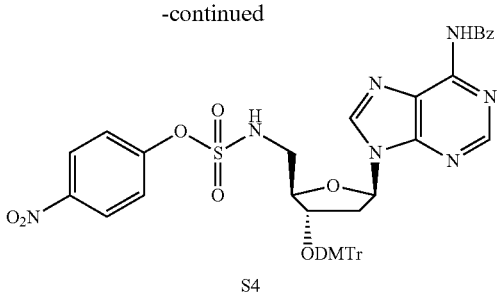

S4

Step 1: A solution of iodine (11.43 g, 45.03 mmol) in THF (50 mL) was added dropwise to a mixture of intermediate 16a (8.0 g, 22.51 mmol), triphenylphosphine (11.81 g, 45.03 mmol) and imidazole (4.6 g, 67.54 mmol) in anhydrous THF (100 mL) at 0° C. The reaction mixture was warmed to room temperature and stirred overnight. The precipitate was removed by filtration and the filtrate concentrated under reduced pressure. The resulting residue was re-dissolved in DCM (300 mL) and washed with saturated aqueous $Na_2S_2O_3$. After 10 min of standing, a white solid precipitated out from the organic layer and was removed by filtration. The aqueous layer was extracted with DCM. The combined organic layers were concentrated under reduced pressure, the resulting residue was triturated in a minimal amount of DCM for 20 min. The resulting precipitate was isolated by filtration. This process (concentration of filtrate, trituration with DCM and filtration) was repeated two times. The collected product was dried under high vacuum to give intermediate 16b (7.5 g, yield: 68%). ESI-MS: m/z 466.0 $[M+H]^+$.

Step 2: A solution of intermediate 16b (7.5 g, 15.26 mmol) and $NaN_3$ (4.96 g, 76.31 mmol) in DMF (160 mL) was stirred at 35° C. overnight. The reaction mixture was cooled to room temperature, diluted with saturated aqueous $Na_2CO_3$ (100 mL) and extracted with EtOAc and DCM. The combined organic layers were dried with anhydrous $Na_2SO_4$ and evaporated under reduced pressure. The residue was purified by silica gel column chromatography (gradient elution: 0-100% EtOAc in petroleum ether, followed by 0 to 10% MeOH in EtOAc) to give intermediate 16c as a white solid (5.4 g, yield: 91%). ESI-MS: m/z 380.9 $[M+H]^+$.

Step 3: DMTrCl (7.18 g, 21.2 mmol) and DMAP (647 mg, 5.3 mmol) were added to a solution of intermediate 16c (4.1 g, 10.6 mmol) in pyridine (80 mL) at 0° C. The reaction mixture was stirred at 55° C. overnight after which it was cooled to room temperature and quenched with methanol (40 mL). Next, water was added and extraction was carried out with EtOAc. The combined organic layers were dried with anhydrous $Na_2SO_4$, filtered and concentrated. The crude product was purified by silica gel column chromatography (gradient elution: 0 to 60% EtOAc in petroleum ether) to give intermediate 16d (6.8 g, yield: 92%). ESI-MS: m/z 683.2 $[M+H]^+$.

Step 4: Triphenylphosphine (3.43 g, 13.06 mmol) was added to a solution of intermediate 16d (6.5 g, 9.33 mmol) in THF (70 mL). The reaction mixture was stirred at 40° C. for 2 h under $N_2$. Next, water (35 mL) was added and stirring was continued at 40° C. overnight. The reaction solution was partially concentrated under pressure, followed by the addition of DCM and water. The water layer was separated and extracted with DCM. The combined organic layers were dried with $Na_2SO_4$, filtered and concentrated under reduced pressure. The crude product was purified by column chromatography over silica (triphenylphosphine oxide was first eluted by isocratic elution with EtOAc, after which a 0 to 10% MeOH in DCM gradient was applied) to give intermediate 16e (5.0 g, yield: 78%). ESI-MS: m/z 657.1 $[M+H]^+$.

Step 5: A solution of intermediate 16e (4.5 g, 6.54 mmol) in DCM (110 ml), to which 4-nitrophenol (9.10 g, 65.43 mmol), $Et_3N$ (3.97 g, 39.26 mmol) and activated molecular sieves were added, was stirred at room temperature for 30 min. The reaction mixture was cooled to −78° C. followed by the addition of 4-nitrophenyl chlorosulfate (7.77 g, 32.71 mmol) in dry DCM (40 mL). Stirring was continued for 2.5 h at −78° C., after which the reaction mixture was allowed to warm to room temperature overnight. The molecular sieves were removed by filtration. The filtrate was washed with saturated aqueous $NaHCO_3$, dried with $Na_2SO_4$ and concentrated under reduced pressure. The crude product was purified by column chromatography over silica gel (gradient elution: 0 to 65% EtOAc in petroleum ether) to give intermediate S4 (4.95 g, yield: 88%). $^1$H NMR (400 MHz, DMSO-$d_6$) δ ppm 11.16 (1H, s), 8.88-8.98 (1H, m), 8.57 (2H, s), 8.21 (2H, br d, J=8.07 Hz), 7.99 (2H, br d, J=7.58 Hz), 7.58-7.65 (1H, m), 7.48-7.55 (2H, m), 7.41 (5H, M), 7.30 (5H, m), 7.18-7.25 (1H, m), 6.88 (4H, br d, J=8.07 Hz), 6.49 (1H, br t, J =7.09 Hz), 4.37 (1H, br s), 3.9' (1H, br s), 3.67 (6H, s), 2.94-3.15 (2H, m), 2.57-2.68 (1H, m), 1.92-2.00 (2H, m); ESI-MS: m/z 858.6 $[M+H]^+$.

Example 17: Synthesis of Intermediate S5

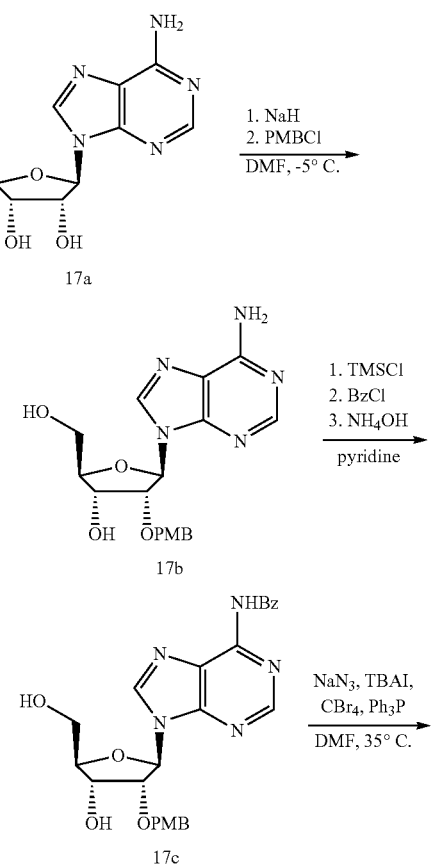

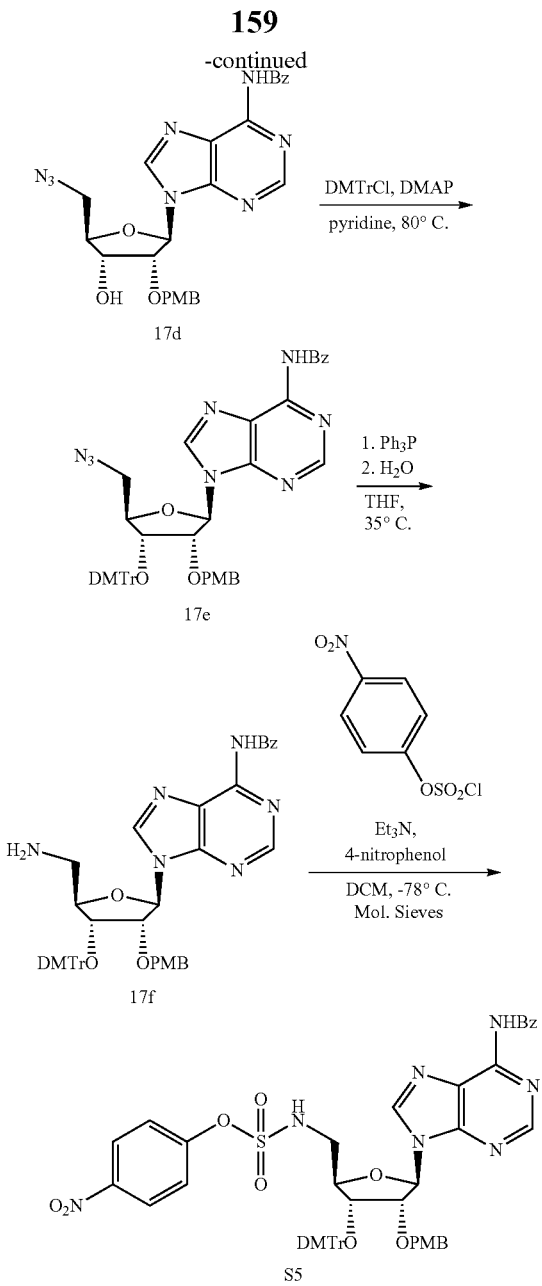

Step 1: NaH (60% in mineral oil, 4.86 g, 121.6 mmol) was added to a solution of adenosine (17a, 25 g, 93.55 mmol) in DMF (900 mL) at −5° C. The reaction mixture was stirred for 1 h followed by the dropwise addition (1 h) of 4-methoxybenzyl chloride (15.2 mL, 112.26 mmol) in DMF (100 mL). The resulting reaction solution was stirred for 12 h at room temperature. Water (30 mL) was added and stirring was continued for 10 min. Concentration under reduced pressure, followed by purification by column chromatography over silica (gradient elution: 0 to 2% MeOH in DCM) resulted in a pure fraction of intermediate 17b (10 g, yield: 28%) and a fraction containing intermediate 17b and its 3'-PMB-protected regio-isomer which was further separated by preparative reversed phase HPLC (Stationary phase: Phenomenex Synergi Max-RP, 10 µm, 250×35 mm; Mobile phase: water (A)-MeCN (B); gradient elution) to give an additional amount of pure intermediate 17b (5 g, yield: 14%). ESI-MS: m/z 387.9 [M+H]$^+$.

Step 2: TMSCl (23.73 mL, 187.15 mmol) was added to a solution of intermediate 17b (14.5 g, 37.43 mmol, dried by co-evaporation with anhydrous pyridine) in dry pyridine (200 mL) at 0° C. The solution was stirred for 2 h at room temperature after which it was cooled again in an ice-bath followed by the addition of benzoyl chloride (8.62 mL, 74.8 mmol). The resulting reaction mixture was stirred at room temperature for 12 h. Next, water (50 mL) and aqueous ammonia (100 mL) were carefully added at 0° C. The resulting solution was stirred for 30 min at room temperature after which it was diluted with brine and extracted with DCM. The combined organic layers were dried over anhydrous Na$_2$SO$_4$, filtered and concentrated under reduced pressure. The residue was triturated in a mixture of EtOAc (150 mL) and MeOH (4 mL) to give intermediate 17c (17 g, yield: 92%) as a white solid. ESI-MS: m/z 491.9 [M+H]$^+$.

Step 3: CBr$_4$ (8.6 g, 25.94 mmol) was added portionwise to a stirred suspension of intermediate 17c (8.5 g, 17.29 mmol), triphenylphosphine (6.80g, 25.94 mmol), TBAI (1.28 g, 3.46 mmol) and NaN$_3$ (6.42 g, 98.75 mmol) in DMF (150 mL) at 0° C. The reaction mixture was stirred for 2 h at room temperature followed by stirring for 36 h at 35° C. Next, saturated aqueous NaHCO$_3$ and brine were added (room temperature), the resulting mixture was extracted with EtOAc. The combined organic layers were washed with brine, dried on Na$_2$SO$_4$ and concentrated under pressure. The crude product was purified by column chromatography over silica (gradient elution: 0 to 100% EtOAc/DCM (1/1) in petroleum ether) to give intermediate 17d (15 g, yield: 83%) as a white foam. ESI-MS: m/z 516.8 [M+H]$^+$.

Step 4: DMAP (1.8 g, 30.1 mmol) and DMTrCl (9.8 g, 29.0 mmol) were added to a solution of intermediate 17d (7.5 g, 14.5 mmol) in pyridine (100 mL). The reaction mixture was stirred at 80° C. for 24 h after which it was allowed to cool to room temperature and quenched with methanol (5 mL). Stirring was continued for 10 min, followed by the removal of the solvent under reduced pressure. The resulting residue was re-dissolved DCM. The organic layer was washed with water and brine, dried over anhydrous Na$_2$SO$_4$, filtered and concentrated. The crude product was purified by silica gel column chromatography (0 to 67% EtOAc/DCM (1/1) in petroleum ether) to give intermediate 17e (10 g, yield: 84%) as a yellow solid. ESI-MS: m/z 819.2 [M+H]$^+$.

Step 5: Triphenylphosphine (2.24 g, 8.55 mmol) was added to a solution of intermediate 17e (5.0 g, 6.1 mmol) in THF (50 mL). The reaction mixture was stirred at 40° C. for 2 h under N$_2$, water (25 mL) was added and stirring was continued at 40° C. for 12 h. Next, the reaction solution was cooled to room temperature, diluted with brine and extracted with DCM. The organic layer was washed with brine, dried with Na$_2$SO$_4$ and concentrated under reduced pressure. The crude product was purified by column chromatography over silica (gradient elution: 0 to 9% MeOH in DCM) to give intermediate 17f (4 g, yield: 82%). ESI-MS: m/z 794.3 [M+H]$^+$.

Step 6: A solution of intermediate 17f (4.0 g, 5.0 mmol) in DCM (100 ml), to which 4-nitrophenol (2.1 g, 15 mmol), Et$_3$N (3.1 g, 30 mmol) and activated molecular sieves were added, was stirred at room temperature for 30 min under N$_2$. Next, the reaction mixture was cooled to −78° C. and 4-nitrophenyl chlorosulfate (3.6 g, 15 mmol) in dry DCM (30 mL) was added. Stirring was continued for 2 h at −78° C. after which the reaction mixture was allowed to warm to room temperature and stirred for an additional 1 h. The molecular sieves were removed by filtration and the filtrate washed with saturated aqueous NaHCO$_3$. The aqueous layer was extracted with DCM. The combined organic layers were dried with Na₂SO₄ and concentrated under reduced pressure. The crude product was purified by column chromatography over silica gel (gradient elution: 0 to 65% EtOAc in petroleum ether) to give intermediate S5 (4.4 g, yield: 88%). $^1$H NMR (400 MHz, CD₃CN) δ ppm 9.32 (br s, 1H), 9.30 (br s, 1H), 8.12 (s, 1H), 8.08 (d, J=9.0 Hz, 2H), 7.98-8.03 (m, 3H), 7.61-7.68 (m, 3H), 7.50-7.60 (m, 4H), 7.46 (d, J=8.8 Hz, 2H), 7.32-7.39 (m, 2H), 7.24-7.32 (m, 3H), 6.91 (br d, J=7.8 Hz, 4H), 6.80 (d, J=8.3 Hz, 2H), 6.40 (d, J=8.3 Hz, 2H), 6.12 (d, J=7.8 Hz, 1H), 4.62 (d, J=12.0 Hz, 1H), 4.58 (dd, J=7.7, 5.4 Hz, 1H), 4.48 (d, J=5.3 Hz, 1H), 4.10 (d, J=12.3 Hz, 1H), 3.78 (s, 3H), 3.77 (s, 3H), 3.57 (s, 3H), 3.43 (br s, 1H), 2.98 (br d, J=14.1 Hz, 1H), 2.68-2.80 (m, 1H); ESI-MS: m/z 994.3 [M+H]⁺.

Example 18: Synthesis of Intermediate S6

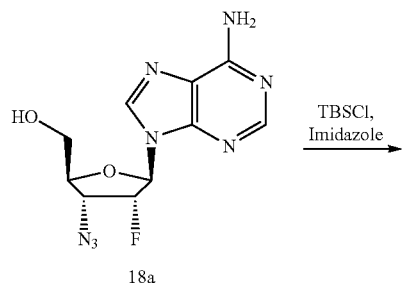
18a

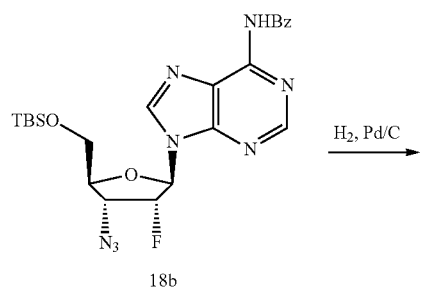
18b

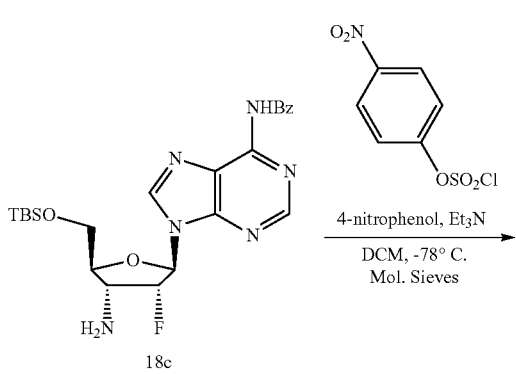
18c

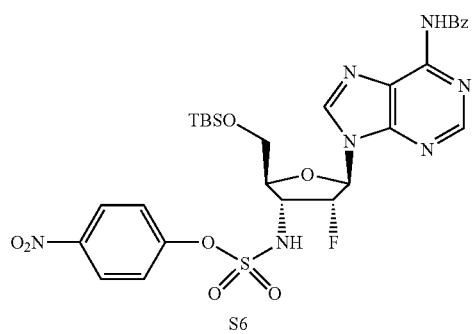
S6

Step 1: A solution of azide 18a (2 g, 5.02 mmol, CAS: 2241580-02-7) in DMF (10 mL), to which imidazole (1.02 g, 15.06 mmol) and TBSCl (1.51 g, 10.04 mmol) were added, was stirred for 2 h at room temperature. The reaction mixture was diluted with EtOAc and washed with water. The aqueous layer was extracted with EtOAc. The combined organic layers were washed with saturated aqueous NaHCO₃ and brine, dried over Na₂SO₄, filtered and concentrated. The crude product was purified by column chromatography over silica gel (gradient elution: 0 to 15% MeOH in DCM) to give intermediate 18b as a yellow solid (2.57 g, yield: 100%). ESI-MS: m/z 513.2 [M+H]⁺.

Step 2: A solution of intermediate 18b (1.29 g, 2.51 mmol) in EtOAc (150 mL) was hydrogenated on Pd/C (10%, 2.95 g) under atmospheric pressure for 2 h. The reaction mixture was next filtered and the filtrate concentrated under reduced pressure. The crude product was purified by column chromatography over silica gel (gradient elution: 0 to 5% MeOH in DCM) to afford intermediate 18c (yield: 69%) as a white solid. $^1$H NMR (400 MHz, CHLOROFORM-c) δ ppm 9.12 (br s, 1H), 8.78 (s, 1H), 8.40 (s, 1H), 8.23 (d, J=9.0 Hz, 2H), 8.02 (d, J=7.9 Hz, 2H), 7.60-7.67 (m, 1H), 7.50-7.58 (m, 2H), 7.45 (d, J=9.0 Hz, 2H), 6.47 (br s, 1H), 6.37 (d, J=18.5 Hz, 1H), 5.66 (dd, J=52.3, 4.2 Hz, 1H), 4.98 (br d, J=26.2 Hz, 1H), 4.29 (br d, J=9.5 Hz, 1H), 4.15 (br d, J=12.1 Hz, 1H), 3.94 (dd, J=12.0, 2.1 Hz, 1H), 0.86 (s, 9H), 0.07 (s, 3H), 0.04 (s, 3H); ESI-MS: m/z 487.1 [M+H]⁺.

Step 3: A solution of intermediate 18c (1.05 g, 2.16 mmol) in DCM (40 ml), to which 4-nitrophenol (900 mg, 6.47 mmol), Et₃N (1.79 mL, 12.95 mmol) and activated molecular sieves were added, was stirred at room temperature for 30 min. The mixture was cooled to −78° C., after which 4-nitrophenyl chlorosulfate (1.54 g, 6.47 mmol) in DCM (10 mL) was added, stirring was continued for 2.5 h at −78° C. The reaction mixture was filtered and washed with aqueous NaHCO₃, the aqueous washing layers were extracted with DCM. The combined organic layers were dried with Na₂SO₄, filtered and concentrated under reduced pressure. The crude product was purified by column chromatography over silica gel (gradient elution: 0 to 100% EtOAc in petroleum ether) to give intermediate S6 as a white solid (1.24 g, yield: 83.5%). ESI-MS: m/z 688.2 [M+H]⁺.

Example 19: Synthesis of Intermediate S7

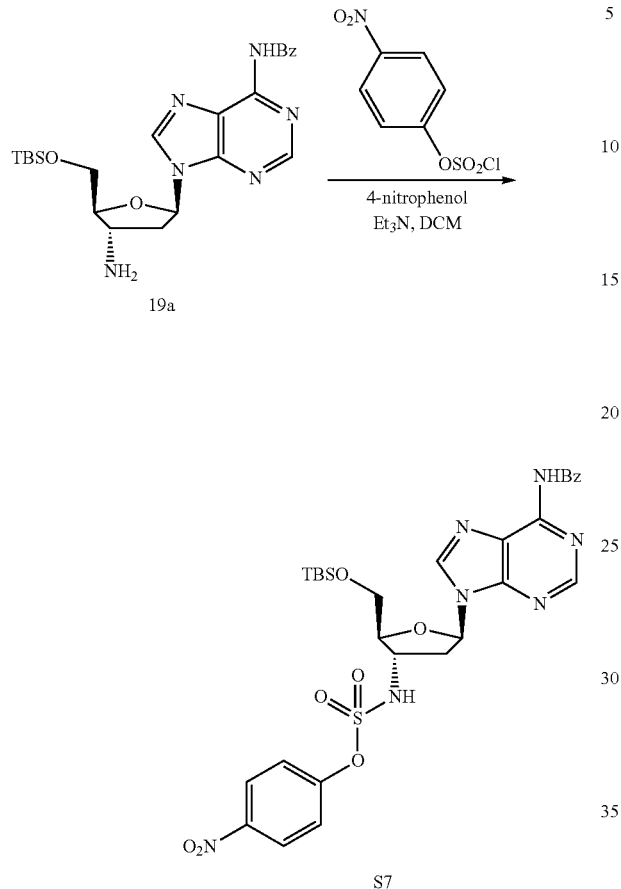

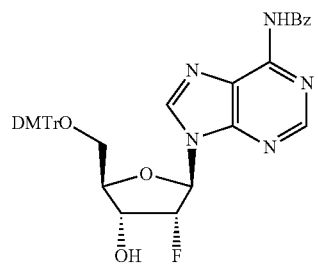

A1

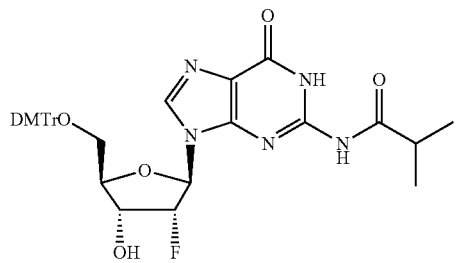

A2

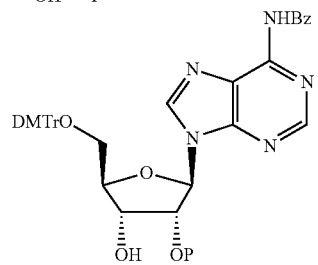

A3a: P = PMB
A3b: P = Bn

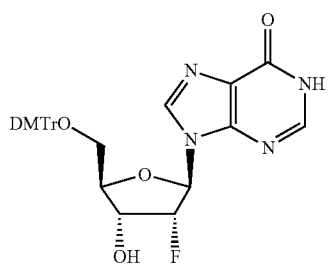

A4

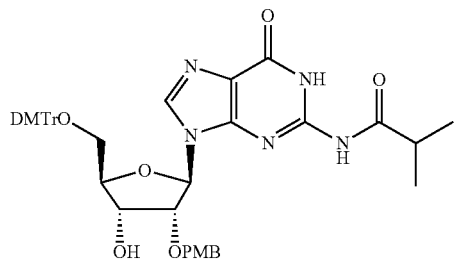

A5

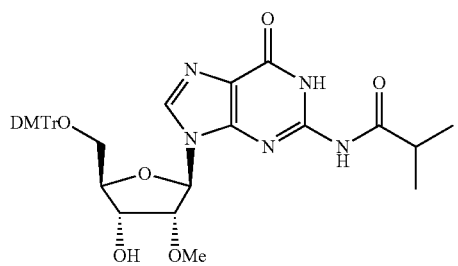

A6

A mixture of amine 19a (3.0 g, 6.40 mmol, CAS: 195375-61-2), 4-nitrophenol (8.90 g, 64 mmol) and Et$_3$N (10.7 mL, 76.8 mmol) in DCM (22 ml) was cooled to −78° C. followed by the dropwise addition of a solution of 4-nitrophenyl chlorosulfate (3.04 g, 12.8 mmol) in DCM (45 mL). The resulting mixture was stirred overnight at room temperature after which it was diluted with DCM (50 mL) and washed with 1.0 M aqueous NaH$_2$PO$_4$. The organic phase was dried with Na$_2$SO$_4$, filtered and concentrated under reduced pressure. The crude material was purified by silica gel column chromatography (gradient elution: 20 to 80% EtOAc in DCM) to give pure intermediate S7 (2.68 g, yield: 62.5%). $^1$H NMR (300 MHz, DMSO-d$_6$) δ ppm 11.20 (br s, 1H), 9.45 (d, J=7.6 Hz, 1H), 8.75 (s, 1H), 8.60 (s, 1H), 8.34-8.39 (m, 2H), 8.02-8.07 (m, 2H), 7.53-7.68 (m, 6H), 6.49 (dd, J=6.7, 5.0 Hz, 1H), 4.50 (quin, J=6.9 Hz, 1H), 3.99-4.07 (m, 1H), 3.87 (dd, J=11.7, 4.1 Hz, 1H), 3.75 (dd, J=11.1, 4.7 Hz, 1H), 3.02-3.12 (m, 1H), 2.59 (dt, J=13.6, 7.0 Hz, 1H), 0.80 (s, 9H), −0.03 (s, 3H), −0.05 (s, 3H); ESI-MS: m/z 670.8 [M+H]$^+$.

The hydroxyl nucleosides mentioned below were used as intermediates representing examples of formula VII, XVII, XXV and XXXIII as defined hereinbefore. Those for which no commercial source, nor literature procedure were available, were prepared through procedures described in examples 20-35.

A7
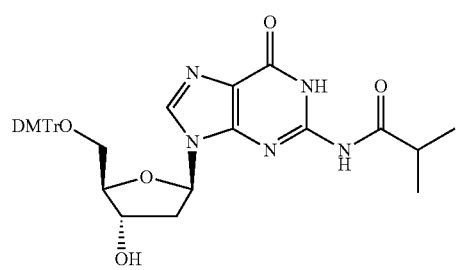
A8
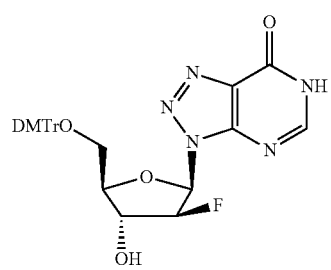
A9
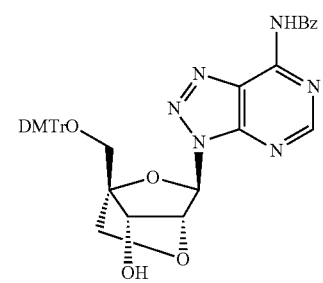
A10
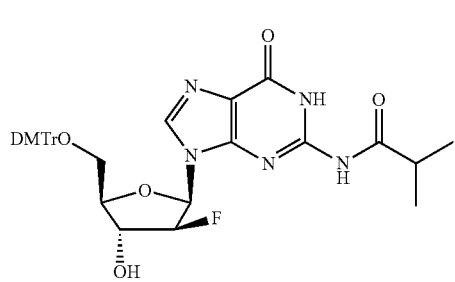
A11
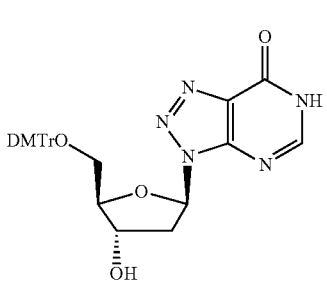
A12
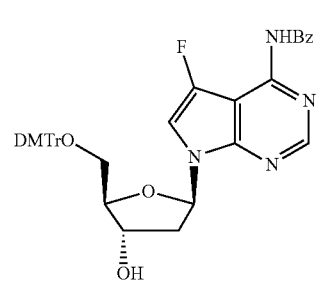
A13
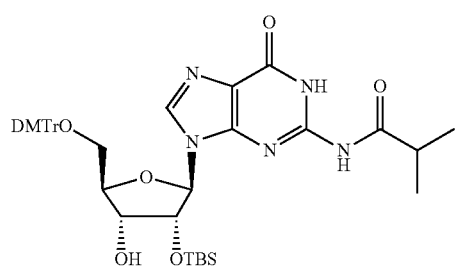
A14
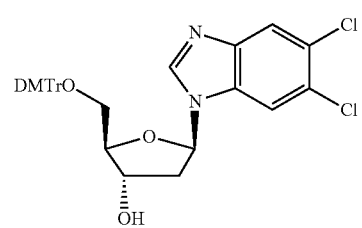
A15
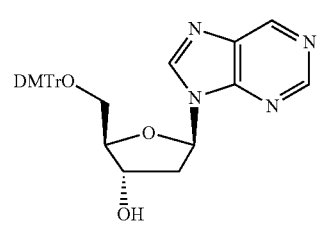
A16
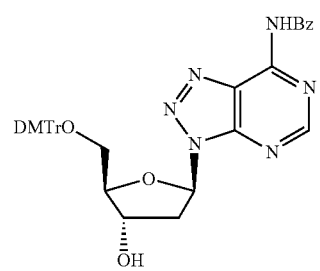
A17
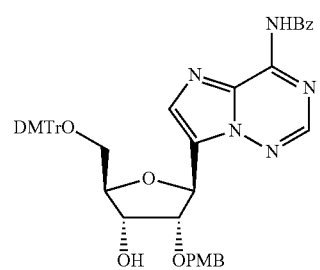
A18
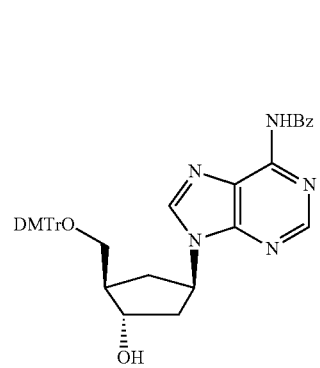

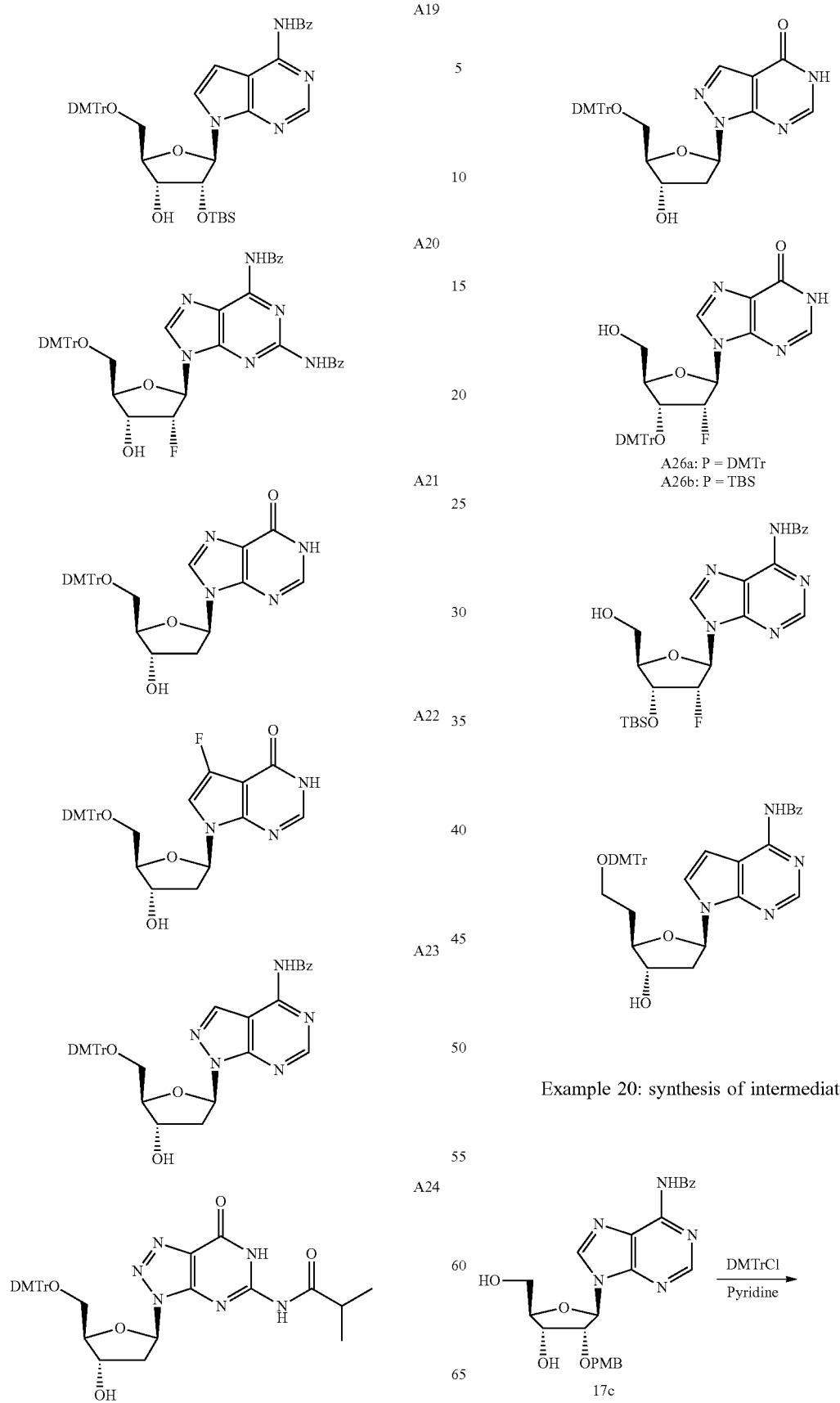
Example 20: synthesis of intermediate A3a

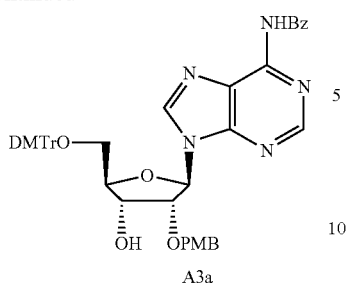

A3a

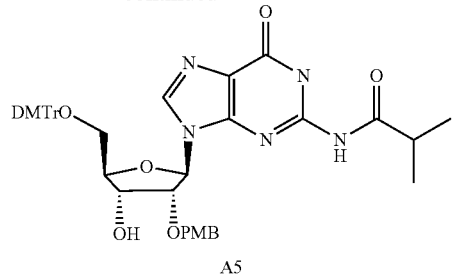

A5

DMTrCl (3.10 g, 9.15 mmol) was added portionwise to a stirred solution of intermediate 17c (3.0 g, 6.1 mmol) in dry pyridine (50 mL) at 0° C. The reaction mixture was stirred at room temperature until complete conversion (ca. 2 h), after which it was diluted with EtOAc and washed with saturated aqueous NaHCO₃ and brine. The organic phase was dried on MgSO₄, filtered, and concentrated. Purification was done by column chromatography over silica (gradient elution: 0 to 100% EtOAc in petroleum ether) to give intermediate A3a as a white solid (4.77 g, yield: 96%). $^1$H NMR (400 MHz, DMSO-d₆) δ ppm 12.07 (s, 1H), 11.56 (s, 1H), 8.02 (s, 1H), 7.28-7.33 (m, 2H), 7.20-7.28 (m, 2H), 7.13-7.20 (m, 7H), 6.71-6.88 (m, 6H), 5.95 (d, J=5.4 Hz, 1H), 5.29 (d, J=5.9 Hz, 1H), 4.63 (d, J=11.7 Hz, 1H), 4.39-4.52 (m, 2H), 4.29-4.39 (m, 1H), 4.04-4.08 (m, 1H), 3.71 (s, 6H), 3.66-3.69 (m, 3H), 3.25 (br dd, J=10.4, 5.7 Hz, 1H), 3.15 (br dd, J=10.5, 2.9 Hz, 1H), 2.74 (spt, J=6.8 Hz, 1H), 1.10 (d, J=6.8 Hz, 6H); ESI-MS: m/z=794.3 [M+H]⁺.

Example 21: Synthesis of Intermediate A5

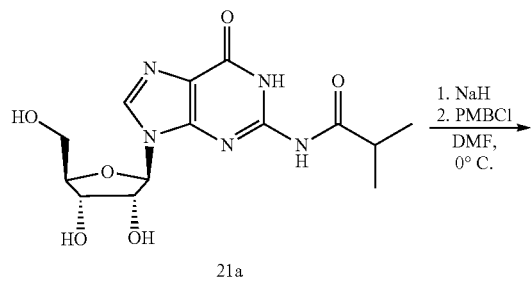

21a

Step 1: NaH (60% in mineral oil, 1.41 g, 35.4 mmol) was added to a suspension of N-isobutyrylguanosine (21a, 5.0 g, 14 mmol, CAS: 64350-24-9) in DMF (120 mL) at 0° C. The reaction mixture was stirred for 90 min after which a solution of 4-methoxybenzyl chloride (2.87 mL, 21.2 mmol) in DMF (10 mL) was added dropwise (1 h), stirring was continued overnight at room temperature Next, the reaction solution was neutralized with 1 N aqueous HCl and evaporated under reduced pressure. The residue was purified by column chromatography over silica (gradient elution: 0 to 10% MeOH in DCM) to give a mixture of intermediate 21b and its 3'-PMB protected regioisomer (structure not shown). Further purification by preparative reversed phase HPLC (stationary phase: Phenomenex Synergi Max-RP, 10 μm, 250×35 mm; mobile phase: water (A)-MeCN (B); gradient elution) afforded pure intermediate 21b (1.5 g, yield: 22%) as the first eluting isomer. ESI-MS: m/z 574.3 [M+H]⁺.

Step 2: A solution of intermediate 21b (1.5 g, 3.2 mmol) and DMTrCl (1.72 g, 5.07 mmol) in pyridine (15 mL), was stirred at room temperature until full conversion. The reaction mixture was diluted with an excess of DCM and washed with saturated aqueous NaHCO₃. The organic phase was dried over anhydrous Na₂SO₄, filtered and concentrated under reduced pressure. The residue was purified by column chromatography over silica (gradient elution: 0 to 100% EtOAc in petroleum ether) to give intermediate A5 as a white solid (1.7 g, yield: 69%). $^1$H NMR (400 MHz, DMSO-d₆) δ ppm 12.07 (s, 1H), 11.56 (s, 1H), 8.02 (s, 1H), 7.28-7.33 (m, 2H), 7.20-7.28 (m, 2H), 7.13-7.20 (m, 7H), 6.71-6.88 (m, 6H), 5.95 (d, J=5.4 Hz, 1H), 5.29 (d, J=5.9 Hz, 1H), 4.63 (d, J=11.7 Hz, 1H), 4.39-4.52 (m, 2H), 4.29-4.39 (m, 1H), 4.04-4.08 (m, 1H), 3.71 (s, 6H), 3.66-3.69 (m, 3H), 3.25 (br dd, J=10.4, 5.7 Hz, 1H), 3.15 (br dd, J=10.5, 2.9 Hz, 1H), 2.74 (spt, J=6.8 Hz, 1H), 1.10 (d, J=6.8 Hz, 6H); ESI-MS: m/z 776.5 [M+H]⁺.

Example 22: Synthesis of Intermediate A9

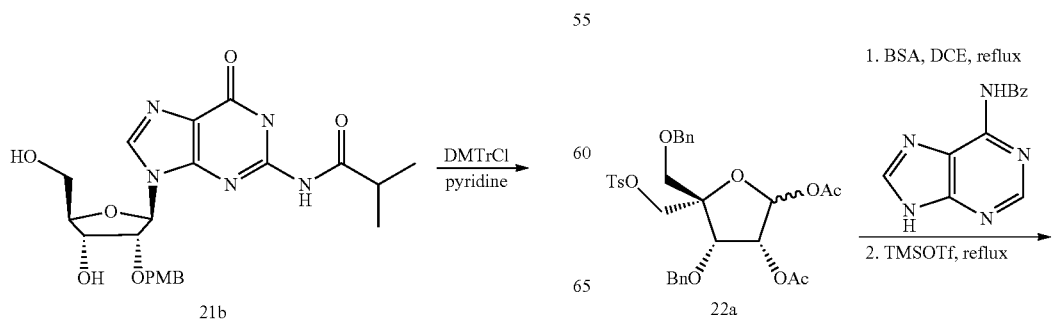

21b                                22a

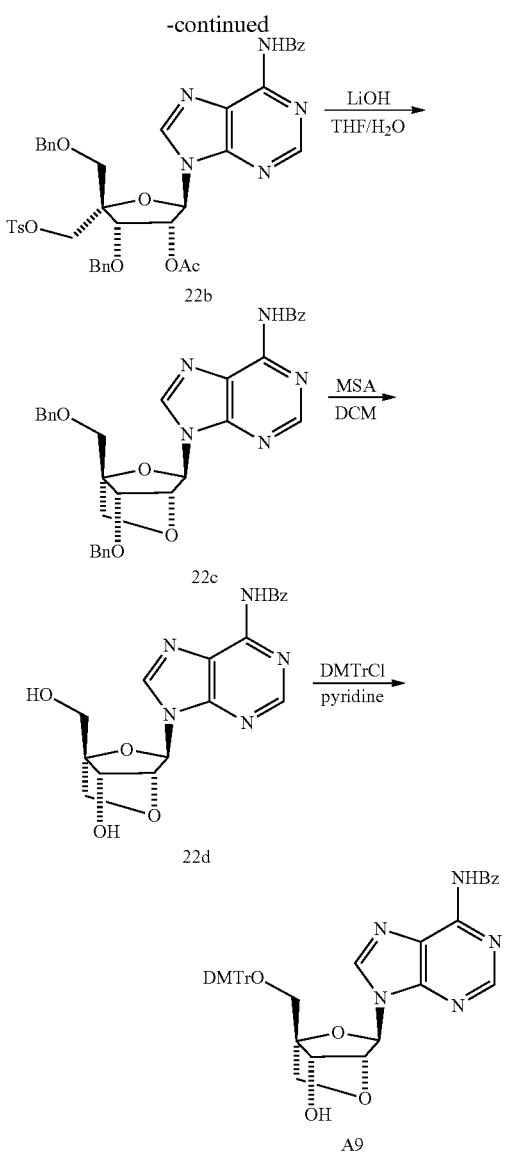

after which it was diluted with EtOAc. The organic phase was separated and washed with brine, the aqueous layer was extracted with DCM. The combined organic layers were dried over anhydrous $Na_2SO_4$, filtered and concentrated under reduced pressure. The residue was purified by silica gel column chromatography (gradient elution: 0 to 100% EtOAc in petroleum ether) to give intermediate 22c (yield: 77%) as a faint yellow solid. ESI-MS: m/z 564.1 $[M+H]^+$.

Step 3: Methanesulfonic acid (MSA, 46 mL g, 1.42 mol) was added to a stirred solution of intermediate 22c (10.0 g, 17.74 mmol) in DCM (150 mL) at 0° C. The reaction mixture was stirred room temperature for 2.5 h, after which it was slowly added to a suspension of solid $NaHCO_3$ (100 g) in DCM (180 mL). After stirring for 1.5 h, MeOH (10 mL) was added and stirring was continued for an addition 30 min. The reaction mixture was filtered and the filtrate was concentrated under reduced pressure. The residue was purified by silica gel column chromatography (gradient elution: 0 to 10% MeOH in DCM) to give intermediate 22d (yield: 77%) as an off-white solid (5.6 g, yield: 82%). ESI-MS: m/z 383.9 $[M+H]^+$.

Step 4: DMTrCl (530 mg, 1.57 mmol) was added to a solution of intermediate 22d (500 mg, 1.30 mmol) in pyridine (5 mL) and stirred at room temperature for 1 h. Next, the reaction mixture was diluted with DCM and washed with saturated aqueous $NaHCO_3$ and brine. The aqueous layer was extracted with DCM. The combined organic layers were dried over anhydrous $Na_2SO_4$, filtered and concentrated under reduced pressure. The residue purified by silica gel column chromatography (gradient elution: 0 to 5% MeOH in DCM) to give intermediate A9 as a white solid (421 mg: yield: 46%). $^1$H NMR (400 MHz, METHANOL-$d_4$) δ ppm 8.74 (s, 1H), 8.51 (s, 1H), 8.09 (d, J=7.3 Hz, 2H), 7.62-7.69 (m, 1H), 7.55-7.61 (m, 2H), 7.46-7.51 (m, 2H), 7.34-7.39 (m, 4H), 7.26-7.33 (m, 2H), 7.19-7.26 (m, 1H), 6.85-6.90 (m, 4H), 6.18 (s, 1H), 4.66 (s, 1H), 4.51 (s, 1H), 3.98-4.06 (m, 2H), 3.78 (s, 6H), 3.62 (d, J=10.8 Hz, 1H), 3.51 (d, J=11.0 Hz, 1H); ESI-MS: m/z 686.3 $[M+H]^+$.

Example 23: Synthesis of Intermediate A10

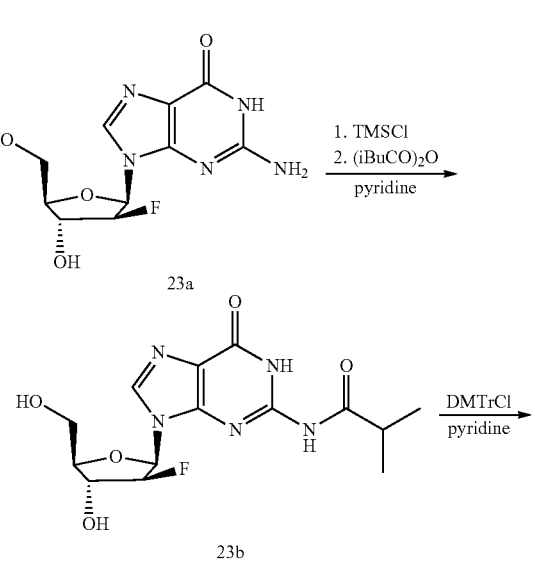

Step 1: To a suspension of 4-C-[(phenylmethoxy)methyl]-3-O-(phenylmethyl)-, 1,2-diacetate 5-(4-methylbenzenesulfonate)-L-lyxofuranose (22a, 10.21 g, 19.55 mmol, CAS: 209968-86-5) and 6-N-benzoyladenine (5.61 g, 23.45 mmol, CAS: 4005-49-6) in anhydrous 1,2-dichloroethane (255 mL) was added bis(trimethylsilyl)acetamide (BSA, 10.34 g, 50.82 mmol), the mixture was refluxed for 1 h. The reaction mixture was cooled to room temperature, TMSOTf (8.69 g, 39.09 mmol) was added and stirred again at reflux temperature for 16 h. The resulting reaction solution was next cooled to room temperature, poured into ice-cold saturated aqueous $NaHCO_3$, stirred for 30 min and filtered. The organic layer was separated and washed with saturated aqueous $NaHCO_3$, dried over anhydrous $Na_2SO_4$, filtered and concentrated under reduced pressure. Purification of the residue by flash column chromatography on silica gel (gradient elution: 1 to 1.5% MeOH in DCM) gave intermediate 22b (12.4 g, yield: 74%) as a light yellow solid. ESI-MS: m/z 702.1 $[M+H]^+$.

Step 2: $LiOH·H_2O$ (0.86 g, 20.49 mmol) was added to a solution of intermediate 22b (2.88 g, 4.10 mmol) in a THF/water solvent mixture (6/4, 45 mL) at 0° C. The reaction mixture was stirred for 5 h at room temperature

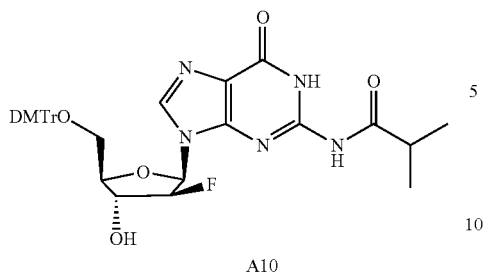

A10

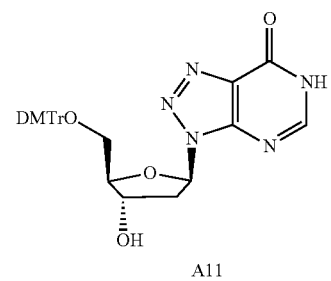

A11

Step 1: TMSCl (3.81 g, 35.06 mmol) was added dropwise to a solution of 9-(2'-deoxy-2'-fluoro-p-D-arabinofuranosyl) guanine (23a, 2.0 g, 7.01 mmol, CAS: 103884-98-6) in dry pyridine at −5° C. under N$_2$. The reaction mixture was stirred at room temperature for 2 h. The resulting reaction solution was cooled again to −5° C., isobutyric anhydride (1.33 g, 8.41 mmol) was added dropwise, stirring was continued at 0° C. for 20 h. Next, 5% aqueous NaHCO$_3$ (30 mL) was added, the resulting mixture was stirred for 1 h at room temperature and then neutralized (pH 7) with 6 M aqueous HCl (6.5 mL). The mixture was concentrated under vacuum to give crude intermediate 23b which was used as such in the next step. ESI-MS: m/z 355.9 [M+H]$^+$.

Step 2: DMTrCl (3.00 g, 8.44 mmol) was added to a solution of the above intermediate 23b (co-evaporated with anhydrous pyridine before use) in pyridine at −5° C. under N$_2$. The reaction mixture was stirred at 0° C. for 15 h. The mixture was next adjusted to pH 7 with solid NaHCO$_3$ (1.3 g, 2.2 eq) and 50 ml water. The mixture was next concentrated under vacuum to remove pyridine. The residue was dissolved in DCM and washed with water. The organic phase was dried over with anhydrous Na$_2$SO$_4$, filtered and concentrated under reduced pressure. The crude product was purified by column chromatography over silica (gradient elution: 50 to 100% EtOAc in heptane) to afford intermediate A10 as a yellowish foam (4.0 g, yield: 87% over two steps). $^1$H NMR (600 MHz, DMSO-d$_6$) δ ppm 12.11 (s, 1H), 11.68 (s, 1H), 7.91 (d, J=2.2 Hz, 1H), 7.39 (d, J=7.6 Hz, 2H), 7.21-7.30 (m, 7H), 6.86 (d, J=9.0 Hz, 2H), 6.85 (d, J=9.0 Hz, 2H), 6.29 (dd, J=15.1, 4.5 Hz, 1H), 6.00 (d, J=4.9 Hz, 1H), 5.20 (dt, J=52.2, 4.0 Hz, 1H), 4.39-4.51 (m, 1H), 4.03-4.07 (m, 1H), 3.73 (s, 6H), 3.38 (dd, J=10.2, 7.2 Hz, 1H), 3.23 (dd, J=10.4, 3.3 Hz, 1H), 2.76 (spt, J=6.8 Hz, 1H), 1.12 (d, J=6.8 Hz, 3H), 1.12 (d, J=6.5 Hz, 3H); ESI-MS: m/z 658.1 [M+H]$^+$ Example 24: Synthesis of Intermediate A11

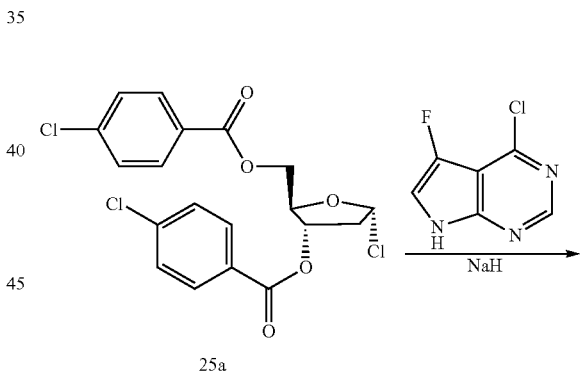

24a

A solution of DMTrCl (4.42 g, 11.40 mmol) in dry pyridine (10 mL) was added to a solution of 24a (2.75g, 10.86 mmol, CAS: 56220-50-9) in dry pyridine (20.0 mL) at 0° C. The reaction mixture was stirred at 5° C. for 20 h, next diluted with EtOAc, washed with saturated aqueous NaHCO$_3$, water, and brine. The organic layer was dried over Na$_2$SO$_4$, filtered, and concentrated under reduced pressure. The residue was purified by silica gel column chromatography (gradient elution: 20 to 80% EtOAc in heptane) to give intermediate A11 as a white solid (4.3 g, yield: 71%). $^1$H NMR (600 MHz, DMSO-d$_6$) δ ppm 12.81 (br s, 1H), 8.24-8.32 (m, 1H), 7.22-7.28 (m, 2H), 7.14-7.20 (m, 3H), 7.12 (d, J=8.7 Hz, 4H), 6.77 (d, J=9.0 Hz, 2H), 6.73 (d, J=9.0 Hz, 2H), 6.62 (dd, J=7.1, 3.5 Hz, 1H), 5.45 (br d, J=3.0 Hz, 1H), 4.56-4.64 (m, 1H), 4.02 (td, J=5.8, 3.4 Hz, 1H), 3.71 (s, 3H), 3.70 (s, 3H), 3.09 (dd, J=10.4, 3.3 Hz, 1H), 2.95-3.04 (m, 2H), 2.45-2.53 (m, 1H); ESI-MS: (m z) 554.1 [M-H]$^-$.

Example 25: Synthesis of Intermediate A12

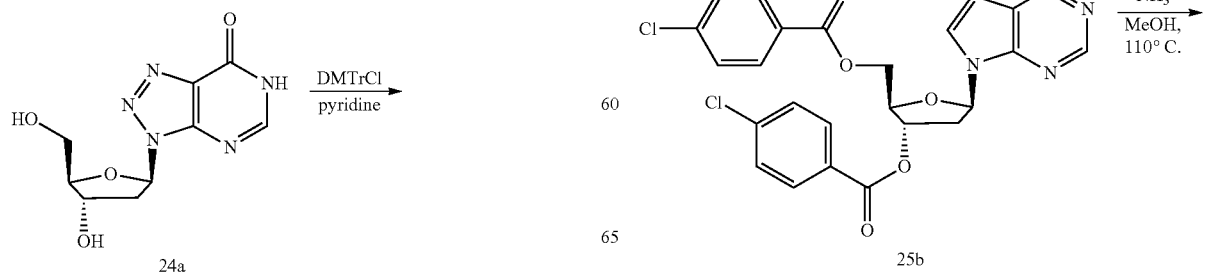

25a

25b

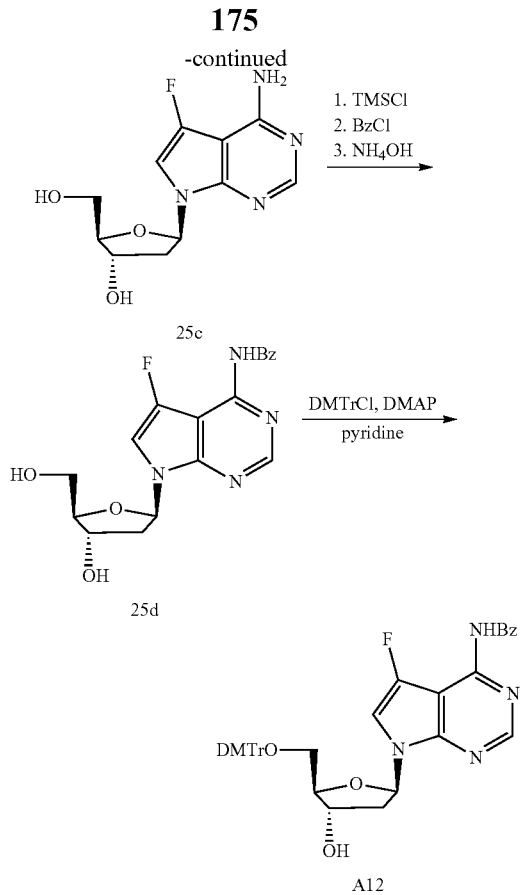

12.1 mL) after 15 min, stirring was continued for 30 min. The reaction solution was neutralized with acetic acid and concentrated under vacuum. Purification was done by column chromatography over silica (gradient elution: 0 to 4% MeOH in DCM) to give intermediate 25d as white solid (1.97 g, yield: 88%). ESI-MS: m/z 373.0 [M+H]$^+$.

Step 4: A solution of intermediate 25d (3.7 g, 9.9 mmol) in dry pyridine (55.5 mL), to which DMAP (0.6 g, 4.9 mmol) and DMTrCl (5.36 g, 15.8 mmol) were added (portionwise), was stirred at room temperature until complete conversion (ca. 2 h). The reaction mixture was quenched with methanol (30 mL) and concentrated under reduced pressure. The obtained residue was dissolved in EtOAc and washed with water. The organic layer was dried over anhydrous Na$_2$SO$_4$, filtered and concentrated under reduced pressure. Purification was done by column chromatography over silica (gradient elution: 0 to 0.5% MeOH in DCM) to give intermediate A12 as an off-white foam (6.0 g, yield: 89%). $^1$H NMR (500 MHz, DMSO-d$_6$) δ ppm 11.29 (br s, 1H), 8.66 (s, 1H), 7.99-8.08 (m, 2H), 7.61-7.69 (m, 1H), 7.52-7.59 (m, 3H), 7.34-7.39 (m, 2H), 7.16-7.31 (m, 7H), 6.82-6.87 (m, 4H), 6.73 (t, J=6.2 Hz, 1H), 5.38 (d, J=4.8 Hz, 1H), 4.33-4.42 (m, 1H), 3.93-4.00 (m, 1H), 3.72 (s, 3H), 3.72 (s, 3H), 3.20 (dd, J=10.3, 6.2 Hz, 1H), 3.13 (dd, J=10.3, 3.4 Hz, 1H), 2.59 (dt, J=13.3, 6.8 Hz, 1H), 2.31 (ddd, J=13.8, 6.2, 4.1 Hz, 1H); ESI-MS: m/z 675.4 [M+H]$^+$.

Intermediate A28 may be prepared using this route for the preparation of intermediate A12, but using (2R,3S,5R)-5-(4-amino-7H-pyrrolo[2,3-d]pyrimidin-7-yl)-2-(2-hydroxyethyl)tetrahydrofuran-3-ol in place of compound 33a.

Example 26: Synthesis of Intermediate A14

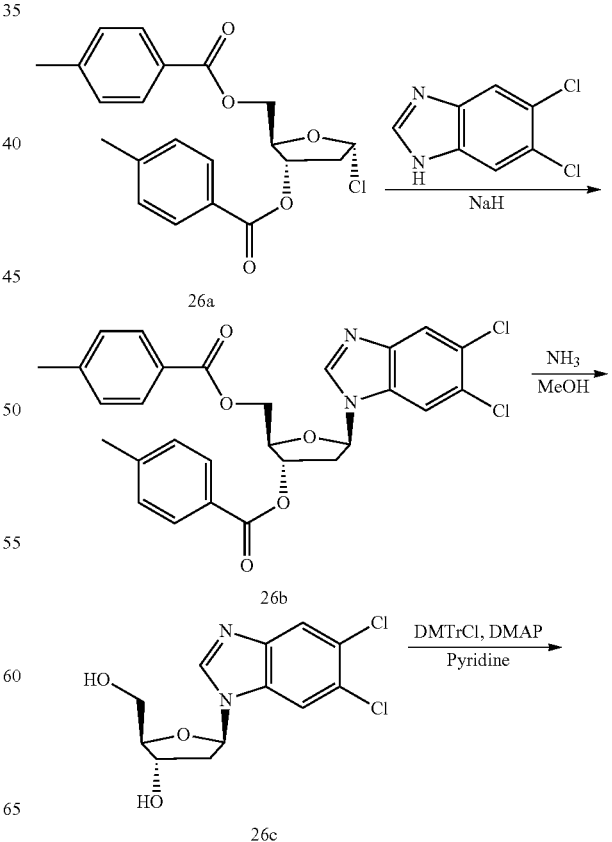

Step 1: NaH (60% dispersion in mineral oil, 0.51 g, 12.8 mmol) was portionwise added to a solution of 4-chloro-5-fluoro-7H-pyrrolo[2,3-d]pyrimidine (2.0 g, 11.6 mmol, CAS: 582313-57-3) in dry MeCN (30 mL) at 0° C. The reaction mixture was warmed to room temperature. After 1 h of stirring, 1-chloro-3,5-di-(4-chlorobenzoyl)-2-deoxy-D-ribose (25a, 6.02 g, 14.0 mmol, CAS: 21740-23-8) was added and stirring was continued for 2 h. Subsequently, the reaction solution was quenched with ice-cold water and stirred for an additional 20 min. Next, the solvent was decanted and the resulting residue was dissolved in diethyl ether, stirred for 20 min and concentrated under reduced pressure. Purification was done by column chromatography over silica (gradient elution: 0 to 10% EtOAc in hexane) to give intermediate 25b as an off-white foam (3.6 g, yield: 54%). ESI-MS: m/z 564.0 [M+H]$^+$.

Step 2: Intermediate 25b (3.6 g, 6.3 mmol) was stirred in a saturated methanolic ammonia solution (72 mL) in a sealed tube at 110° C. until complete conversion (ca. 2 days). The reaction mixture was concentrated under reduced pressure. Purification was done by column chromatography over silica (gradient elution: 0 to 10% MeOH in DCM) to give intermediate 25c as an off-white powder (1.6 g, yield: 73%). ESI-MS: m/z 269.0 [M+H]$^+$.

Step 3: TMSCl (3.78 mL, 29.8 mmol) was added dropwise to a solution of intermediate 25c (1.6 g, 5.94 mmol) in dry pyridine (22.4 mL) at 0° C. The reaction solution was stirred at room temperature for 1 h after which it was cooled again to 0° C. Next, benzoyl chloride (3.46 mL, 29.8 mmol) was added dropwise over a period of 15 min and stirring was continued at room temperature until complete conversion. Next, the reaction mixture was cooled to 0° C., water was added followed by the addition of aqueous ammonia (25%,

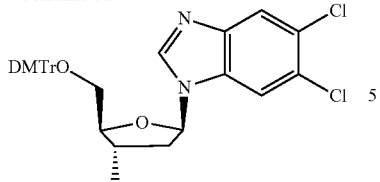

A14

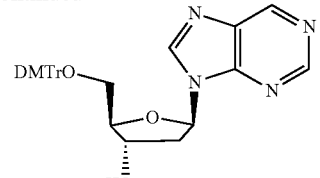

A15

Step 1: NaH (1.36 g, 31.1 mmol) was added portionwise to a solution of 5,6-dichloro-1H-benzimidazole (5.3 g, 28.34 mmol, CAS: 6478-73-5) in dry MeCN (185 mL) at 0° C. After stirring for 1 h at room temperature, the reaction mixture was cooled again to 0° C. and 1-chloro-3,5-di-(4-chlorobenzoyl)-2-deoxy-D-ribose (26a, 11 g, 28.34 mmol) was added portionwise. Stirring was continued at room temperature until complete conversion (ca. 2 h). Next, the reaction mixture was diluted with EtOAc and washed with water. The organic layer was dried over anhydrous Na$_2$SO$_4$, filtered and concentrated under reduced pressure. Purification was done by column chromatography over silica (gradient elution: 0 to 40% EtOAc in hexane) to give intermediate 26b as an off-white foam (14 g, yield: 92%). ESI-MS: m/z 539 [M+H]$^+$.

Step 2: A solution of intermediate 26b (14 g, 25.9 mmol) in a saturated methanolic ammonia solution (280 mL) was stirred at room temperature in a sealed tube until complete conversion (ca. 16 h). The reaction solution was next concentrated under reduced pressure and the crude residue washed with DCM to give intermediate 26c as a white solid (7 g, yield: 89%). ESI-MS: m/z 302 [M+H]$^+$.

Step 3: A solution of intermediate 26c (7 g, 23.17 mmol) in dry pyridine (105 mL), to which DMAP (1.41 g, 11.5 mmol) and DMTrCl (11.7 g, 34.7 mmol) were added (portionwise), was stirred at room temperature until complete conversion (ca. 6 h). The reaction mixture was quenched with methanol (10 mL) and concentrated under reduced pressure. The obtained residue was dissolved in DCM and washed with water. The organic layer was dried over anhydrous Na$_2$SO$_4$, filtered and concentrated under reduced pressure. Purification was done by column chromatography over silica (gradient elution: 0 to 0.5% MeOH in DCM) to give intermediate A14 as an off-white foam (8 g, yield: 57%). $^1$H NMR (500 MHz, DMSO-d$_6$) δ ppm 8.53 (s, 1H), 8.03 (s, 1H), 7.98 (s, 1H), 7.23-7.28 (m, 2H), 7.17-7.22 (m, 3H), 7.11-7.16 (m, 4H), 6.75 (m, J=8.6, 8.6 Hz, 4H), 6.41 (t, J=5.9 Hz, 1H), 5.40 (d, J=4.8 Hz, 1H), 4.42 (quin, J=5.2 Hz, 1H), 3.94-4.03 (m, 1H), 3.71 (s, 6H), 3.13 (dd, J=10.3, 2.8 Hz, 1H), 3.06 (dd, J=10.3, 6.2 Hz, 1H), 2.78 (dt, J=12.9, 6.3 Hz, 1H), 2.41 (dt, J=12.9, 6.3 Hz, 1H). ESI-MS: m/z 605[M+H]$^+$.

Example 27: Synthesis of Intermediate A15

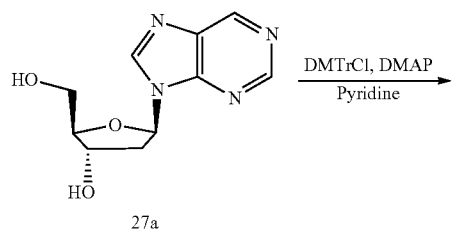

Intermediate A15 was prepared from 2'-deoxynebularine (27a, CAS: 4546-68-3) using the procedure as exemplified for the preparation of intermediate A14 from 26b. $^1$H NMR (500 MHz DMSO-d$_6$) δ ppm: 9.18 (s, 1H), 8.87 (s, 1H), 8.72 (s, 1H), 7.30 (d, J=6.9 Hz, 2H), 7.18 (m, 7H), 6.79 (d, J=9.0 Hz, 2H), 6.74 (d, J=9.0 Hz, 2H), 6.51 (t, J=6.2 Hz, 1H), 5.41 (d, J=4.1 Hz, 1H), 4.53 (m, 1H), 4.03 (q, J=4.6 Hz, 1H), 3.72 (s, 3H), 3.71 (s, 3H), 3.18 (m, 2H), 2.96 (m, 1H), 2.40 (m, 1H). ESI-MS: m/z 539 [M+H]$^+$.

Example 28: Synthesis of Intermediate A16

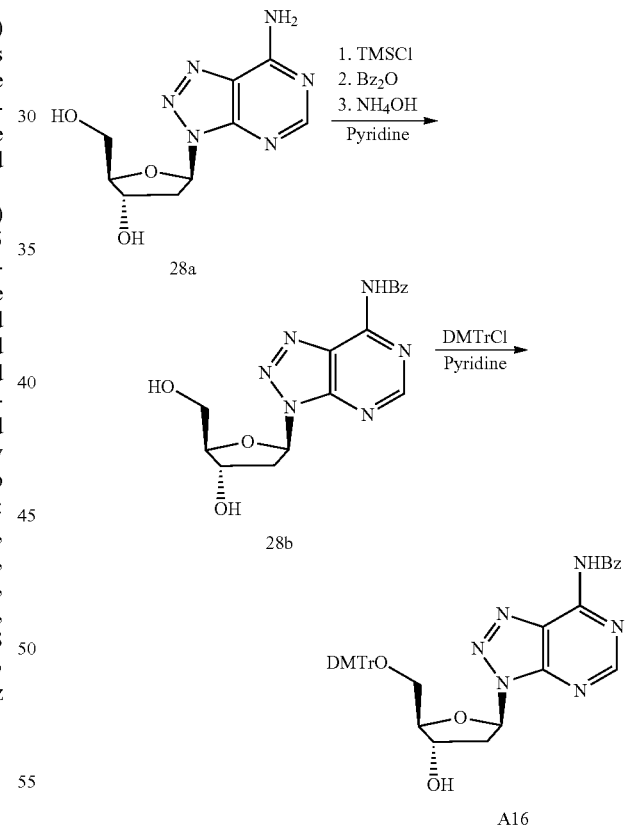

A16

Step 1: TMSCl (6.46 g, 59.47 mmol) was added dropwise to a solution of 8-aza-2'-deoxyadenosine (28a, 3.0 g, 11.9 mmol, CAS: 34536-05-5) in dry pyridine at −5° C. under N$_2$. The reaction solution was stirred at room temperature for 2 h after which it was cooled again to −5° C. Benzoic anhydride (4.04 g, 17.84 mmol) was added and stirring was continued at 0° C. for 20 h. 5% Aqueous NaHCO$_3$ (35 mL) was added, the resulting mixture was stirred at room temperature for 1 h. Next, ammonia was added (until pH 8) and stirring was continued for 1 h at room temperature. The resulting reaction solution was neutralized (pH 7) with 6 M HCl and concentrated under vacuum to give crude intermediate 28b which was used as such in the next step. ESI-MS: m/z 357.8 [M+H]$^+$.

Step 2: DMTrCl (4.84 g, 14.28 mmol) in dry pyridine (10.0 mL) was added to a solution of the above intermediate 28b in dry pyridine (50.0 mL) at 0° C. The reaction mixture was stirred at 0° C. for 12 h after which EtOAc was added. The resulting solution was washed with saturated aqueous NaHCO$_3$, water, and brine, dried over Na$_2$SO$_4$, filtered, and concentrated under reduced pressure. The residue was purified by silica gel column chromatography (gradient elution: 20 to 50% EtOAc in heptane) to give intermediate A16 as a white solid (6.0 g, yield: 77% over two steps). $^1$H NMR (500 MHz, DMSO-d$_6$) δ ppm 11.91 (br s, 1H), 8.93 (br s, 1H), 8.09 (br d, J=7.3 Hz, 2H), 7.69 (t, J=7.3 Hz, 1H), 7.59 (t, J=7.8 Hz, 2H), 7.20-7.26 (m, 2H), 7.09-7.20 (m, 7H), 6.83 (br s, 1H), 6.76 (d, J=8.7 Hz, 2H), 6.70 (d, J=8.7 Hz, 2H), 5.49 (d, J=5.0 Hz, 1H), 4.67 (quin, J=5.7 Hz, 1H), 4.05-4.09 (m, 1H), 3.69 (s, 3H), 3.68 (s, 3H), 3.12 (br dd, J=10.1, 3.2 Hz, 2H), 3.05 (dd, J=10.1, 6.9 Hz, 1H), 2.52-2.59 (m, 1H); ESI-MS: m/z 659.4 [M+H]$^+$.

Example 29: Synthesis of Intermediate A17

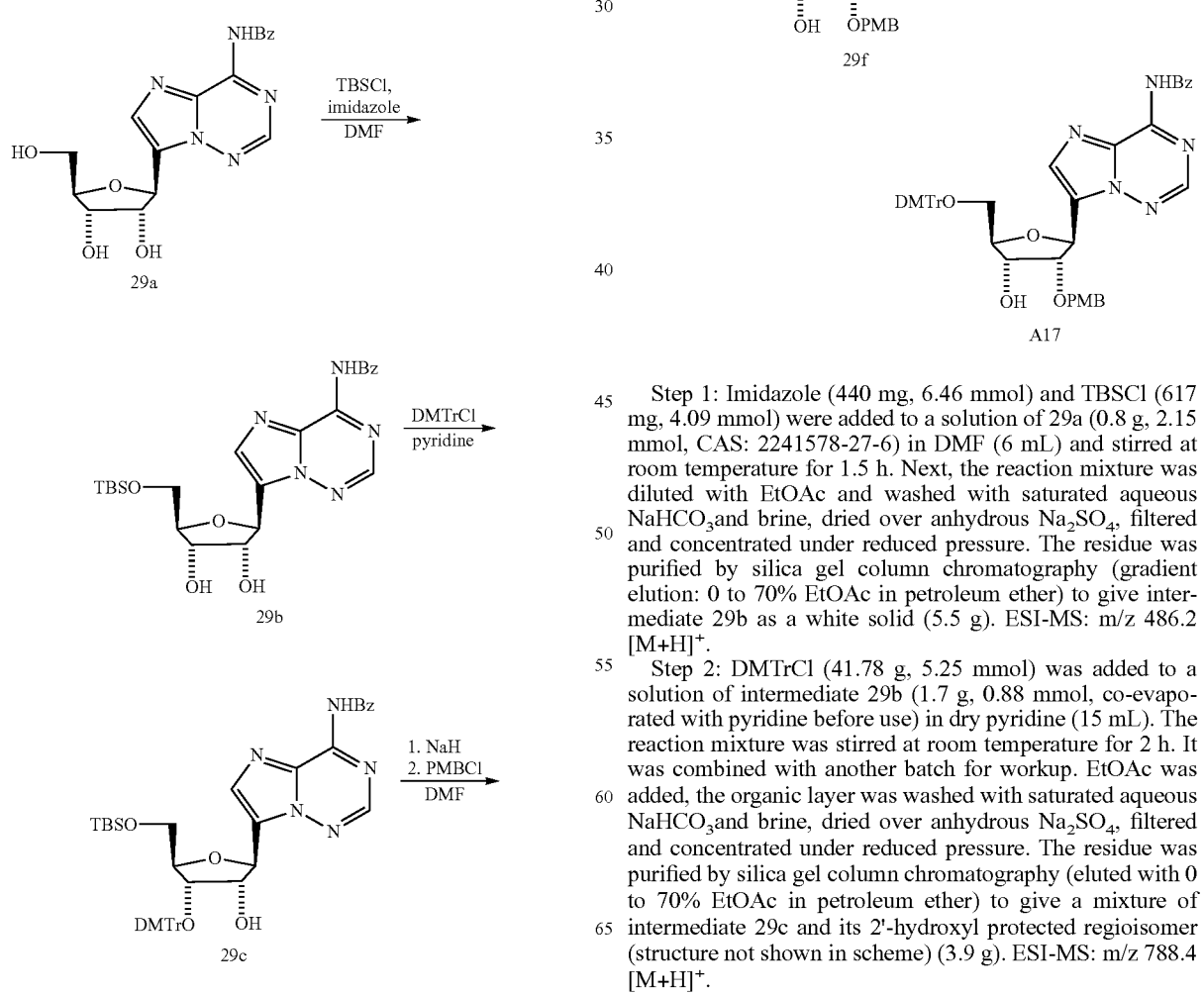

Step 1: Imidazole (440 mg, 6.46 mmol) and TBSCl (617 mg, 4.09 mmol) were added to a solution of 29a (0.8 g, 2.15 mmol, CAS: 2241578-27-6) in DMF (6 mL) and stirred at room temperature for 1.5 h. Next, the reaction mixture was diluted with EtOAc and washed with saturated aqueous NaHCO$_3$ and brine, dried over anhydrous Na$_2$SO$_4$, filtered and concentrated under reduced pressure. The residue was purified by silica gel column chromatography (gradient elution: 0 to 70% EtOAc in petroleum ether) to give intermediate 29b as a white solid (5.5 g). ESI-MS: m/z 486.2 [M+H]$^+$.

Step 2: DMTrCl (41.78 g, 5.25 mmol) was added to a solution of intermediate 29b (1.7 g, 0.88 mmol, co-evaporated with pyridine before use) in dry pyridine (15 mL). The reaction mixture was stirred at room temperature for 2 h. It was combined with another batch for workup. EtOAc was added, the organic layer was washed with saturated aqueous NaHCO$_3$ and brine, dried over anhydrous Na$_2$SO$_4$, filtered and concentrated under reduced pressure. The residue was purified by silica gel column chromatography (eluted with 0 to 70% EtOAc in petroleum ether) to give a mixture of intermediate 29c and its 2'-hydroxyl protected regioisomer (structure not shown in scheme) (3.9 g). ESI-MS: m/z 788.4 [M+H]$^+$.

Step 3: NaH (60% in mineral oil, 482 mg, 12.05 mmol) was added to a solution of intermediate 29c and its 2'-hydroxyl protected regioisomer (2.5 g, 3.17 mmol) in DMF (25 mL) at 0° C. After stirring for 1 h at 0° C., a solution of 4-methoxybenzyl chloride (745 mg, 4.76 mmol) in DMF (5 mL) was added dropwise (ca. 10 min). The reaction mixture was stirred at room temperature for 2 h, after which it was quenched by the dropwise addition of water (5 mL). Next, EtOAc was added, the resulting solution was successively washed with saturated aqueous NaHCO$_3$ and brine, dried over anhydrous Na$_2$SO$_4$, filtered and concentrated under reduced pressure. The residue was purified by silica gel column chromatography (gradient elution: 0 to 40% EtOAc in petroleum ether) to give mixture of intermediate 29d and its regioisomer (1.9 g). ESI-MS: m/z 908.4 [M+H]$^+$.

Step 4: A solution of the above isomeric mixture (1.9 g, 2.09 mmol) in DCM (30 mL) was treated with DCA (690 µL, 8.37 mmol) and water (380 µL, 20.92 mmol). The resulting yellow solution was stirred at room temperature for 2 h after which it was quenched by the addition of MeOH (150 µL) and pyridine (662 mg). After stirring for an additional 15 min, the reaction mixture was concentrated under reduced pressure and purified by column chromatography on silica gel to give a mixture of intermediate 29e and its 2'3'-protected regioisomer (1.05 g, yield: 60%). ESI-MS: m/z 606.1 [M+H]$^+$.

Step 5: A solution of the above isomeric mixture (intermediate 29e+2'3'-protected regioisomer, 1.2 g, 1.98 mmol) in THF (12 mL) was treated with TBAF (1 M in THF, 3.0 mL, 3.0 mmol) and stirred at room temperature for 3 h. The resulting reaction solution was diluted with EtOAc and subsequently washed with saturated aqueous NaHCO$_3$. The organic layer was dried over anhydrous Na$_2$SO$_4$, filtered and evaporated in vacuo. Purification by column chromatography on silica gel (isocratic elution: 5% MeOH in DCM) gave a mixture of intermediate 29f and its 3'-PMB protected regioisomer. This compound mixture was triturated with MeOH resulting in the precipitation of the pure 3'-PMB protected isomer (major isomer) which was isolated by filtration and washed with a small amount of cold MeOH. The filtrate was concentrated and purified by reverse phase preparative HPLC to give the desired intermediate 29f as the minor isomer. $^1$H NMR (400 MHz, DMSO-d$_6$) δ ppm 8.61 (br s, 1H), 8.03 (br d, J=8.0 Hz, 2H), 7.92 (br s, 1H), 7.69-7.65 (m, 1H), 7.58-7.54 (m, 2H), 7.33 (d, J=8.0 Hz, 2H), 6.92 (d, J=8.0 Hz, 2H), 5.33 (d, J=8.0 Hz, 1H), 5.21 (br d, J=8.0 Hz, 1H), 4.87 (t, J=8.0 Hz, 1H), 4.66 (d, J=8.0 Hz, 1H), 4.57-4.49 (m, 1H), 4.01 (q, J=4.0 Hz, 1H), 3.95 (t, J=4.0 Hz, 1H), 3.75 (s, 3H), 3.60-3.55 (m, 1H), 3.50-3.45 (m, 1H); ESI-MS: m/z 492.3 [M+H]$^+$.

3'-PMB regioisomer: $^1$H NMR (400 MHz, DMSO-d$_6$) δ 8.51 (s, 1H), 8.03 (br d, J=8.0 Hz, 2H), 7.81 (s, 1H), 7.67-7.63 (m, 1H), 7.57-7.53 (m, 2H), 7.17 (d, J=8.0 Hz, 2H), 6.80 (d, J=8.0 Hz, 2H), 5.28 (d, J=8.0 Hz, 1H), 5.09 (br d, J=4.0 Hz, 1H), 4.83 (br t, J=4.0 Hz, 1H), 4.64 (d, J=12 Hz, 1H), 4.47 (d, J=12 Hz, 1H), 4.28 (t, J=4.0 Hz, 1H), 4.20 (q, J=4.0 Hz, 1H), 3.91 (q, J=4.0 Hz, 1H), 3.70 (s, 3H), 3.61-3.58 (m, 1H), 3.51-3.47 (m, 1H); ESI-MS: m/z 492.2 [M+H]$^+$.

Step 6: DMTrCl (99 mg, 0.29 mmol) was added to a solution of intermediate 29f (110 mg, 0.22 mmol) in pyridine (5 mL) and stirred at room temperature overnight. The resulting reaction solution was concentrated. The residue was dissolved in DCM, washed with saturated aqueous NaHCO$_3$, dried with anhydrous Na$_2$SO$_4$, filtered and concentrated under reduced pressure. The crude product was purified by column chromatography on silica gel to give intermediate A17 (yield: ca. 47%). ESI-MS: m/z 794.4 [M+H]$^+$.

Example 30: Synthesis of Intermediate A20

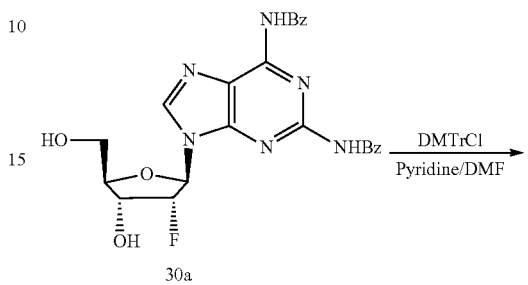

30a

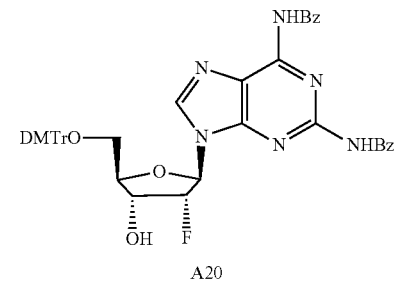

A20

DMTrCl (4.85 g, 14.3 mmol) was added to a solution of N-benzoyl-2-(benzoylamino)-2'-deoxy-2'-fluoro-adenosine (30a, 7.02 g, 14.3 mmol, CAS: 1786418-21-0) in a pyridine/DMF solvent mixture (2/1, 81 mL) at 10° C. under argon. The reaction mixture was allowed to warm to room temperature overnight after which it was diluted with DCM and washed with saturated aqueous NaHCO$_3$. The aqueous phase was back extracted with DCM. The combined organic layers were dried over Na$_2$SO$_4$, filtered and concentrated. The crude product was purified by silica column chromatography (gradient elution: 1 to 2% MeOH in DCM) to give intermediate A20 (7.48 g, yield: 66%). $^1$H NMR (300 MHz, DMSO-d$_6$) δ ppm 11.20 (s, 1H), 10.90 (s, 1H), 8.51 (s, 1H), 8.02-8.09 (m, 2H), 7.81-7.88 (m, 2H), 7.46-7.68 (m, 6H), 7.22-7.31 (m, 2H), 7.06-7.15 (m, 7H), 6.68 (d, J=9.4 Hz, 2H), 6.62 (d, J=8.8 Hz, 2H), 6.39 (d, J=20.5 Hz, 1H), 5.54 (d, J=7.0 Hz, 1H), 5.54 (dd, J=52.7, 4.7 Hz, 1H), 4.85-5.06 (m, 1H), 4.02-4.18 (m, 1H), 3.66 (s, 3H), 3.64 (s, 3H), 3.51 (dd, J=11.1, 7.0 Hz, 1H), 3.12 (br d, J=10.4 Hz, 1H); ESI-MS: m/z 795.3 [M+H]$^+$.

Example 31: Synthesis of Intermediate A21

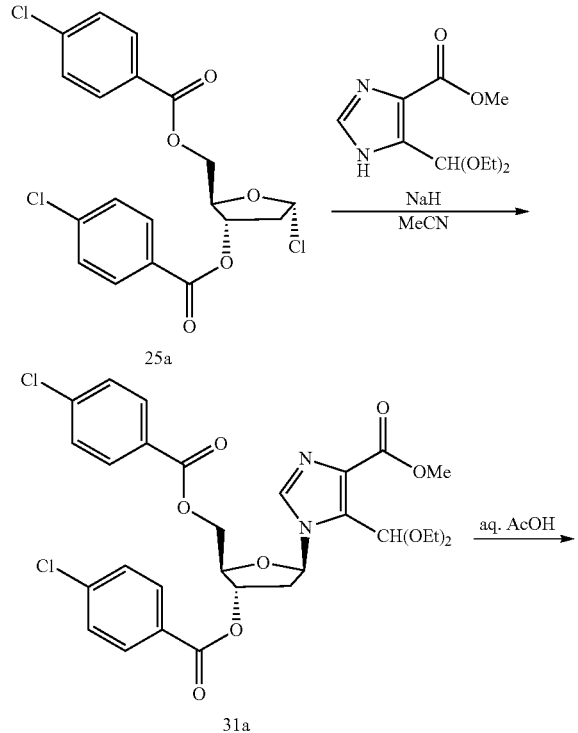

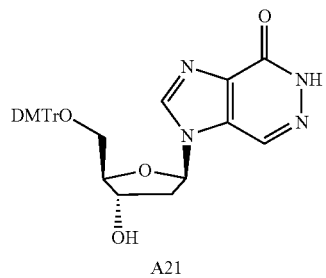

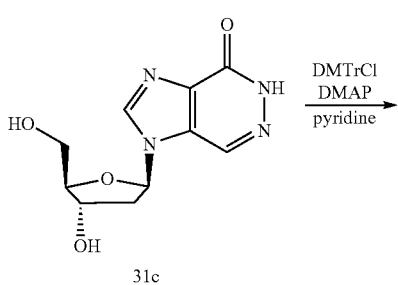

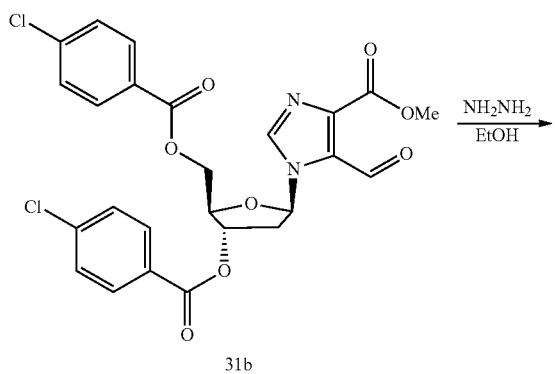

Step 1: NaH (~55% dispersion in mineral oil, 1.15 g, 48.1 mmol) was portionwise added to a solution of methyl 5-(diethoxymethyl)-1H-imidazole-4-carboxylate (10 g, 43.7 mmol, CAS: 85109-99-5) in dry MeCN (500 mL) at 0° C. and then stirred for 1 h at room temperature. The reaction mixture was cooled again to 0° C., followed by the portionwise addition of 1-chloro-3,5-di-(4-chlorobenzoyl)-2-deoxy-D-ribose (25a, 18.7 g, 43.7 mmol, CAS: 582313-57-3). Stirring at room temperature was continued until complete conversion (ca. 2 h). Next, the reaction mixture was diluted with EtOAc and washed with water. The organic layer was dried over anhydrous $Na_2SO_4$, filtered and concentrated under reduced pressure. Purification was done by column chromatography over silica (gradient elution: 0 to 40% EtOAc in hexane) to give intermediate 31a as an off-white foam (10 g, yield: 37%). ESI-MS: m/z 621.0 $[M+H]^+$.

Step 2: A solution of intermediate 31a (10 g, 16.1 mmol) in 80% aqueous acetic acid (100 mL), was stirred at room temperature for 14 h. The resulting solid was isolated by filtration, washed with water and dried under vacuum to give intermediate 31b as a white solid (4.5 g, yield: 51%). ESI-MS: m/z 569.0 $[M+Na]^+$.

Step 3: 1 M hydrazine in THF (164 mL, 164 mmol) was added to a solution of intermediate 31b (4.5 g, 8.2 mmol) in anhydrous EtOH (50 mL). The reaction solution was stirred at reflux temperature until complete conversion (ca. 72 h), allowing complete evaporation of THF (note: the reaction was very slow in presence of THF). The resulting solid was filtered, washed with ethanol and dried under high vacuum to give intermediate 31c as off white solid (1.4 g, yield: 67%).

Step 4: DMTrCl (3.0 g, 8.8 mmol) was added portionwise to a solution of intermediate 31c (1.4 g, 5.5 mmol, dried by co-evaporation with anhydrous toluene and dry pyridine) and DMAP (0.339 g, 2.8 mmol) in dry pyridine (30 mL), and stirred until complete conversion. The reaction mixture was next quenched with methanol (10 mL) and concentrated under reduced pressure. The obtained residue was dissolved in DCM and washed with water. The organic layer was dried over anhydrous $Na_2SO_4$, filtered and concentrated under reduced pressure. Purification by column chromatography over silica (gradient elution: 0 to 2.5% MeOH in DCM) to afforded intermediate A21 as an off-white solid (2.1 g, yield: 68%). $^1$H NMR (400 MHz, DMSO-$d_6$) δ ppm 12.75 (s, 1H), 8.52 (s, 1H), 8.48 (s, 1H), 7.19-7.28 (m, 5H), 7.11-7.16 (m, 4H), 6.76-6.81 (m, 4H), 6.41 (t, J=6.0 Hz, 1H), 5.43 (d, J=4.9 Hz, 1H), 4.40 (quin, J=5.2 Hz, 1H), 3.98-4.05 (m, 1H), 3.72 (s, 6H), 3.13 (dd, J=10.4, 2.7 Hz, 1H), 3.08 (dd, J=10.4, 5.5 Hz, 1H), 2.69-2.79 (m, 1H), 2.40-2.49 (m, 1H). ESI-MS: m/z 553.1 $[M+H]^+$.

Example 32: Synthesis of Intermediate A22

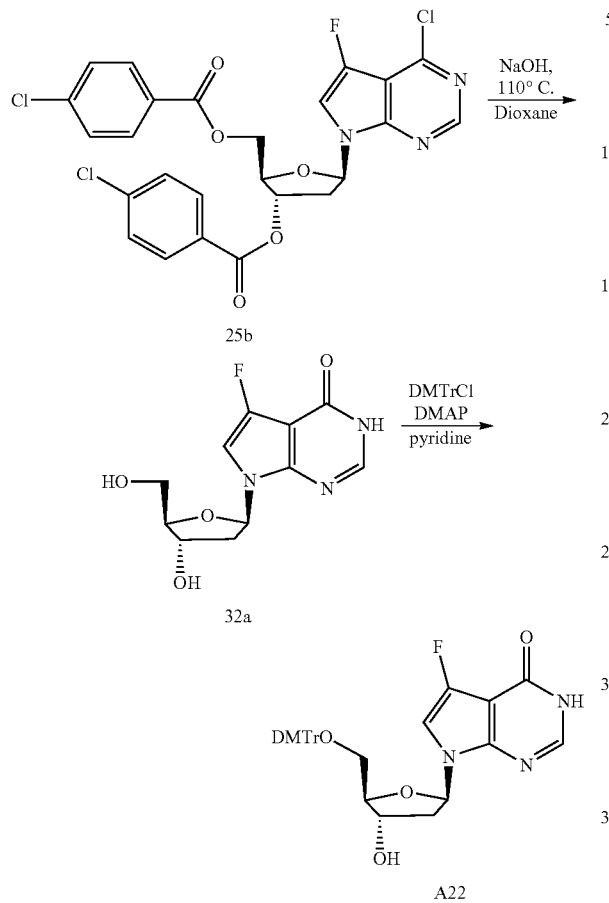

Step 1: A mixture of 2 N aqueous NaOH and 1,4-dioxane (1:1, 132 mL) was added to intermediate 25b (6.6 g, 11.6 mmol). The resulting solution was stirred at room temperature for 10 min after which it was heated to 110° C. for 3 h. The reaction mixture was next cooled to room temperature, neutralized with 2 N aqueous HCl and concentrated under reduced pressure. Purification was done by column chromatography over silica (gradient elution: 0 to 7% MeOH in DCM) to give intermediate 32a as an off-white powder (1.6 g, yield: 51%). ESI-MS: m/z 291.9 [M+Na]+.

Step 2: DMAP (0.36 g, 2.9 mmol) was added to a solution of intermediate 32a (1.6 g, 5.9 mmol, dried before use by co-evaporation with anhydrous toluene and dry pyridine) in dry pyridine (24 mL), next DMTrCl (3.2 g, 9.5 mmol) was added portionwise. The reaction mixture was stirred at room temperature for 4 h after which it was quenched with methanol (20 mL) and concentrated under reduced pressure. The obtained residue was dissolved in EtOAc and washed with water. The organic layer was dried over anhydrous Na$_2$SO$_4$, filtered and concentrated under reduced pressure. Purification was done by column chromatography over silica (gradient elution: 0 to 1% MeOH in DCM) to give intermediate A22 as an off-purple foam (2.7 g, yield: 80%). $^1$H NMR (500 MHz, DMSO-d$_6$) δ ppm 12.10 (br s, 1H), 7.93 (s, 1H), 7.32-7.39 (m, 2H), 7.19-7.30 (m, 7H), 7.13 (d, J=2.1 Hz, 1H), 6.84 (dd, J=9.0, 6.2 Hz, 4H), 6.48-6.55 (m, 1H), 5.34 (d, J=4.8 Hz, 1H), 4.29-4.37 (m, 1H), 3.87-3.94 (m, 1H), 3.73 (s, 6H), 3.15 (dd, J=10.3, 6.2 Hz, 1H), 3.11 (dd, J=10.3, 4.1 Hz, 1H), 2.42-2.50 (m, 1H), 2.25 (ddd, J=13.4, 6.5, 4.1 Hz, 1H); ESI-MS: m/z 570.1 [M−H]−.

Example 33: Synthesis of Intermediate A23

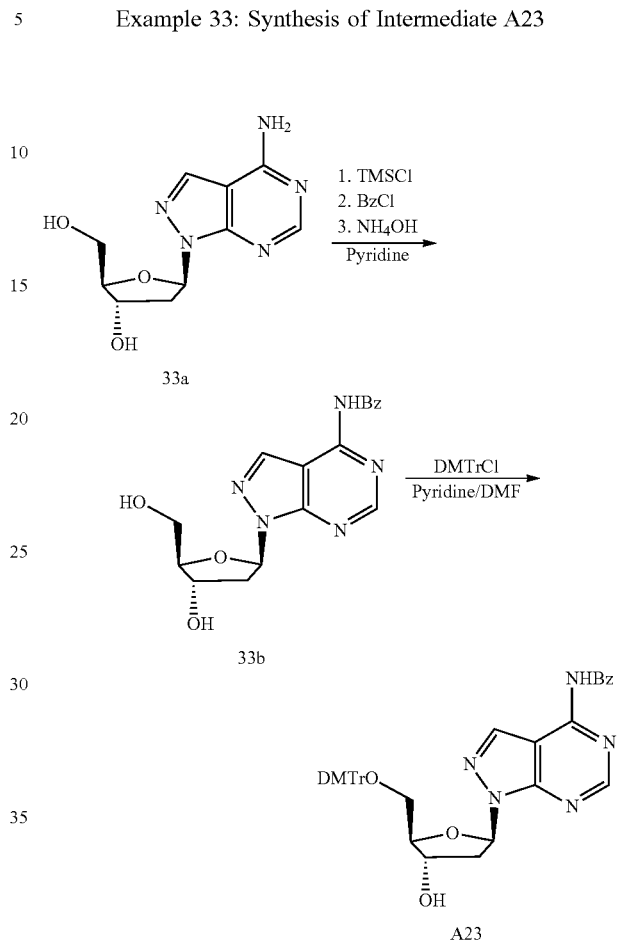

Step 1: TMSCl (10.6 mL, 83.3 mmol) was added dropwise to a solution of 8-aza-7-deaza-2'-deoxyadenosine (33a, 3.0 g, 11.9 mmol, CAS: 17318-21-7) in anhydrous pyridine (47.6 mL) at −5° C. under inert atmosphere. The resulting reaction mixture was stirred for 2 h at −5° C. Benzoyl chloride (1.39 mL, 11.9 mmol) was added dropwise and stirring was continued for 1.5 h at room temperature. The reaction solution was next cooled to 0° C. followed by the addition of water (1.0 mL) and aqueous ammonia (20 mL). The resulting mixture was stirred at 0° C. for 30 min and an additional 2 h at room temperature. The pH of the solution was adjusted to 6-7 by the addition of 6 M aqueous HCl, after which stirring was continued for 10 h. The mixture was partially concentrated (up to 50 mL), resulting in the precipitation of intermediate 33b which was collected by filtration, washed with water and dried under high vacuum (4.37 g, yield: quantitative). ESI-MS: m/z 356.1 [M+H]+.

Step 2: DMTrCl (4.03 g, 11.9 mmol) was added to a solution of intermediate 33b (4.37 g, 11.9 mmol) in a pyridine/DMF solvent mixture (1/2, 48 mL) at 10° C. under inert atmosphere. The reaction mixture was stirred at room temperature overnight after which DCM and solid NaHCO$_3$ (3.0 g) were added. The resulting mixture was stirred for 10 min and subsequently washed with water. The aqueous phase was back extracted with DCM. The combined organic layers were dried over Na$_2$SO$_4$, filtered and concentrated.

The crude product was purified by silica gel chromatography (elution gradient: 0 to 5% MeOH in DCM) to give pure intermediate A23 (4.18 g, yield: 53% yield). $^1$H NMR (300 MHz, DMSO-d$_6$) δ ppm 11.69 (br s, 1H), 8.79 (s, 1H), 8.42 (s, 1H), 8.01-8.13 (m, 2H), 7.61-7.70 (m, 1H), 7.49-7.59 (m, 2H), 7.22-7.33 (m, 2H), 7.09-7.17 (m, 7H), 6.61-6.80 (m, 5H), 5.36 (d, J=4.7 Hz, 1H), 4.46-4.60 (m, 1H), 3.88-3.99 (m, 1 H), 3.67 (s, 3H), 3.65 (s, 3H), 3.05 (dd, J=10.0, 4.1 Hz, 1H), 2.98 (dd, J=10.0, 6.4 Hz, 1H), 2.79-2.89 (m, 1H), 2.29-2.42 (m, 1H); ESI-MS: m/z 658.6 [M+H]$^+$.

Example 34: Synthesis of Intermediate A24

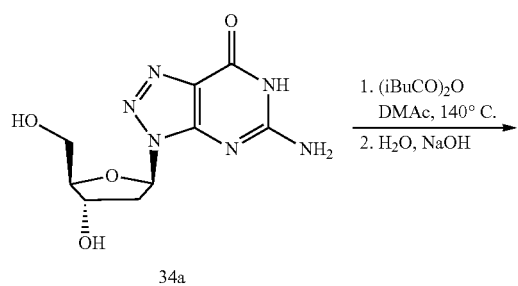

concentrated in vacuo and the residue purified by preparative reversed phase HPLC to give intermediate 34b (1.37 g, yield: 52%). ESI-MS: m/z 339.0 [M+H]$^+$.

Step 2: A solution of DMTrCl (1.51 g, 4.45 mmol) in dry pyridine (5.0 mL) was added to a solution of intermediate 34b (1.37 g, 4.05 mmol) in dry pyridine (20.0 mL) at 0° C. The reaction mixture was stirred at 5° C. for 12 h, next diluted with EtOAc, washed with saturated aqueous NaHCO$_3$, water and brine. The organic layer was dried over Na$_2$SO$_4$, filtered, and concentrated to dryness under reduced pressure. The residue was purified by silica gel column chromatography (gradient elution: 20 to 80% EtOAc in heptane) to give intermediate A24 as a white solid (1.65 g, yield: 64%). $^1$H NMR (500 MHz, DMSO-d$_6$) δ ppm 12.18 (br s, 1H), 12.05 (br s, 1H), 7.22-7.26 (m, 2H), 7.14-7.21 (m, 3H), 7.12 (dd, J=8.9, 3.0 Hz, 4H), 6.77 (d, J=9.2 Hz, 2H), 6.71-6.75 (m, 2H), 6.48 (dd, J=7.1, 3.4 Hz, 1H), 5.43 (d, J=5.0 Hz, 1H), 4.56-4.64 (m, 1H), 3.98-4.02 (m, 1H), 3.71 (s, 3H), 3.70 (s, 3H), 3.07-3.12 (m, 1H), 2.98-3.06 (m, 2H), 2.80 (spt, J=6.9 Hz, 1H), 2.44-2.50 (m, 1H), 1.14 (d, J=6.9 Hz, 3H), 1.14 (d, J=6.9 Hz, 3H); ESI-MS: m/z 641.1 [M+H]$^+$.

Example 35: Synthesis of Intermediate A25

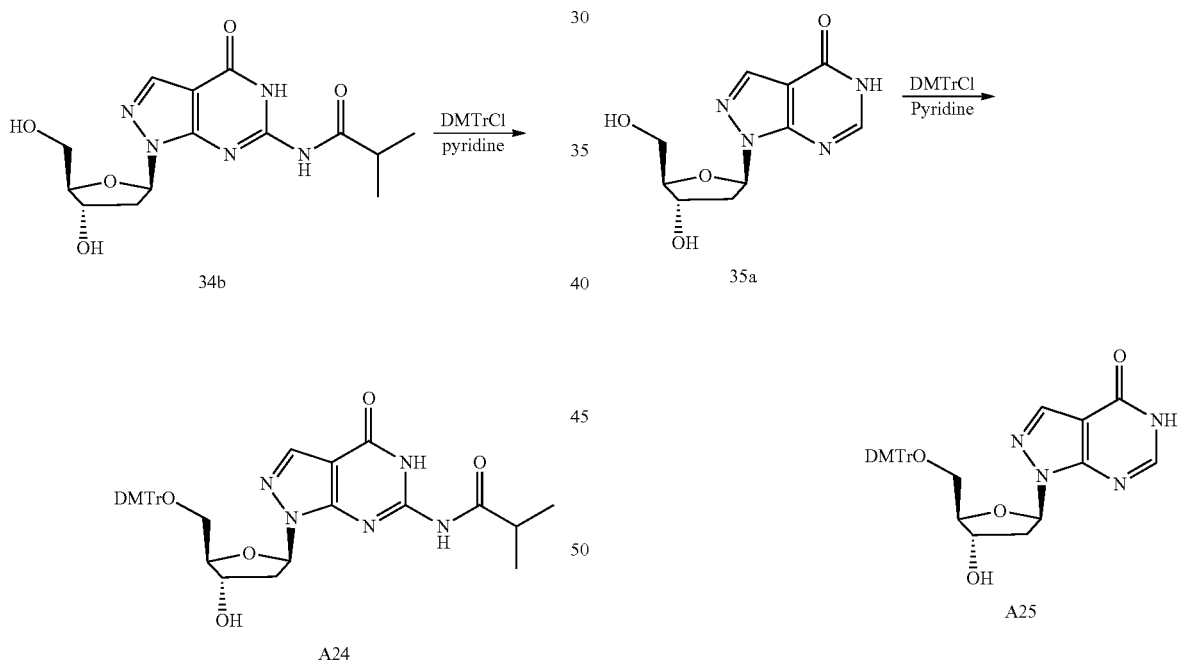

Step 1: Isobutyric anhydride (6.19 g, 39.15 mmol) was added dropwise to a solution of 8-aza-2'-deoxyguanosine (34a, CAS: 4546-73-0, 2.1 g, 7.83 mmol) in anhydrous dimethylacetamide (DMAc, 60 mL). The reaction mixture was stirred at 140° C. for 2 h after which it was cooled to room temperature prior the addition of water (20 mL) and NaOH (4.38 g, 109.61 mmol). The resulting mixture was stirred for an additional 2 h after which the pH was adjusted to 7 with a 6 M HCl solution. The resulting solution was Intermediate A25 was prepared from 35a (CAS: 95087-12-0) using the procedure as exemplified for the preparation of intermediate A11 $^1$H NMR (600 MHz, DMSO-d$_6$) δ ppm 12.30 (br s, 1H), 8.15 (s, 1H), 8.08 (s, 1H), 7.31 (d, J=7.2 Hz, 2H), 7.21-7.15 (m, 7H), 6.79 (d, J=9.0 Hz, 2H), 6.75 (d, J=9.0 Hz, 2H), 6.55 (dd, J=6.6, 3.6 Hz, 1H), 5.32 (d, J=4.8 Hz, 1H), 4.56-4.52 (m, 1H), 3.94 (q, J=5.4 Hz, 1H), 3.71 (s, 3H), 3.71 (s, 3H), 3.06 (dd, J=3.6, 10.2 Hz, 1H), 3.00 (dd, J=6.6, 10.2 Hz, 1H), 2.77-2.74 (m, 1H), 2.35-2.30 (m, 1H); ESI-MS: m/z 553.1 [M−H]$^-$.

Example 36: Synthesis of Compounds 49-59
Compounds 49-57 are prepared using the procedures, reagents and intermediates described in Examples 1-36.
49
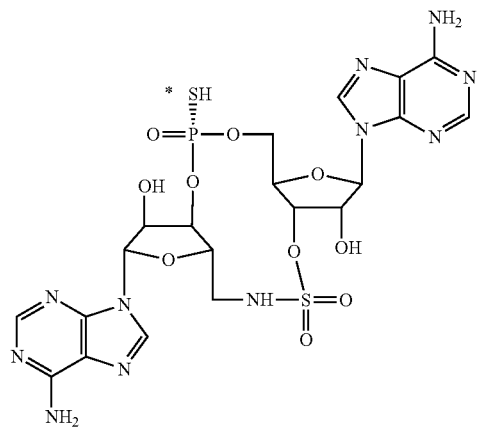
50
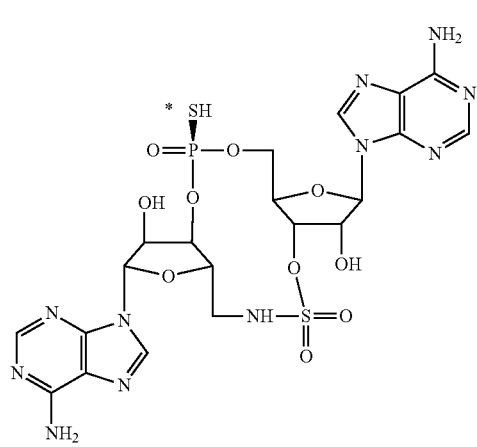
51
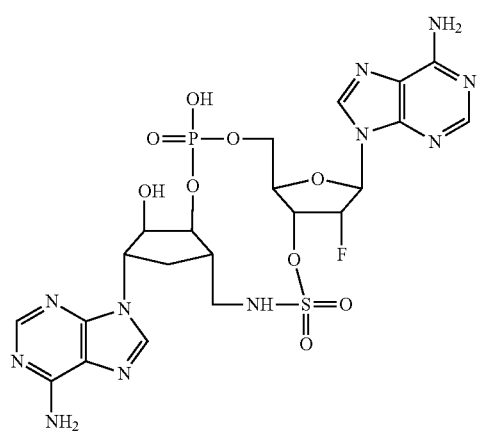
52
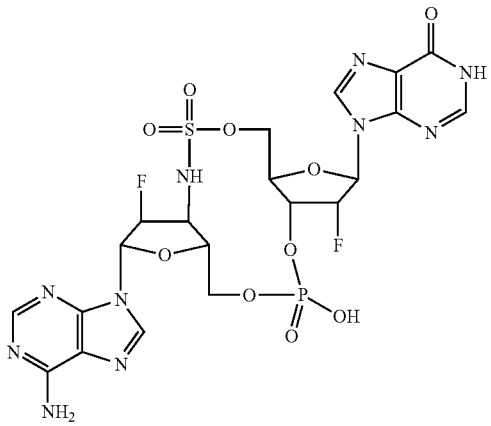
53
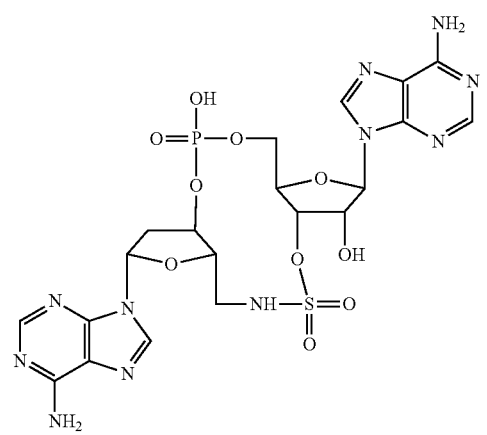
54
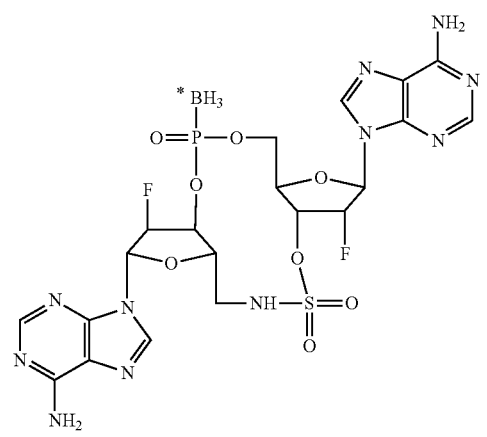

55
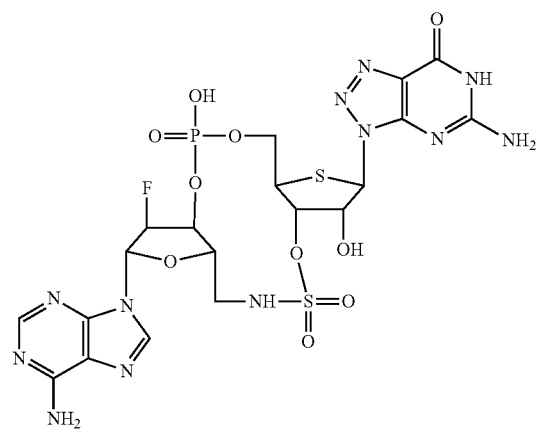
56
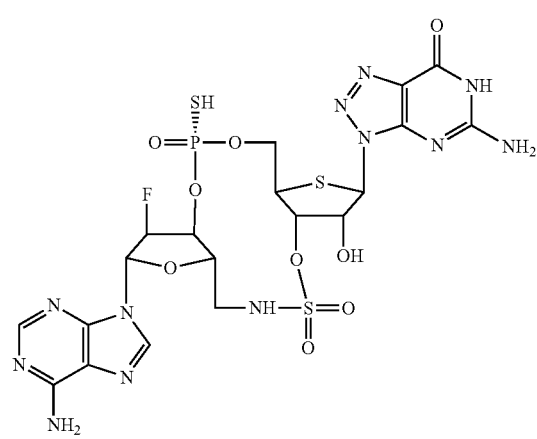
57
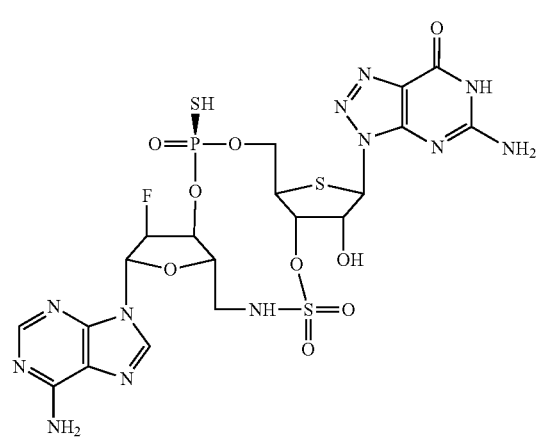
58
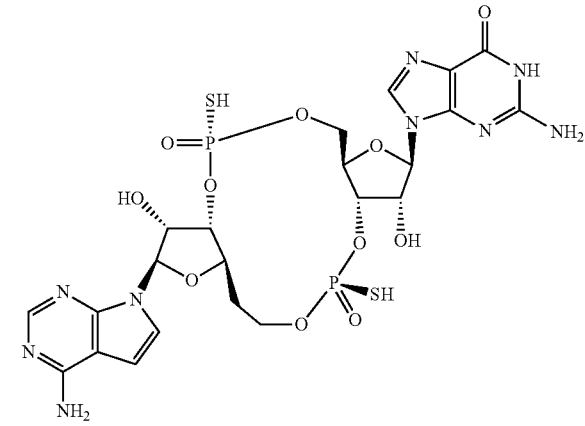
59
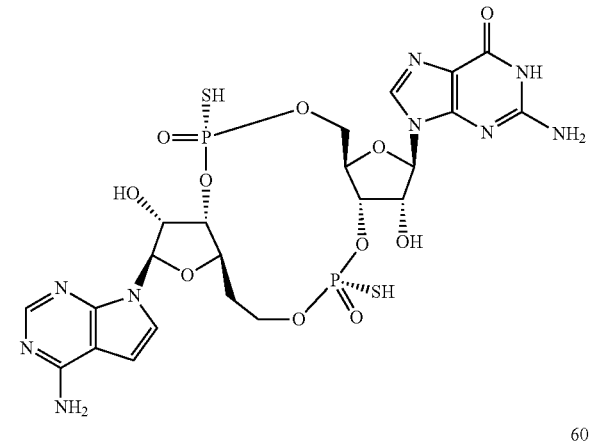
60
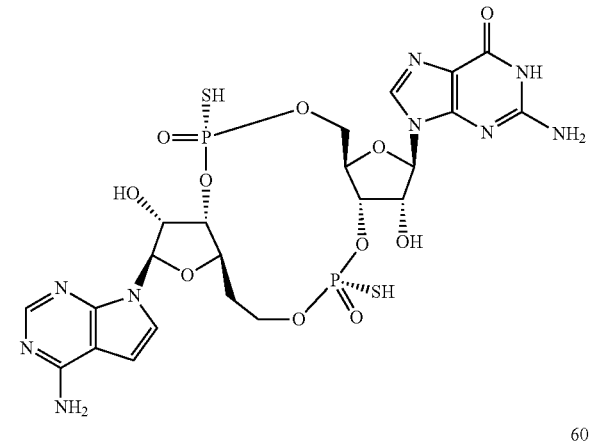
TABLE 2
| Compound Number | NMR (δ ppm) and LCMS | Synthesis in analogy to example |
|---|---|---|
| 10 | $^1$H NMR (400 MHz, D$_2$O) 7.96 (s, 1H), 7.72 (s, 1H), 7.30 (s, 1H), 6.46-6.29 (m, 1H), 6.09 (d, J = 16.3 Hz, 1H), 5.68-5.49 (m, 1H), 5.47-5.34 (m, 1H), 5.31-5.11 (m, 1H), 5.04-4.86 (m, 1H), 4.58-4.35 (m, 3H), 4.08 (dd, J = 4.6, 11.9 Hz, 1H), 3.81 (br d, J = 11.5 Hz, 1H), 3.47 (br d, J = 12.5 Hz, 1H); $^{31}$P NMR (162 MHz, | 8 |

TABLE 2-continued

| Compound Number | NMR (δ ppm) and LCMS | Synthesis in analogy to example |
|---|---|---|
| | D$_2$O) −1.60 (s, 1P); $^{19}$F NMR (376 MHz, D$_2$O) −197.68 (s, 1F), −200.28 (s, 1F); ESI-MS: m/z = 678 [M + H]$^+$. | |
| 8 | $^1$H NMR (400 MHz, DMSO-d$_6$) 9.50 (br, s, 1H), 8.49 (s, 1H), 8.31 (br, d, J = 12.8 Hz, 1H), 8.08 (s, 1H), 7.76 (s, 1H), 7.59-7.35 (m, 4H), 6.53-6.30 (m, 2H), 6.03 (s, 1H), 5.58-5.35 (m, 1H), 5.21-5.06 (m, 2H), 4.71 (br, s, 1H), 4.35 (br, d, J = 6.5 Hz, 1H), 4.27 (br, d, J = 8.5 Hz, 1H), 4.16 (br, d, J = 12.0Hz, 1H), 3.86-3.77 (m, 1H), 3.59 (br, d, J = 11.0 Hz, 1H); $^{19}$F NMR (376.5 MHz, DMSO-d$_6$) −197.68 (1 1F); $^{31}$P NMR (162 MHz, DMSO-d$_6$) −2.74 (s, 1P); ESI-MS: m/z = 660.1 [M + H]$^+$. | 6 |
| 46 | $^1$H NMR (400 MHz, D$_2$O) 8.10 (s, 1 H), 8.08 (s, 1 H), 7.92 (s, 1 H), 7.41 (br s, 1 H), 7.25-7.31 (m, 2 H), 7.13-7.21 (m, 3 H), 6.40 (dd, J = 8.1, 2.8 Hz, 1 H), 6.07 (s, 1 H), 5.43 (dd, J = 8.7, 5.1 Hz, 1 H), 5.13-5.22 (m, 1 H), 5.11 (br d, J = 5.3 Hz, 1 H), 5.01 (s, 2 H), 4.47 (br d, J = 8.1 Hz, 1 H), 4.39 (br d, J = 12.2 Hz, 1 H), 4.30 (br dt, J = 7.7, 2.3 Hz, 1 H), 4.07 (dd, J = 11.2, 5.1 Hz, 1 H), 3.71 (dd, J = 13.0, 2.8 Hz, 1 H), 3.50 (br dd, J = 13.0, 2.0 Hz, 1 H), 2.67-2.81 (m, 2 H); $^{31}$P NMR (162 MHz, D$_2$O) −0.95 (s, 1 P); ESI-MS: m/z-732.4 [M + H]$^+$. | 5 |
| 6 | $^1$H NMR (400 MHz, D$_2$O) 7.94 (s, 1 H), 7.89 (s, 1 H), 7.76 (s, 1 H), 7.13 (br s, 1 H), 6.10-6.19 (m, 2 H), 5.29-5.39 (m, 1 H), 4.95-5.03 (m, 1 H), 4.53 (br d, J = 9.05 Hz, 2 H), 4.35 (br d, J = 11.49 Hz, 1 H), 4.14 (br d, J = 8.07 Hz, 1H), 3.98 (dd, J = 12.10, 5.26 Hz, 1 H), 3.53-3.59 (m, 1 H), 3.35 (br d, J = 12.23 Hz, 1 H), 2.55-2.66 (m, 2 H); $^{19}$F NMR (376 MHz, D$_2$O) −200.63 (br d, J = 47.68 Hz, 1 F); $^{31}$P NMR (162 MHz, D$_2$O) −1.02 (s, 1 P); ESI-MS: m/z 644.1 [M + H]$^+$ | 5 |
| (*R) 16 | $^1$H NMR (400 MHz, D$_2$O) 8.40 (s, 1H), 8.01 (s, 1H), 7.77 (s, 1H), 6.41 (d, J = 17.8 Hz, 1H), 6.20-6.12 (m, 1H), 5.88 (br, d, J = 4.5 Hz, 0.5 H), 5.74 (br, dd, J = 4.3, 11.5 Hz, 1H), 5.64-5.53 (m, 1.5 H), 5.20-5.00 (m, 1H), 4.57 (br, d, J = 8.8 Hz, 1H), 4.49-4.33 (m, 2H), 4.14 (br, dd, J = 4.5, 11.8 Hz, 1H), 3.74-3.61 (m, 1H), 3.45 (br, d, J = 12.8 Hz, 1H); $^{19}$F NMR (376 MHz, D$_2$O) −198.45 (s, 1F), −199.72 (s, 1F); $^{31}$P NMR (162 MHz, D$_2$O) 55.34 (s, 1P); ESI-MS: m/z = 694.1 [M + H]$^+$. | 2 |
| (*S) 16 | $^1$H NMR (400 MHz, D$_2$O) 8.00 (br, s, 1H), 7.88 (s, 1H), 7.70 (s, 1H), 6.12- 5.69 (m, 5H), 5.34-5.13 (m, 1H), 4.68 (br d, J = 9.0 Hz, 1H), 4.56-4.40 (m, 2H), 4.11 (br, dd, J = 7.8, 12.3 Hz, 1H), 3.78 (br, d, J = 11.5 Hz, 1H), 3.44 (br, d, J = 13.8 Hz, 1H); $^{19}$F NMR (376 MHz, D$_2$O) −200.85 (s, 1F), −201.15 (s, 1F); $^{31}$P NMR (162 MHz, D$_2$O) 55.41 (s, 1P); ESI-MS: m/z = 694.1 [M + H]$^+$. | 2 |
| (*S) 18 | $^1$H NMR (400 MHz, DMSO-d6) 10.64 (br s, 1H), 9.66 (br s, 1H), 8.41 (br s, 1H), 8.11-7.93 (m, 2H), 7.54 (br s, 2H), 6.62-6.47 (m, 1H), 6.53 (br s, 1H), 6.44-6.34 (m, 1H), 6.39 (br d, J = 19.8 Hz, 1H), 6.47-6.31 (m, 1H), 6.20 (d, J = 17.6 Hz, 1H), 5.72-5.36 (m, 2H), 5.35-5.13 (m, 2H), 4.45-4.18 (m, 3H), 3.84 (br d, J = 12.5 Hz, 1H), 3.61 (br d, J = 9.8 Hz, 1H); $^{31}$P NMR (162 MHz, DMSO-d6) 52.73 (s, 1P); $^{19}$F NMR (376 MHz, DMSO-d6) −198.70 (s, 1F), −199.48 (s, 1F); ESI-MS: m/z = 694.1 [M + H]$^+$. | 2 |
| (*R) 18 | $^1$H NMR (400 MHz, D$_2$O) 7.90 (s, 1H), 7.68 (s, 1H), 7.25 (s, 1H), 6.40-6.24 (m, 1H), 6.04 (d, J = 16.4 Hz, 1H), 5.59-5.40 (m, 1H), 5.38-5.25 (m, 1H), 5.23-5.06 (m, 1H), 5.05-4.91 (m, 1H), 4.53-4.36 (m, 3H), 3.95 (dd, J = 6.0, 12.3 Hz, 1H), 3.81-3.69 (m, 1H), 3.81-3.69 (m, 1H), 3.36 (br d, J = 13.0 Hz, 1H); $^{31}$P NMR (162 MHz, D$_2$O) 55.12 (s, 1P); $^{19}$F NMR (376 MHz, D$_2$O) −196.95 (s, 1F), −200.13 (s, 1F); ESI-MS: m/z = 694.0 [M + H]$^+$. | 2 |
| (*S) 19 | $^1$H NMR (400 MHz, D$_2$O) 8.73 (s, 1H), 8.36 (br, s, 1H), 8.25 (s, 1H), 7.81 (br, s, 1H), 6.63-6.52 (m, 1H), 6.34 (s, 1H), 5.95-5.78 (m, 1H), 5.42-5.30 (m, 2H), 5.01 (br, d, J = 4.3 Hz, 1H), 4.75-4.72 (m, 1H), 4.67 (br, d, J = 9.3 Hz, 1H), 4.59 (br, d, J = 12.0 Hz, 1H), 4.26 (br, dd, J = 4.1, 11.9 Hz, 1H), 3.92 (br, d, J = 11.5Hz, | 7 |

TABLE 2-continued

| Compound Number | NMR (δ ppm) and LCMS | Synthesis in analogy to example |
|---|---|---|
| | 1H), 3.63 (br, d, J = 13.3 Hz, 1H); $^{19}$F NMR (376.5 MHz, D$_2$O) −197.60 (s, 1F); $^{31}$P NMR (162 MHz, D2O) 54.67 (s, 1P); ESI-MS: m/z = 676.1 [M + H]$^+$. | |
| (*R) 19 | $^1$H NMR (400 MHz, D$_2$O) 8.38 (s, 1H), 8.25 (s, 1H), 8.23 (br, s, 1H), 7.42 (br, s, 1H), 6.55-6.47 (m, 1H), 6.21 (s, 1H), 5.54 (br, d, J = 4.0 Hz, 0.5H), 5.40 (td, J = 4.6, 9.6 Hz, 1.5 H), 5.35-5.22 (m, 1H), 5.14 (d, J = 4.5 Hz, 1H), 4.75 (dd, J = 1.5, 2.5 Hz, 1H), 4.73-4.68 (m, 1H), 4.64 (br, d, J = 9.5 Hz, 1H), 4.20 (br, dd, J = 6.0, 12.0 Hz, 1H), 3.94 (br, d, J = 12.5 Hz, 1H), 3.62 (br, d, J = 13.1 Hz, 1H); $^{19}$F NMR (376.5 MHz, D$_2$O) −196.38 (s, 1F); $^{31}$P NMR (162 MHz, D$_2$O) 54.702 (s, 1P); ESI-MS: m/z = 676.1 [M + H]$^+$. | 7 |
| (*S) 20 | $^1$H NMR (400 MHz, D$_2$O) 8.36 (d, J = 6.25 Hz, 2 H), 8.04-8.11 (m, 1 H), 8.08 (s, 1 H), 7.85 (s, 1 H), 7.72 (s, 1 H), 6.31-6.42 (m, 2 H), 5.58-5.79 (m, 1 H), 5.40-5.53 (m, 1 H), 5.02-5.13 (m, 1 H), 4.55 (br d, J = 8.88 Hz, 1 H), 4.32 (br d, J = 12.13 Hz, 1 H), 4.23 (br d, J = 4.50 Hz, 1 H), 4.06 (dd, J = 11.82, 5.19 Hz, 1 H), 3.54 (dd, J = 13.63, 4.50 Hz, 1 H), 3.36-3.44 (m, 1 H), 2.96 (ddd, J = 14.32, 7.19, 3.63 Hz, 1 H), 2.66-2.78 (m, 1 H); $^{19}$F NMR (377 MHz, D$_2$O) −200.29 (s, 1 F); $^{31}$P NMR (162 MHz, D$_2$O) 54.85 (s, 1 P); ESI-MS: m/z = 660.0 [M + H]$^+$ | 2 |
| (*R) 20 | $^1$H NMR (400 MHz, D$_2$O) 8.35 (s, 1 H), 8.04 (s, 1 H), 7.96 (s, 1 H), 7.86 (s, 1 H), 6.19-6.28 (m, 2H), 5.68-5.86 (m, 1 H), 5.33-5.46 (m, 1 H), 5.17 (quin, J = 8.13 Hz, 1 H), 4.62 (br d, J = 9.51 Hz, 1 H), 4.49 (br d, J = 12.13 Hz, 1 H), 4.47-4.53 (m, 1 H), 4.21 (br d, J = 8.00 Hz, 1 H), 4.00 (dd, J = 12.26, 6.50 Hz, 1 H), 3.59-3.69 (m, 1 H), 3.39 (br d, J = 12.63 Hz, 1 H), 2.65-2.74 (m, 2 H); $^{19}$F NMR (377 MHz, D$_2$O) −200.59 (br s, 1 F); $^{31}$P NMR (162 MHz, D$_2$O) 54.74 (s, 1 P); ESI-MS: m/z = 660.0 [M + H]$^+$. | 2 |
| 21 | $^1$H NMR (400 MHz, D$_2$O) 8.11 (s, 1 H), 7.89 (s, 1 H), 7.71 (s, 1 H), 7.64 (s, 1 H), 6.12 (dd, J = 15.06, 10.54 Hz, 2 H), 5.47-5.88 (m, 2 H), 5.05-5.22 (m, 1 H), 4.61 (d, J = 9.29 Hz, 1 H), 4.38-4.52 (m, 4 H), 4.07 (dd, J = 11.92, 5.90 Hz, 1 H); $^{19}$F NMR (377 MHz, D$_2$O) −200.64 (br s, 1 F), −204.13 (br s, 1 F); $^{31}$P NMR (162 MHz, D$_2$O) −1.93 (s, 1 P); ESI-MS: m/z = 663.1 [M + H]$^+$ | 12 |
| 7 | $^1$H NMR (400 MHz, D$_2$O) 8.24 (s, 1 H), 8.07 (s, 1H), 7.82 (br s, 1H), 6.54-6.48 (m, 1H), 5.53 (br s, 0.5H), 5.40 (br s, 0.5H), 5.27-5.20 (m, 3H), 5.01 (br s, 1H), 4.59-4.48 (m, 3H), 4.19-4.16 (m, 1H), 3.87-3.84 (m, 1H), 3.61-3.58 (m, 1H); $^{31}$P NMR (162 MHz, D$_2$O) −2.04 (s, 1 P); $^{19}$F NMR (377 MHz, D$_2$O) −197.6 to −197.8 (m, 1 F); ESI-MS: m/z = 674.4 [M + H]$^−$ | 6 |
| (*R) 22 | $^1$H NMR (400 MHz, D$_2$O) 8.04 (s, 1 H), 7.78 (s, 1 H), 7.69 (br s, 1 H), 7.64 (d, J = 1.47 Hz, 1 H), 6.07 (t, J = 14.06 Hz, 2 H), 5.47-5.70 (m, 2 H), 5.02-5.21 (m, 1 H), 4.72 (br d, J = 11.74 Hz, 1 H), 4.55 (br d, J = 9.29 Hz, 1 H), 4.35-4.52 (m, 4 H), 3.95 (br dd, J = 12.23, 7.09 Hz, 1 H); $^{19}$F NMR (377 MHz, D$_2$O) −200.51 (br s, 1 F), −203.41 (br s, 1 F); $^{31}$P NMR (162 MHz, D$_2$O) 55.05 (br s, 1 P); ESI-MS: m/z = 679.1 [M + H]$^+$ | 2 |
| (*S) 22 | $^1$H NMR (400 MHz, D$_2$O) 8.21-8.31 (m, 1 H), 7.87-7.95 (m, 1 H), 7.66-7.78 (m, 2 H), 6.08-6.27 (m, 2 H), 5.85-6.05 (m, 1 H), 5.27-5.48 (m, 1 H), 4.87-5.05 (m, 1 H), 4.57 (br d, J = 12.47 Hz, 1 H), 4.48 (br d, J = 8.80 Hz, 1 H), 4.15-4.39 (m, 4 H), 4.00 (br dd, J = 11.74, 5.38 Hz, 1 H); 19F NMR (377 MHz, D$_2$O) −199.61 (br s, 1 F), −202.36 (br s, 1 F); $^{31}$P NMR (162 MHz, D$_2$O) 54.08 (br s, 1 P); ESI-MS: m/z = 679.1 [M + H]$^+$ | 2 |
| 11 | $^1$H NMR (400 MHz, D$_2$O) 7.96-7.85 (m, 2H), 7.81 (s, 1H), 7.01 (br s, 1H), 5.94-5.73 (m, 2H), 5.18 (br dd, J = 4.2, 9.3 Hz, 1H), 4.87 (d, J = 4.4 Hz, 1H), 4.81-4.72 (m, 2H), 4.42 (br s, 2H), 4.37-4.27 (m, 2H), 3.97 (dd, J = 4.8, 11.9 Hz, 1H), 3.67-3.58 (m, 1H), 3.31 (br d, J = 12.7 Hz, 1H); $^{31}$P NMR (162 MHz, D$_2$O) −1.51; ESI-MS: m/z = 658.2 [M + H]$^+$. | 6 |
| (*R) 12 | $^1$H NMR (400 MHz, D$_2$O) 7.95-7.73 (m, 3H), 6.93 (br s, 1H), 5.97-5.70 (m, 2H), 5.12 (dd, J = 4.3, 9.2 Hz, 1H), 4.91-4.76 (m, 2H), 4.48-4.33 (m, 3H), 4.28 (br d, | 7 |

TABLE 2-continued

| Compound Number | NMR (δ ppm) and LCMS | Synthesis in analogy to example |
|---|---|---|
| | J = 9, 3 Hz, 1H), 3.88 (br dd, J = 6.2, 11.6 Hz, 1H), 3.66-3.54 (m, 1H), 3.26 (br d, J = 12.5 Hz, 1H); $^{31}$P NMR (162 MHz, D$_2$O) 54.59 (s, 1P); ESI-MS: m/z = 674.0 [M + H]$^+$. | |
| 4 | $^1$H NMR (400 MHz, D$_2$O) 8.03 (s, 1H), 7.83 (s, 1H), 7.44-7.41 (m, 1H), 7.43 (s, 1H), 6.52-6.44 (m, 1H), 5.97 (s, 1H), 5.45 (br dd, J = 4.8, 9.2 Hz, 1H), 5.37 (br d, J =3.6 Hz, 1H), 5.24 (br d, J =4.0 Hz, 1H), 5.11-4.95 (m, 1H), 4.58 (br d, J =9.6 Hz, 1H), 4.52-4.45 (m, 2H), 4.13 (br dd, J =4.4, 12.0 Hz, 1H), 3.91 (br s, 1H), 3.88 (s, 3H), 3.54 (br d, J = 13.6 Hz, 1H); $^{31}$P NMR (162 MHz, D$_2$O) −1.64 (s, 1P); $^{19}$F NMR (376 MHz, D$_2$O) −197.35 to −198.00 (m, 1F); ESI-MS: m/z = 690.2 [M + H]$^+$. | 9 |
| 23 | $^1$H NMR (400 MHz, D$_2$O) 8.07 (s, 1H), 7.85 (s, 1H), 7.60 (s, 1H), 6.50-6.42 (m, 1H), 6.18 (br d, J = 7.2 Hz, 1H), 5.55-5.47 (m, 1H), 5.43-5.28 (m, 1H), 5.21-5.07 (m, 1H), 4.56 (br d, J =9.6 Hz, 1H), 4.44-4.36 (m, 2H), 4.16 (br dd, J =5.2, 11.2 Hz, 1H), 3.85 (br d, J = 11.2 Hz, 1H), 3.51 (br d, J =13.2 Hz, 1H), 3.25-3.15 (m, 1H), 2.98-2.88 (m, 1H); $^{31}$P NMR (162 MHz, D$_2$O) −1.56 (s, 1P); $^{19}$F NMR (376 MHz, D$_2$O) −197.18 to −197.92 (m, 1F); ESI-MS: m/z = 660.0 [M + H]$^+$. | 9 |
| 25 | $^1$H NMR (400 MHz, D$_2$O) 7.99 (m, 1H), 7.93 (s, 1H), 7.83 (s, 1H), 6.88 (t, J = 8.0 Hz, 1H), 6.34-6.28 (m, 1H), 6.07-5.91 (m, 1H), 5.83-5.75 (m, 1H), 5.44-5.32 (m, 2H), 4.40 (br dd, J = 8.0, 20 Hz, 2H), 4.19 (br d, J = 12 Hz, 1H), 4.05 (br dd, J = 4.0, 12 Hz, 1H), 3.81-3.78 (m, 1H), 3.48 (br d, J = 12.0 Hz, 1H); $^{19}$F NMR (376 MHz, D$_2$O) −122.16 (br s, 1F), −197.92 (br s, 1F); $^{31}$P NMR (162 MHz, D$_2$O) −1.97 (br s, 1P); ESI-MS: m/z = 664.1 [M + H]$^+$ | 8 |
| 38 | $^1$H NMR (400 MHz, D$_2$O) 8.38-8.02 (m, 1H), 7.98-7.57 (m, 1H), 8.32-7.56 (m, 1H), 7.15-6.72 (m, 1H), 6.56-6.28 (m, 1H), 6.10 (br s, 1H), 5.62-5.26 (m, 1H), 5.11-4.83 (m, 2H), 5.11-4.83 (m, 1H), 4.54-3.31 (m, 6H); $^{19}$F NMR (376 MHz, D$_2$O) −197.23 (br s, 1F); $^{31}$P NMR (162 MHz, D$_2$O) −2.69 (br s, 1P); ESI-MS: m/z = 672.2 [M + H]$^+$ | 9 |
| 26 | $^1$H NMR (400 MHz, D$_2$O) 8.29 (br s, 1 H), 7.84-8.01 (m, 2 H), 6.29-6.46 (m, 2 H), 5.57-5.79 (m, 1 H), 5.09-5.40 (m, 3 H), 4.41 (br d, J = 8.03 Hz, 1 H), 4.19-4.31 (m, 2 H), 4.07 (br dd, J = 10.04, 4.77 Hz, 1 H), 3.68 (br d, J = 13.30 Hz, 1 H), 3.39 (br d, J = 12.30 Hz, 1 H); $^{19}$F NMR (376 MHz, D$_2$O) −193.30 (br d, J = 22.01 Hz, 1 F), −193.47 (br s, 1 F); $^{31}$P NMR (162 MHz, D$_2$O) −1.51 (s, 1 P); ESI-MS: m/z = 678.1 [M + H]$^+$ | 9 |
| 27 | $^1$H NMR (400 MHz, D$_2$O) 8.03 (s, 1 H), 8.00 (br s, 1 H), 7.89 (s, 1 H), 7.36 (br s, 1 H), 6.22 (d, J = 20.8 Hz, 1 H), 5.26 (dd, J = 51.6, 4.5 Hz, 1 H), 4.77-5.02 (m, 3 H), 4.35 (br d, J = 9.5 Hz, 1 H), 3.97 (br s, 2 H), 3.63 (br d, J = 11.3 Hz, 1 H), 3.35 (br d, J = 13.3 Hz, 1 H), 2.29-2.57 (m, 4 H), 2.08-2.24 (m, 1 H); $^{19}$F NMR (376 MHz, D$_2$O) −197.69 (s, 1F); $^{31}$P NMR (162 MHz, D$_2$O) −1.71 (s, 1P); ESI-MS: m/z = 642.2 [M + H]$^+$ | 8 |
| 29 | $^1$H NMR (400 MHz, D$_2$O) 7.97 (s, 1H), 7.80 (s, 1H), 7.58 (s, 1H), 6.96 (d, J = 1.8 Hz, 1H), 6.37-6.21 (m, 2H), 5.39 (d, J = 4.5 Hz, 1H), 5.43-5.20 (m, 1H), 5.19-5.04 (m, 1H), 4.40 (br d, J = 9.3 Hz, 1H), 4.27-4.12 (m, 2H), 4.02 (br dd, J = 5.3, 10.5 Hz, 1H), 3.74-3.63 (m, 1H), 3.37 (br d, J = 12.8 Hz, 1H), 2.87-2.70 (m, 2H); $^{19}$F NMR (376 MHz, D$_2$O) −167.62 (s, 1F), −197.49 (s, 1F); $^{31}$P NMR (162 MHz, D$_2$O) −1.68 (s, 1P); ESI-MS: m/z = 661.2 [M + H]$^+$ | 5 |
| (*R) 31 | $^1$H NMR (400 MHz, D$_2$O) 8.29 (s, 1H), 8.05 (s, 1H), 7.71 (s, 2H), 6.35 (s, 1H), 6.30 (d, J = 4.0 Hz, 1H), 5.78-5.49 (m, 2H), 5.41-5.34 (m, 1H), 5.13-5.01 (m, 1H), 4.47 (br d, J = 8.0 Hz, 1H), 4.41 (br d, J = 8.0 Hz, 1H), 4.33 (br d, J = 12.0 Hz, 1H), 4.04 (br dd, J = 4.0, 12.0 Hz, 1H), 3.65-3.62 (m, 1H), 3.36 (br d, J = 12.0 Hz, 1H); $^{19}$F NMR (376 MHz, D$_2$O) −197.93 (br s, 1F), −199.41 (br s, 1F); $^{31}$P NMR (162 MHz, D$_2$O) 54.86 (s, 1P); ESI-MS: m/z = 679.0 [M + H]$^+$. | 2 |
| (*S) 31 | $^1$H NMR (400 MHz, D$_2$O) 7.95-7.94 (m, 2H), 7.74 (s, 1H), 7.64 (s, 1H), 6.14-6.04 (m, 2H), 5.74-5.54 (m, 2H), 5.42-5.37 (m, 1H), 5.10-5.02 (m, 1H), 4.55 (br d, | 2 |

TABLE 2-continued

| Compound Number | NMR (δ ppm) and LCMS | Synthesis in analogy to example |
|---|---|---|
| | J = 8.0 Hz, 1H), 4.44-4.38 (m, 2H), 4.00 (br dd, J = 8.0, 12.0 Hz, 1H), 3.70-3.66 (m, 1H), 3.35 (br d, J = 16.0 Hz, 1H); $^{19}$F NMR (376 MHz, D$_2$O) −199.01 (br s, 1F), −200.64 (br s, 1F); $^{31}$P NMR (162 MHz, D$_2$O) 55.23 (br s, 1P); ESI-MS: m/z = 679.0 [M + H]$^+$. | |
| 32 | $^1$H NMR (400 MHz, D$_2$O) 8.11 (s, 1H), 7.91 (s, 1H), 7.36 (br d, J = 16.0 Hz, 2H), 7.22 (br s, 1H), 6.17 (br d, J = 8.0 Hz, 2H), 5.33-5.19 (m, 2H), 4.99-4.94 (m, 1H), 4.39 (br d, J = 8.0 Hz, 1H), 4.28-4.25 (m, 2H), 4.05 (br dd, J = 4.0, 12.0 Hz, 1H), 3.69 (br d, J = 12.0 Hz, 1H), 3.36 (br d, J = 13.0 Hz, 1H), 2.85-2.79 (m, 1H), 2.70-2.65 (m, 1H); $^{19}$F NMR (376 MHz, D$_2$O) −198.33 (br s, 1F); $^{31}$P NMR (162 MHz, D$_2$O) −1.91 (s, 1P); ESI-MS: m/z = 695.0 [M + H]$^+$ | 5 |
| 33 | $^1$H NMR (400 MHz, D$_2$O) 8.58 (s, 1H), 8.41 (br s, 1H), 8.36-8.23 (m, 1H), 8.02 (br s, 1H), 7.30 (br s, 1H), 6.35 (br s, 1H), 6.22 (br s, 1H), 5.47 (br d, J = 7.3 Hz, 1H), 5.43-5.23 (m, 1H), 5.06 (br d, J = 18.8 Hz, 1H), 4.52-4.31 (m, 3H), 4.18-4.05 (m, 1H), 3.72 (br d, J = 13.2 Hz, 1H), 3.42 (br d, J = 13.0 Hz, 1H), 3.31-3.17 (m, 1H), 3.00 (m, 1H); $^{19}$F NMR (376 MHz, D$_2$O) −197.74 (s, 1F); $^{31}$P NMR (162 MHz, D$_2$O) −1.69 (s, 1P); ESI-MS: m/z = 629.2 [M + H]$^+$ | 9 |
| (*R) 34 | $^1$H NMR (400 MHz, DMSO-d$_6$) 10.66 (s, 1 H), 9.88 (br s, 1 H), 8.31 (br s, 1 H), 8.06 (s, 1 H), 7.75 (d, J = 1.76 Hz, 1 H), 7.57 (br s, 2 H), 6.54 (br s, 2 H), 6.33-6.46 (m, 1 H), 6.17 (br dd, J = 17.86, 3.53 Hz, 1 H), 5.31-5.68 (m, 3 H), 5.14 (br d, J = 17.64 Hz, 1 H), 4.32 (br s, 1 H), 4.20 (br s, 1 H), 4.08 (br s, 1 H), 3.84 (br d, J = 10.80 Hz, 1 H), 3.58 (br d, J = 10.14 Hz, 1 H); $^{19}$F NMR (376 MHz, DMSO-d$_6$) −197.33 to −196.59 (m, 1 F), −199.39 (br s, 1 F); $^{31}$P NMR (162 MHz, DMSO-d$_6$) 53.37 (s, 1 P); ESI-MS: m/z = 694.0 [M + H]$^+$ | 2 |
| (*S) 34 | $^1$H NMR (400 MHz, D$_2$O) 8.00 (s, 1 H), 7.75 (d, J = 2.69 Hz, 2 H), 6.23-6.32 (m, 2 H), 5.52-5.75 (m, 1 H), 5.18-5.38 (m, 2 H), 4.98-5.17 (m, 1 H), 4.36 (br d, J = 9.54 Hz, 1 H), 4.15-4.27 (m, 2 H), 3.99 (br dd, J = 9.54, 6.11 Hz, 1 H), 3.61-3.76 (m, 1 H), 3.36 (br d, J = 13.21 Hz, 1 H); $^{19}$F NMR (376 MHz, D$_2$O) −193.64 (br d, J = 48.42 Hz, 1 F), −197.65 (br s, 1 F); $^{31}$P NMR (162 MHz, D$_2$O) 55.34 (br s, 1 P); ESI-MS: m/z = 694.1 [M + H]$^+$ | 2 |
| 35 | $^1$H NMR (400 MHz, DMSO-d$_6$) 9.86 (br s, 1H), 8.41 (br s, 1H), 8.33 (s, 1H), 8.31 (s, 1H), 8.16-8.15 (m, 1H), 7.71 (br s, 1H), 6.69 (dd, J = 3.2, 8.0 Hz, 1H), 6.48-6.40 (m, 1H), 5.68 (q, J = 7.2 Hz, 1H), 5.49-5.32 (m, 1H), 5.26-5.13 (m, 1H), 4.32 (br d, J = 9.2 Hz, 1H), 4.24 (br s, 1H), 3.86-3.78 (m, 2H), 3.61(br d, J = 4.0 Hz, 1H), 3.50 (ddd, J = 3.6, 7.6, 14.0 Hz, 1H), 3.33 (br d, J = 12.4 Hz, 1H), 3.03-2.93 (m, 1H); $^{19}$F NMR (376 MHz, DMSO-d$_6$) −197.52 (s, 1F); $^{31}$P NMR (162 MHz, DMSO-d$_6$) −2.89 (s, 1P); ESI-MS: m/z = 645.1 [M + H]$^+$ | 5 |
| 36 | $^1$H NMR (400 MHz, D$_2$O) 7.93 (s, 1H), 7.86 (s, 1H), 7.30 (br s, 1H), 7.11 (br s, 1H), 6.28-6.12 (m, 1H), 5.41-5.18 (m, 2H), 5.10 (br d, J = 5.6 Hz, 1H), 4.97-4.82 (m, 2H), 4.42 (br d, J = 10.0 Hz, 1H), 4.39-4.29 (m, 1H), 4.39-4.29 (m, 1H), 4.00 (br dd, J = 4.8, 11.6 Hz, 1H), 4.06-3.94 (m, 1H), 3.70 (br d, J = 11.6 Hz, 1H), 3.41 (br d, J = 13.2 Hz, 1H); $^{31}$P NMR (162 MHz, D$_2$O) −1.53 (br s, 1P); $^{19}$F NMR (376 MHz, D$_2$O) −198.26 (br s, 1F); ESI-MS: m/z-660.0 [M + H]$^+$ | 6 |
| 48 | $^1$H NMR (400 MHz, DMSO-d$^6$) d ppm 3.60 (br d, J = 13.05 Hz, 1 H), 3.80 (br d, J = 10.79 Hz, 1 H), 4.10 (br d, J = 12.30 Hz, 1 H), 4.24-4.33 (m, 2 H), 4.42 (br s, 1 H), 5.08 (dd, J = 7.91, 4.64 Hz, 1 H), 5.12-5.24 (m, 1 H), 5.24-5.40 (m, 1 H), 6.20 (d, J = 1.51 Hz, 1 H), 6.30 (d, J = 5.77 Hz, 1 H), 6.38-6.47 (m, 1 H), 6.50 (d, J = 3.76 Hz, 1 H), 7.27 (br s, 2 H), 7.49 (d, J = 3.51 Hz, 1 H), 7.61 (br s, 2 H), 7.89 (s, 1 H), 8.09 (s, 1 H), 8.34 (s, 1 H), 9.55 (br d, J = 3.26 Hz, 1 H); $^{19}$F NMR (376 MHz, DMSO-d$_6$) −197.63 (br s, 1 F); $^{31}$P NMR (162 MHz, DMSO-d$_6$) −2.36 (br s, 1 P); ESI-MS: m/z 659.2 [M + H]$^+$ | 11 |

TABLE 2-continued

| Compound Number | NMR (δ ppm) and LCMS | Synthesis in analogy to example |
|---|---|---|
| 39 | $^1$H NMR (400 MHz, D$_2$O) 8.03-8.02 (m, 2H), 7.85 (d, J = 8.0 Hz, 2H), 6.55 (dd, J = 2.6, 8.0 Hz, 1H), 6.34-6.28 (m, 1H), 5.55 (q, J = 8.0Hz, 1H), 5.43-5.30 (m, 1H), 5.24-5.13 (m, 1H), 4.40 (br d, J = 8.0 Hz, 1H), 4.24 (br dd, J = 4.0, 8.0 Hz, 1H), 3.99-3.92 (m, 2H), 3.70 (dd, J = 4.0, 12.0 Hz, 1H), 3.40 (br d, J = 16.0 Hz, 1H), 3.22-3.19 (m, 1H), 2.93-2.86 (m, 1H); $^{19}$F NMR (376 MHz, D$_2$O) −197.79 (br s, 1F); $^{31}$P NMR (162 MHz, D$_2$O) −1.68 (s, 1P); ESI-MS: m/z = 645.0 [M + H]$^+$ | 5 |
| 41 | $^1$H NMR (400 MHz, D$_2$O) 8.08 (s, 1H), 7.83 (s, 1H), 7.58 (s, 1H), 7.12 (d, J = 1.8Hz, 1H), 6.49-6.35 (m, 2H), 5.48-5.29 (m, 2H), 5.27-5.12 (m, 1H), 4.52 (br d, J = 9.5 Hz, 1H), 4.40-4.27 (m, 2H), 4.13 (br dd, J = 5.4, 10.9 Hz, 1H), 3.86-3.75 (m, 1H), 3.50 (d, J = 12.5 Hz, 1H), 3.12-2.99 (m, 1H), 2.97-2.83 (m, 1H); $^{19}$F NMR (376 MHz, D$_2$O) −165.99 (br s, 1F), −197.33 (br s, 1F); $^{31}$P NMR (162 MHz, D$_2$O) −1.75 (s, 1P); ESI-MS: m/z = 662.0 [M + H]$^+$. | 5 |
| 42 | $^1$H NMR (400 MHz, D$_2$O) 8.13 (s, 1H), 8.10 (s, 1H), 7.85 (s, 1H), 6.69 (d, J = 8.0 Hz, 1H), 6.37-6.32 (m, 1H), 5.76 (q, J = 8.0 Hz, 1H), 5.32-5.12 (m, 2H), 4.42-4.34 (m, 2H), 4.00-3.91 (m, 2H), 3.73 (dd, J = 4.0, 12.0 Hz, 1H), 3.42-3.39 (m, 2H), 3.03 (td, J = 8.0, 12.0 Hz, 1H); $^{19}$F NMR (376 MHz, D$_2$O) −197.76 (s, 1F); $^{31}$P NMR (162 MHz, D$_2$O) −1.98 (s, 1P); ESI-MS: m/z = 646.1 [M + H]$^+$ | 9 |
| 43 | $^1$H NMR (400 MHz, D$_2$O) 8.34 (s, 1H), 8.24 (s, 1H), 7.94 (s, 1H), 7.03 (s, 1H), 6.39-6.33 (m, 2H), 5.41-5.34 (m, 1H), 5.27-5.13 ( m, 1H), 5.01-4.90 (m, 1H), 4.48-4.38 (m, 3H), 4.09 (br dd, J = 4.0, 12.0 Hz, 1H), 3.75 (br d, J = 8.0 Hz, 1H), 3.43 (br d, J = 12.0 Hz, 1H), 3.17-3.12 (m, 1H), 3.09-3.01 (m, 1H); $^{19}$F NMR (376 MHz, D$_2$O) −196.91 (br s, 1F); $^{31}$P NMR (162 MHz, D$_2$O) −1.59 (s, 1P); ESI-MS: m/z = 645.2 [M + H]$^+$ | 9 |
| 44 | $^1$H NMR (400 MHz, D$_2$O) 8.11 (s, 1H), 7.89 (br s, 1H), 7.61 (br s, 1H), 6.54-6.28 (m, 1H), 6.19 (br d, J = 15.3 Hz, 1H), 5.91-5.68 (m, 1H), 5.64-5.33 (m, 2H), 5.23-5.04 (m, 1H), 4.70 (br d, J = 9.5 Hz, 1H), 4.64-4.51 (m, 2H), 4.21 (dd, J = 4.9, 12.2 Hz, 1H), 4.00-3.86 (m, 1H), 3.58 (br d, J = 13.3 Hz, 1H); $^{31}$P NMR (162 MHz, D$_2$O) −1.80 (br s, 1P); $^{19}$F NMR (376 MHz, D$_2$O) −197.70 to −198.12 (m, 1F), −200.46 to −200.88 (m, 1F); ESI-MS: m/z = 677.2 [M + H]$^+$ | 5 |
| 45 | $^1$H NMR (400 MHz, D$_2$O) 8.00-7.77 (m, 4H), 6.66 (br d, J =8.0 Hz, 1H), 6.29-6.23 (m, 1H), 5.84-5.70 (m, 1H), 5.41 (q, J =8.0 Hz, 1H), 5.14-5.04 (m, 1H), 4.42 (br d, J =8.0 Hz, 1H), 4.23-4.18 (m, 1H), 4.05-3.94 (m, 2H), 3.73 (br d, J =12.0 Hz, 1H), 3.47-3.40 (m, 2H), 3.09 (br d, J =4.0 Hz, 1H); $^{19}$F NMR (376 MHz, D$_2$O) −197.36 (br s, 1F); $^{31}$P NMR (162 MHz, D$_2$O) −1.42 (br s, 1P); ESI-MS: m/z = 644.2 [M + H]$^+$ | 9 |
| 15-S | $^1$H NMR (400 MHz, D$_2$O) δ ppm 8.95 (br, s, 1H), 8.83-8.60 (m, 3H), 7.85 (br, s, 2H), 7.40 (br, s, 2H), 7.00 (br, s, 1H), 6.75 (br, s, 1H), 6.42-5.80 (m, 4H), 5.37 (br, s, 4H), 5.07 (br, s, 1H), 4.68-4.55 (m, 1H), 4.33 (br, d, J = 17.3 Hz, 4H), 4.09(br, s, 1H). $^{19}$F NMR (376.5 MHz, D$_2$O) δ ppm-195.166; $^{31}$P NMR (162 MHz, D$_2$O) δ ppm 58.053; LCMS: ESI-MS: m/z = 796.4 [M + H]$^+$. LCMS: ESI-MS: m/z = 796.0 [M + H]$^+$. | 2 |
| 15-R | $^1$H NMR (400 MHz, D$_2$O) δ ppm 8.86 (s, 1H), 8.71 (s, 1H), 8.64 (s, 1H), 8.08 (s, 1H), 7.85 (d, J = 8.5 Hz, 1H), 7.35 (d, J = 8.8 Hz, 2H), 6.98-6.90 (m, 1H), 6.71 (s, 1H), 5.95 −5.68 (m, 3H), 5.52-5.40 (m, 3H), 5.07-4.97 (m, 3H), 4.55 (br, dd, J = 5.9, 10.9 Hz, 1H), 4.37-4.28 (m, 4H), 4.00 (br, d, J = 12.3 Hz, 1H). $^{19}$F NMR (376.5 MHz, D$_2$O) δ ppm-195.958. $^{31}$P NMR (162 MHz, D$_2$O) δ ppm 55.336 | 2 |

Biological Examples

In Vitro Assays

Example 1

STING SPA Binding Assay

The human STING SPA binding assay measures displacement of tritium labeled 2',3'cGAMP (cyclic (guanosine-(2'->5')-monophosphate-adenosine-(3'→5')monophosphate) to biotinylated STING protein. A soluble version of recombinant STING was expressed in E. coli that lacks the four transmembrane domains and contains residues 139-379 of Q86WV6 with an R at position 232 (H232R). Based on the allele frequency of 58% of the population, H232R is considered to be a wild type (Yi, et. al., "Single 20 Nucleotide Polymorphisms of Human STING can affect innate immune response to cyclic dinucleotides" PLOS ONE. 2013, 8(10), e77846). The STING construct has an N-terminal HIS tag, followed by a TEV protease cleavage site and an AVI tag to allow directed biotinylation by BirA biotin ligase (Beckett et al., A minimal peptide substrate in biotin holoenzyme synthetase-catalyzed biotinylation. (1999) Protein Science 8, 921-929). The HIS tag is cleaved after purification and prior to biotinylation.

The assay was run in 1536-well plates in a total volume of 8 μL per well by adding 8 nM [$^3$H]-2'3'-cGAMP and 40 nM biotin-STING protein in assay buffer [25 mM HEPES (Corning 25-060-C1) pH 7.5, 150 mM NaCl (Sigma S5150), 0.5 mg/mL BSA (Gibco 15260-037), 0.001% Tween-20 (Sigma P7949), molecular grade water (Corning 46-000-CM)]. Test compounds (80 nL) were added with an acoustic dispenser (EDC Biosystems) in 100% DMSO for a final assay concentration of 1% DMSO. Plates were centrifuged for 1 min and incubated for 60 min at room temperature. Finally, (2 μL) polystyrene streptavidin SPA beads (PerkinElmer RPNQ0306) were added and plates were sealed and centrifuged for 1 min at room temperature. Plates were dark adapted for 2 h and read on a ViewLux (Perkin Elmer) for 12 min per plate. A saturation binding curve for [$^3$H]-2'3'cGAMP showed a $K_D$ of 3.6±0.3 nM for binding to STING, comparable to reported values for the natural ligand (Zhang et al., Cyclic GMP-AMP containing mixed phosphodiester linkages is an endogenous high-affinity ligand for STING (Molecular Cell 2013 51(2):10.1016/j.molcel.2013.05.022.).

Other natural ligands including cyclic-di-GMP also returned values in this assay within the expected range. Reference compound is cGAMP and results are reported as percent inhibition and $IC_{50}$ values. Binding to mouse STING used a construct similar to the one described above containing residues 138-378 of Q3TBT3.

Full Length Human STING Binding Assay

Human STING from residues 1-379 of Q86WV6 with an R at position 232 (H232R) with an N-terminal 6HIS tag followed by a FLAG tag, a TEV protease cleavage site and an AVI tag for biotinylation was recombinantly expressed in HEK293-EXPI cells. Purified membranes were prepared from these cells and STING expression was confirmed and quantified by immunoblot. STING containing membranes were combined with test compound in a Greiner 384-well assay plate and incubated at room temperature for one hour in the same assay buffer used for the STING SPA binding assay. Next, [$^3$H]-2'3'cGAMP was added and plates were incubated for 30 min at room temperature. Reactions were transferred to a prewashed Pall 5073 filter plate and each well was washed 3 times with 50 μL assay buffer. Filter plates were dried at 50° C. for 1 h. To each well, 10 μL of Microscint scintillation fluid was added and plates were sealed and read on a TopCount (Perkin Elmer) for 1 min per well.

STING SPR Binding Assay

Compounds were analyzed on an S200 biacore SPR instrument (GE Healthcare). E. coli produced truncated STING protein was immobilized on a series S streptavidin chip via biotin capture (GE Healthcare #BR100531). Compounds were screened at 1:2 dilutions from 100 uM to 0.195 uM in run buffer (10 mM HEPES, pH 7.4, 150 mM NaCl, 0.005% P20, 1 mM TECEP). Steady state affinity and kinetic evaluations were carried out using 1:1 binding model (STING was treated as a dimer). Run parameters were as follows: 60 sec on, 300 sec off for cyclic-di-GMP (60 sec on/60 sec off), thiol isomer 1 (60 sec on/300 sec off) and cGAMP (60 sec on/1200 sec off) with a flow rate of 50 μL/min and data collection at 40 Hz at 25° C.

STING Human Cell Reporter Assay

Agonism of the human STING pathway is assessed in THP1-ISG cells (Invivogen, cat #thp-isg) derived from human THP1 monocyte cell line by stable integration of an interferon regulatory factor (IRF)-inducible SEAP reporter construct. THP1-Blue ISG cells express a secreted embryonic alkaline phosphatase (SEAP) reporter gene under the control of an ISG54 minimal promoter in conjunction with five interferon (IFN)-stimulated response elements. As a result, THP1-Blue ISG cells allow the monitoring of IRF activation by determining the activity of SEAP. The levels of IRF-induced SEAP in the cell culture supernatant are readily assessed with alkaline phosphatase detection medium, a SEAP detection reagent. These cells are resistant to Zeocin. 2'3'cGAMP was used as a positive control in this assay. To run the assay, 60,000 cells were dispensed in 30 μL/well of a white, opaque bottom tissue culture treated 384-well plate.

Test compounds were added in a volume of 10 μL (1% DMSO final concentration). Compounds are initially prepared in 100% DMSO, spotted on an intermediate dilution plate and then diluted in media prior to transfer. The assay was incubated for 24 h at 37° C., 5% $CO_2$ then plates were centrifuged at 1200 rpm (120×g) for 5 min. After final incubation, 90 μL of alkaline phosphatase detection medium-substrate was added to each well of a new 384-well clear plate and 10 μL of the cell supernatant was transferred from the assay plate to the new alkaline phosphatase detection medium-plate using a Biomek FX and mixed 4 times. Plates were incubated at RT for 20 min then absorbance at 655 nm was determined on the Tecan Safire2.

STING Mouse Cell Reporter Assay

Agonism of the mouse STING pathway is assessed in RAW Lucia cells (Invivogen, cat #rawl-isg) derived from mouse RAW-264.7 macrophage cell line by stable integration of an interferon-inducible Lucia luciferase reporter construct. RAW Lucia cells express a secreted luciferase reporter gene under the control of an ISG54 minimal promoter in conjunction with five interferon (IFN)-stimulated response elements. As a result, RAW Lucia cells allow the monitoring of IRF activation by determining the activity of luciferase. The levels of IRF-induced luciferase in the cell culture supernatant are readily assessed with QUANTI-Luc™, a luciferase detection reagent. These cells are resistant to Zeocin. 2'3'cGAMP is used as a positive control in this assay. To run the assay, 100,000 cells were dispensed in 90 μL/well of a clear, flat bottom tissue culture treated 96-well plate. Test compounds were added in a volume of 10 μL. The assay was incubated for 24 and 48 hours at 37° C., 5% C02. After incubation, 20 μL of the cell supernatant from the assay plate was transferred to a new 96-well white plate and 50 uL of QUANTI-Luc substrate was added. The plate was incubated, shaking, at RT for 5 minutes then luminescence was read on an EnVision 2104 with 0.1s integration time.

Human Interferon-β Induction Assay

THP1-Dual cells (Invivogen, cat #thpd-nfis) are used to measure the secretion of IFN-β into the culture supernatant following STING pathway activation. The THP1-Dual cell line is similar to the THP1-Blue ISG but has two stably integrated reporter genes to measure IRF and NFkB pathway activity simultaneously. IRF activity is monitored by secreted Lucia luciferase under the control of ISG54 and five interferon-stimulated response elements and NFkB activity is monitored by SEAP under the control of an IFN-β minimal promoter fused to five NFkB response elements and three copies of the c-Rel binding site. To run the assay, anti-IFN-0 capture antibodies were coated on 96 well MultiArray plates (Mesoscale Discovery). After a one hour incubation, plates were washed and 50 μL supernatant from the STING human cell reporter assay plates or IFN-β standards were mixed with 20 μL Sulfotag-conjugated detection antibody in the coated plates. Plates were incubated, shaking for 2 h, washed, and read buffer was applied. Electrochemiluminescence was measured on the SectorImager.

STING Cell Signaling Pathway Assessment

Agonism of the STING pathway was measured in THP1 BLUE ISG or THP1-Dual cells by western blot of phospho-STING (S366), phospho-TBK1 (S172) and phospho-IRF3 (S396). Protein changes were measured six hours after compound addition to the culture media or 1 hour after electroporation. For electroporation, 5 million cells in 90 μL nucleofection buffer were mixed with 10 μL test compounds. These mixtures were electroporated using program V-001 on an Amaxa Nucleofector (Lonza). Cells were transferred into 12 well plates with fresh media and allowed to recover for one hour at 37° C., 5% $CO_2$. The following applies to both electroporation and direct compound addition methods: Cells were then washed in cold HBSS and lysed in RIPA buffer. Samples were total protein normalized and either diluted in ProteinSimple sample buffer or LDS loading buffer. Samples were heat denatured at 95° C. for 5 min, then PeggySue (ProteinSimple) was used to measure phospho- and total STING and IRF3 while the NuPAGE (Invitrogen) system was used to measure TBK1. Data was analyzed using Compass or Licor Odyssey software, respectively.

STING In Vivo Activity

For all studies, female Balb/c mice were obtained from Charles River Labs (Wilmington, Mass.) and used when they were 6-8 weeks of age and weighed approximately 20 g. All animals were allowed to acclimate and recover from any shipping-related stress for a minimum of 5 days prior to experimental use. Reverse osmosis chlorinated water and irradiated food (Laboratory Autoclavable Rodent Diet 5010, Lab Diet) were provided ad libitum, and the animals were maintained on a 12 h light and dark cycle. Cages and bedding were autoclaved before use and changed weekly. All experiments were carried out in accordance with The Guide for the Care and Use of Laboratory Animals and were approved by the Institutional Animal Care and Use Committee of Janssen R & D, Spring House, Pa. Each experimental group contained 8 mice. In vivo efficacy in a mouse CT26 tumor model was determined by implanting 500,000 CT26 colon carcinoma tumor cells subcutaneously into Balb/c mice and allowing tumors to establish to 100-300 $mm^3$.

Compounds were injected intratumorally formulated in phosphate buffered saline in a volume of 0.1 mL per injection. Mice were administered 0.05 mg every three days for a total of three doses. Efficacy was measured as the percent tumor growth inhibition (TGI) calculated by the reduction in size of the Treated tumor volume (T) over the Control tumor volume (C) according to the following formula: ((C-T)/(C))*100 when all control animals were still on study. Cures were defined as the number of animals with no measurable tumor detected 10 tumor volume doubling times (TVDT) after the last dose was administered.

The resultant data are presented in Table 3.

TABLE 3

| Compound # | hSTING SPA $IC_{50}$ (μM) | human cell reporter $EC_{50}$ (μM) |
|---|---|---|
| 41 | >100 (1) | >100 (1) |
| 4 | >100 (1) | 64.07 (1) |
| 20-S | >100 (1) | 61.85 (1) |
| 9 | 28.84 (1) | 6.24 (1) |
| 34-S | 8.76 (1) | 47.66 (1) |
| 12 | >100 (1) | 35.43 (2) |
| 8 | >100 (1) | 5.9 (1) |
| 7 | 71.02 (1) | 4.3 (1) |
| 17-S | 43.72 (1) | 4.23 (1) |
| 25 | >100 (1) | 33.79 (1) |
| 34-R | >100 (1) | 23.71 (2) |
| 46 | >100 (1) | >100 (1) |
| 14-S | 77.98 (1) | >100 (1) |
| 15-S | >100 (1) | >100 (1) |
| 15-R | >100 (1) | >100 (1) |
| 11 | >100 (1) | >100 (1) |
| 27 | >100 (1) | >100 (1) |
| 29 | >100 (1) | >100 (1) |
| 35 | >100 (1) | >100 (1) |
| 48 | >100 (1) | >100 (1) |
| 39 | >100 (1) | >100 (1) |
| 18-S | 18.65 (1) | 21.1 (1) |
| 6 | >100 (1) | 2.94 (2) |
| 44 | 14.42 (1) | 2.65 (1) |
| 23 | 32.48 (1) | 2.28 (1) |
| 17-R | 0.35 (1) | 0.98 (2) |
| 14-R | 13.86 (1) | 1.83 (1) |
| 16-R | 5.16 (1) | 1.83 (2) |
| 31-S | 0.062 (2) | 0.97 (2) |
| 31-R | 8.38 (2) | 0.93 (2) |
| 37-R | 13.4 (1) | 0.88 (1) |
| 19-S | 32.65 (1) | 0.86 (1) |
| 28 | 2.84 (1) | 0.73 (1) |
| 33 | >100 (1) | 0.73 (1) |
| 43 | >100 (1) | 0.73 (1) |
| 37-S | 1.09 (1) | 0.64 (1) |
| 5 | 3.79 (2) | 0.32 (2) |
| 36 | >100 (1) | 0.62 (1) |
| 30 | 33.41 (2) | 0.58; >100 |
| 3 | 18.04 (2) | 0.54 (4) |
| 1 | 5.21 (6) | 0.16 (6) |
| 38 | 5.44 (1) | 0.38 (1) |
| 20-R | 44.79 (1) | 0.35 (1) |
| 19-R | 64.26 (2) | 0.31 (2) |
| 47 | >100 (1) | 0.29 (1) |
| 22-S | 1.62 (1) | 0.097 (2) |
| 32 | >100 (1) | 0.18 (1) |
| 40 | 33.66 (1) | 0.15 (1) |
| 21 | 0.13 (1) | 0.072 (2) |
| 10 | 2.07 (2) | 0.13 (2) |
| 18-R | 0.79 (1) | 0.093 (1) |
| 24 | 0.19 (1) | 0.07 (1) |
| 22-R | 0.03 (1) | 0.029 (2) |
| 26 | >100 (1) | 0.03 (1) |
| 13 | 0.21 (2) | 0.02 (4) |
| 16-S | 0.094 (1) | 0.0046 (3) |

TABLE 3-continued

| Compound # | hSTING SPA IC$_{50}$ (μM) | human cell reporter EC$_{50}$ (μM) |
|---|---|---|
| 2 | 0.5 (5) | 0.012 (5) |
| 42 | >100 (1) | 100 (1) |
| 45 | >100 (1) | 0.09; >100 | human IFN-β ranking value determined by Ranking value determined by total cumulative IFNβ induction over the dose range tested (0.78 to 50 uM) in THP-1 cells.
* IC$_{50}$ and EC$_{50}$ are means of at least three values.

Biological Example 2

STING Primary Human PBMC Cytokine Induction Assay

Agonism of the human STING pathway is assessed in primary human peripheral blood mononuclear cells (PBMC) derived from human whole blood. 1 pint (approximately 420 mL) of fresh donor blood (AllCells Inc., Alameda, Calif.) is layered over Lymphocyte Separation Medium (1.077-1.080 g/mL, Corning, Manassas, Va.), then centrifuged at 500 g for 20 min at rt without applying break. The PBMC collected at the interface between serum and Lymphocyte Separation Medium are harvested, washed, then counted. PBMC are composed of subtypes of lymphocytes and monocytes, such as B cells, T cells, etc., and these subtypes have been characterized in the literature to express different levels of the STING protein. In response to STING agonists, such as 2'3'-cGAMP, these cells become activated and are induced to express a variety of proinflammatory and antiviral cytokines. Also, upon stimulation with STING agonists, these cells upregulate activation markers. The levels of cytokine induction can be measured by a variety of methods including ELISA, Luminex and MSD. The levels of activation marker upregulation can be measured by flow cytometry.

To run the assay, 1,000,000 cells may be dispensed into 225 μL/well of flat-bottom, tissue culture treated, 96-well plates. Test compounds may be added in a volume of 25 μL at 10× concentration. Some compounds may be solubilized in 100% DMSO and the final concentration of DMSO in the cultures receiving these compounds may be 1%. The assay may be incubated for 48 h at 37° C., 5% $CO_2$. 200 μl of supernatants may be harvested without disturbing cells on the bottom of the plate, then frozen at −20° C. until time of Luminex measurement. Luminex assays may be performed using G-CSF, IFN□2, IFN□, IL-Ib, IL-6, IL-10, IL-12 (p40), IL-12 (p70), TNFa from MILLIPLEX MAP Human Cytokine/Chemokine Magnetic Bead Panel—Immunology Multiplex Assay kit and IFNβ1 analyte from MILLIPLEX MAP Human Cytokine/Chemokine Magnetic Bead Panel IV kit (EMD Millipore, Billerica, Mass.), following the manufacturer's protocol. Cytokine induction may be measured using a Luminex FlexMAP 3D® instrument (Luminex Corporation, Radnor, Pa.). Analysis of collected Luminex data may be performed using MILLIPLEX Analyst software (EMD Millipore).

Suppression of HBV virus in PHH cells using conditioned media from STING activated primary human PBMC Primary human hepatocytes can be infected with hepatitis B virus and during an established infection, will produce viral proteins such as HBsAg and HBeAg that can be detected by ELISA. Therapeutic treatment with compounds such as entecavir can suppress HBV reproduction, which can be measured by decreased viral protein production. (# of cells) 4×10$^5$ cells/well primary human hepatocytes (BioRec-lamation, Westbury, N.Y.) may be dispensed into 500 μL/well of flat-bottom, tissue culture treated, 24-well plates. 24 h later, cells may be infected with 30-75 moi of HBV. On the next day, the PHH may be washed 3× and fresh maintenance media may be added to the cells. Concurrently, PBMC may be isolated as described previously. To stimulate the PBMC, 10,000,000 cells may be dispensed into 400 μL/well of flat-bottom, tissue culture treated, 24-well plates. Test compounds may be added in a volume of 100 μL, then the cultures may be incubated for 48 h at 37° C., 5% C02. Supernatants may be harvested. Cells may be measured for activation marker upregulation using flow cytometry. Briefly, cells may be stained with fluorescently labeled antibodies directed to CD56, CD19, CD3, CD8a, CD14, CD69, CD54, CD161, CD4 and CD80. Samples may be analyzed on an Attune N×T flow cytometer (Thermo Fisher, Carlsbad, Calif.)

From the stimulated PBMC cultures, a portion of supernatant may be reserved for cytokine detection by Luminex, as described previously. The rest of the supernatant may be divided in half, and one aliquot may be stored at 4° C. for use on d8 of the assay. The other aliquot of supernatant may be diluted 1:1 with 2×PHH media, then may be added to the d4 infected PHH cells. After 96 h, the spent media may be changed and supernatant may be added at a dilution of 1:1 with 2×PHH media. At this point an interim measurement of HBsAg may be performed using an HBsAg ELISA kit (Wantai Bio-pharm, Beijing, China). Following 96 h, the media may be collected and HBsAg may be measured.

While the foregoing specification teaches the principles of the present invention, with examples provided for the purposes of illustration, it will be understood that the practice of the invention encompasses the usual variations, adaptations and/or modifications as come within the scope of the following claims and their equivalents.

The invention claimed is:
1. A compound of Formula (I):

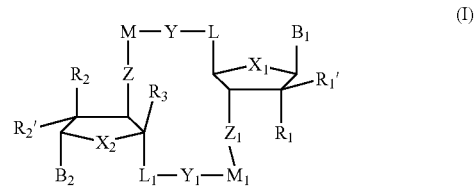

wherein
B$_1$ and B$_2$ are, independently, b1, b2, b3, b4, b5, b6, b7, b8, b9, b10, b11, b12, b13, b14, b15, b16, b17, b18, b19, b20, b21, b22, b23, b24, b25, b26, b27, b28, b29, or b30:

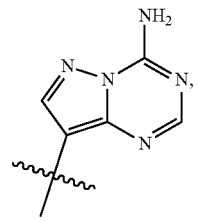

-continued
| | | |
|---|---|---|
| 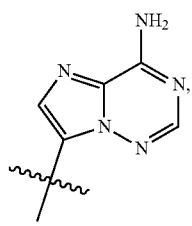 | b2 | 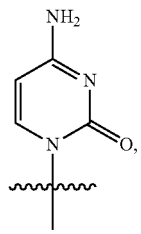 b9 |
| 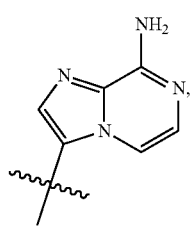 | b3 | 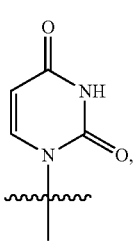 b10 |
| 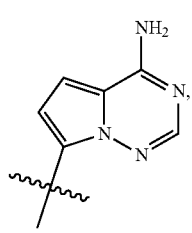 | b4 | 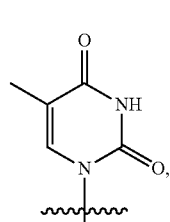 b11 |
| 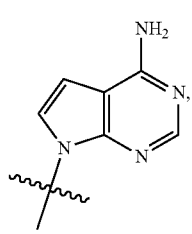 | b5 | 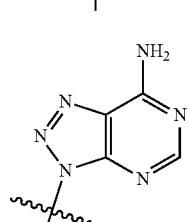 b12 |
| 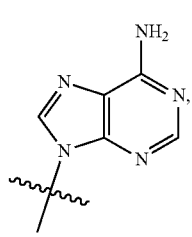 | b6 | 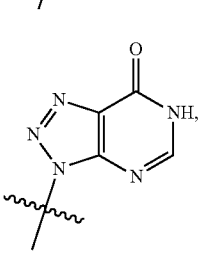 b13 |
| 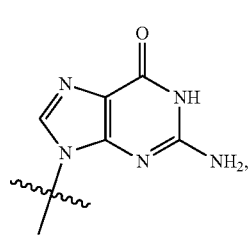 | b7 | 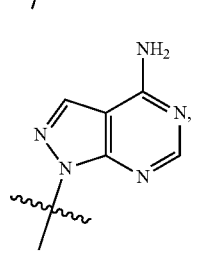 b14 |
| 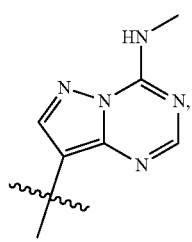 | b8 | 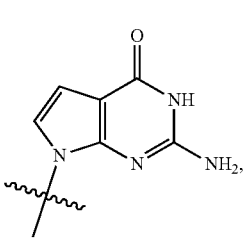 b15 |

-continued
| | |
|---|---|
| 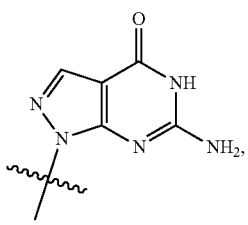 b16 | 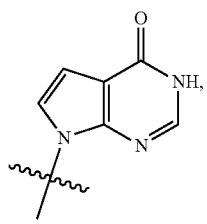 b23 |
| 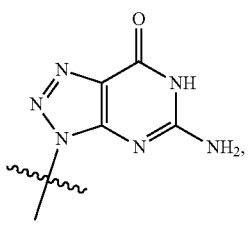 b17 | 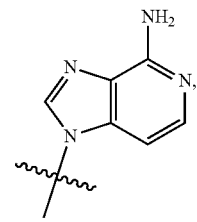 b24 |
| 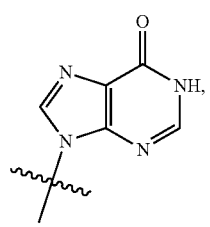 b18 | 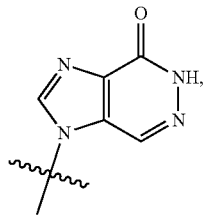 b25 |
| 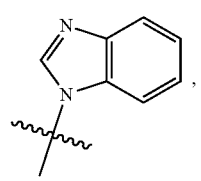 b19 | 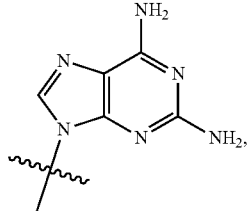 b26 |
| 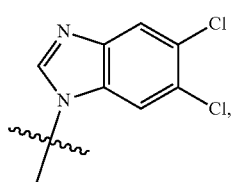 b20 | 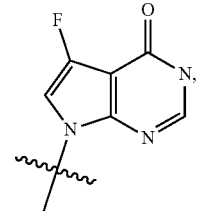 b27 |
| 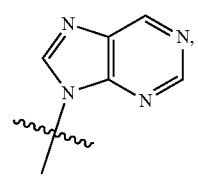 b21 | 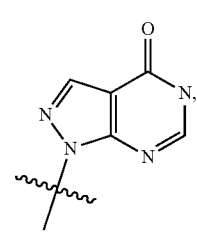 b28 |
| 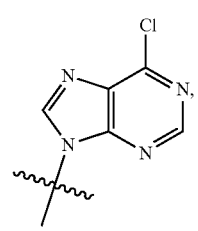 b22 | 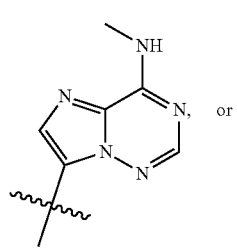 b29 |

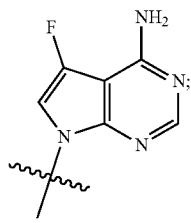

R$_1$ is hydrogen; hydroxy; fluoro; optionally substituted C$_{1-3}$alkoxy; C$_{3-6}$alkenyloxy; C$_{2-6}$alkynyloxy; hydroxy(C$_{1-3}$alkoxy); or optionally substituted C$_{1-3}$alkyl;

R$_1$' is hydrogen, fluoro, or hydroxy; provided that when R$_1$' is fluoro, R$_1$ is hydrogen or fluoro;

R$_2$ is hydrogen; hydroxy; fluoro; optionally substituted C$_{1-3}$alkoxy; C$_{3-6}$alkenyloxy; C$_{2-6}$alkynyloxy; hydroxy(C$_{1-3}$alkoxy); or optionally substituted C$_{1-3}$alkyl; and R$_3$ is hydrogen;

or, R$_3$ is —CH$_2$—, and R$_2$ is —O—; such that R$_2$, R$_3$ and the atoms to which they are attached form a 5-membered ring;

R$_2$' is hydrogen, fluoro, or hydroxy; provided that when R$_2$' is fluoro, R$_2$ is hydrogen or fluoro;

R$_3$ hydrogen, fluoro, CH$_3$, or CH$_2$F;

X$_1$ and X$_2$ are, independently, O, S, or CH$_2$;

L and L$_1$ are, independently, —CH$_2$— or —CH$_2$CH$_2$—;

Y and Y$_1$ are, independently, absent, 0, or NH;

Z and Z$_1$ are, independently, 0 or NH;

one of M and M$_1$ is

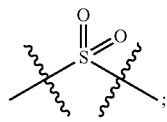

and the other of M and M$_1$ is

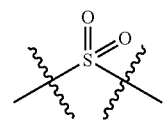

or

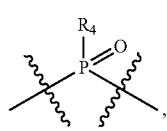

wherein:
(i) when M is

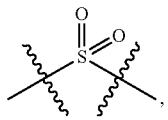

one of Y and Z is NH, and the other of Y and Z is O; and
(ii) when M$_1$ is

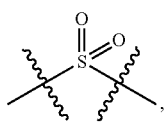

one of Y$_1$ and Z$_1$ is NH, and the other of Y$_1$ and Z$_1$ is O;
(iii) when Y is absent, L is —CH$_2$CH$_2$, and M is

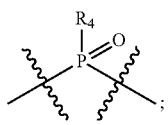

and
(iv) when Y$_1$ is absent, L$_1$ is absent, and M$_1$ is

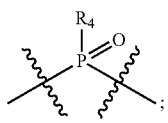

R$_4$ is hydroxy, methyl, BH$_3$, or —SR$_5$; wherein:
R$_5$ is hydrogen, —CH$_2$OC(O)R$_6$, —CH$_2$OC(O)OR$_6$, —CH$_2$CH$_2$SC(O)R$_6$, or —CH$_2$CH$_2$S—SCH$_2$R$_6$; and
R$_6$ is C$_{6-10}$aryl, heteroaryl, heterocycloalkyl, C$_{3-12}$cycloalkyl, or optionally substituted C$_{1-20}$alkyl;
or an enantiomer, diastereomer, or pharmaceutically acceptable salt form thereof.

2. The compound of claim 1, wherein R$_1$ or R$_2$ is C$_{1-3}$alkoxy optionally substituted with one to seven halogen, methoxy, or optionally substituted C$_{6-10}$aryl.

3. The compound of claim 2, wherein the C$_{6-10}$aryl is optionally substituted with one to two fluoro, chloro, bromo, iodo, C$_{1-3}$alkoxy, C$_{1-3}$alkyl, hydroxy, nitro or cyano.

4. The compound of claim 1, wherein R$_1$ or R$_2$ is C$_{1-3}$alkyl substituted with one to three fluoro, chloro, bromo, iodo, or hydroxy.

5. The compound of claim 1, wherein R$_1$ is F.
6. The compound of claim 1, wherein R$_1$ is H.
7. The compound of claim 1, wherein R$_1$ is OH.
8. The compound of claim 1, wherein R$_1$ is H.
9. The compound of claim 1, wherein R$_1$' is F.

10. The compound of claim 1, wherein $R_2$ is F.
11. The compound of claim 1, wherein $R_2$ is H.
12. The compound of claim 1, wherein $R_2$ is OH.
13. The compound of claim 1, wherein $R_2'$ is H.
14. The compound of claim 1, wherein $R_3$ is H.
15. The compound of claim 1, wherein L is $CH_2$.
16. The compound of claim 1, wherein $L_1$ is $CH_2$.
17. The compound of claim 1, wherein M is P(O)(OH).
18. The compound of claim 1, wherein M is P(O)(SH).
19. The compound of claim 1, wherein M is $S(O)_2$.
20. The compound of claim 1, wherein $M_1$ is $S(O)_2$.
21. The compound of claim 1, wherein $M_1$ is P(O)(OH).
22. The compound of claim 1, wherein $M_1$ is P(O)(SH).
23. The compound of claim 1, wherein X is O.
24. The compound of claim 1, wherein X is $CH_2$.
25. The compound of claim 1, wherein $X_1$ is O.
26. The compound of claim 1, wherein $X_1$ is $CH_2$.
27. The compound of claim 1, wherein Y is O.
28. The compound of claim 1, wherein Y is NH.
29. The compound of claim 1, wherein $Y_1$ is NH.
30. The compound of claim 1, wherein $Y_1$ is O.
31. The compound of claim 1, wherein Z is O.
32. The compound of claim 1, wherein Z is NH.
33. The compound of claim 1, wherein $Z_1$ is O.
34. The compound of claim 1, wherein $Z_1$ is $CH_2$.
35. The compound of claim 1, wherein $Z_1$ is NH.
36. The compound of claim 1, wherein $B_1$ and $B_2$ are each b6:

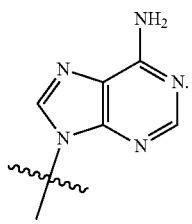
b6

37. The compound of claim 1, wherein $B_1$ is b7 and $B_2$ is b6

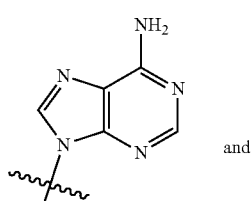
b6 and

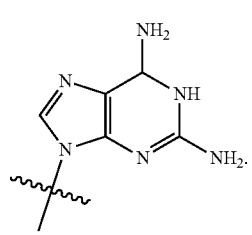
b7

38. The compound of claim 1, that is of the following structure:

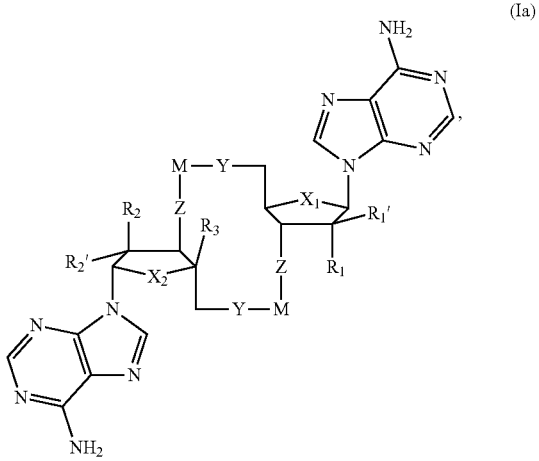
(Ia)

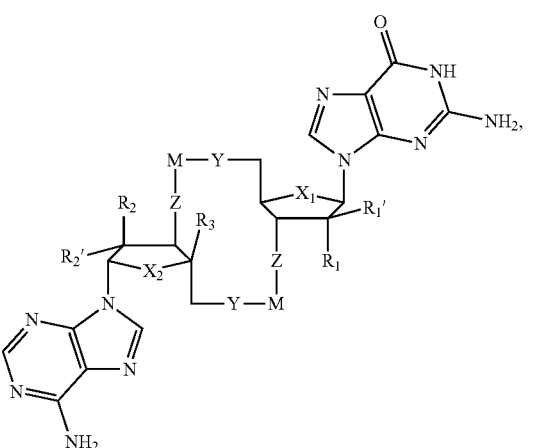
(Ib)

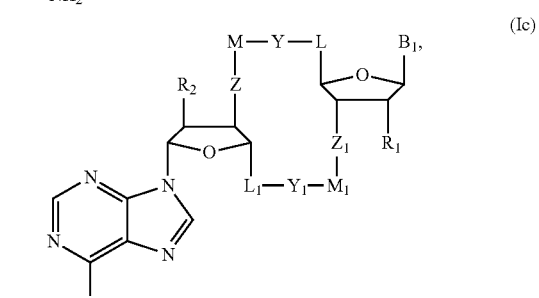
(Ic)

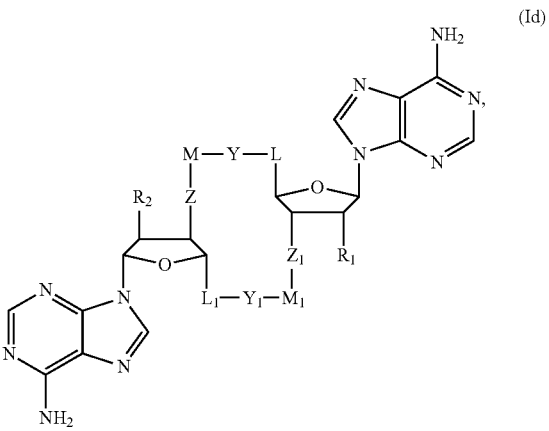
(Id)

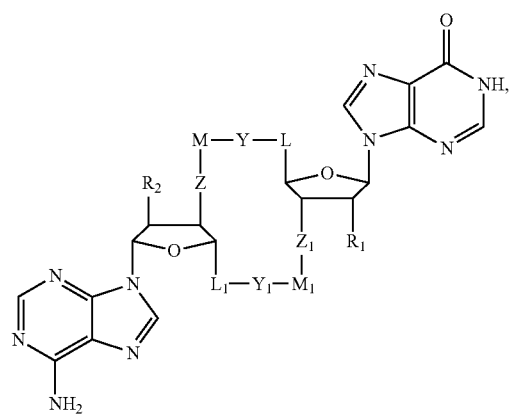
(Ie)
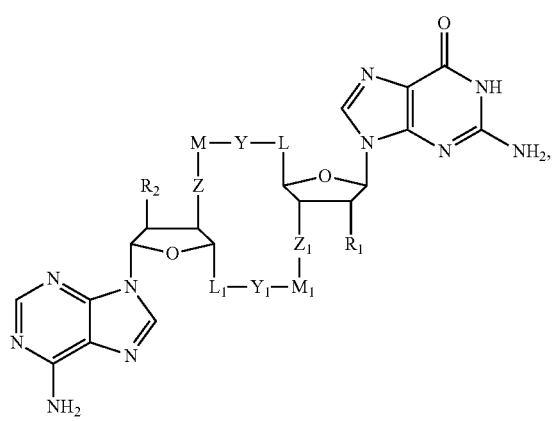
(If)
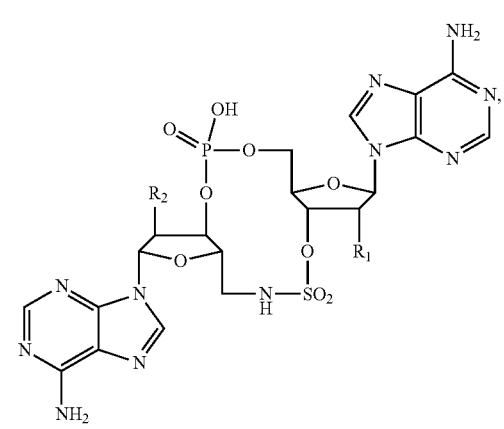
(Ig)
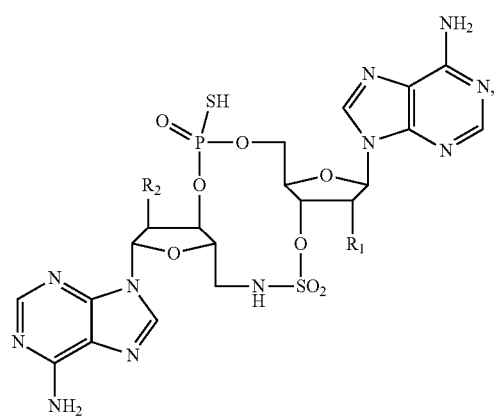
(Ih)
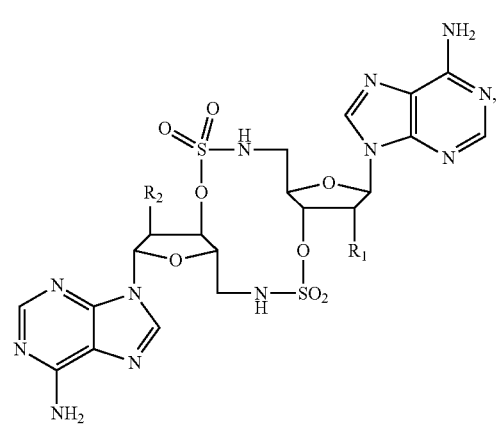
(Ij)
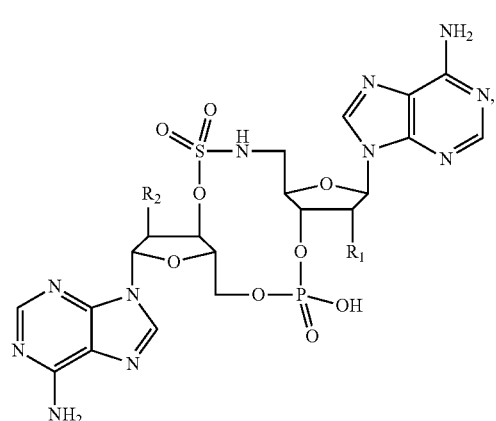
(Ik)
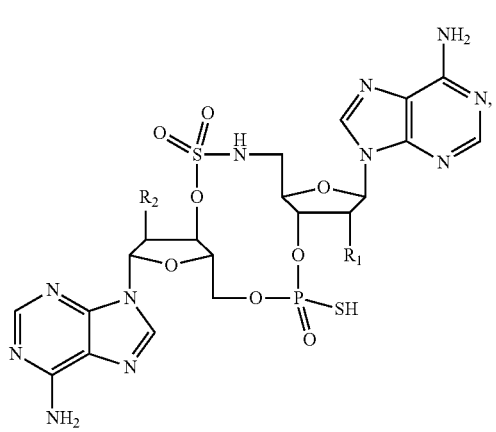
(Im)

(In)
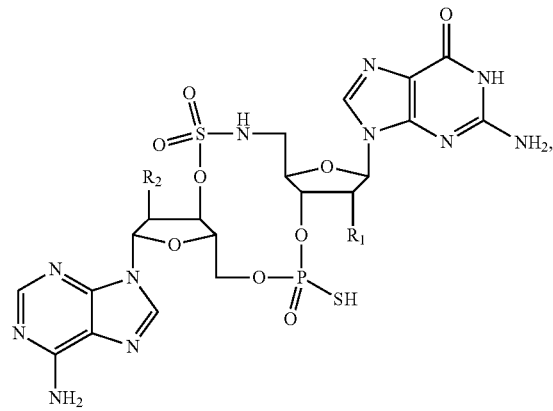
(Ip)
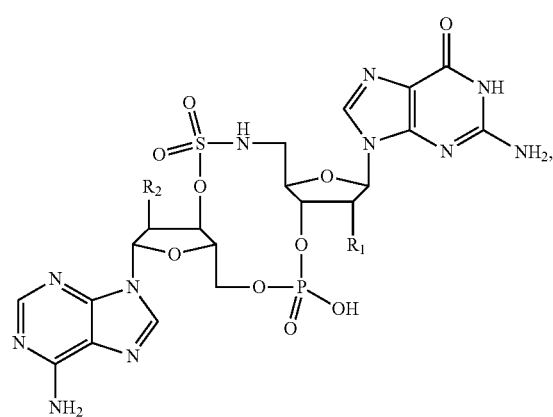
(Iq)
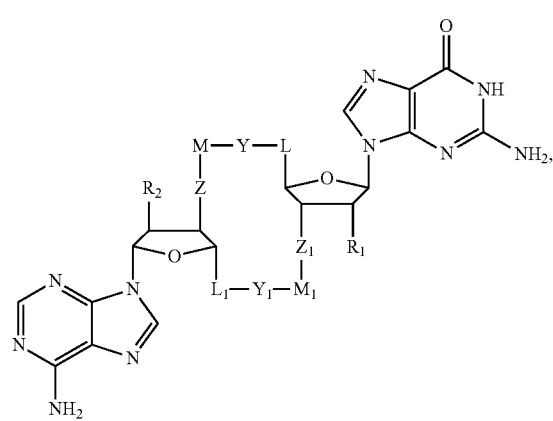
or
(Ir)
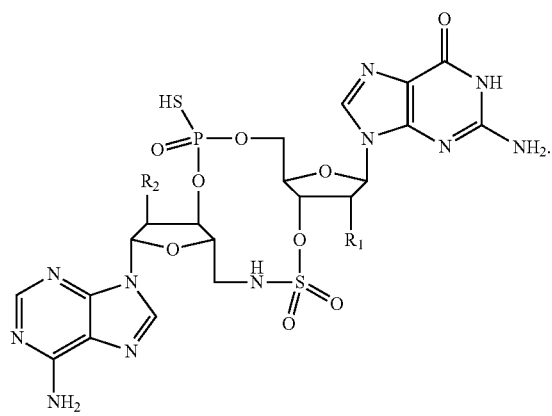
39. The compound of claim 1, wherein the compound is:
1
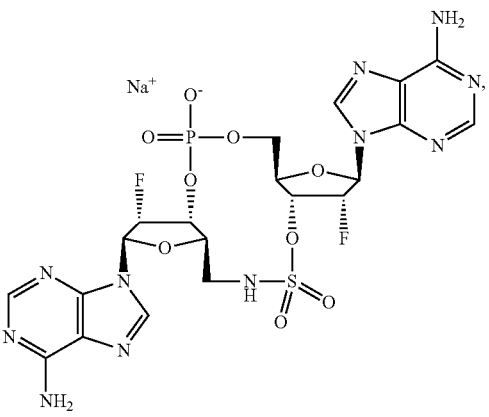
2
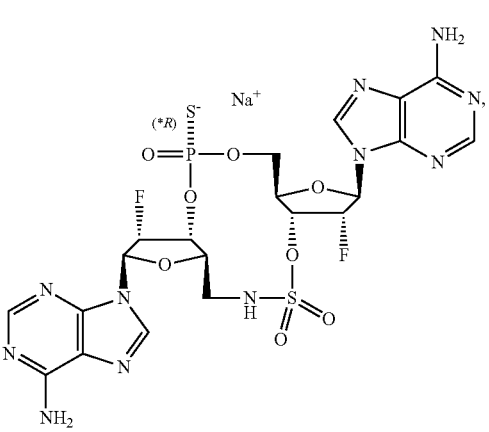

221
-continued
3
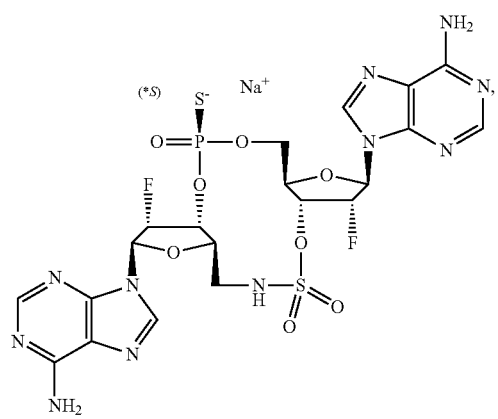
4
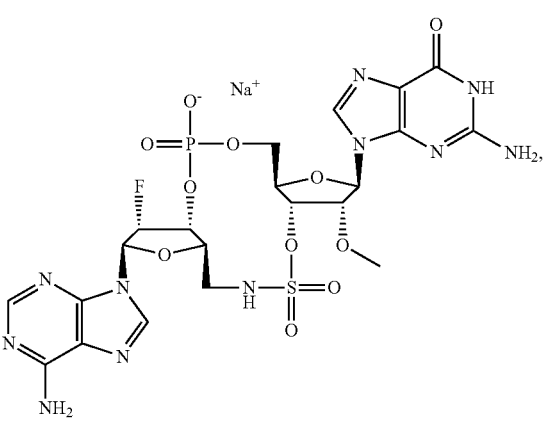
5
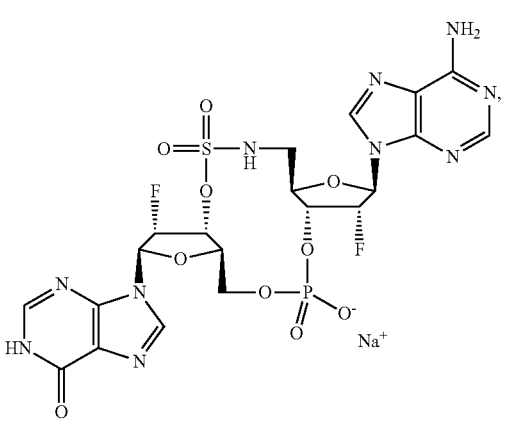
222
-continued
6
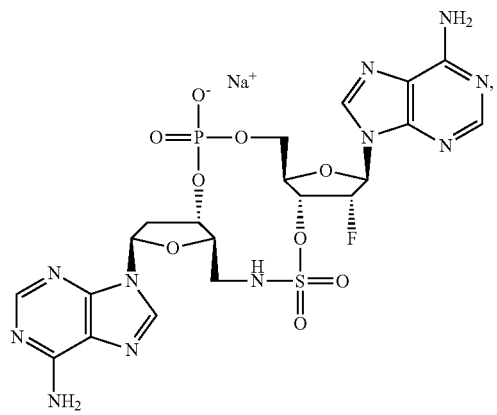
7
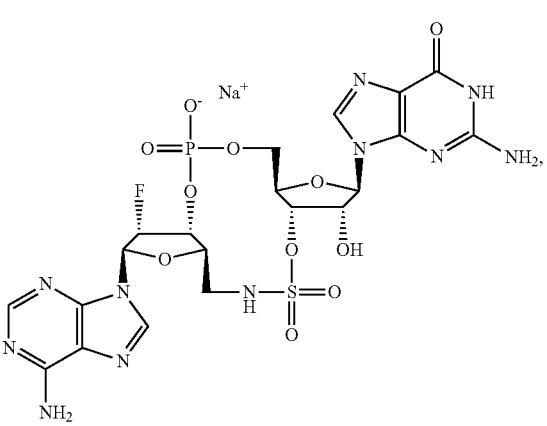
8
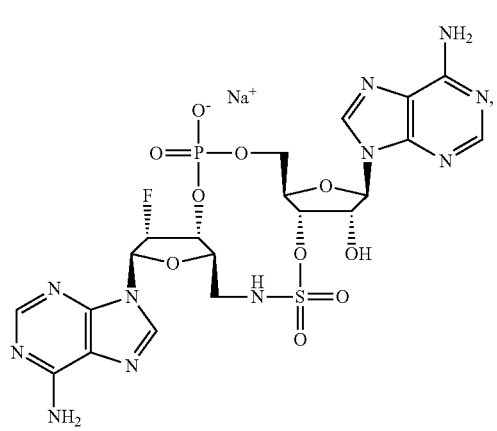

-continued
9
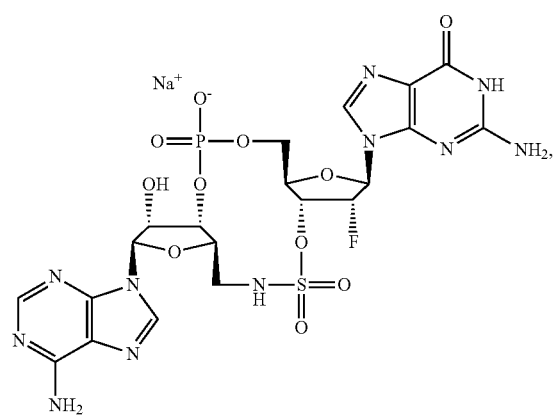
10
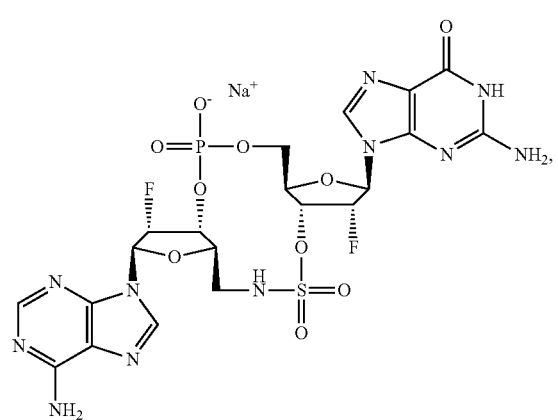
11
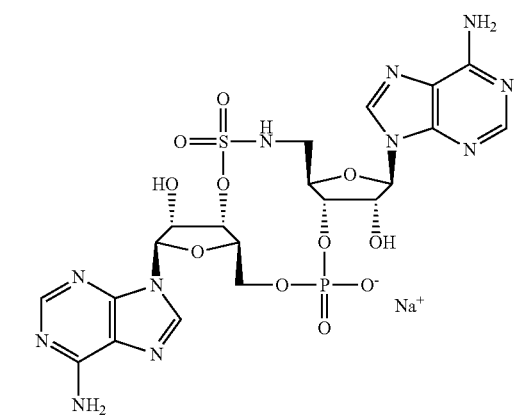
-continued
12-R
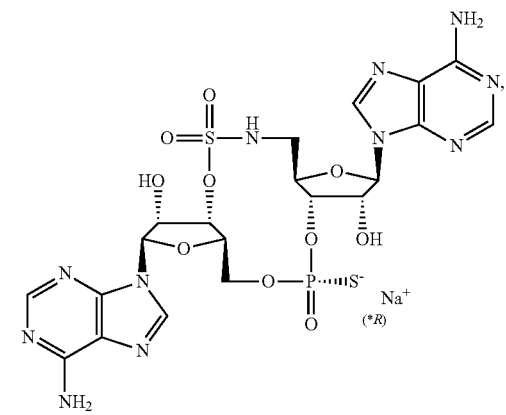
13
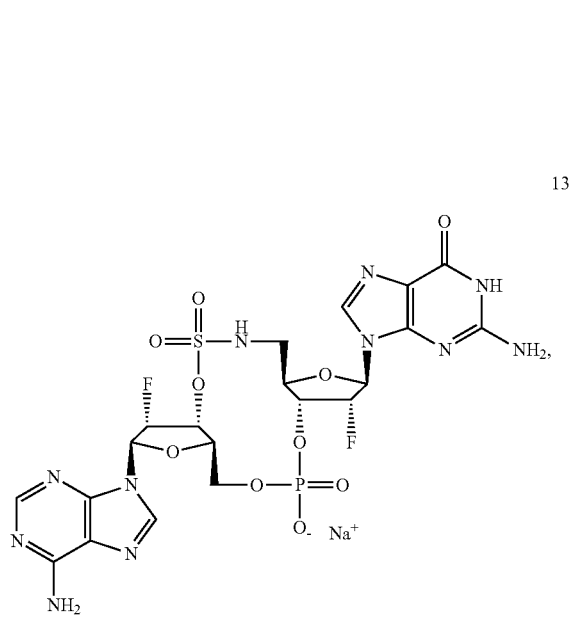
14-R
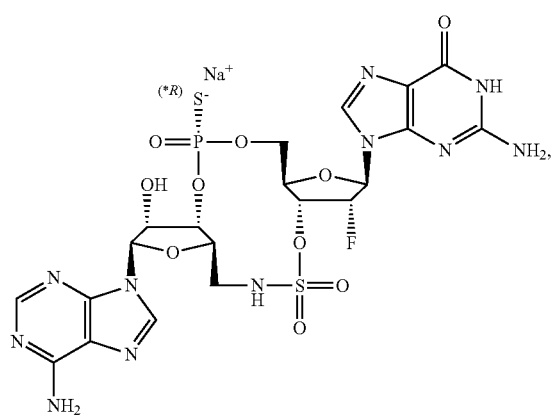

-continued
14-S
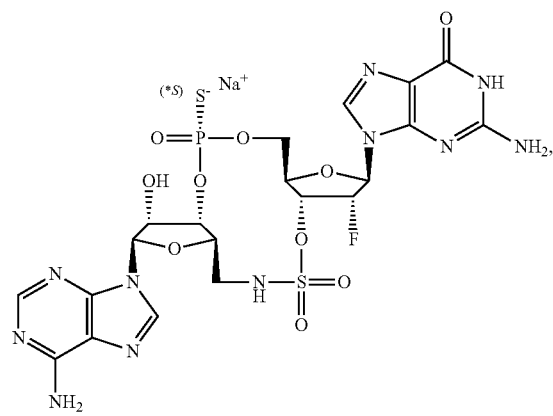
16-R
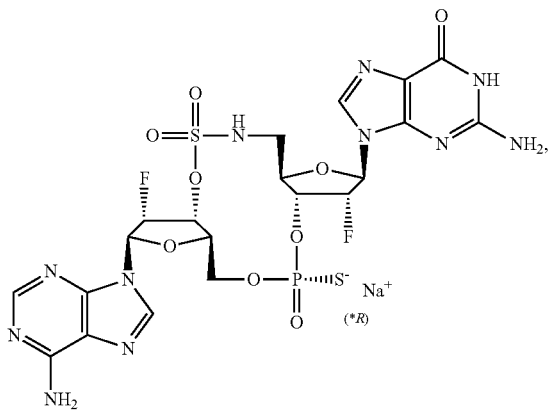
15-S
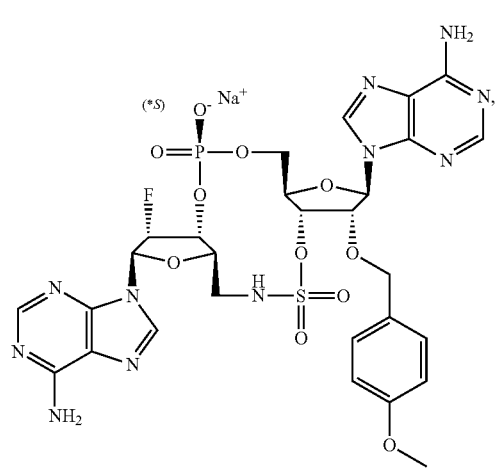
16-S
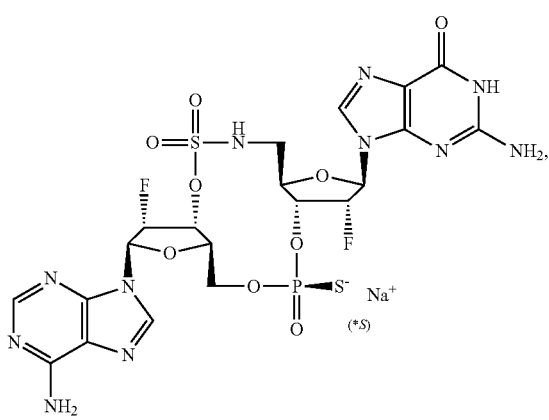
15-R
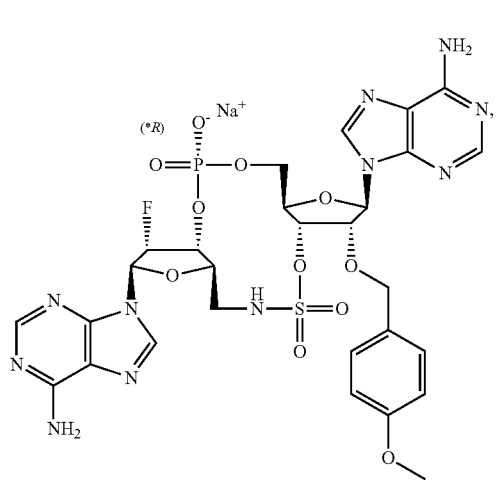
17-R
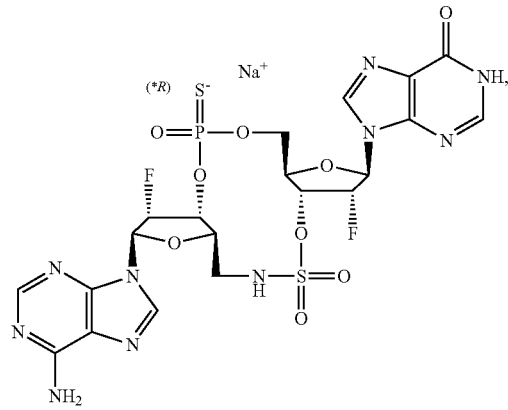

-continued
17-S
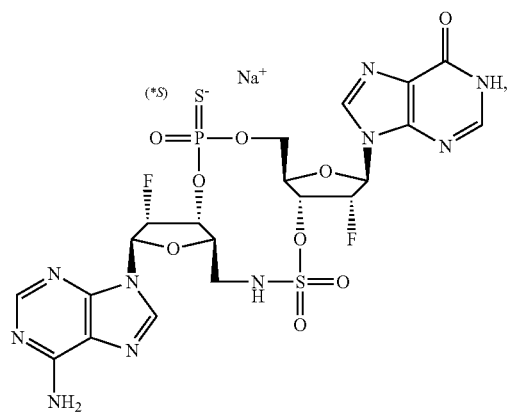
18-S
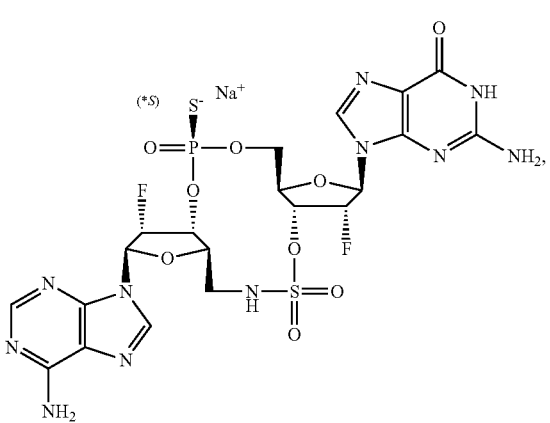
18-R
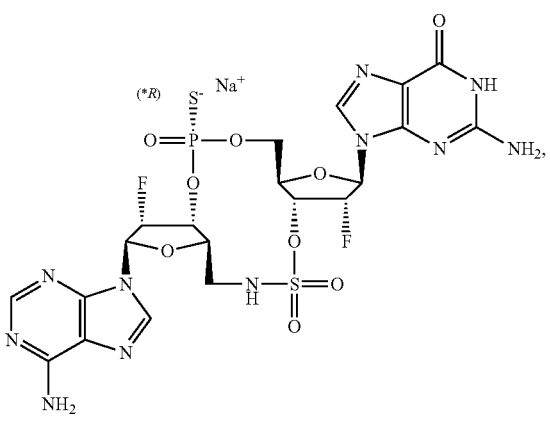
-continued
19-S
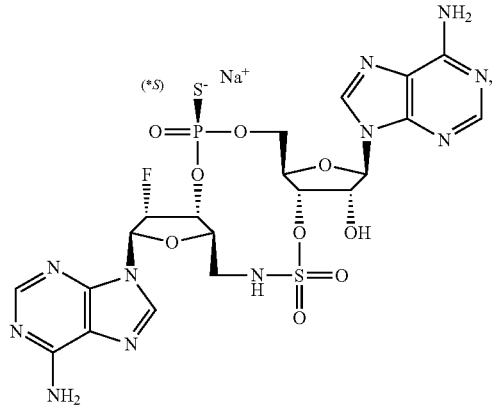
19-R
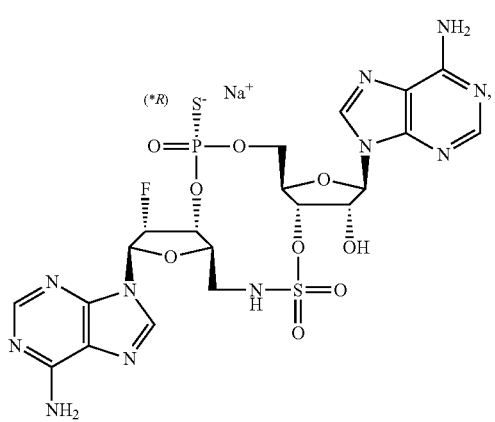
20-S
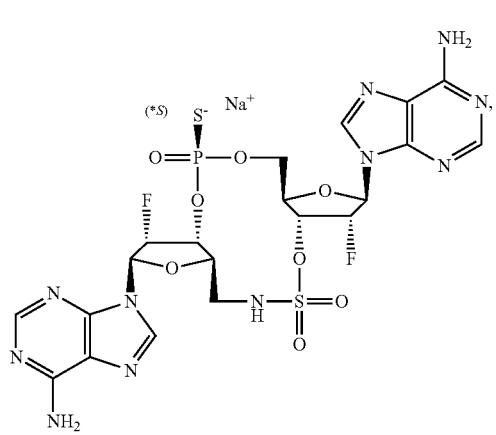
20-R
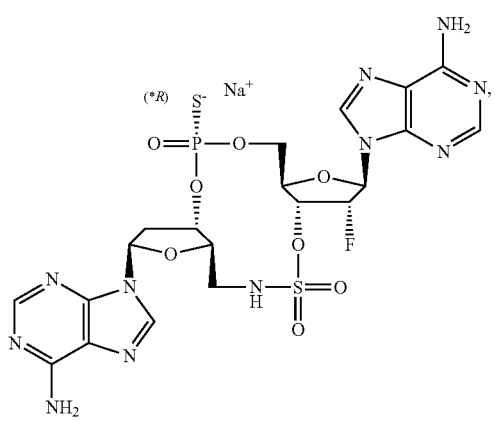

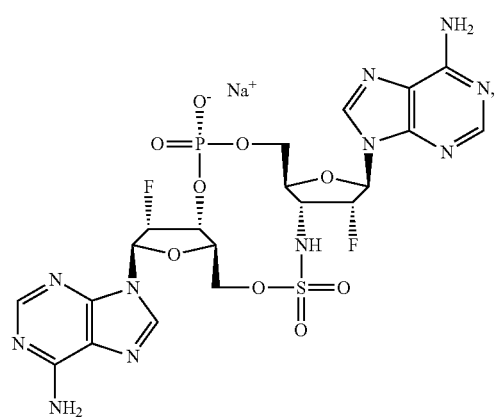
21
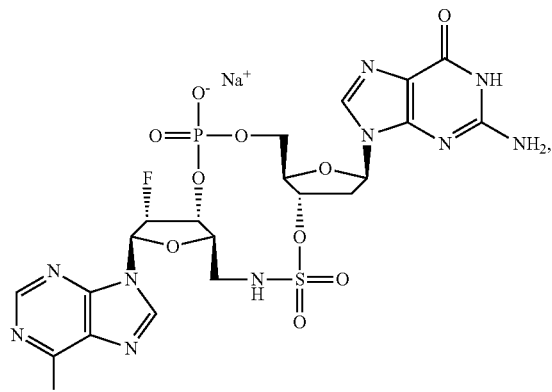
23
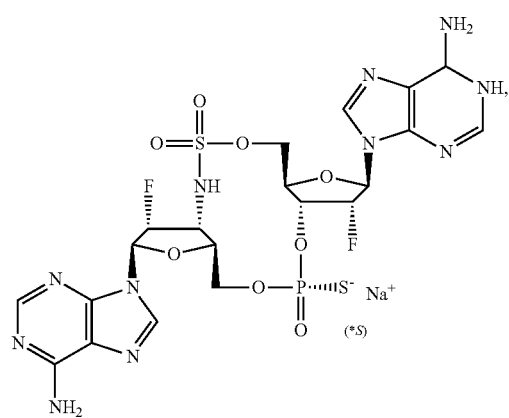
22-R
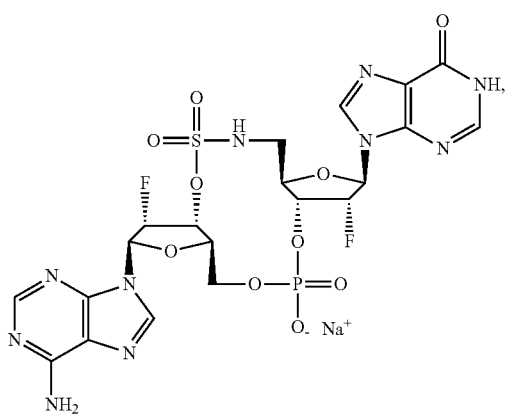
24
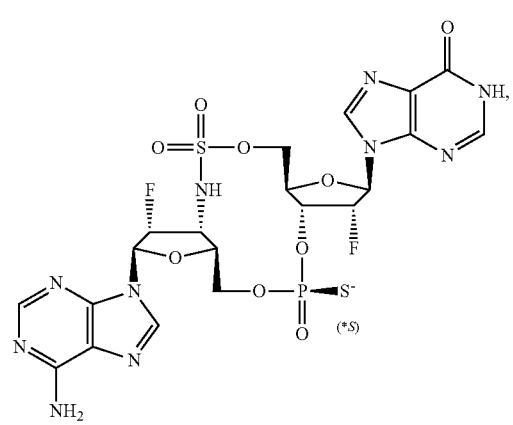
22-S
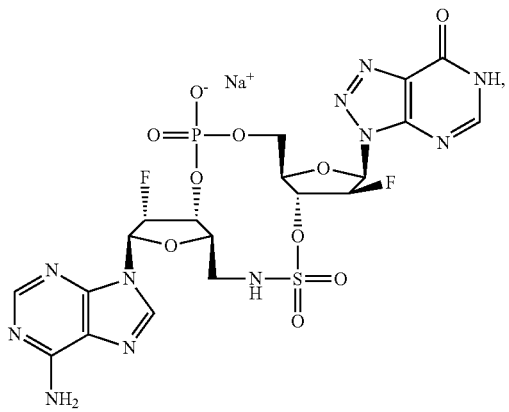
25

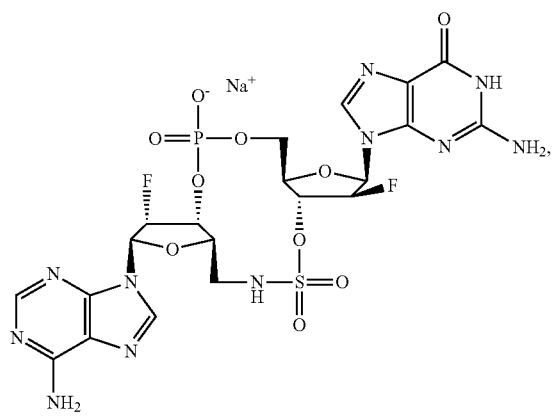
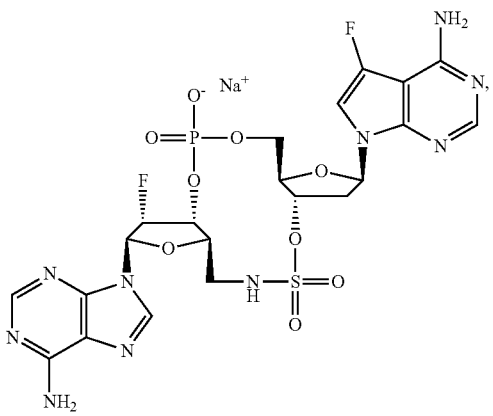
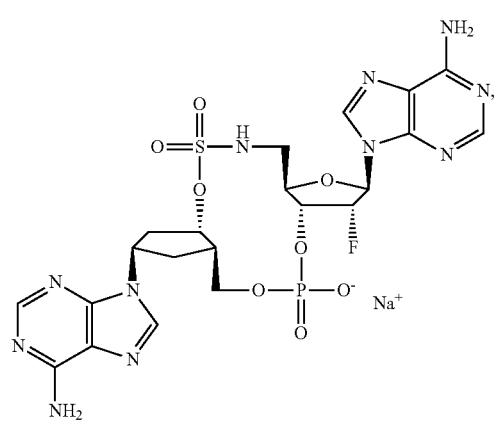
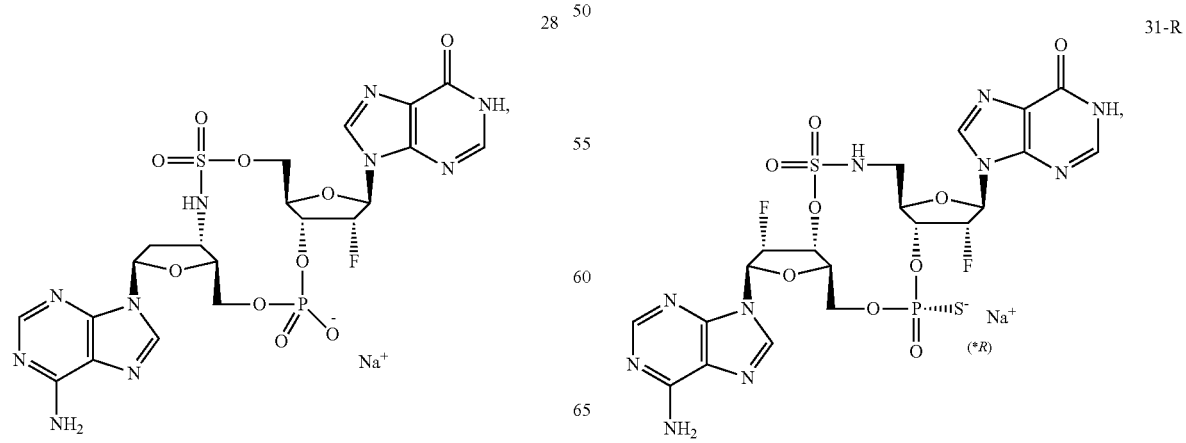

-continued
31-S
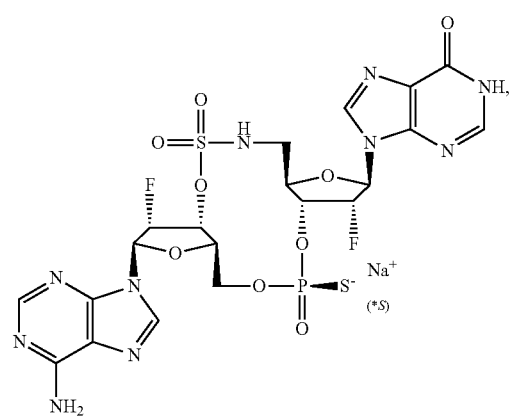
32
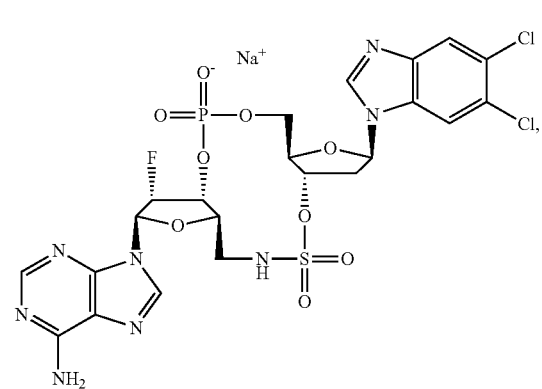
33
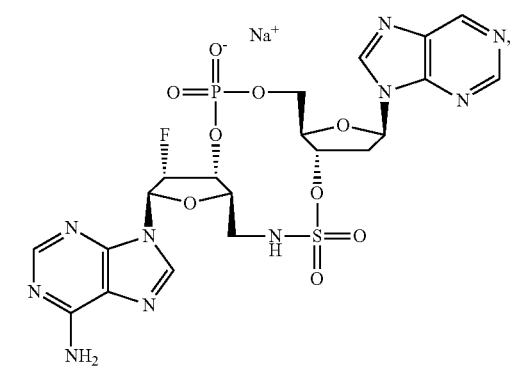
34-S
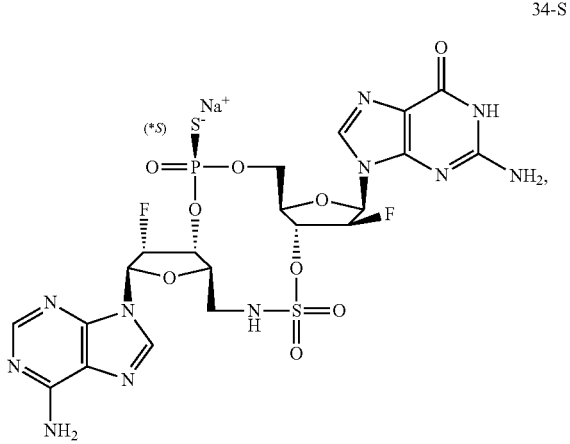
-continued
34-R
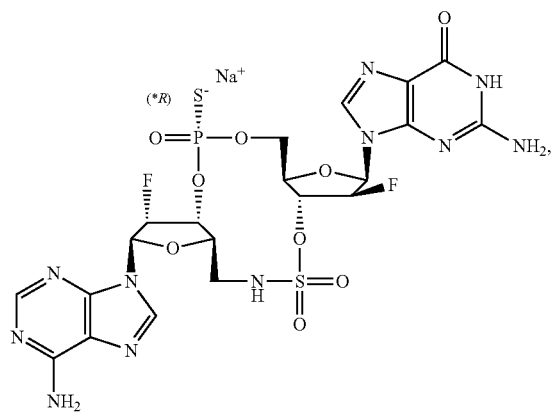
35
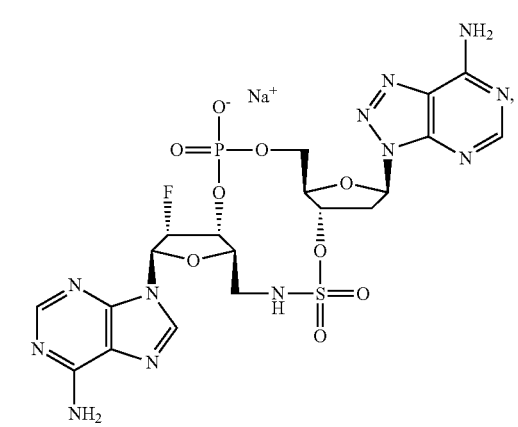
36
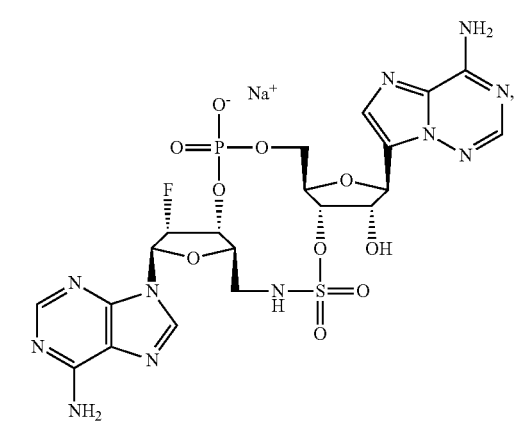

-continued
37-R
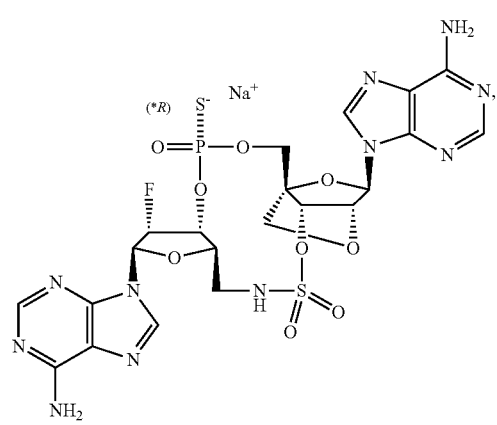
37-S
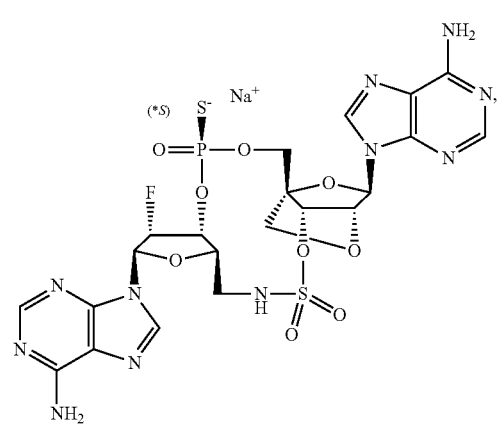
38
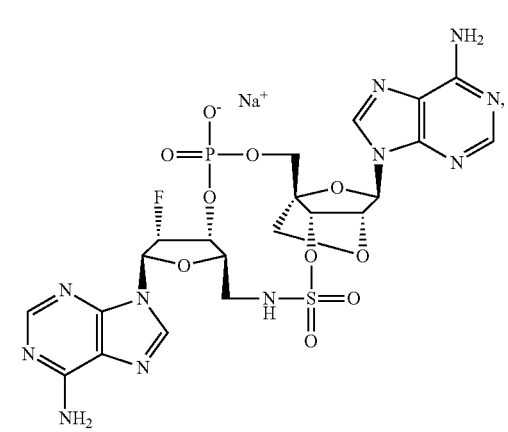
39
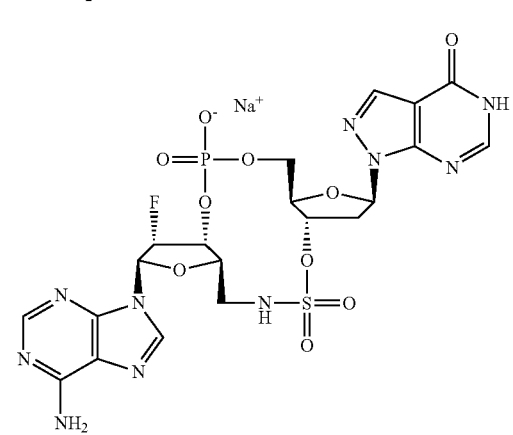
-continued
40
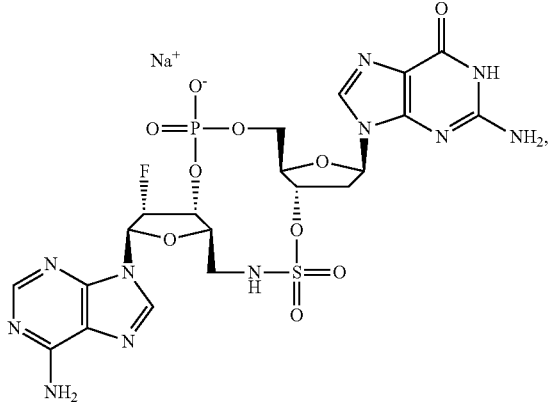
41
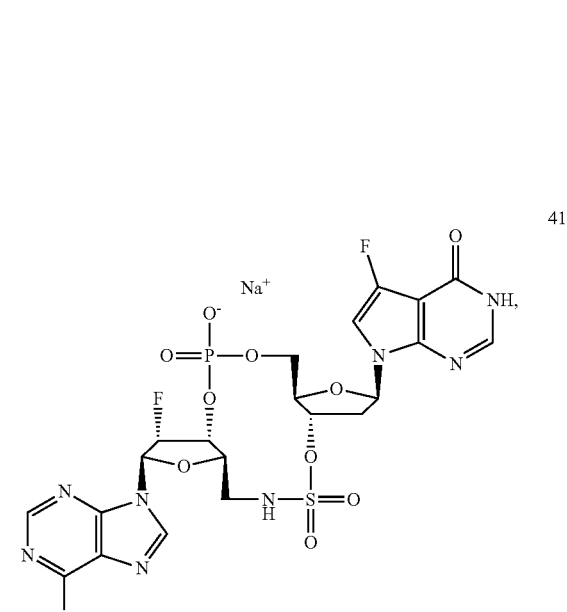
42
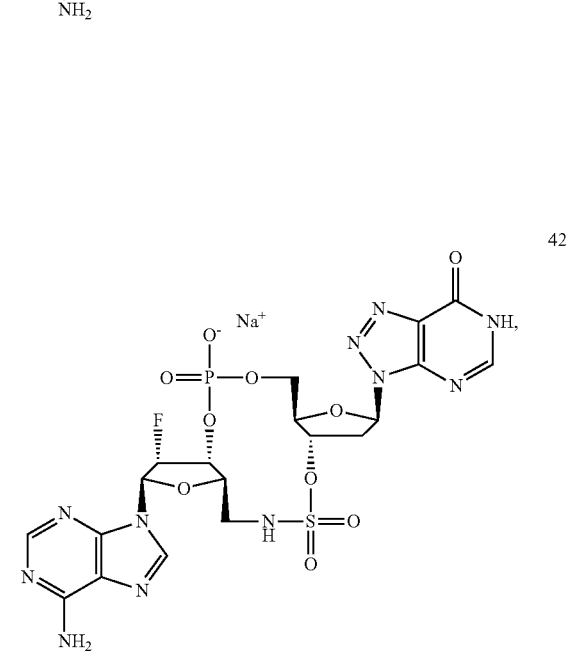

237
-continued
43
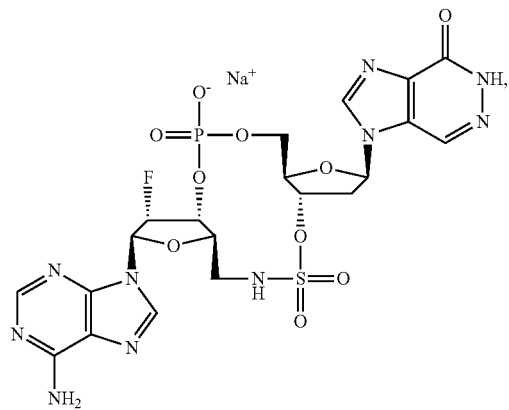
44
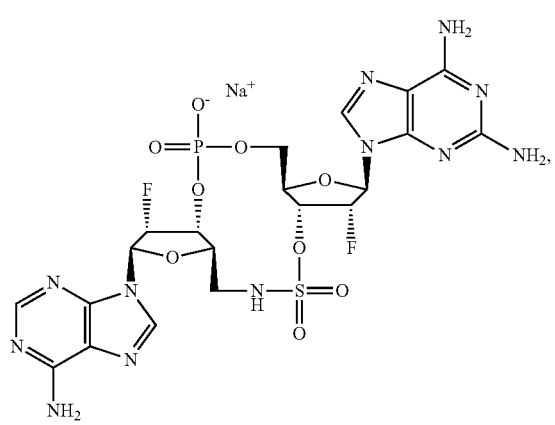
45
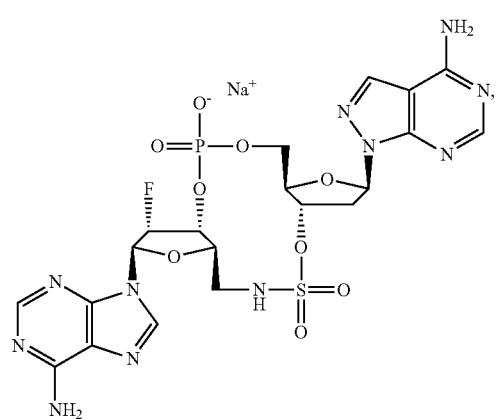
238
-continued
46
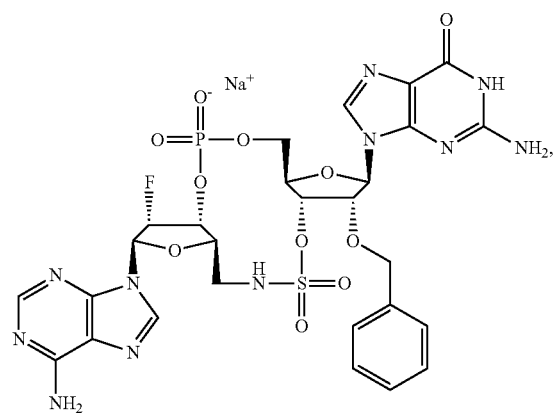
47
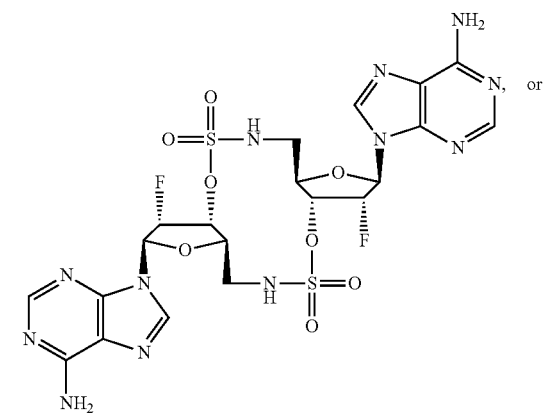
48
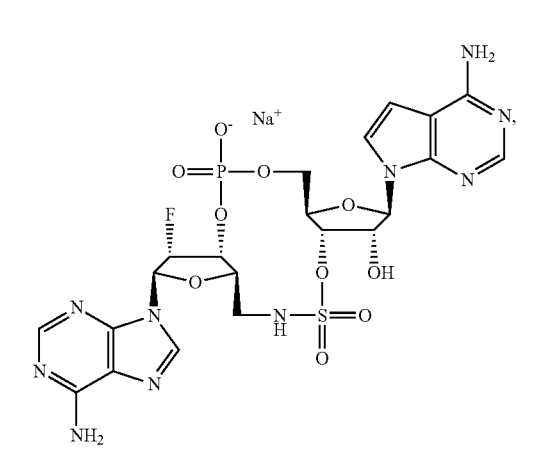
or a pharmaceutically acceptable salt form thereof.

40. The compound of claim 1, that is:
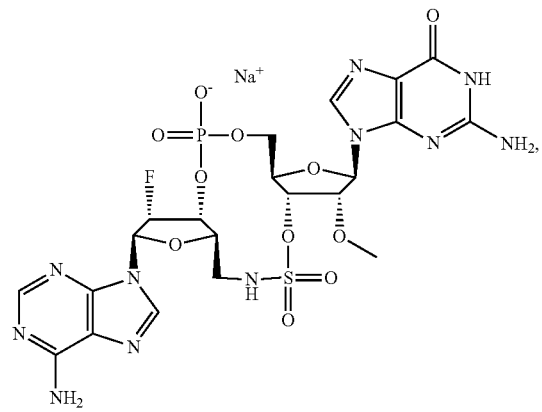
4
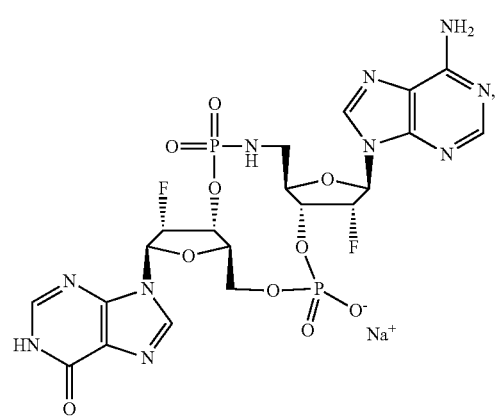
5
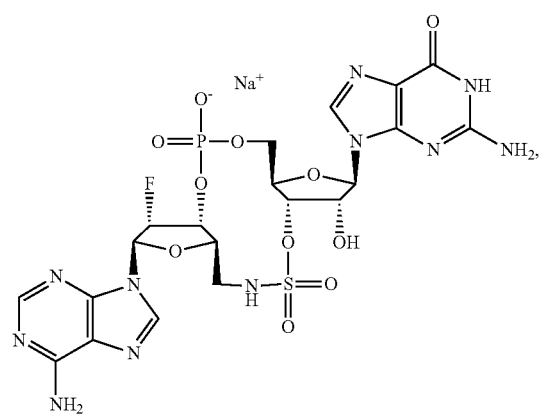
7
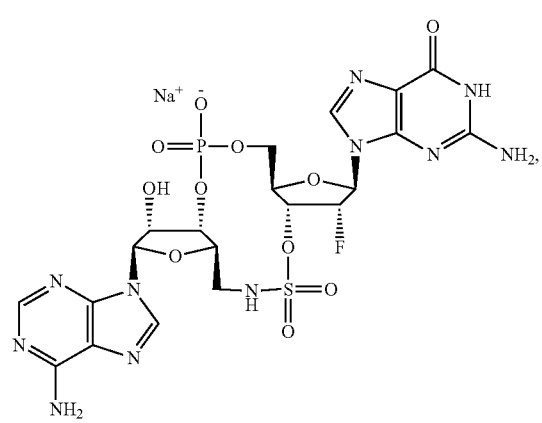
9
-continued
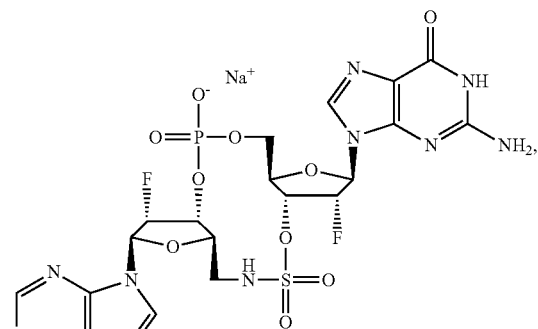
10
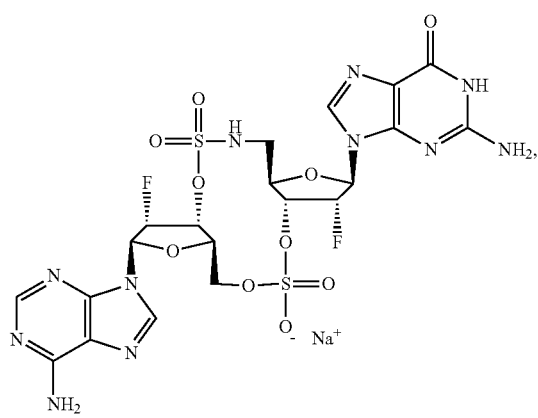
13
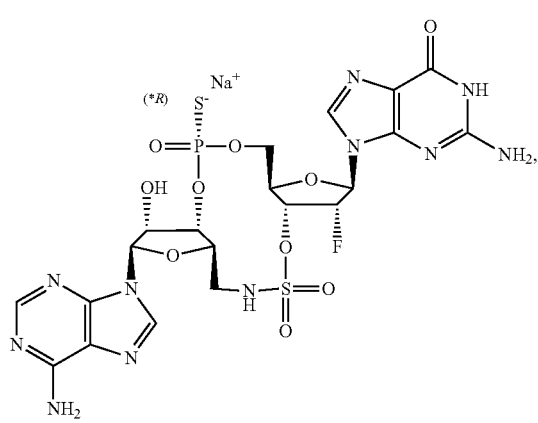
14-R -continued
14-S
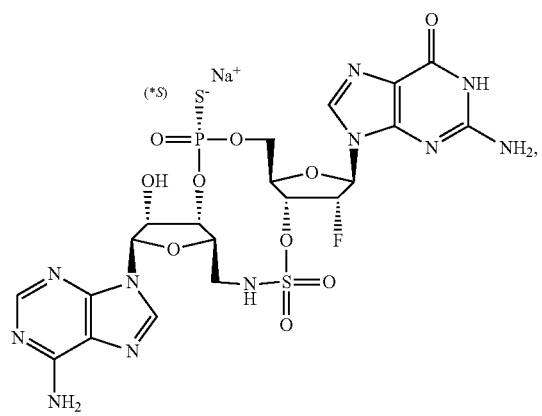
16-R
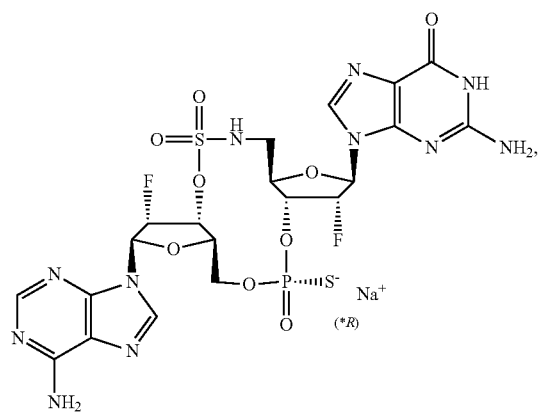
16-S
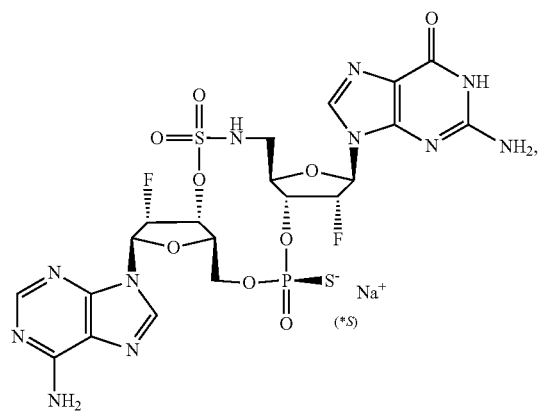
-continued
17-R
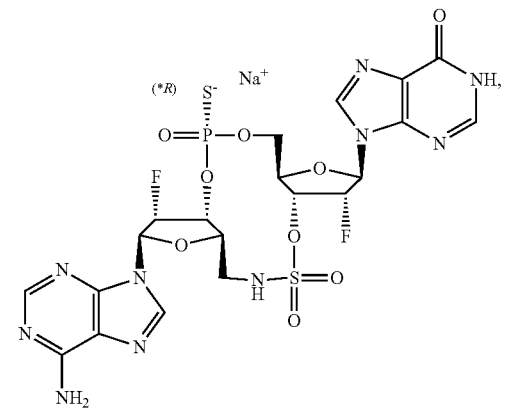
17-S
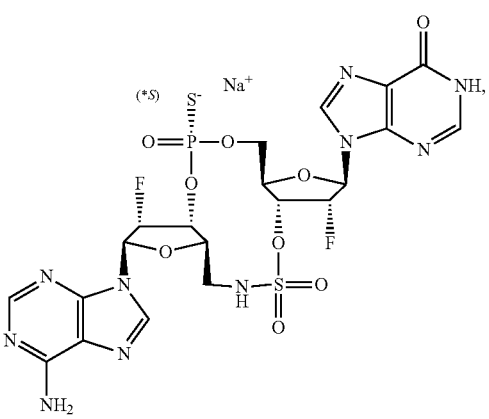
18-S
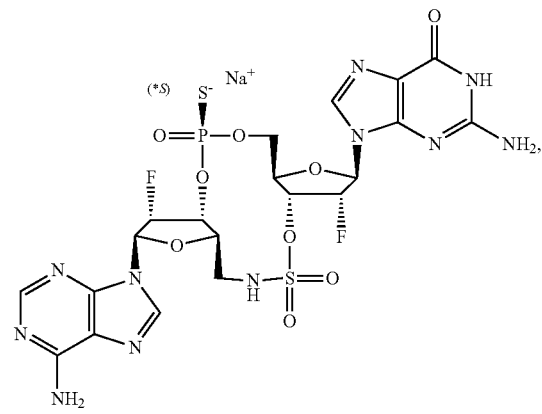

243
-continued
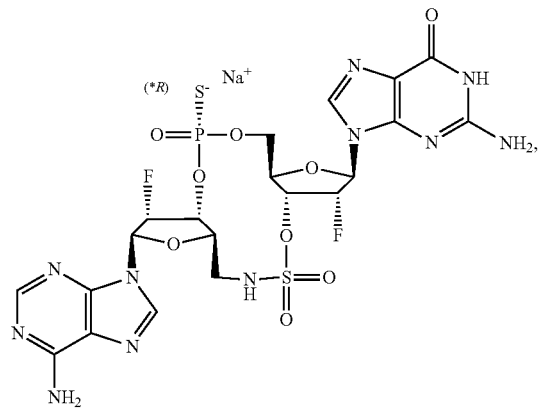
18-R
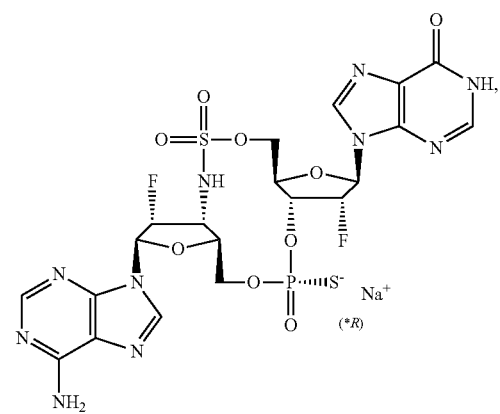
22-R
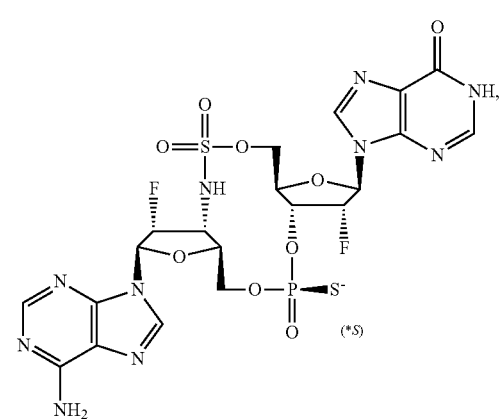
22-S
244
-continued
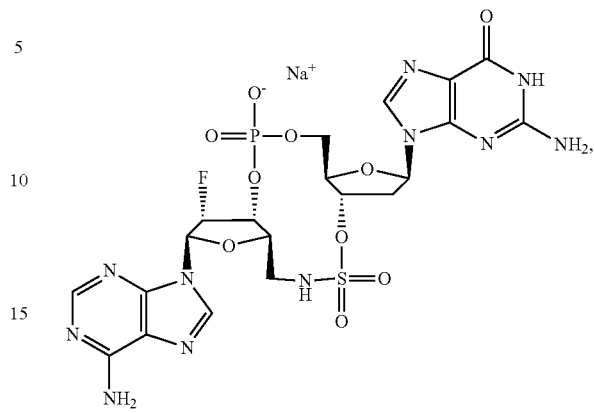
23
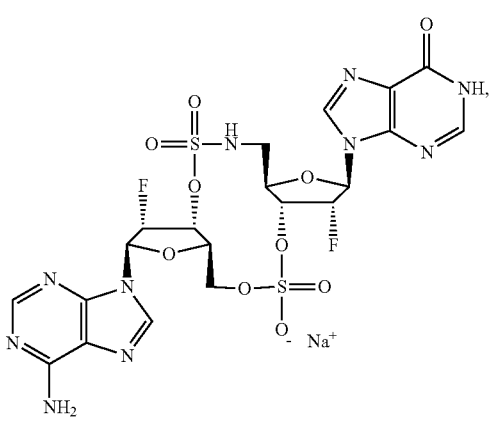
24
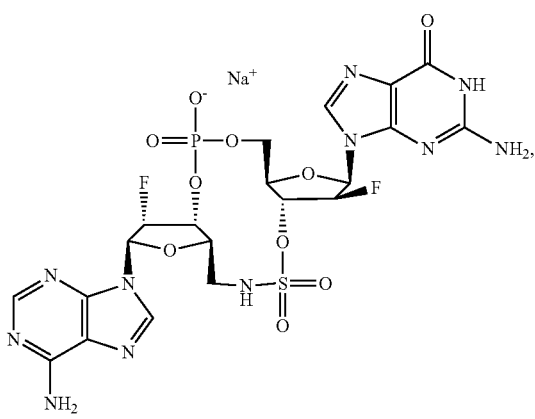
26

245
-continued
28
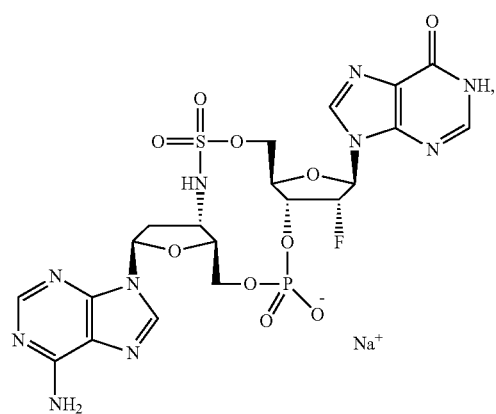
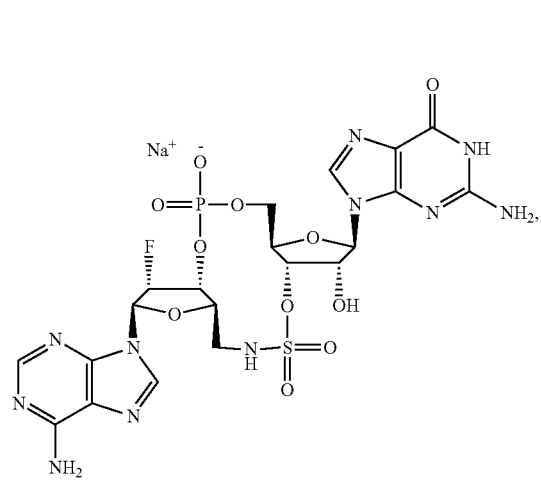
31-R
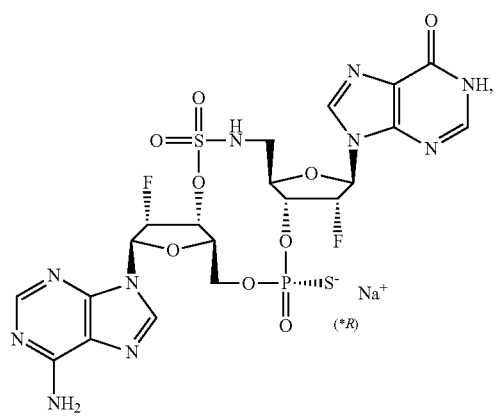
246
-continued
31-S
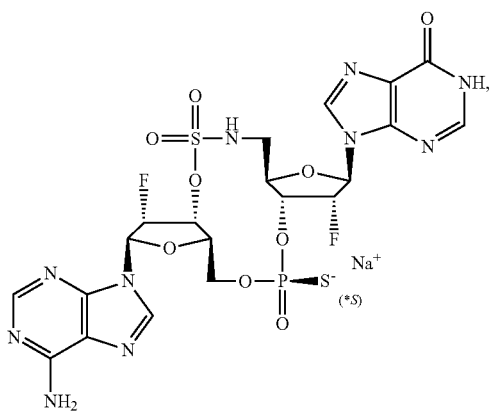
34-R
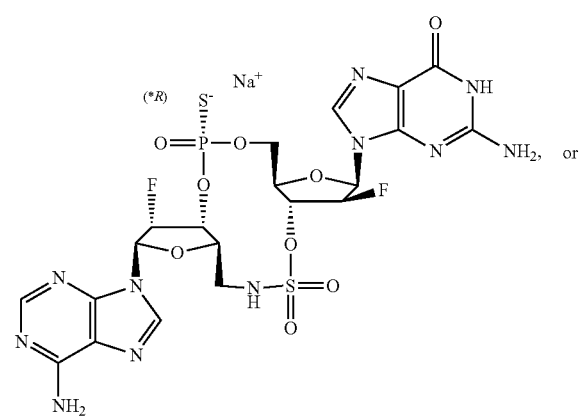
or
34-S
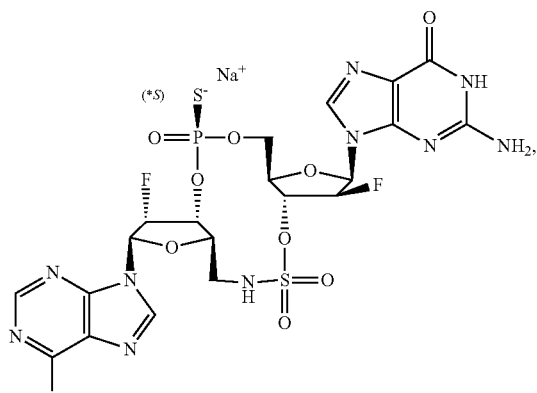
or a pharmaceutically acceptable salt thereof.

41. The compound of claim 1, that is:
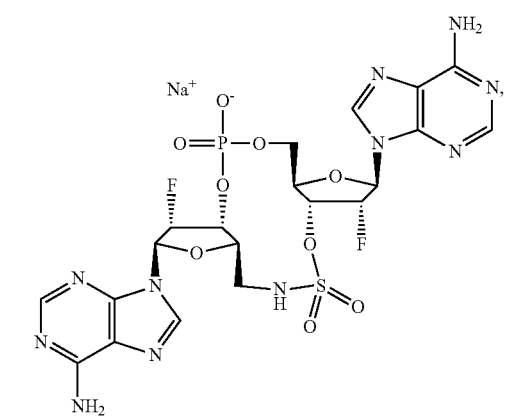
1
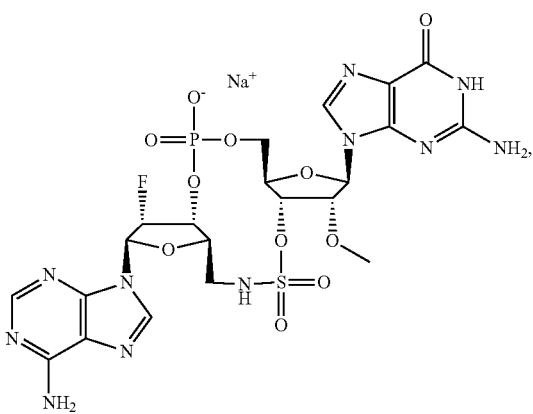
4
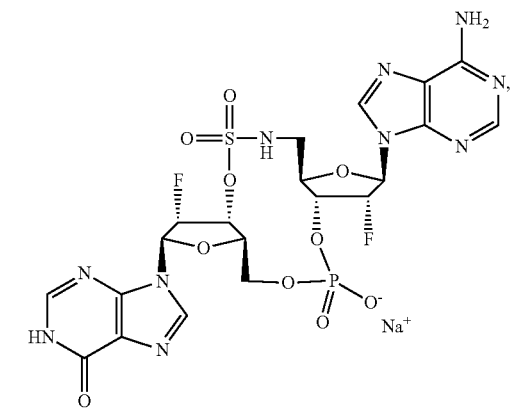
5
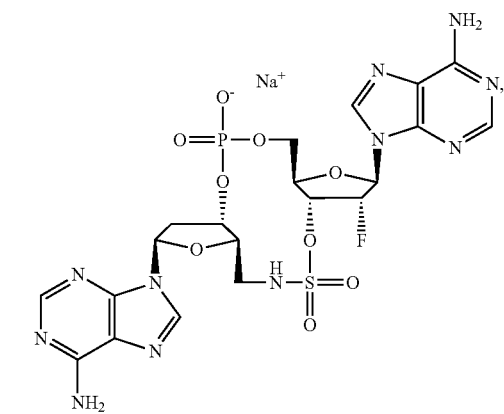
6
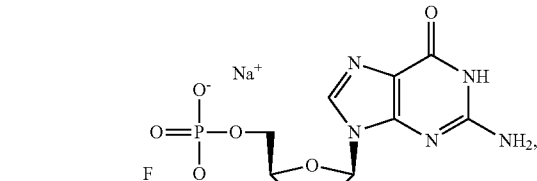
7
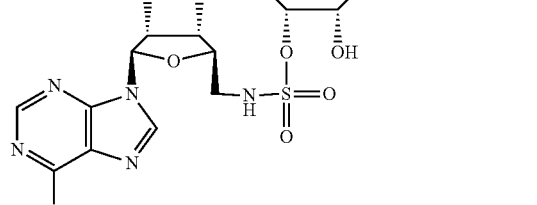
8
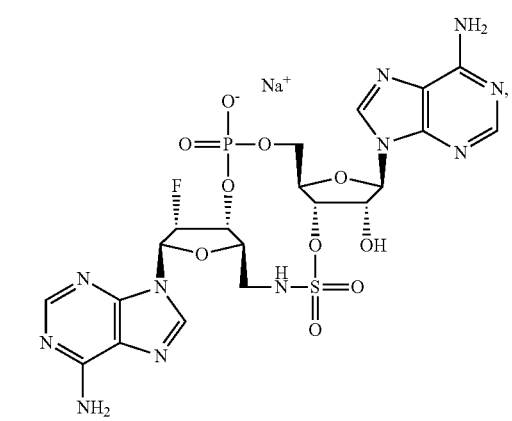
9
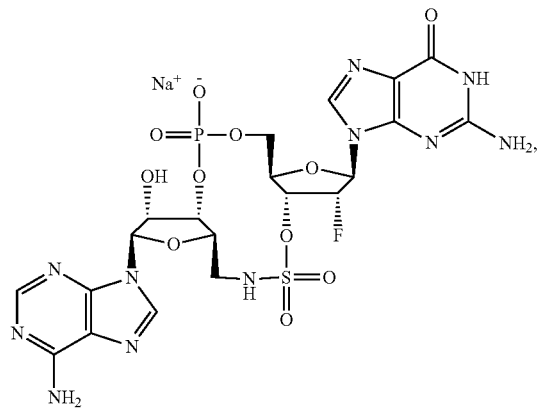
9
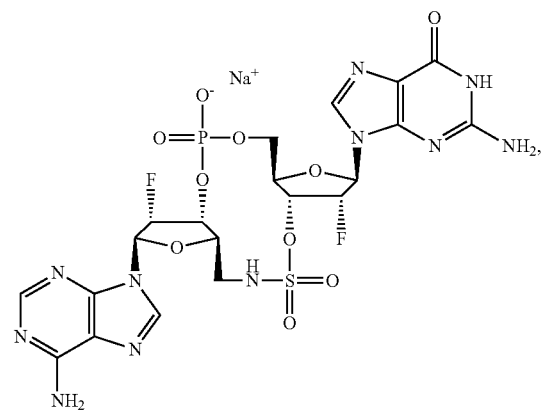
10

11
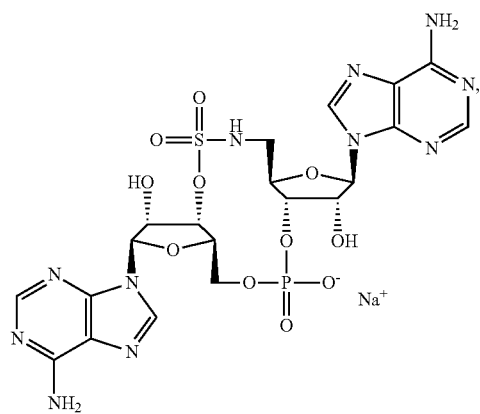
13
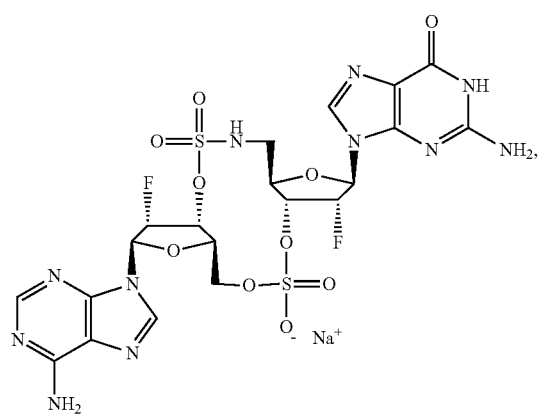
21
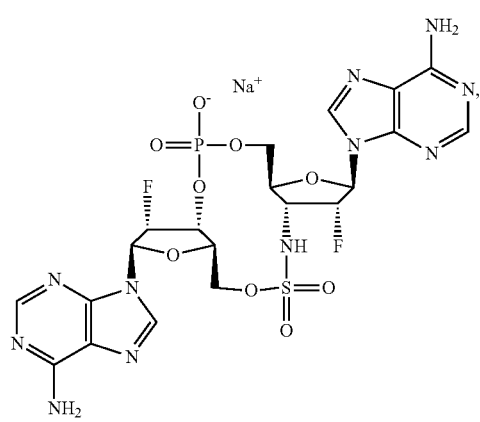
23
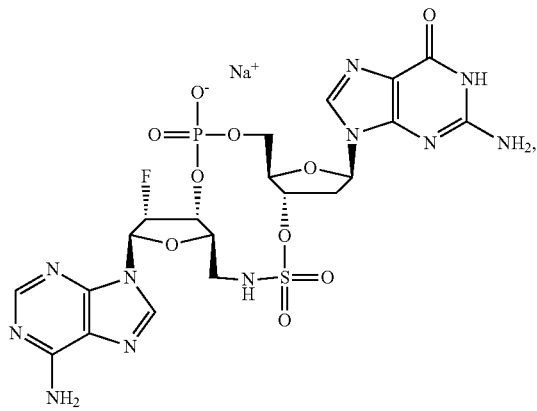
24
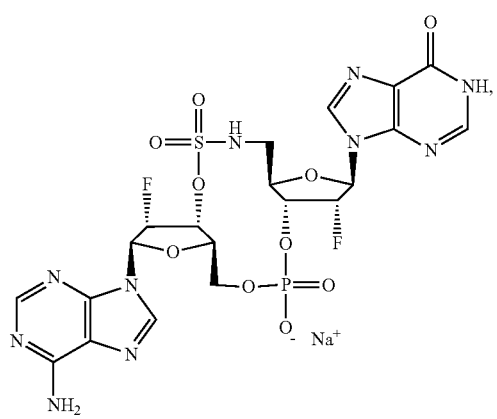
25
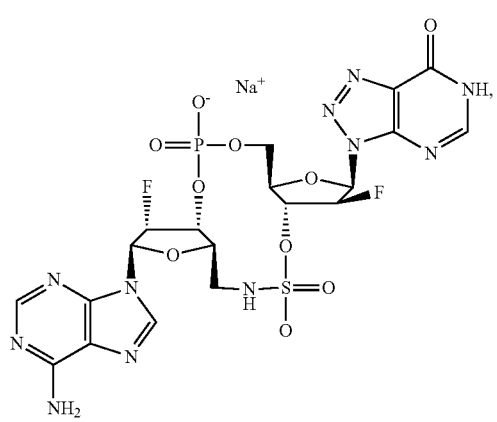

251
-continued
26
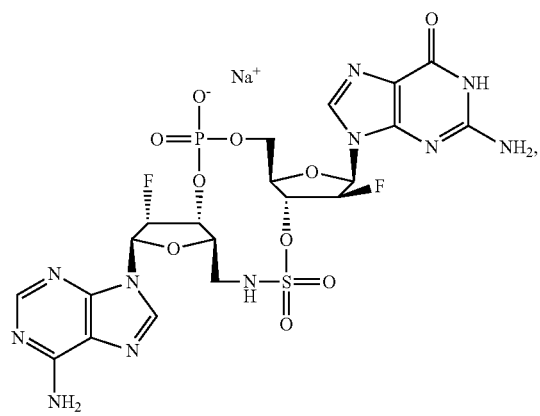
27
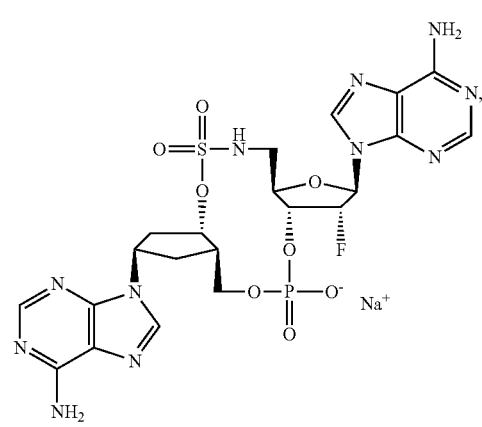
28
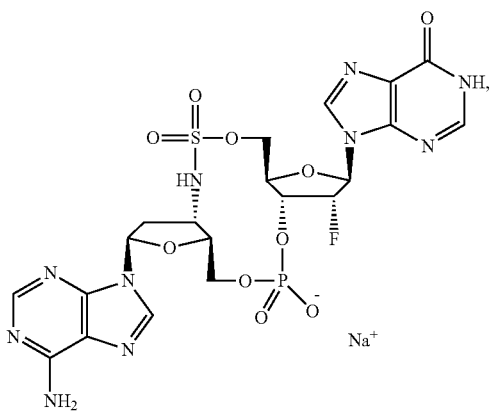
252
-continued
29
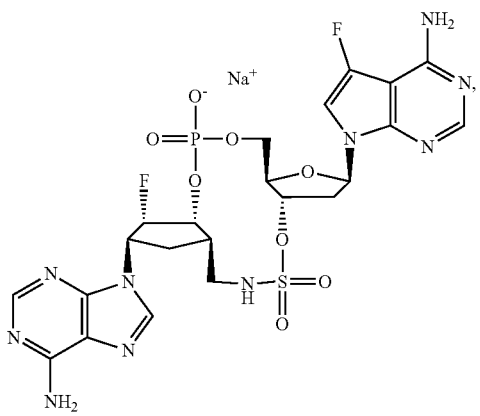
30
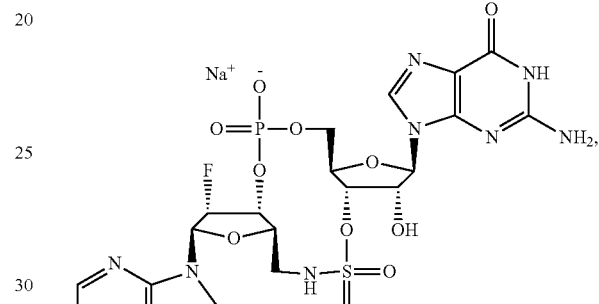
32
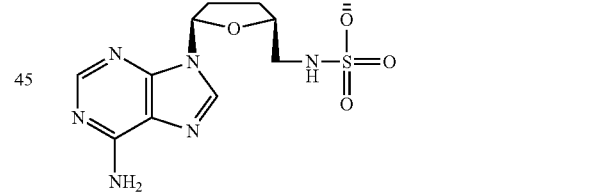
33
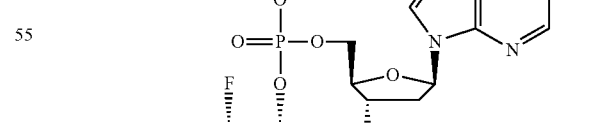

35
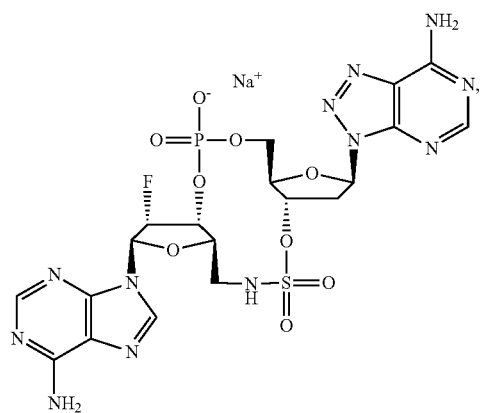
36
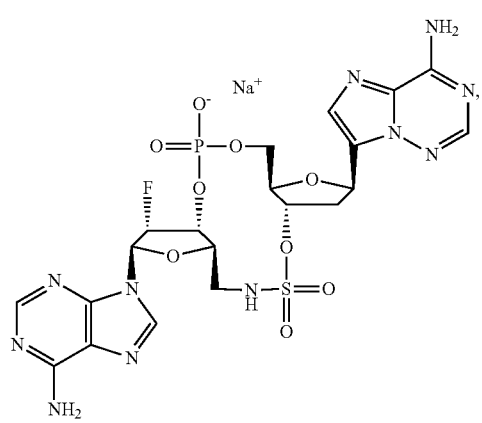
38
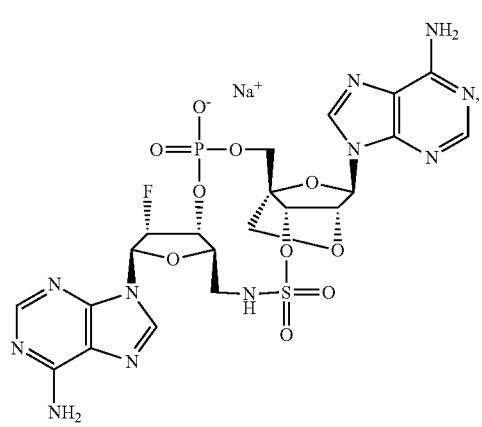
39
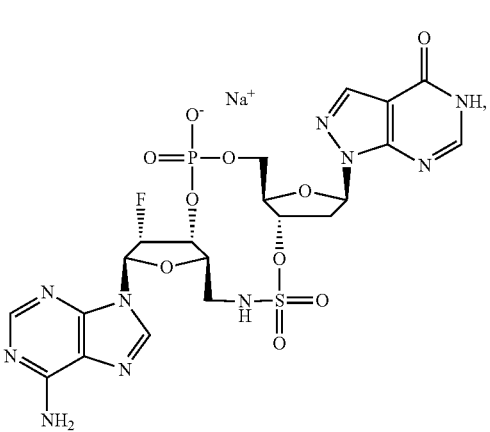
40
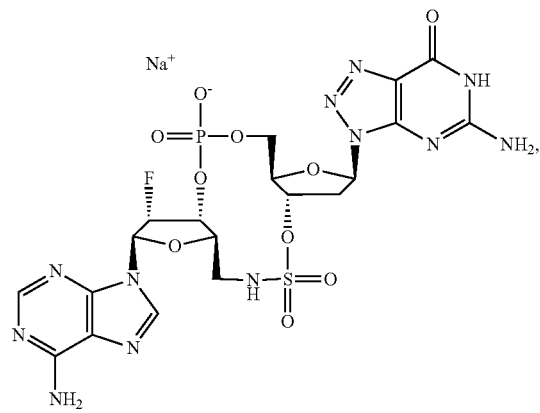
41
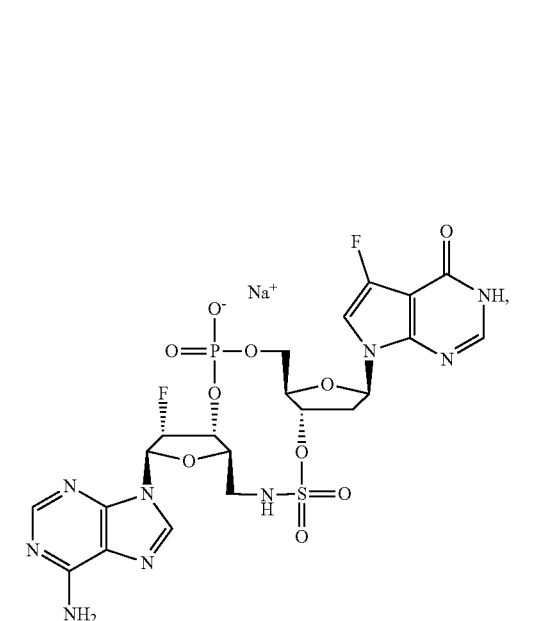
42
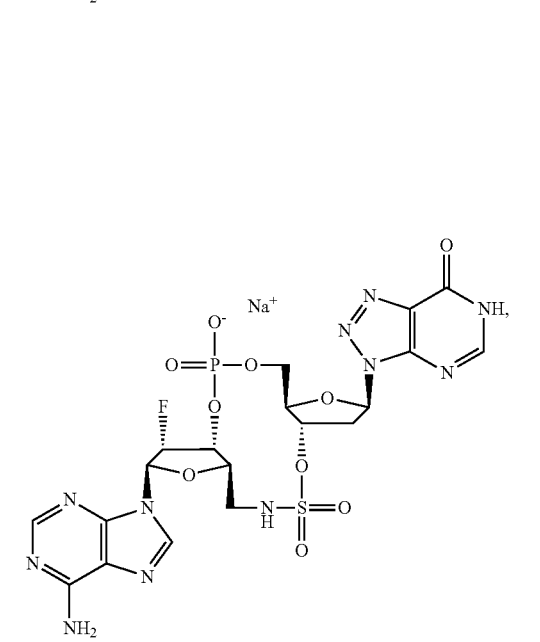

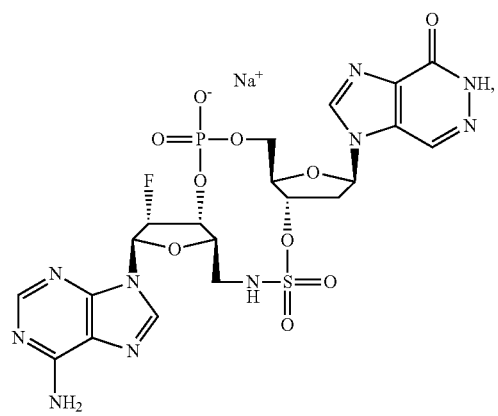
43
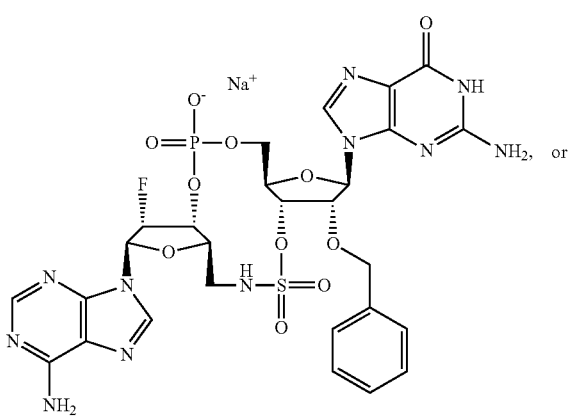
46
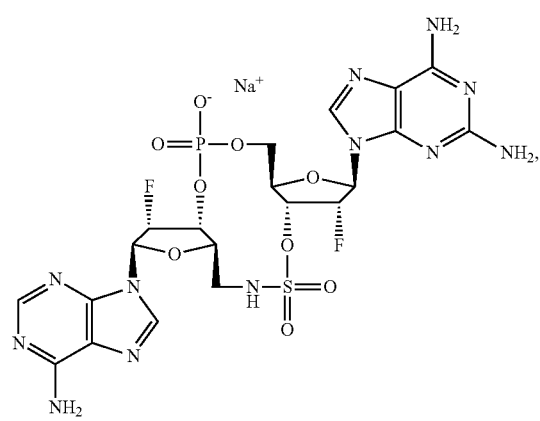
44
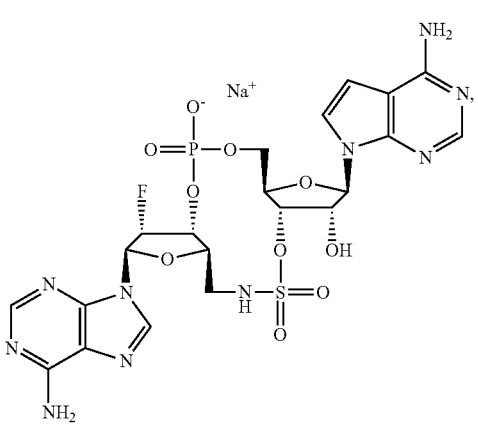
48
or a pharmaceutically acceptable salt thereof.
42. The compound of claim 1, that is:
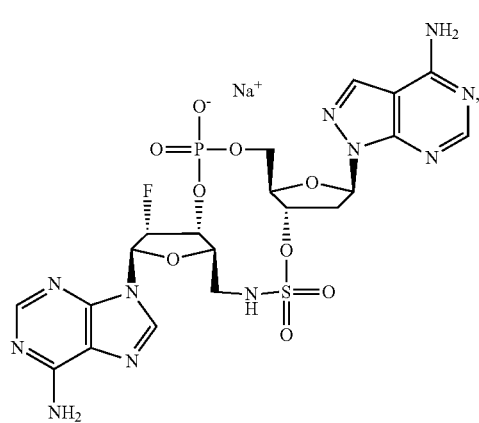
45
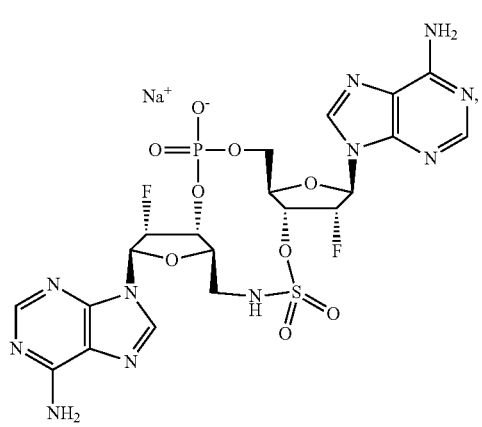
1

-continued
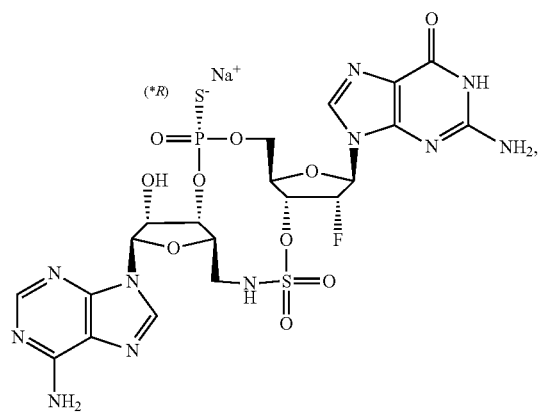
14-R
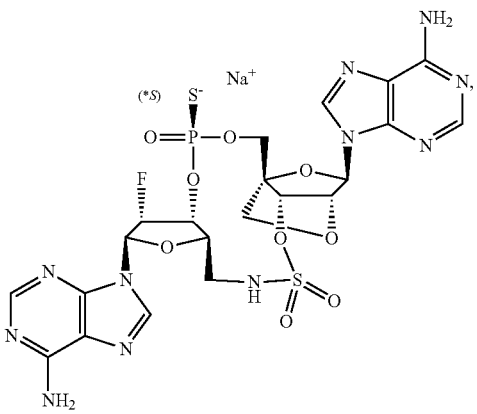
37-S
or a pharmaceutically acceptable salt thereof.
43. The compound of claim 1, that is:
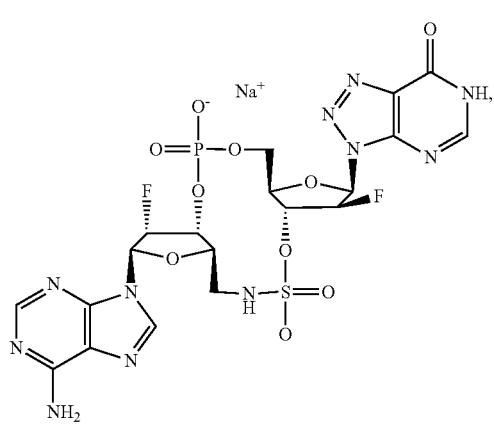
25
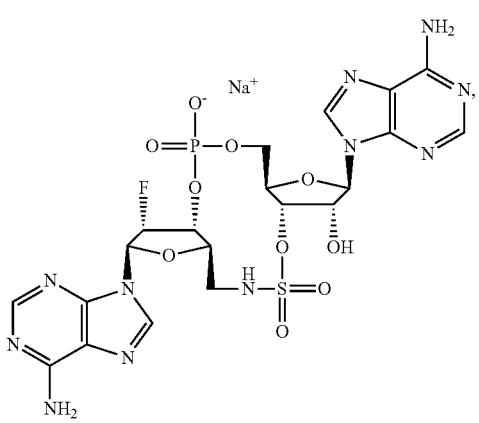
8
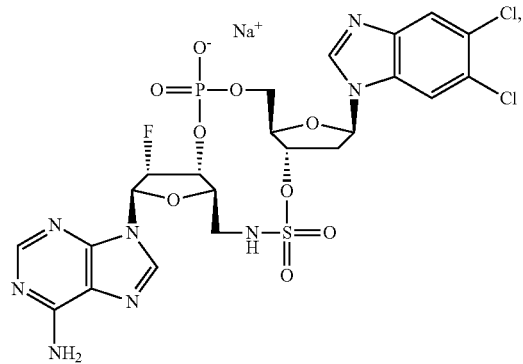
32
or
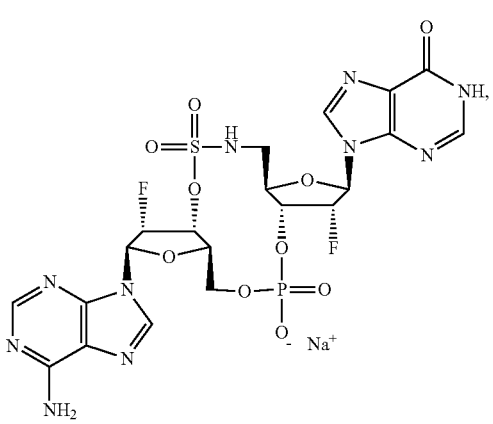
24

-continued
31-R
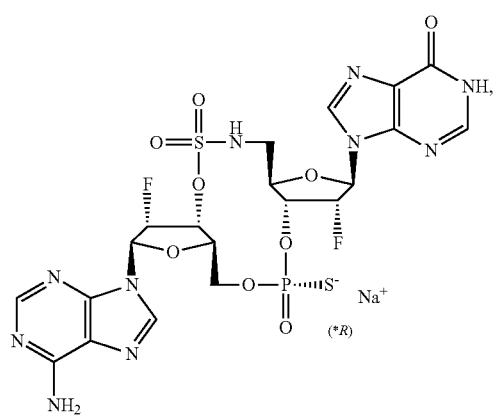
37-S
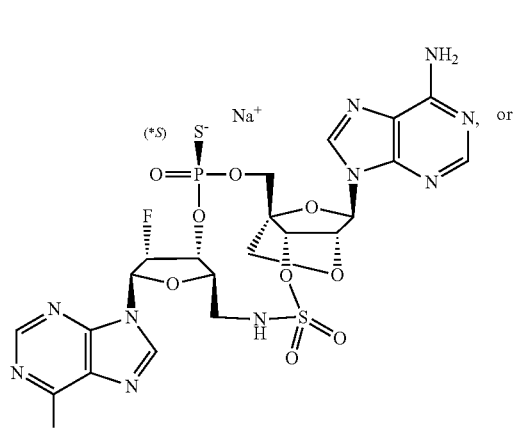
or a pharmaceutically acceptable salt thereof.
44. The compound of claim 1, that is:
5
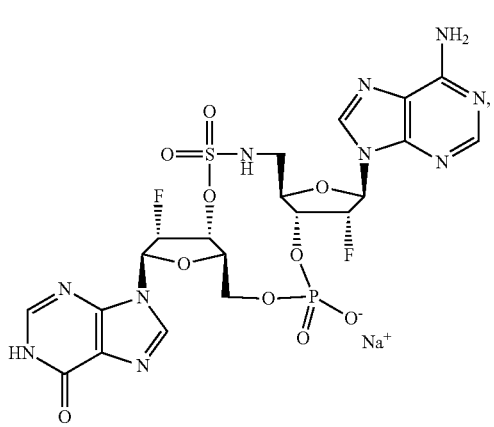
23
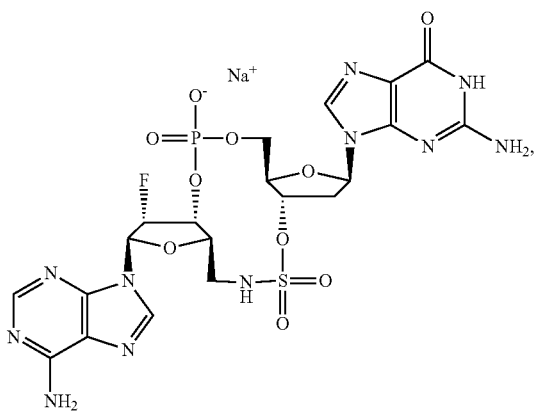
48
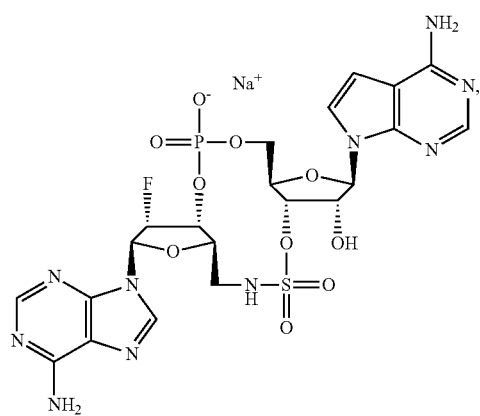
29
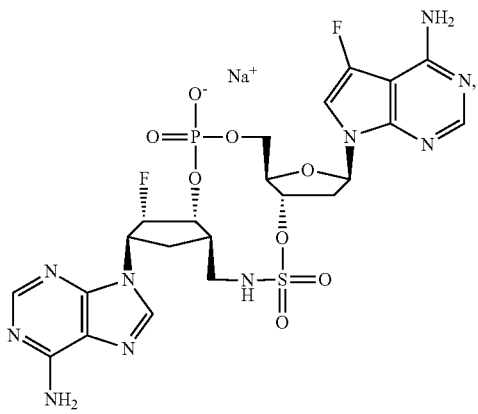

261

-continued

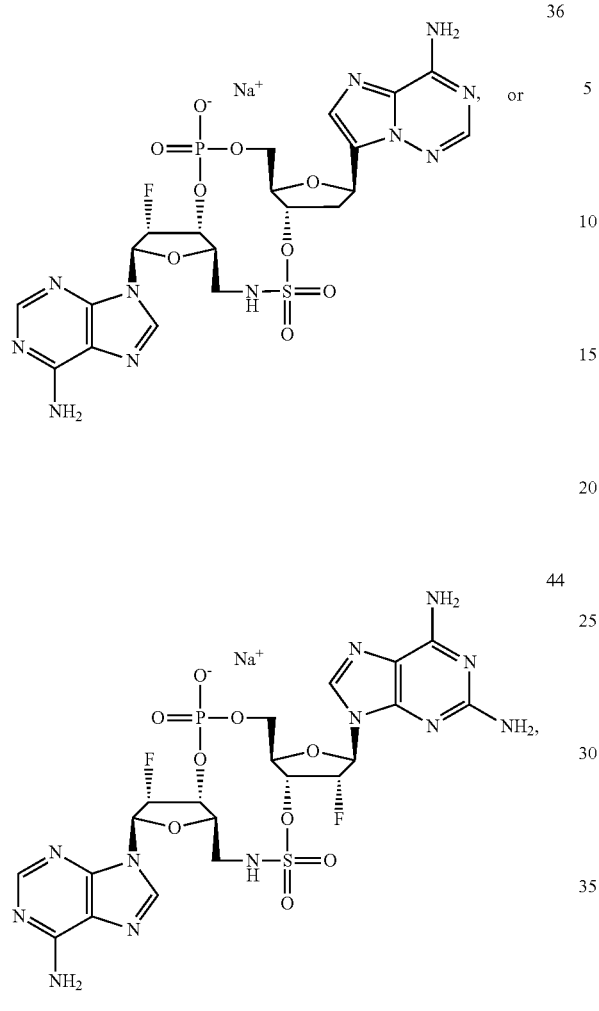

or a pharmaceutically acceptable salt thereof.

45. A pharmaceutical composition comprising a compound of claim 1 and at least one of a pharmaceutically acceptable carrier, a pharmaceutically acceptable excipient, and a pharmaceutically acceptable diluent.

46. The pharmaceutical composition of claim 45, wherein the composition is a solid oral dosage form.

47. The pharmaceutical composition of claim 45, wherein the composition is a syrup, an elixir or a suspension.

48. A method of treating a disease, syndrome, or condition that is viral infection, melanoma, colon cancer, breast cancer, prostate cancer, lung cancer, or fibrosarcoma, comprising administering to a subject in need thereof a therapeutically effective amount of the composition of claim 45.

49. The method of claim 48, wherein said disease, syndrome, or condition is cancer.

50. The method of claim 48, wherein said cancer is melanoma, colon cancer, breast cancer, prostate cancer, lung cancer, or fibrosarcoma.

51. The method of claim 48, wherein said disease, syndrome, or condition is a viral infection.

52. The method of claim 48, wherein the viral infection is hepatitis B.

262

53. A compound that is:

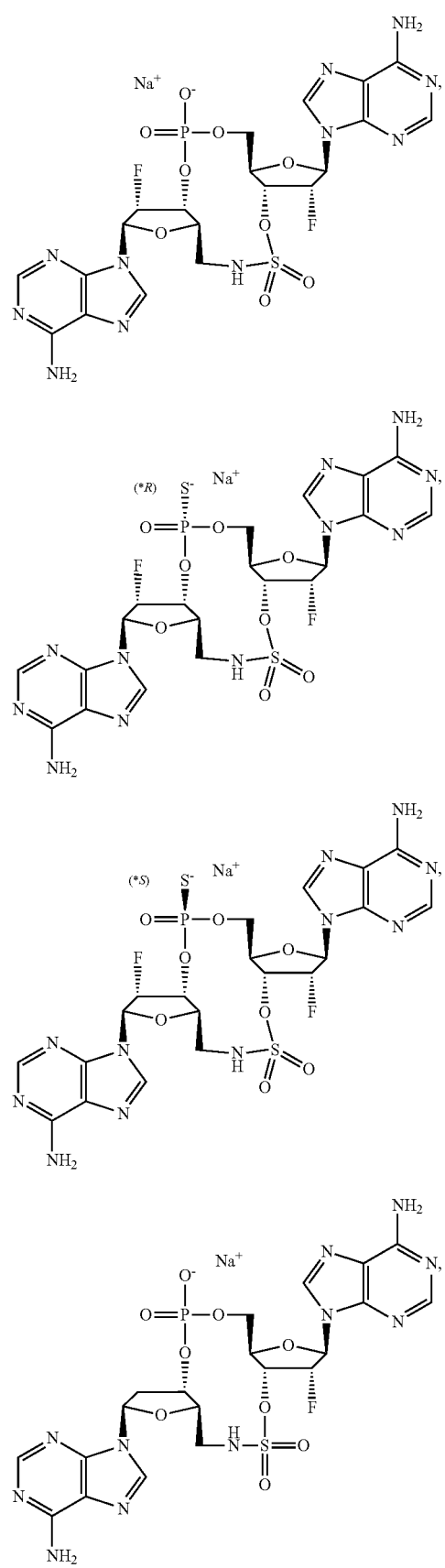

263
-continued
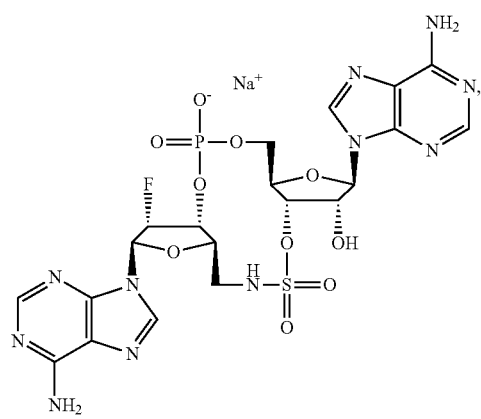
8
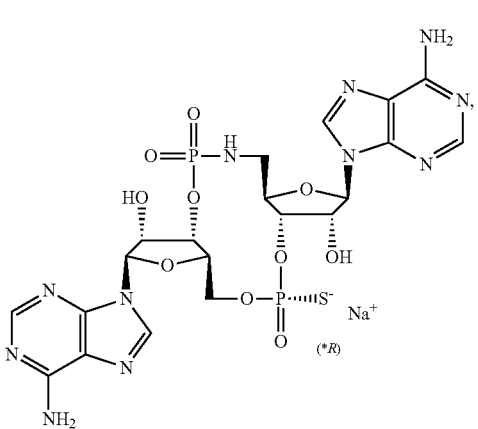
12-R
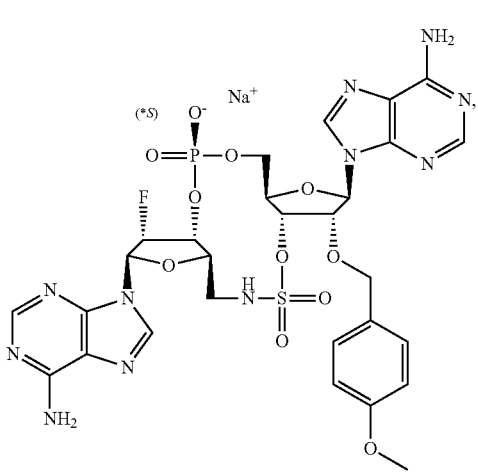
15-S
264
-continued
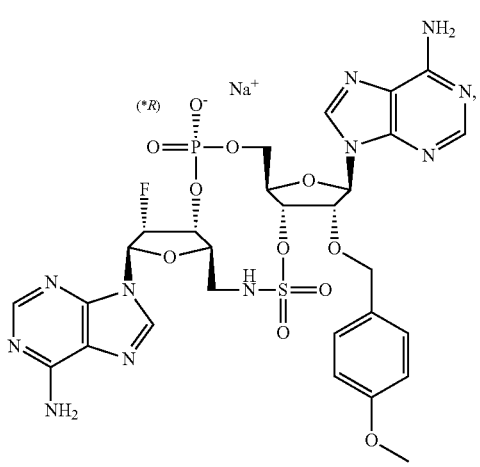
15-R
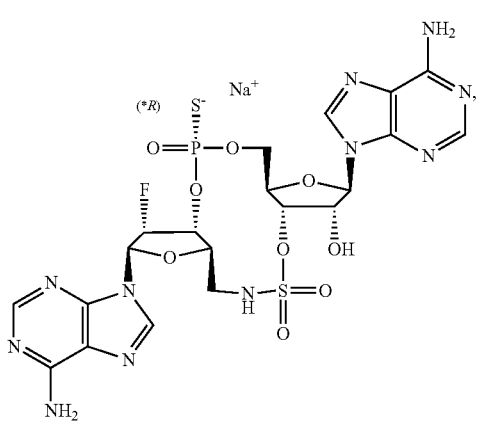
19-R
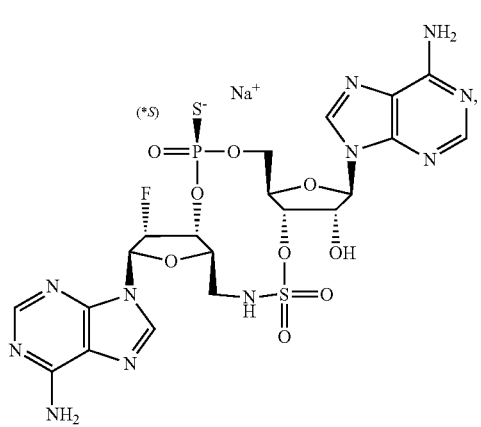
19-S

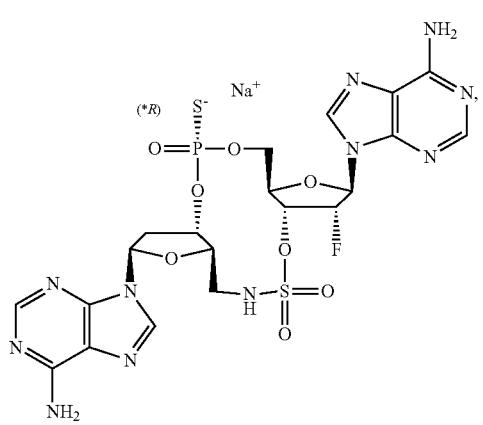
20-R
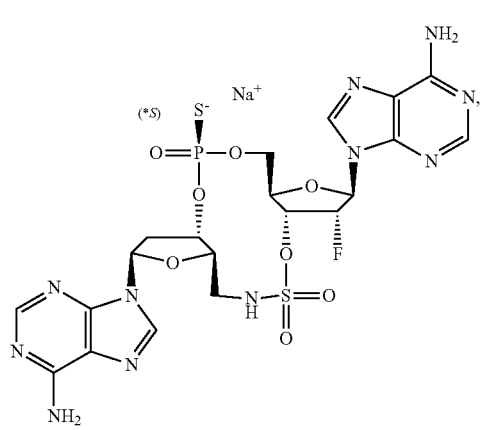
20-S
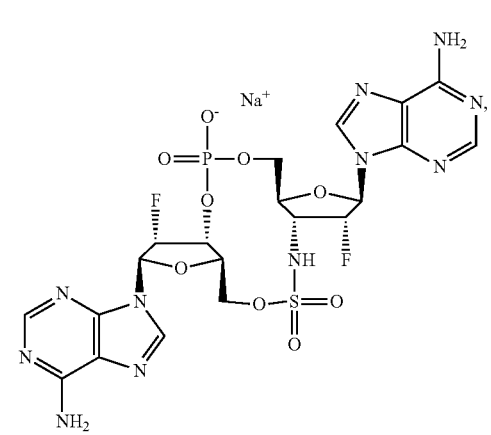
21
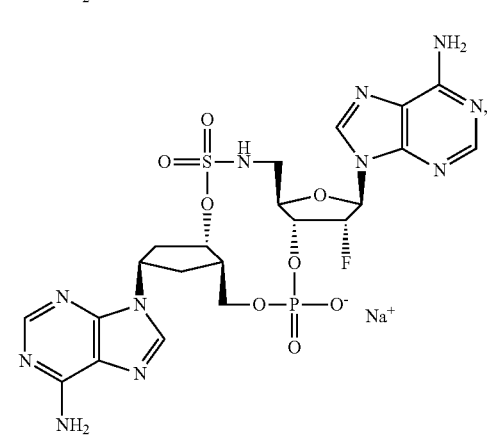
27
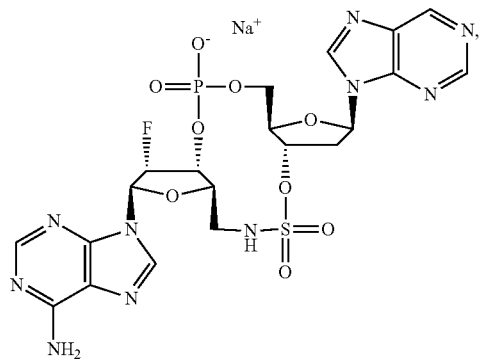
33
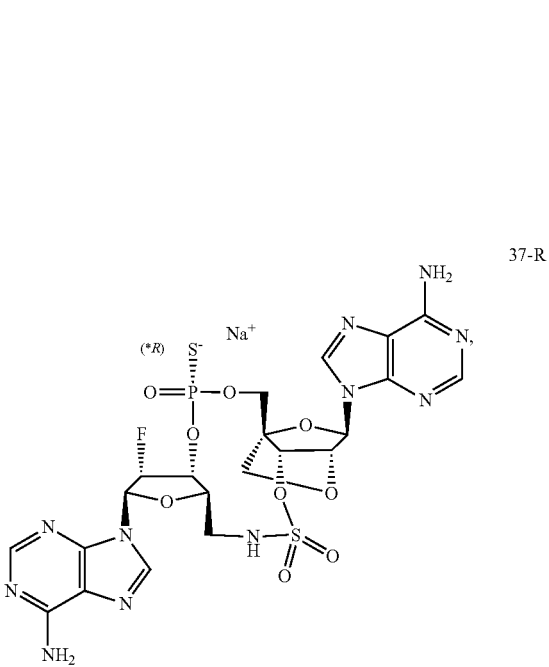
37-R
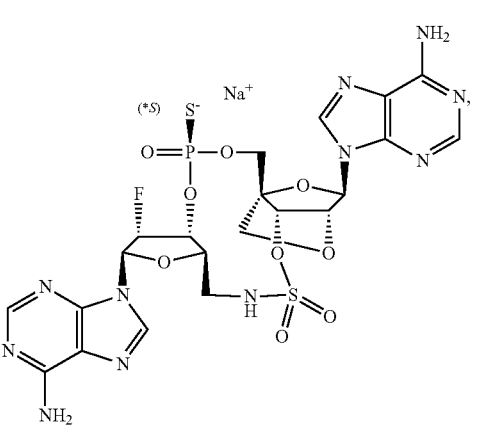
37-S -continued
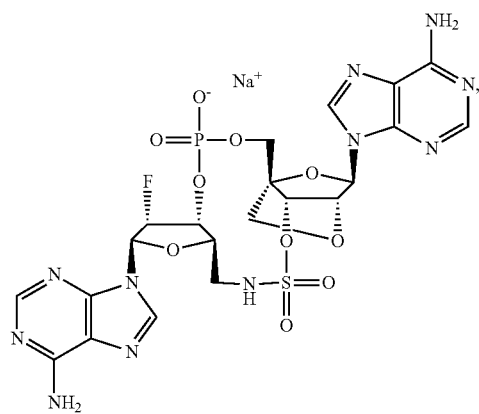
38
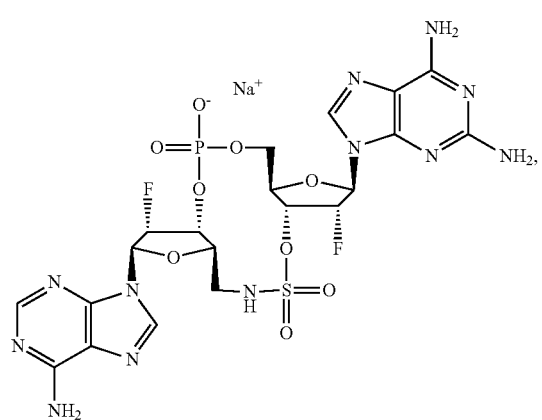
44
-continued
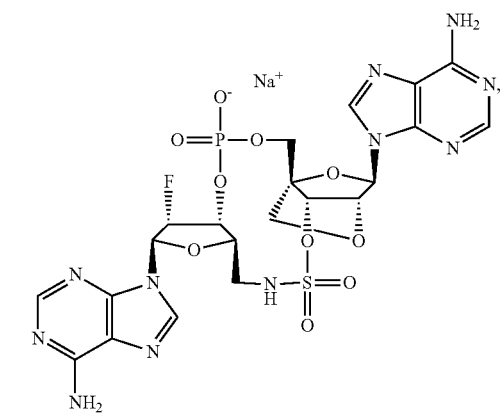
46
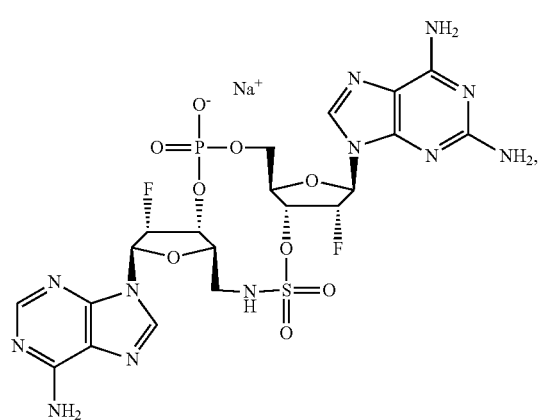
47
or a pharmaceutically acceptable salt form thereof.
* * * * *